United States Patent
Seitz et al.

(10) Patent No.: US 9,822,103 B2
(45) Date of Patent: Nov. 21, 2017

(54) INHIBITORS OF LYSINE METHYL TRANSFERASE

(71) Applicant: BRISTOL-MYERS SQUIBB COMPANY, Princeton, NJ (US)

(72) Inventors: Steven P. Seitz, Swarthmore, PA (US); Jay A. Markwalder, Lahaska, PA (US); Ashok Vinayak Purandare, Pennington, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 15/037,066

(22) PCT Filed: Nov. 18, 2014

(86) PCT No.: PCT/US2014/066032
§ 371 (c)(1),
(2) Date: May 17, 2016

(87) PCT Pub. No.: WO2015/077194
PCT Pub. Date: May 28, 2015

(65) Prior Publication Data
US 2016/0297805 A1    Oct. 13, 2016

Related U.S. Application Data

(60) Provisional application No. 61/907,527, filed on Nov. 22, 2013.

(51) Int. Cl.
| | | |
|---|---|---|
| *A61K 31/4427* | (2006.01) | |
| *C07D 405/12* | (2006.01) | |
| *C07D 405/14* | (2006.01) | |
| *C07D 413/14* | (2006.01) | |
| *A61K 31/443* | (2006.01) | |
| *A61K 31/444* | (2006.01) | |
| *A61K 31/496* | (2006.01) | |
| *A61K 31/506* | (2006.01) | |
| *A61K 31/5377* | (2006.01) | |
| *A61K 45/06* | (2006.01) | |

(52) U.S. Cl.
CPC ......... *C07D 405/12* (2013.01); *A61K 31/443* (2013.01); *A61K 31/444* (2013.01); *A61K 31/4427* (2013.01); *A61K 31/496* (2013.01); *A61K 31/506* (2013.01); *A61K 31/5377* (2013.01); *A61K 45/06* (2013.01); *C07D 405/14* (2013.01); *C07D 413/14* (2013.01)

(58) Field of Classification Search
None
See application file for complete search history.

(56) References Cited

FOREIGN PATENT DOCUMENTS

| WO | WO 2011/140324 | 11/2011 |
|---|---|---|
| WO | WO 2011/140325 | 11/2011 |
| WO | WO 2012/075080 | 6/2012 |
| WO | WO 2012/118812 | 9/2012 |
| WO | WO 2012/142504 | 10/2012 |
| WO | WO 2012/142513 | 10/2012 |
| WO | WO 2013/049770 | 4/2013 |
| WO | WO 2013/067296 | 5/2013 |
| WO | WO 2013/067300 | 5/2013 |
| WO | WO 2013/075084 | 5/2013 |
| WO | WO 2013/173441 | 11/2013 |
| WO | WO 2015/077193 | 5/2015 |

OTHER PUBLICATIONS

Simon, Jeffrey. Mutation Research 647 (2008) 21-29.*
Myeloproliferative disorders: University of Maryland Medical Center. (2016).Web: <http://umm.edu/health/medical/altmed/condition/myeloproliferative-disorders>.*
MedicineNet.com (2004) Web <http://www.medterms.com>.*
Konze et al., ACS Chemical Biology, vol. 8, No. 6, pp. 1324-1334 (2013).

* cited by examiner

*Primary Examiner* — Deepak Rao
*Assistant Examiner* — Laura Daniel
(74) *Attorney, Agent, or Firm* — Elliott Korsen

(57) ABSTRACT

There are disclosed compounds that are inhibitors of EZH2, pharmaceutical compositions containing said compounds and methods of treating hyperproliferative, inflammatory, infectious, and immunoregulatory disorders and diseases utilizing the compounds of the invention.

7 Claims, No Drawings

INHIBITORS OF LYSINE METHYL TRANSFERASE

CROSS-REFERENCES TO RELATED APPLICATION

This application claims priority benefit under Title 35 §119(e) of U.S. provisional Application 61/907,527 filed Nov. 22, 2013, the contents of which are herein incorporated by reference in its entirety.

FIELD OF THE INVENTION

The present invention relates to novel compounds which are inhibitors of Enhancer of Zeste 2 (EZH2), to methods of using such compounds for inhibiting protein methyl transferases in the treatment of hyperproliferative, inflammatory, infectious, and immunoregulatory disorders and diseases, and to pharmaceutical compositions containing such compounds.

The invention also encompasses pharmaceutical compositions containing these compounds. The compounds and pharmaceutical compositions of the invention are particularly well suited as inhibitors of protein methyl transferases and consequently can be advantageously used as therapeutic agents for the treatment of diseases and disorders including cancer, asthma, COPD, and allergic diseases, rheumatoid arthritis, atherosclerosis, psoriasis, solid organ transplant rejection, osteoarthritis and inflammatory bowel syndrome. This invention also relates to methods of using the compounds of this invention alone or in combination with other pharmaceutically active agents.

BACKGROUND OF THE INVENTION

Cells in an organism, regardless of their function, contain identical genetic material yet vary greatly in gene expression and phenotype. Gene transcription is controlled in part through the architecture of its chromatin and through recruitment of transcription factors to specific regulatory elements. These mechanisms are regulated through covalent modifications of DNA and histone proteins that leave the underlying DNA sequence unaltered. Posttranslational modifications of histone proteins are mediated by enzymes that can add or subtract covalent attachments at specific residues. Histones can be methylated, acetylated, phosphorylated, or ubiquitinated and, depending on the residue being modified, identical chemical modifications can have opposing consequences. Histone methyl transferases (HMTs) are enzymes that catalyze the transfer of methyl groups from S-Adenosyl-L-Methionine (SAM) to specific lysine residues of proteins.

Enhancer of Zeste 2 (EZH2) is a HMT that catalyzes methylation of H3K27. Along with cofactors SUZ12, EED, and RbAp46/48, EZH2 forms the Polycomb Repressive Complex 2 (PRC2) (Morey L et al, *Trends Biochem Sci* 2010; 35 p 323-32.). EZH2 is overexpressed in a wide range of cancers, including advanced-stage and high-grade prostate, breast, and lung tumors (Albert M. et. al., *Semin Cell Dev Biol,* 2010, 21, p 209-20). EZH2 and PRC2 are critical for the control of gene expression in embryonic stem cells, maintaining self-renewal while inhibiting differentiation (Bracken A P, *Genes Dev* 2006; 20, p 1123-36), and these properties of EZH2 appear active when the gene is overexpressed in tumors. EZH2 overexpression induces cell migration and colony formation and induces genomic instability by repression of regulators of DNA repair (Kleer C G, et al. *Proc Natl Acad Sci USA* 2003, 100, p 11606-11.). Conversely, EZH2 depletion suppresses proliferation and attenuates tumor formation in vivo (Gonzalez M E, et al., *Oncogene,* 2009, 28, p 843-53.). Recently, somatic mutations and deletions of EZH2 were identified in hematologic malignancies, leading to the gain or loss of EZH2 function. Approximately 30% of diffuse large B-cell lymphomas (DLBCL) and 10% of follicular lymphomas contain a mutation at tyrosine 641 (Y641) within the SET domain, predicted to alter the substrate recognition pocket within the enzyme (Morin R D et al., *Nat Genet,* 2010, 42, p 181-5.). These mutations are always heterozygous, suggesting that they are either dominant to or cooperate with the wild-type (WT) EZH2 protein. Enzymatic studies showed that WT EZH2 converted unmethylated H3K27 to H3K27me1 and to a lesser extent the me2 and me3 states (Sneeringer C J et al, *Proc Natl Acad Sci USA.,* 2010, 107, p 20980-5). By contrast, EZH2Y641X failed to recognize unmethylated H3K27 but readily converted H3K27me1 (created by WT EZH2) to H3K27me2 or me3. Accordingly, DLBCL cells harboring EZH2Y641X display increased levels of H3K27me3. EZH2 is silenced in resting, mature B cells and is transiently upregulated in germinal center B cells, where, along with BCL6, it blocks DNA damage response pathways allowing cells to survive the somatic hypermutation of antibody maturation (Velichutina I et al *Blood* 2010, 116, p 5247-55). By amplifying these functions and targeting additional pathways, EZH2 mutations may stimulate malignant transformation. In myeloid neoplasia, EZH2 is most often affected by deletions and nonsense mutations that yield loss of function, and leukemia cell lines harboring EZH2 mutations show decreased H3K27 methylation (Ernst T et al *Nat Genet* 2010, 42, p 722-6.). The presence of activating and inactivating EZH2 mutations in different cancers suggest a complex, context-dependent role of Polycomb proteins in oncogenesis. It is unclear whether EZH2 affects different sets of genes in different malignancies or whether global histone changes may interfere with other chromatin functions such as replication and DNA repair. Nevertheless, the frequent occurrence of genetic lesions affecting H3K27 suggests that this mark is under tight control, which may present a challenge in the design of safe and effective EZH2 inhibitors. The S-adenosylhomocysteine (SAH) hydrolase inhibitor 3-Deazaneplanocin A (DZNeP) is an early example of an EZH2 inhibitor (Tan J, et al. *Genes Dev* 2007, 21, p 1050-63.). DZNeP can inhibit HMTs by increasing SAH levels, inducing the degradation of EZH2 and leading to a global decrease of H3K27 methylation accompanied by apoptosis of cancer cells. However, in some cells, DZNeP decreases methylation of multiple other histone residues, perhaps as a result of the ability of SAH to compete with the AdoMet cofactor (Miranda T B et al. *Mol Cancer Ther* 2009, 8, p 1579-88.). Hence, more specific inhibitors of EZH2 are required to address various lesions in cancer. Recently inhibitors of EZH2, acting as a SAM competitor and affecting specifically the HMT activity of EZH2 (McCabe M T et al, *Nature,* 2012, 492, p 108-112.) have been reported. They also show antiproliferative activity in DLBCL cell lines expressing mutant EZH2, suggesting that direct inhibition of EZH2 activity presents a promising avenue for treatment in the clinic.

SUMMARY OF THE INVENTION

The present invention provides compounds, pharmaceutical compositions containing said compounds, and methods for treating various medical conditions using said compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in therapy.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect of the invention, there are provided compounds of formula (I)

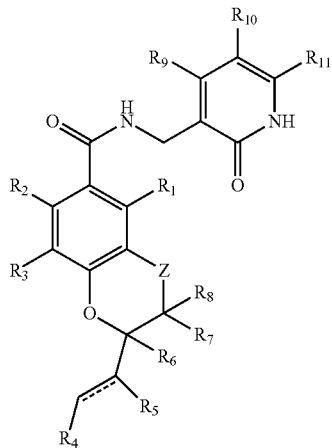

(I)

wherein
the dotted line represents an optional double bond;
Z is O, $CH_2$ or a direct bond;
$R_1$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl, $C_1$-$C_6$ alkynyl, optionally substituted aryl or optionally substituted heterocyclo;
$R_2$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl, $C_1$-$C_6$ alkynyl, optionally substituted aryl or optionally substituted heterocyclo;
$R_3$ is hydrogen, halogen, —CN, —$CONR_{12}R_{13}$, optionally substituted $C_3$-$C_6$ mono or bicyclic aryl, optionally substituted $C_3$-$C_{11}$ mono or bicyclic heteroaryl, optionally substituted $C_1$-$C_6$ alkyl $C_3$-$C_6$aryl or optionally substituted $C_1$-$C_6$ alkyl $C_3$-$C_8$ heteroaryl, wherein the optional substituents are halogen, $C_1$-$C_6$ alkyl, $C_1$-$C_6$ alkoxy, —$CONR_{12}R_{13}$ or heterocyclo;
$R_4$, $R_5$, $R_6$, $R_7$ and $R_8$ are independently one or more hydrogen, flourine, $CF_3$ or optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl, $C_1$-$C_6$ alkenyl, optionally substituted aryl or optionally substituted heterocyclo; or
$R_6$ and $R_7$ may be taken together to form a fused $C_3$-$C_8$ cycloalkyl group,
$R_4$ and $R_6$ may be taken together to form a spiro $C_3$-$C_8$ cycloalkyl group; or
$R_7$ and $R_8$ may be taken together to form a spiro $C_3$-$C_8$ cycloalkyl group;
$R_9$, $R_{10}$ and $R_{11}$ are independently hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl, $C_1$-$C_6$ alkenyl, optionally substituted aryl or optionally substituted heterocyclo;
$R_{12}$ and $R_{13}$ are independently hydrogen, $C_1$-$C_6$ alkyl, or
$R_{12}$ and $R_{13}$ are taken together with the nitrogen atom to which they are attached to form an optionally substituted heterocyclo group;
or a pharmaceutically acceptable salt, tautomer or stereoisomer thereof.

In a second aspect of the invention, there is provided a compound of formula I

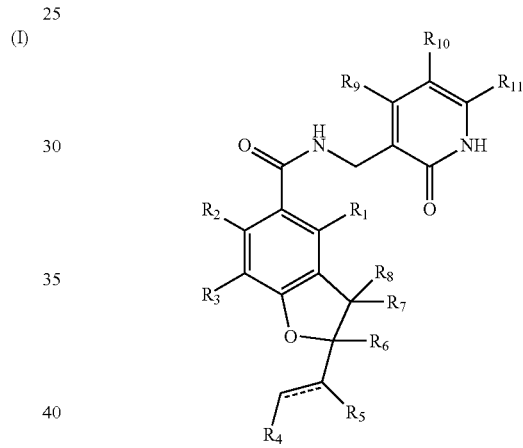

wherein
$R_1$ is hydrogen, halogen, $CF_3$ or optionally substituted $C_1$-$C_6$ alkyl;
$R_2$ is hydrogen, halogen, $CF_3$ or optionally substituted $C_1$-$C_6$ alkyl;
$R_3$ is hydrogen, halogen, —CN, —$CONR_{12}R_{13}$, optionally substituted $C_3$-$C_6$ mono or bicyclic aryl, optionally substituted $C_3$-$C_{11}$ mono or bicyclic heteroaryl, optionally substituted $C_1$-$C_6$ alkyl $C_3$-$C_6$aryl or optionally substituted $C_1$-$C_6$ alkyl $C_3$-$C_8$ heteroaryl, wherein the optional substituents are halogen, $C_1$-$C_6$ alkyl, $C_1$-$C_6$ alkoxy, —$CONR_{12}R_{13}$ or heterocyclo;
$R_4$, $R_5$, $R_6$, $R_7$ and $R_8$ are independently one or more hydrogen, flourine, $CF_3$ or optionally substituted $C_1$-$C_6$ alkyl; or
$R_6$ and $R_7$ may be taken together to form a fused $C_3$-$C_8$ cycloalkyl group,
$R_4$ and $R_6$ may be taken together to form a spiro $C_3$-$C_8$ cycloalkyl group; or
$R_7$ and $R_8$ may be taken together to form a spiro $C_3$-$C_8$ cycloalkyl group;
$R_9$, $R_{10}$ and $R_{11}$ are independently hydrogen, halogen, $CF_3$ or optionally substituted $C_1$-$C_6$ alkyl;

$R_{12}$ and $R_{13}$ are independently hydrogen, $C_1$-$C_6$ alkyl, or $R_{12}$ and $R_{13}$ are taken together with the nitrogen atom to which they are attached to form an optionally substituted heterocyclo group;

or a pharmaceutically acceptable salt, tautomer or stereoisomer thereof.

In a third aspect of the invention within the prior aspects, there is provided a compound of formula I

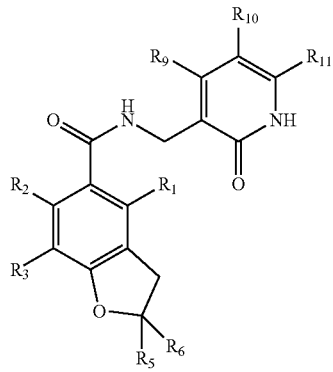

$R_1$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;

$R_2$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;

$R_3$ is hydrogen, halogen, —CN, —$CONR_{12}R_{13}$, optionally substituted $C_3$-$C_6$ mono or bicyclic aryl, optionally substituted $C_3$-$C_{11}$ mono or bicyclic heteroaryl, optionally substituted $C_1$-$C_6$ alkyl $C_3$-$C_6$aryl or optionally substituted $C_1$-$C_6$ alkyl $C_3$-$C_8$ heteroaryl, wherein the optional substituents are halogen, $C_1$-$C_6$ alkyl, $C_1$-$C_6$ alkoxy, —$CONR_{12}R_{13}$ or heterocyclo;

$R_5$ and $R_6$ are independently one or more hydrogen, fluorine, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo; or $R_9$, $R_{10}$ and $R_{11}$ are independently hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl or $C_1$-$C_6$ alkynyl, optionally substituted aryl or optionally substituted heterocyclo;

$R_{12}$ and $R_{13}$ are independently hydrogen, $C_1$-$C_6$ alkyl, or $R_{12}$ and $R_{13}$ are taken together with the nitrogen atom to which they are attached to form an optionally substituted heterocyclo group;

or a pharmaceutically acceptable salt, tautomer or stereoisomer thereof.

In a fourth aspect of the invention within the prior aspects, there is provided a compound of formula I

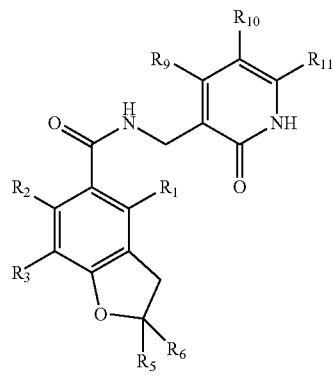

$R_1$ is hydrogen, halogen, $CF_3$ or optionally substituted $C_1$-$C_6$ alkyl;

$R_2$ is hydrogen, halogen, $CF_3$ or optionally substituted $C_1$-$C_6$ alkyl;

$R_3$ is hydrogen, halogen, —CN, —$CONR_{12}R_{13}$, optionally substituted $C_3$-$C_6$ mono or bicyclic aryl, optionally substituted $C_3$-$C_{11}$ mono or bicyclic heteroaryl, optionally substituted $C_1$-$C_6$ alkyl $C_3$-$C_6$aryl or optionally substituted $C_1$-$C_6$ alkyl $C_3$-$C_8$ heteroaryl, wherein the optional substituents are halogen, $C_1$-$C_6$ alkyl, $C_1$-$C_6$ alkoxy, —$CONR_{12}R_{13}$ or heterocyclo;

$R_5$ and $R_6$ are independently one or more hydrogen, fluorine, $CF_3$ or optionally substituted $C_1$-$C_6$ alkyl; or $R_9$, $R_{10}$ and $R_{11}$ are independently hydrogen, halogen, $CF_3$ or optionally substituted $C_1$-$C_6$ alkyl;

$R_{12}$ and $R_{13}$ are independently hydrogen, $C_1$-$C_6$ alkyl, or $R_{12}$ and $R_{13}$ are taken together with the nitrogen atom to which they are attached to form an optionally substituted heterocyclo group;

or a pharmaceutically acceptable salt, tautomer or stereoisomer thereof.

In a fifth aspect of the invention, there is provided a compound of Formula (II)

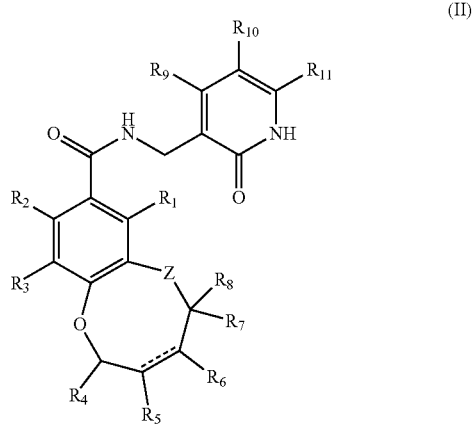

wherein

Z is O, $CH_2$ or a direct bond;

$R_1$ is hydrogen, halogen, $CF_3$, optionally substituted $C_1$-$C_6$ alkyl, optionally substituted $C_1$-$C_6$ alkoxy, optionally substituted $C_3$-$C_8$ cycloalkyl, $C_1$-$C_6$ alkenyl, $C_1$-$C_6$ alkynyl, optionally substituted aryl or optionally substituted heterocyclo;

R₂ is hydrogen, halogen, CF₃, optionally substituted C₁-C₆ alkyl, optionally substituted C₁-C₆ alkoxy, optionally substituted C₃-C₈ cycloalkyl, C₁-C₆ alkenyl, C₁-C₆ alkynyl, optionally substituted aryl or optionally substituted heterocyclo;

R₃ is hydrogen, halogen, —CN, —CONR₁₂R₁₃, optionally substituted C₃-C₆ mono or bicyclic aryl, optionally substituted C₃-C₁₁ mono or bicyclic heteroaryl, optionally substituted C₁-C₆ alkyl C₃-C₆aryl or optionally substituted C₁-C₆ alkyl C₃-C₈ heteroaryl, wherein the optional substituents are halogen, C₁-C₆ alkyl, C₁-C₆ alkoxy, —CONR₁₂R₁₃ or heterocyclo;

R₄, R₅, R₆, R₇ and R₈ are independently one or more hydrogen, fluorine, CF₃, optionally substituted C₁-C₆ alkyl, optionally substituted C₁-C₆alkoxy, optionally substituted C₃-C₈ cycloalkyl, C₁-C₆ alkenyl, C₁-C₆alkynyl, optionally substituted aryl or optionally substituted heterocyclo; or R₆ and R₇ may be taken together to form a fused C₃-C₈ cycloalkyl group, R₇ and R₈ may be taken together to form a spiro C₃-C₈ cycloalkyl group;

R₉, R₁₀ and R₁₁ are independently hydrogen, halogen, CF₃, optionally substituted C₁-C₆ alkyl, optionally substituted C₁-C₆ alkoxy, optionally substituted C₃-C₈ cycloalkyl, C₁-C₆ alkenyl or C₁-C₆alkynyl, optionally substituted aryl or optionally substituted heterocyclo;

R₁₂ and R₁₃ are independently hydrogen, C₁-C₆ alkyl, or R₁₂ and R₁₃ are taken together with the nitrogen atom to which they are attached to form an optionally substituted heterocyclo group;

or a pharmaceutically acceptable salt, tautomer or stereoisomer thereof.

In a sixth aspect of the invention within the fourth aspect, there is provided a compound of Formula (II)

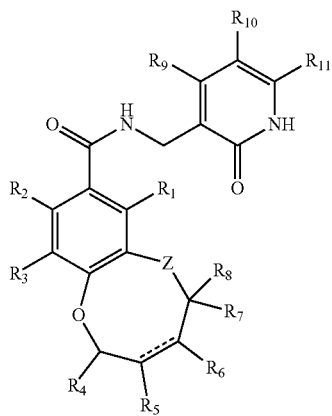

(II)

wherein
Z is O, CH₂ or a direct bond;
R₁ is hydrogen, halogen, CF₃ or optionally substituted C₁-C₆ alkyl;
R₂ is hydrogen, halogen, CF₃ or optionally substituted C₁-C₆ alkyl;
R₃ is hydrogen, halogen, —CN, —CONR₁₂R₁₃, optionally substituted C₃-C₆ mono or bicyclic aryl, optionally substituted C₃-C₁₁ mono or bicyclic heteroaryl, optionally substituted C₁-C₆ alkyl C₃-C₆aryl or optionally substituted C₁-C₆ alkyl C₃-C₈ heteroaryl, wherein the optional substituents are halogen, C₁-C₆ alkyl, C₁-C₆alkoxy, —CONR₁₂R₁₃ or heterocyclo;

R₄, R₅, R₆, R₇ and R₈ are independently one or more hydrogen, fluorine, CF₃ or optionally substituted C₁-C₆ alkyl; or R₆ and R₇ may be taken together to form a fused C₃-C₈ cycloalkyl group, R₇ and R₈ may be taken together to form a spiro C₃-C₈ cycloalkyl group;

R₉, R₁₀ and R₁₁ are independently hydrogen, halogen, CF₃ or optionally substituted C₁-C₆ alkyl;

R₁₂ and R₁₃ are independently hydrogen, C₁-C₆ alkyl, or R₁₂ and R₁₃ are taken together with the nitrogen atom to which they are attached to form an optionally substituted heterocyclo group;

or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another aspect, the invention provides a compound selected from the following 7-Bromo-N-((4,6-dimethyl-2-oxo-1,2-dihydropyridin-3-yl)methyl)-2,2-dimethyl-2,3-dihydrobenzofuran-5-carboxamide, 7-Chloro-N-((4,6-dimethyl-2-oxo-1,2-dihydropyridin-3-yl)methyl)-2,2-dimethyl-2,3-dihydrobenzofuran-5-carboxamide, N-((4,6-Dimethyl-2-oxo-1,2-dihydropyridin-3-yl)methyl)-2,2-dimethyl-2,3-dihydrobenzofuran-5-carboxamide, N-((4,6-Dimethyl-2-oxo-1,2-dihydropyridin-3-yl)methyl)-7-fluoro-2,2-dimethyl-2,3-dihydrobenzofuran-5-carboxamide, N-((4,6-Dimethyl-2-oxo-1,2-dihydropyridin-3-yl)methyl)-2,2,7-trimethyl-2,3-dihydrobenzofuran-5-carboxamide, N-((4,6-Dimethyl-2-oxo-1,2-dihydropyridin-3-yl)methyl)-2,2-dimethyl-7-(trifluoromethyl)-2,3-dihydrobenzofuran-5-carboxamide, 7-Bromo-N-((4,6-dimethyl-2-oxo-1,2-dihydropyridin-3-yl)methyl)-2,2,4-trimethyl-2,3-dihydrobenzofuran-5-carboxamide, N-((4,6-Dimethyl-2-oxo-1,2-dihydropyridin-3-yl)methyl)-2,2,4-trimethyl-2,3-dihydrobenzofuran-5-carboxamide, N-((4,6-Dimethyl-2-oxo-1,2-dihydropyridin-3-yl)methyl)-2,2,4,7-tetramethyl-2,3-dihydrobenzofuran-5-carboxamide, N-((4,6-Dimethyl-2-oxo-1,2-dihydropyridin-3-yl)methyl)-2,2-dimethyl-7-(4-(morpholinomethyl)phenyl)-2,3-dihydrobenzofuran-5-carboxamide, N-((4,6-Dimethyl-2-oxo-1,2-dihydropyridin-3-yl)methyl)-2,2-dimethyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-2,2-dimethyl-7-(6-morpholinopyridin-3-yl)-2,3-dihydrobenzofuran-5-carboxamide, N-((4,6-Dimethyl-2-oxo-1,2-dihydropyridin-3-yl)methyl)-2,2-dimethyl-7-(quinolin-3-yl)-2,3-dihydrobenzofuran-5-carboxamide, N-((4,6-Dimethyl-2-oxo-1,2-dihydropyridin-3-yl)methyl)-7-(6-methoxypyridin-3-yl)-2,2-dimethyl-2,3-dihydrobenzofuran-5-carboxamide, (E)-N-((4,6-Dimethyl-2-oxo-1,2-dihydropyridin-3-yl)methyl)-2,2-dimethyl-7-styryl-2,3-dihydrobenzofuran-5-carboxamide, N-((4,6-Dimethyl-2-oxo-1,2-dihydropyridin-3-yl)methyl)-2,2-dimethyl-7-(4-(4-methylpiperazine-1-carbonyl)phenyl)-2,3-dihydrobenzofuran-5-carboxamide, t-Butyl 4-(5-(5-(((4,6-dimethyl-2-oxo-1,2-dihydropyridin-3-yl)methyl)carbamoyl)-2,2-dimethyl-2,3-dihydrobenzofuran-7-yl)pyrimidin-2-yl)piperazine-1-carboxylate, N-((4,6-Dimethyl-2-oxo-1,2-dihydropyridin-3-yl)methyl)-2,2-dimethyl-7-(4-(piperazin-1-yl)phenyl)-2,3-dihydrobenzofuran-5-carboxamide, N-((4,6-Dimethyl-2-oxo-1,2-dihydropyridin-3-yl)methyl)-2,2-dimethyl-7-(4-(piperidin-1-ylmethyl)phenyl)-2,3-dihydrobenzofuran-5-carboxamide, N-((4,6-Dimethyl-2-oxo-1,2-dihydropyridin-3-yl)methyl)-2,2-dimethyl-7-(2-(piperazin-1-yl)pyrimidin-5-yl)-2,3-dihydrobenzofuran-5-carboxamide, 7-Benzyl-N-((4,6-dimethyl-2-oxo-1,2-dihydropyridin-3-yl)methyl)-2,2-dimethyl-2,3-dihydrobenzofuran-5-carboxamide, 7-Cyano-N-((4,6-dimethyl-2-oxo-1,2-dihydropyridin-3-yl)methyl)-2,2-dimethyl-2,3-dihydrobenzofuran-5-carboxamide, 7-Chloro-2,2-dimethyl-N-((6-methyl-2-oxo-4-propyl-1,2-dihydropyridin-3-yl)methyl)-2,3-dihydrobenzofuran-5-carboxamide, 7-Bromo-2,2-dimethyl-N-((6-methyl-2-oxo-4-propyl-1,2-dihydropyridin-3-yl)methyl)-2,3-dihydrobenzofuran-5-carboxamide, N-((4,6-Dimethyl-2-oxo-1,2-dihydropyridin-3-yl)methyl)-7-(6-methoxypyridin-3-yl)-2,2,4-trimethyl-2,3-dihydrobenzofuran-5-carboxamide, N-((4,6-Dimethyl-2-oxo-1,2-dihydropyridin-3-yl)methyl)-2,2,4-trimethyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-3-methyl-7-(6-morpholinopyridin-3-yl)-2,3-dihydrobenzofuran-5-carboxamide, N-((4,6-Dimethyl-2-oxo-1,2-dihydropyridin-3-yl)methyl)-3-methyl-7-(4-(morpholinomethyl)phenyl)-2,3-dihydrobenzofuran-5-carboxamide, N-((4,6-Dimethyl-2-oxo-1,2-dihydropyridin-3-yl)methyl)-3-methyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-7-(6-methoxypyridin-3-yl)-3-methyl-2,3-dihydrobenzofuran-5-carboxamide, 7-Bromo-N-((4,6-dimethyl-2-oxo-1,2-dihydropyridin-3-yl)methyl)-2-methyl-2,3-dihydrobenzofuran-5-carboxamide, N-((4,6-Dimethyl-2-oxo-1,2-dihydropyridin-3-yl)methyl)-7-(6-methoxypyridin-3-yl)-2-methyl-2,3-dihydrobenzofuran-5-carboxamide, N-((4,6-Dimethyl-2-oxo-1,2-dihydropyridin-3-yl)methyl)-2-methyl-7-(6-morpholinopyridin-3-yl)-2,3-dihydrobenzofuran-5-carboxamide, N-((4,6-Dimethyl-2-oxo-1,2-dihydropyridin-3-yl)methyl)-2-methyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-2-methyl-7-(4-(morpholinomethyl)phenyl)-2,3-dihydrobenzofuran-5-carboxamide, N-((4,6-Dimethyl-2-oxo-1,2-dihydropyridin-3-yl)methyl)-7-(6-methoxypyridin-3-yl)-2,3-dihydrobenzofuran-5-carboxamide, N-((4,6-Dimethyl-2-oxo-1,2-dihydropyridin-3-yl)methyl)-7-(6-morpholinopyridin-3-yl)-2,3-dihydrobenzofuran-5-carboxamide, N-((4,6-Dimethyl-2-oxo-1,2-dihydropyridin-3-yl)methyl)-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-7-(6-methoxypyridin-3-yl)-3,3-dimethyl-2,3-dihydrobenzofuran-5-carboxamide, (2S,3R)-7-Bromo-N-((4,6-dimethyl-2-oxo-1,2-dihydropyridin-3-yl)methyl)-2,3-dimethyl-2,3-dihydrobenzofuran-5-carboxamide, N-((4,6-Dimethyl-2-oxo-1,2-dihydropyridin-3-yl)methyl)-2,2-dimethylchroman-6-carboxamide, 8-Bromo-N-((4,6-dimethyl-2-oxo-1,2-dihydropyridin-3-yl)methyl)-2,2-dimethylchroman-6-carboxamide, N-((4,6-Dimethyl-2-oxo-1,2-dihydropyridin-3-yl)methyl)-8-(6-methoxypyridin-3-yl)-2,2-dimethylchroman-6-carboxamide, 9-Bromo-N-((4,6-dimethyl-2-oxo-1,2-dihydropyridin-3-yl)methyl)-4-methyl-2,5-dihydrobenzo[b]oxepine-7-carboxamide, 9-Bromo-N-((4,6-dimethyl-2-oxo-1,2-dihydropyridin-3-yl)methyl)-4-methyl-2,3,4,5-tetrahydrobenzo[b]oxepine-7-carboxamide, N-((4,6-Dimethyl-2-oxo-1,2-dihydropyridin-3-yl)methyl)-9-(6-methoxypyridin-3-yl)-4-methyl-2,3,4,5-tetrahydrobenzo[b]oxepine-7-carboxamide, N-((4,6-Dimethyl-2-oxo-1,2-dihydropyridin-3-yl)methyl)-2-methyl-2,3-dihydrobenzo[b]oxepine-7-carboxamide, N-((4,6-Dimethyl-2-oxo-1,2-dihydropyridin-3-yl)methyl)-2-methyl-2,3,4,5-tetrahydrobenzo[b]oxepine-7-carboxamide, 9-Bromo-N-((4,6-dimethyl-2-oxo-1,2-dihydropyridin-3-yl)methyl)-2-methyl-2,3,4,5-tetrahydrobenzo[b]oxepine-7-carboxamide, N-((4,6-Dimethyl-2-oxo-1,2-dihydropyridin-3-yl)methyl)-2-methyl-9-(4-(morpholinomethyl)phenyl)-2,3,4,5-tetrahydrobenzo[b]oxepine-7-carboxamide, N-((4,6-Dimethyl-2-oxo-1,2-dihydropyridin-3-yl)methyl)-2-methyl-9-(6-(piperazin-1-yl)pyridin-3-yl)-2,3,4,5-tetrahydrobenzo[b]oxepine-7-carboxamide, N-((4,6-Dimethyl-2-oxo-1,2-dihydropyridin-3-yl)methyl)-9-(6-methoxypyridin-3-yl)-2-methyl-2,3,4,5-tetrahydrobenzo[b]oxepine-7-carboxamide, 9-Bromo-N-((4,6-dimethyl-2-oxo-1,2-dihydropyridin-3-yl)methyl)-3-methyl-2,3,4,5-tetrahydrobenzo[b]oxepine-7-carboxamide, N-((4,6-Dimethyl-2-oxo-1,2-dihydropyridin-3-yl)methyl)-3-methyl-9-(6-(piperazin-1-yl)pyridin-3-yl)-2,3,4,5-tetrahydrobenzo[b]oxepine-7-carboxamide, N-((4,6-Dimethyl-2-oxo-1,2-dihydropyridin-3-yl)methyl)-7-(6-methoxypyridin-3-yl)-2-methyl-2-vinyl-2,3-dihydrobenzofuran-5-carboxamide, 7-Bromo-N-((4,6-dimethyl-2-oxo-1,2-dihydropyridin-3-yl)methyl)-2-methyl-2-vinyl-2,3-dihydrobenzofuran-5-carboxamide, N-((4,6-Dimethyl-2-oxo-1,2-dihydropyridin-3-yl)methyl)-2-methyl-7-(4-(morpholinomethyl)phenyl)-2-vinyl-2,3-dihydrobenzofuran-5-carboxamide, N-((4,6-Dimethyl-2-oxo-1,2-dihydropyridin-3-yl)methyl)-2-methyl-7-(6-(piperazin-1-yl)pyridin-3-yl)-2-vinyl-2,3-dihydrobenzofuran-5-carboxamide, N-((4,6-Dimethyl-2-oxo-1,2-dihydropyridin-3-yl)methyl)-2-ethyl-7-(6-methoxypyridin-3-yl)-2-methyl-2,3-dihydrobenzofuran-5-carboxamide, N-((4,6-Dimethyl-2-oxo-1,2-dihydropyridin-3-yl)methyl)-2-ethyl-2-methyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-2-ethyl-2-methyl-7-(p-tolyl)-2,3-dihydrobenzofuran-5-carboxamide, rac-(3aS,8bS)-5-Bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(6-(piperazin-1-yl)pyridin-3-yl)-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-5-(6-methoxypyridin-3-yl)-3a-methyl-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(4-(piperidin-1-ylmethyl)phenyl)-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(4-(piperazin-1-yl)phenyl)-2,3,3a,8b-tetrahydro-1H-cyclopenta[b]benzofuran-7-carboxamide, rac-(3aS,8bS)-5-Bromo-N-((4,6-dimethyl-2-oxo-1,2-dihydropyridin-3-yl)methyl)-3a,6-dimethyl-2,3,3a,8b-tetrahydro-1H-cyclopenta[b]benzofuran-7-carboxamide, 7-Bromo-N-((4,6-dimethyl-2-oxo-1,2-dihydropyridin-3-yl)methyl)-3H-spiro[benzofuran-2,1'-cyclopentane]-5-carboxamide, N-((4,6-Dimethyl-2-oxo-1,2-dihydropyridin-3-yl)methyl)-7-(6-methoxypyridin-3-yl)-3H-spiro[benzofuran-2,1'-cyclopentane]-5-carboxamide, N-((4,6-Dimethyl-2-oxo-1,2-dihydropyridin-3-yl)methyl)-7-(6-(piperazin-1-yl)pyridin-3-yl)-3H-spiro[benzofuran-2,1'-cyclopentane]-5-carboxamide, tert-Butyl 4-(5-(5-(((4,6-dimethyl-2-oxo-1,2-dihydropyridin-3-yl)methyl)carbamoyl)-3H-spiro[benzofuran-2,1'-cyclopentan]-7-yl)pyrimidin-2-yl)piperazine-1-carboxylate, N-((4,6-Dimethyl-2-oxo-1,2-dihydropyridin-3-yl)methyl)-7-(4-(piperidin-1-ylmethyl)phenyl)-3H-spiro[benzofuran-2,1'-cyclopentane]-5-carboxamide, 7-Bromo-N-((4,6-dimethyl-2-oxo-1,2-dihydropyridin-3-yl)methyl)-2H-spiro[benzofuran-3,1'-cyclopentane]-5-carboxamide, N-((4,6-Dimethyl-2-oxo-1,2-dihydropyridin-3-yl)methyl)-7-(6-methoxypyridin-3-yl)-2H-spiro[benzofuran-3,1'-cyclopentane]-5-carboxamide, N-((4,6-Dimethyl-2-oxo-1,2-dihydropyridin-3-yl)methyl)-7-(6-(piperazin-1-yl)pyridin-3-yl)-2H-spiro[benzofuran-3,1'-cyclopentane]-5-carboxamide, N-((4,6-Dimethyl-2-oxo-1,2-dihydropyridin-3-yl)methyl)-7-(4-(piperidin-1-ylmethyl)phenyl)-2H-spiro[benzofuran-3,1'-cyclopentane]-5-carboxamide, 7-Bromo-N-((4,6-dimethyl-2-oxo-1,2-dihydropyridin-3-yl)methyl)-2-isopropyl-2,3-dihydrobenzofuran-5-carboxamide, N-((4,6-Dimethyl-2-oxo-1,2-dihydropyridin-3-yl)methyl)-2-isopropyl-7-(6-(piperazin-1-yl)pyridin-3-yl)-2,3-dihydrobenzofuran-5-carboxamide, 9-Bromo-N-((4,6-dimethyl-2-oxo-1,2-dihydropyridin-3-yl)methyl)-3,4-dimethyl-2,5-dihydrobenzo[b]oxepine-7-carboxamide, 7-Bromo-N-((4,6-dimethyl-2-oxo-1,2-dihydropyridin-3-yl)methyl)-2-methyl-2-(prop-1-en-2-yl)-2,3-dihydrobenzofuran-5-carboxamide, N-((4,6-dimethyl-2-oxo-1,2-dihydropyridin-3-yl)methyl)-7-(6-methoxypyridin-3-yl)-2-methyl-2-(prop-1-en-2-yl)-2,3-dihydrobenzofuran-5-carboxamide, N-((4,6-Dimethyl-2-oxo-1,2-dihydropyridin-3-yl)methyl)-2-isopropyl-7-(6-methoxypyridin-3-yl)-2-methyl-2,3-dihydrobenzofuran-5-carboxamide, HCl, N-((4,6-Dimethyl-2-oxo-1,2-dihydropyridin-3-yl)methyl)-2-methyl-7-(6-(piperazin-1-yl)pyridin-3-yl)-2-(prop-1-en-2-yl)-2,3-dihydrobenzofuran-5-carboxamide, 2 TFA, 9-Bromo-3,4-dimethyl-N-((6-methyl-2-oxo-4-propyl-1,2-dihydropyridin-3-yl)methyl)-2,5-dihydrobenzo[b]oxepine-7-carboxamide, 2-Methyl-N-((6-methyl-2-oxo-4-propyl-1,2-dihydropyridin-3-yl)methyl)-7-(6-(piperazin-1-yl)pyridin-3-yl)-2-(prop-1-en-2-yl)-2,3-dihydrobenzofuran-5-carboxamide, 2 TFA, 2-isopropyl-2-methyl-N-((6-methyl-2-oxo-4-propyl-1,2-dihydropyridin-3-yl)methyl)-7-(6-(piperazin-1-yl)pyridin-3-yl)-2,3-dihydrobenzofuran-5-carboxamide, 2 HCl, 9-Bromo-N-((4,6-dimethyl-2-oxo-1,2-dihydropyridin-3-yl)methyl)-3,4-dimethyl-2,5-dihydrobenzo[b]oxepine-7-carboxamide, 8-Bromo-N-((4,6-dimethyl-2-oxo-1,2-dihydropyridin-3-yl)methyl)-2-vinyl-2,3-dihydrobenzo[b][1,4]dioxine-6-carboxamide, 8-Bromo-N-((4,6-dimethyl-2-oxo-1,2-dihydropyridin-3-yl)methyl)-2-ethyl-2,3-dihydrobenzo[b][1,4]dioxine-6-carboxamide, N-((4,6-Dimethyl-2-oxo-1,2-dihydropyridin-3-yl)methyl)-2-ethyl-8-(6-(piperazin-1-yl)pyridin-3-yl)-2,3-dihydrobenzo[b][1,4]dioxine-6-carboxamide, 2 TFA, 2-Isopropyl-7-(6-(4-isopropylpiperazin-1-yl)pyridin-3-yl)-2-methyl-N-((6-methyl-2-oxo-4-propyl-1,2-dihydropyridin-3-yl)methyl)-2,3-dihydrobenzofuran-5-carboxamide, 2-Methyl-N-((6-methyl-2-oxo-4-propyl-1,2-dihydropyridin-3-yl)methyl)-7-(2-(piperazin-1-yl)pyrimidin-5-yl)-2-(prop-1-en-2-yl)-2,3-dihydrobenzofuran-5-carboxamide, 2 HCl, or a pharmaceutically acceptable salt, tautomer or stereoisomer thereof.

In one embodiment, the compounds of the invention have $IC_{50}$ values≤5.0 µM.

In another embodiment, the compounds of the invention have $IC_{50}$ values≤0.5 µm.

In another embodiment, the compounds of the invention have $IC_{50}$ values≤0.05 µM.

II. Other Embodiments of the Invention

In another embodiment, the present invention provides a composition comprising one or more compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

III. Therapeutic Applications

The compounds and pharmaceutical compositions of the present invention are useful in treating or preventing any disease or conditions that are sensitive to apoptosis. These include infections (e.g. skin infections, GI infection, urinary tract infections, genito-urinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjogren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

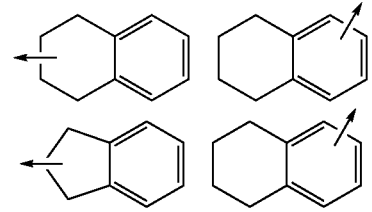

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention may be prepared by methods such as those illustrated in the following schemes and examples utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999).

The starting materials for synthesis of the compounds of the present invention are bromophenols of generic structure A1 (Scheme 1). These materials have been described in the chemical literature or are commercially available or readily-prepared by literature methods using reactions known to those skilled in the art of organic chemistry. Ortho-unsubstituted phenols, for instance are converted to bromophenols a by treatment with bromine in a solvent such as acetic acid or by the action of NBS or other electrophilic brominating agents.

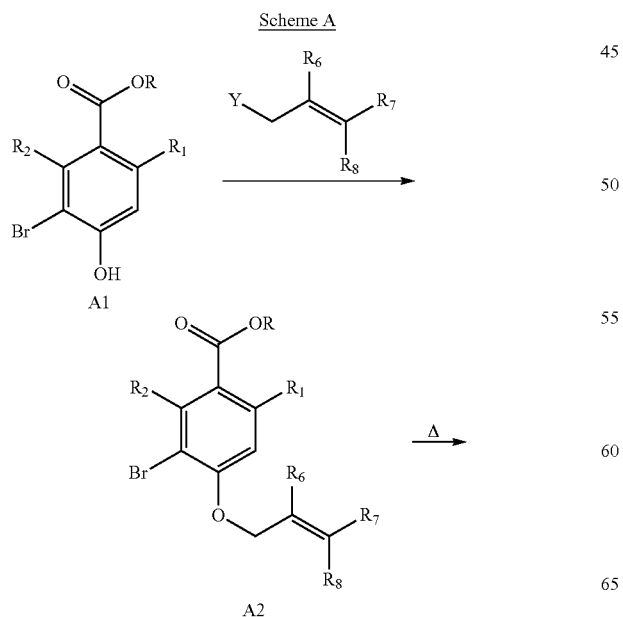

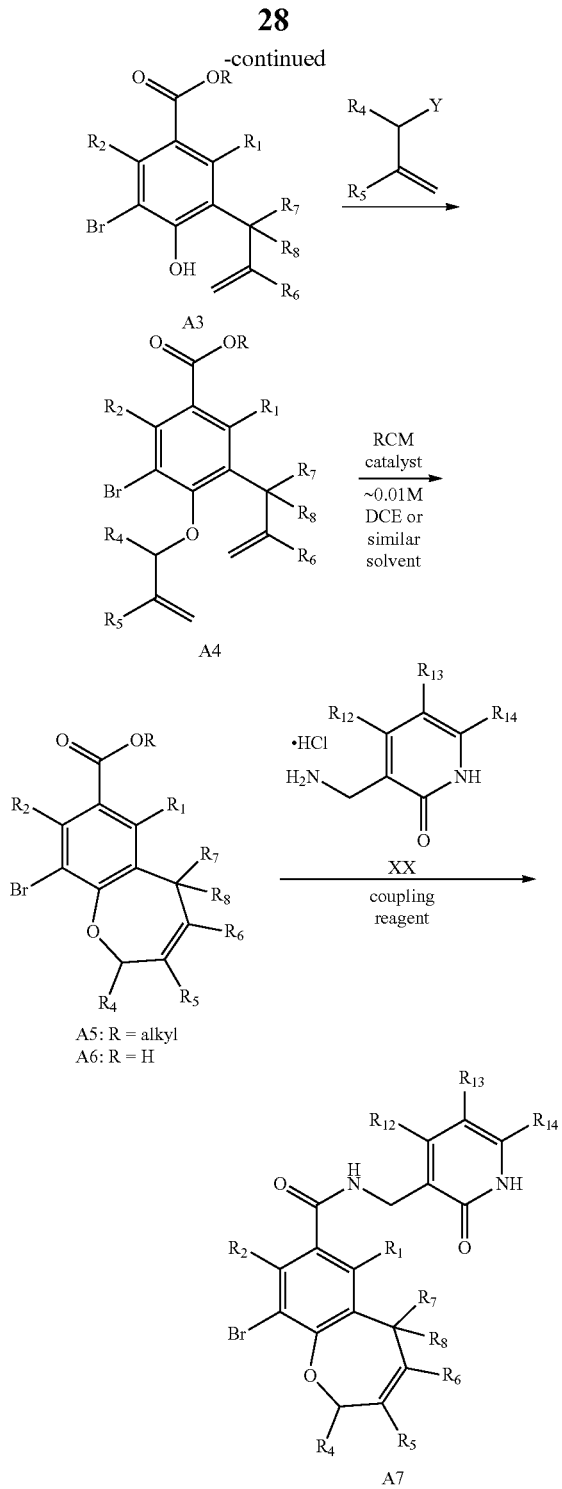

Phenols A1 are converted to allylic ethers A2 by treatment with an allylic electrophile such as a halide or tosylate and a base of the appropriate strength in a solvent. Preferred bases include sodium, potassium, and cesium carbonates. Useful solvents include acetonitrile, DMF, and THF. Heating may be required. Alternatively, Mitsunobu conditions may be employed for this transformation. In this reaction the phenol is combined with an allylic alcohol and triphenylphosphine in a suitable solvent and treated at a temperature between 0° C. and ambient with DIAD, DEAD, or a similar diazodicarboxylate. Allylic ethers A2 undergo [3,3] sigmatropic (Claisen) rearrangement upon heating, typically between 150-200° C. in an appropriate solvent or solvent mixture. Suitable solvents include diglyme and mesitylene for lower temperature reactions and N,N-dimethylaniline, decalin, and Dowtherm® A for reactions performed towards the higher end of this range. Phenols A3 are alkylated under the conditions used for A1 to afford allylic ethers A4. Heating a dilute (typically ~0.01M) solution of A4 in a solvent such as DCM or DCE with a suitable catalyst results in a ring-closing metathesis (RCM) reaction which affords the 7-membered ethers A5. Several RCM catalysts are commercially available with the preferred one for this transformation being the $2^{nd}$ generation Grubbs' catalyst (*Organic Letters* 1 (6), 953-956). Saponification to afford acids A6 is generally accomplished by treatment of the ester A5 with an alkali metal hydroxide such as sodium, lithium, or potassium hydroxide in a mixed aqueous-organic solvent system. In analogs where base-sensitive substituents are present, nucleophilic cleavage using a reagent such as lithium iodide could be employed. Carboxylic acids A6 may be activated with various reagents to afford intermediate "active esters" which condense with amines or amine salts such as XX (vide infra) to give amides A7. Preferred coupling reagents include, but are not limited to, Bop, PyBop, EDC, HATU, and TBTU. Generally, addition of a tertiary amine base is required. Preferred solvents include DMF, NMP, and DCM. The use of such peptide coupling reagents has been reviewed by Han, S-Y et al., *Tetrahedron*, 60:2447-2467 (2004). 9-Bromo-2,5-dihydrobenzo[b]oxepines A7 are compounds of the invention (Ie) and may also serve as intermediates for the preparation of additional compounds of the invention by ring-contraction and/or Suzuki (or related) coupling reactions.

Catechols B1 are converted to allylic ethers B2 using the conditions for the conversion of A1 to A2. These ethers undergo RCM reactions to give 2,5-dihydrobenzo[b][1,4]dioxocines B3 using the conditions for the conversion of A4 to A5. Heating B3 in a solvent such as DMF with a catalyst such as tetrakis(triphenylphosphine)palladium(0) affords the ring-contracted analogs B4, which can be hydrogenated to the saturated analogs B5. Many conditions are known for this transformation, including the use of a catalytic amount of palladium on carbon in ethyl acetate under an atmosphere of $H_2$. Saponification to carboxylic acids B6 and coupling with amines XX proceed under the conditions shown in Scheme A to give B7. 5-Bromo-2,3-dihydrobenzo[b][1,4]dioxines B7 are compounds of the invention (Id) and may also serve as intermediates for the preparation of additional compounds of the invention by Suzuki (or related) coupling reactions.

Scheme B

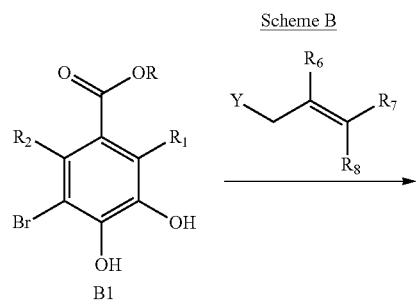

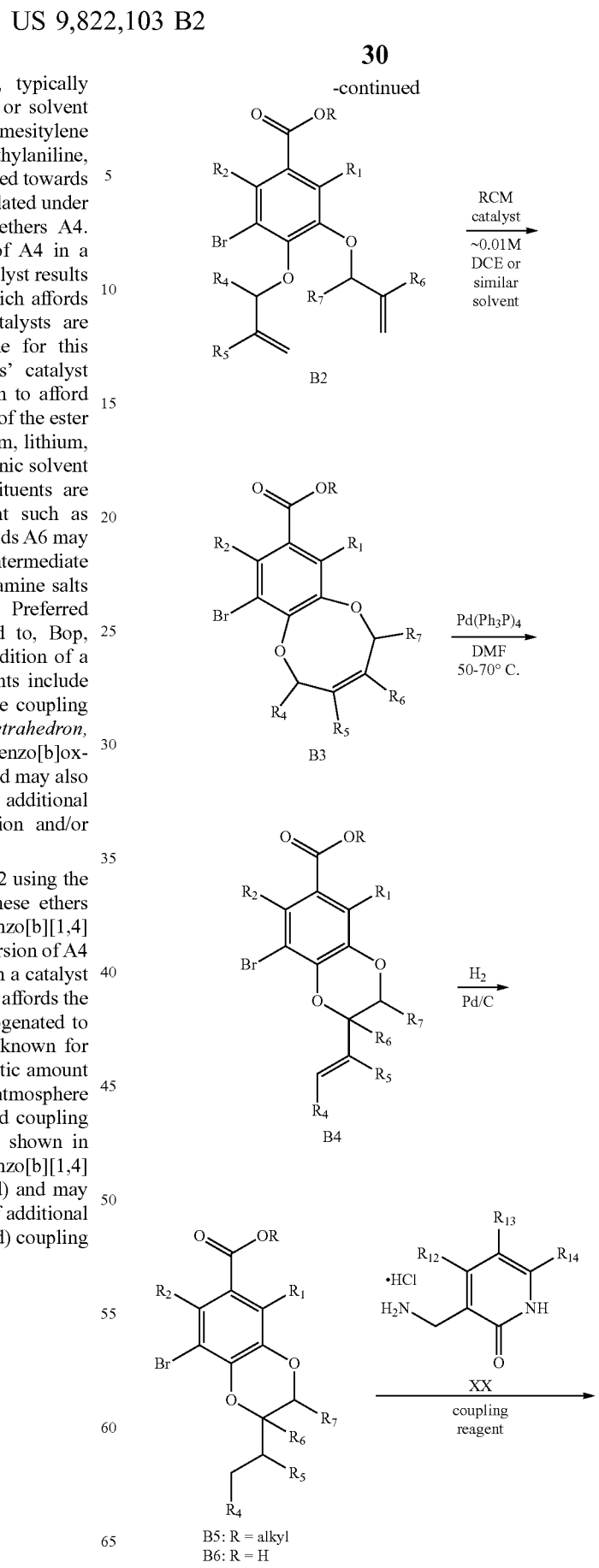

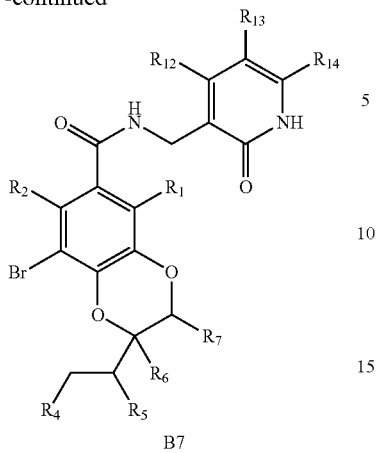

B7

9-Bromo-2,5-dihydrobenzo[b]oxepines A7 can be reduced to 9-bromo-2,3,4,5-tetrahydrobenzo[b]oxepines C1, preferably under an atmosphere of hydrogen, using palladium on

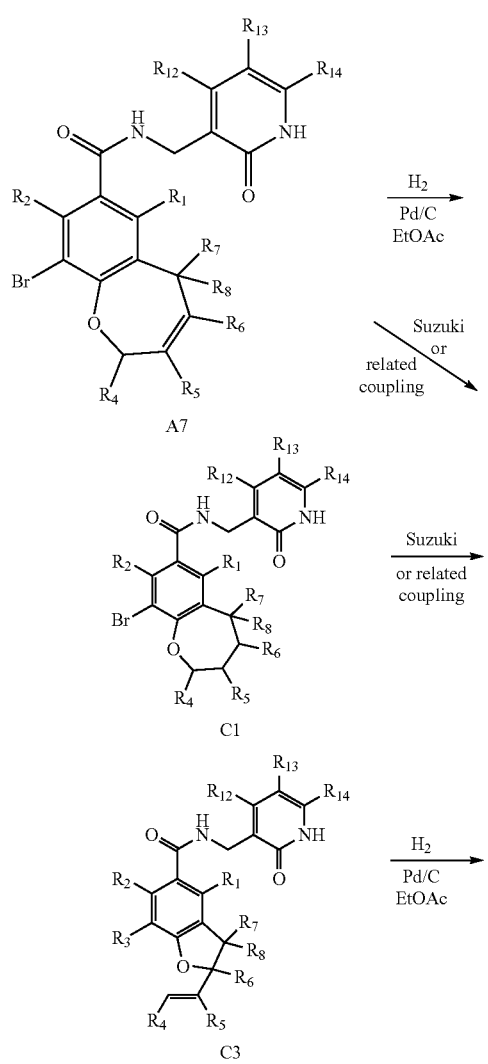

Scheme C

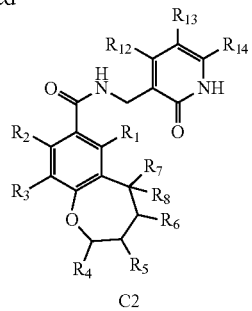

C2

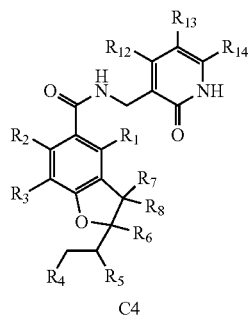

C4 carbon as the catalyst and ethyl acetate as a solvent. Alternatively, this reduction can be done on an earlier intermediate such as A5 or A6, and the resulting tetrahydrobenzo[b]oxepine can be converted to amides C1 using the chemistry described in Scheme A. Analogs C1 are compounds of the invention (If) which may also be coupled with arylboronic acids or esters, preferably under the conditions of Suzuki (see Kotha, S. et al., Tetrahedron, 58:9633-9695 (2002)) to afford analogs C2. Typically, this reaction is performed by heating the halide and the boronic acid or ester to from about 90 to about 100° C. with a base such as aqueous tribasic sodium or potassium phosphate or sodium or potassium carbonate in a solvent such as dioxane, DMF, THF, or NMP using a catalyst such as tetrakis(triphenylphosphine)palladium or $Cl_2Pd(dppf)$. Many variations on this reaction involving the use of different temperatures, solvents, bases, anhydrous conditions, catalysts, boronate derivatives, and halide surrogates such as triflates are known to those skilled in the art of organic/medicinal chemistry. Mild conditions have been reported for the coupling of sensitive boronic acid derivatives. See Kinzel, T. et al., J. Am. Chem. Soc., 132(40):14073-14075 (2010). Related coupling reactions for the conversion of C1 and other aryl halide intermediates described in later Schemes into compounds of the invention include the Heck (olefin) (J. Am. Chem. Soc., 96(4):1133-1136 (1974)), Stille (organostannane) (Synthesis, 803-815 (1992)), Sonogashira (acetylene) (Sonogashira, K. et al., Tetrahedron Lett., 16(50):4467-4470 (1975)), and Negishi (organozinc) (Aldrichimica Acta, 38(3):71-78 (2005)) coupling reactions. Analogs C2 are also compounds of the invention (If). Additionally, analogs A7 can serve as substrates for Suzuki couplings. When the coupling reaction is performed using a catalytic amount of $(Ph_3P)Pd$ in DMF at a temperature between 80 and 100° C. with an appropriate boronic acid or ester $R_3B(OH)_2$ of $R_3B(OR)_2$ and potassium carbonate as the base, dihydrobenzofuran derivatives C3 are obtained. These analogs are compounds of the invention (Ia) which may be further reduced to analogs C4 which are also compounds of the invention (Ib). When the base and boronic acid/ester components are excluded from the Suzuki coupling reactions of analogs A7, analogs C3 are obtained in which $R_3$ is Br. These are also compounds of the invention (Ia). In an alternative route, the 2,5-dihydrobenzo[b]oxepines to 2-vinyl-2,3-dihydrobenzofuran rearrangement can be performed (with or without concommitant Suzuki coupling) on an earlier intermediate such as A5. The resulting products can then be saponified and coupled to amine XX (vide supra) to afford analogs C3.

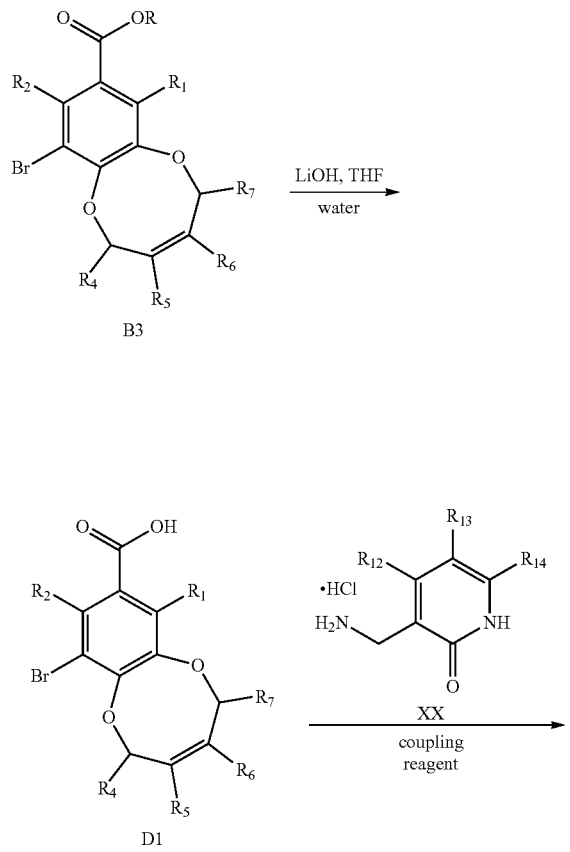

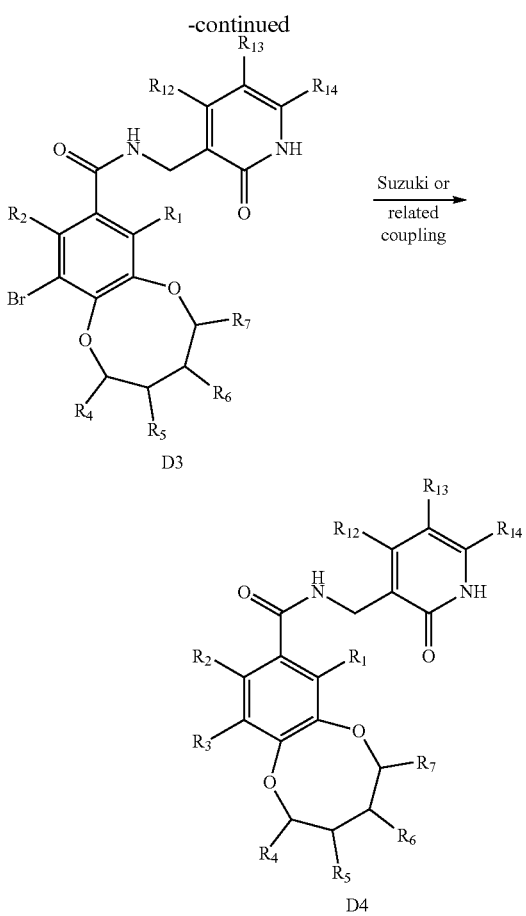

Ester intermediates B3 can be saponified using the conditions described previously to afford carboxylic acids D1. Coupling to amines XX as previously described affords 10-bromo-2,5-dihydrobenzo[b][1,4]dioxocine-8-carboxamides D2 which are compounds of the invention (Ig). Compounds D2 may also serve as intermediates which can be reduced using conditions described above to provide 10-bromo-2,3,4,5-tetrahydrobenzo[b][1,4]dioxocine-8-carboxamides D3. These are compounds of the invention (Ih). Additionally, they can undergo Suzuki or related coupling reactions to afford analogs D4 which are also compounds of the invention (Ih).

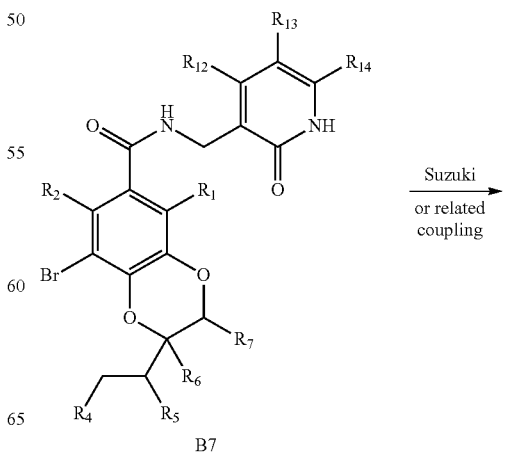

Scheme F

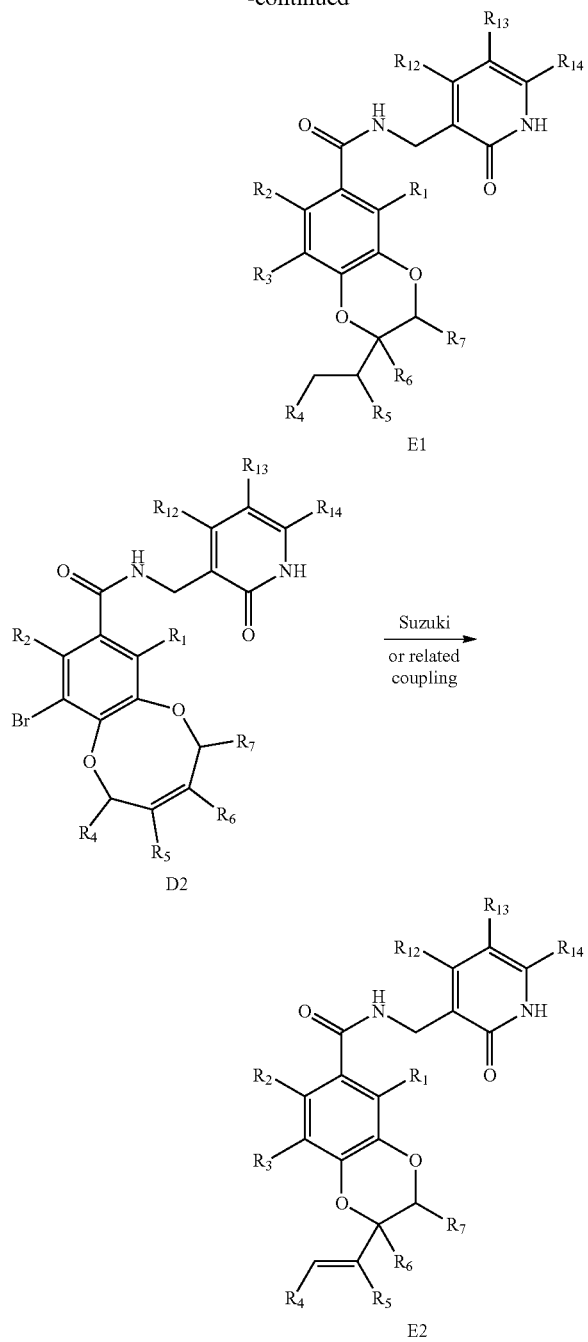
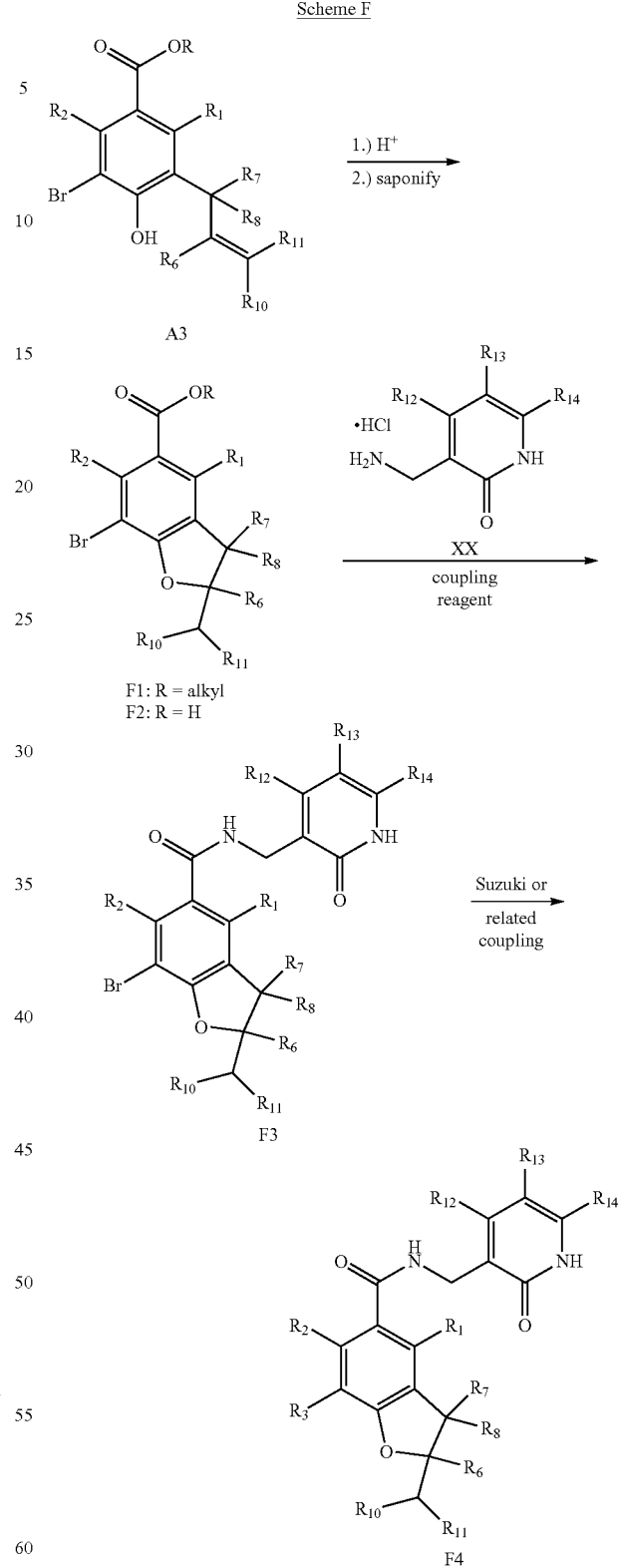

Ester intermediates B7 can undergo Suzuki or related couplings using the conditions described previously to afford E1 which are further compounds of the invention (Id). Compounds of the invention (Ic) are prepared by performing Suzuki or related coupling reactions on intermediates D2 to afford benzodioxanes E2.

Phenols A3 cyclize under acidic conditions, preferably using a neat acid such as formic acid at about 110° C., to afford benzofuran esters F1. Saponification and coupling as above affords amides F3 which are compounds of the invention (Ii). These can react under Suzuki or related conditions to afford F4 which are further compounds of the invention (Ii).

General Experimental

Air- or moisture-sensitive reactions were generally performed under an atmosphere of nitrogen or argon in anhydrous solvents (EMD DRISOLV®). Reaction concentrations are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/F254 were used with visualization by UV light at ~254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous $MgSO_4$ followed by filtration and rinsing the residual solids with an appropriate organic solvent. "Stripped" means concentration under reduced pressure, generally on a rotary evaporator. "Silica gel chromatography", "flash chromatography", or "chromatographed on silica gel" refers to glass column chromatography performed in a manner similar to that described by Still (*J. Org. Chem.*, 43:2923 (1978)). Typically silica gel 60 (EMD, 230-400 mesh ASTM) is used with solvents from JT Baker or Mallinckrodt. HPLC refers to purification by reverse-phase high-performance liquid chromatography generally on C18 columns using the stated mobile phases. Analytical HPLC runs were performed using the columns, flow rates, and mobile phases indicated. It is understood that analytical HPLC retention times ($T_r$) are reported in minutes, and may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Melting points were determined on a Thomas-Hoover Uni-Melt apparatus and are uncorrected. Generally, mass spectral results are reported as the $(M+H)^+$ value. For halogenated compounds where two or more peaks are significant, m/z for one peak in the cluster, generally the most intense, is reported. $^1$H NMR spectra were recorded on dilute solutions at 400 or 500 MHz on Bruker® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Unless otherwise specified, the various substituents of the compounds as employed herein are defined in the same manner as compounds of the invention of Formula (I).

For ease of reference, the following abbreviations are used herein.

| Abbreviations | |
|---|---|
| AcOH, HOAc | acetic acid |
| ACN | acetonitrile |
| $Ac_2O$ | acetic anhydride |
| ADDP | 1,1'-(azodicarbonyl)dipiperidine |
| aq. | aqueous |
| Bn | benzyl |
| Boc | t-butyl carbamate |
| $Boc_2O$ | di-t-butyl dicarbonate |
| BOP | Benzotriazol-1-yloxytris(dimethylamino)phosphonium hexafluorophosphate |
| Bu | butyl |
| Cbz | benzyl carbamate |
| conc. | concentrated |
| DCE | 1,2-dichloroethane |
| DCM | dichloromethane |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethylsulfoxide |
| DMT-MM | 4-(4,6-dimethoxy-1,3,5-triazin-2-yl)-4-methylmorpholinium chloride |
| EDC | 1-(3-(dimethylamino)propyl)-3-ethylcarbodiimide hydrochloride |
| Et | ethyl |
| EtOAc | ethyl acetate |
| EtOH | ethanol |
| $Et_2O$ | diethyl ether |
| $Et_3N$ | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high performance liquid chromatography |
| i-PrOH | isopropanol |
| KOAc | potassium acetate |
| LAH | Lithium aluminum hydride |
| min | minute(s) |
| Me | methyl |
| MeCN | acetonitrile |
| MeOH | methanol |
| $Me_2NH$ | dimethylamine |
| NaHMDS | sodium bis(trimethylsilyl)amide |
| $Na(OAc)_3BH$ | sodium triacetoxyborohydride |
| n-BuLi | n-butyllithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| $Pd(dppf)_2Cl_2$ | [1,1'-bis(diphenylphosphino)ferrocene]dichloropalladium(II) |
| $Pd(OAc)_2$ | palladium acetate |
| $Pd(PPh_3)_4$ | tetrakis(triphenylphosphine)palladium |
| $Pd_2(dba)_3$ | tris(dibenzylideneacetone)dipalladium(0) |
| PE | Petroleum ether |
| Ph | phenyl |
| PhMe | toluene |
| $Ph_2TfN$ | 1,1,1-trifluoro-N-phenyl-N-(trifluoromethyl)sulfonyl methanesulfonamide |
| $PPh_3$ | triphenylphosphine |
| RB | Round-bottom flask |
| rt | room temperature |
| RCM | Ring-closing metathesis |
| sat. | saturated |
| t-Bu | tertiary butyl |
| t-BuOH | tertiary butanol |
| TFA | trifluoroacetic acid |
| $Tf_2O$ | trifluoromethylsulfonic anhydride |
| THF | tetrahydrofuran |
| TMS | trimethylsilyl |
| TsO | p-toluenesulfonyl |

Example 1

7-Bromo-N-((4,6-dimethyl-2-oxo-1,2-dihydropyridin-3-yl)methyl)-2,2-dimethyl-2,3-dihydrobenzofuran-5-carboxamide

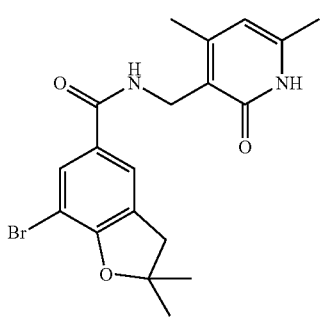 [SMILES: Cc1cc(C)c(CNC(=O)c2cc(Br)c3c(c2)CC(C)(C)O3)c(=O)[nH]1]

1A. Methyl 3-bromo-4-((2-methylallyl)oxy)benzoate

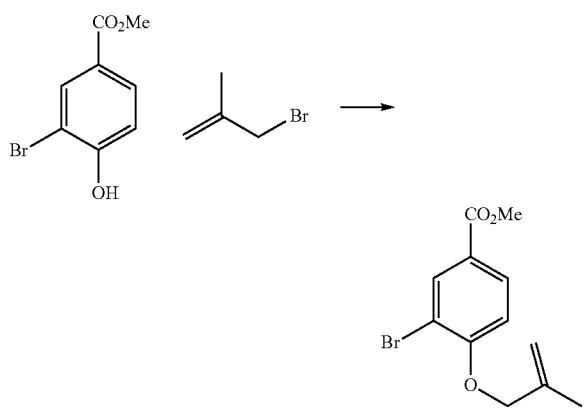

Methyl 3-bromo-4-hydroxybenzoate (2.2 g, 9.52 mmol) was dissolved in acetonitrile (20 mL) under nitrogen. Potassium carbonate (1.579 g, 11.43 mmol) was added and stirring continued for 5 minutes. 3-Bromo-2-methylprop-1-ene (1.152 ml, 11.43 mmol) was then added and the reaction stirred overnight. The reaction was quenched with water and transferred to a reparatory funnel. The reaction was extracted with ether. The organic layer was washed with water and then brine. The organic phase was dried over magnesium sulfate, filtered and evaporated. The crude material was applied to an 80 g Isco silica gel column and eluted with 0-25% ethyl acetate in hexanes. Evaporation of the appropriate fractions gave methyl 3-bromo-4-((2-methylallyl)oxy)benzoate (2.39 g, 8.21 mmol, 86% yield) as a colorless solid.

$^1$H NMR (400 MHz, CHLOROFORM-d) δ 8.28 (d, J=2.0 Hz, 1H), 7.98 (dd, J=8.7, 2.1 Hz, 1H), 6.93 (d, J=8.6 Hz, 1H), 5.20 (t, J=1.1 Hz, 1H), 5.12-4.98 (m, 1H), 4.60 (s, 2H), 3.93 (s, 3H), 1.90 (d, J=0.4 Hz, 3H).

1B. Methyl 7-bromo-2,2-dimethyl-2,3-dihydrobenzofuran-5-carboxylate

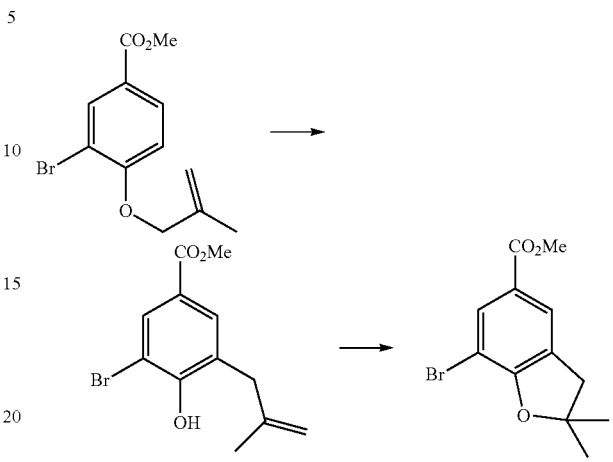

A reaction vial was charged with methyl 3-bromo-4-((2-methylallyl)oxy)benzoate (456 mg, 1.599 mmol) and Dowtherm (0.5 mL). The vial was sealed and heated to 200° C. for 2 hours. The reaction was cooled and applied directly to a 40 g Isco silica gel column and eluted with 0-20% ethyl acetate in hexanes. Evaporation of the appropriate fractions gave methyl 3-bromo-4-hydroxy-5-(2-methylallyl)benzoate (352 mg, 1.235 mmol, 77% yield) as a viscous oil. 1H-NMR suggested the presence of some minor impurities, but the material was carried into the next step. The material was dissolved in formic acid (6 mL) under nitrogen. The reaction was warmed to 110° C. for 3 hours. The reaction was then cooled and stirred for 5 days. The material was transferred to a separatory funnel and diluted with ether. The organic layer was washed with saturated sodium bicarbonate solution until weakly alkaline and then brine. The ether layer was dried over magnesium sulfate, filtered and evaporated. The crude product was applied to a 40 g Isco silica gel column and eluted with 0-20% ethyl acetate in hexanes. Concentration of the appropriate fractions provided methyl 7-bromo-2,2-dimethyl-2,3-dihydrobenzofuran-5-carboxylate (206 mg, 0.708 mmol, 57.4% yield) as a colorless solid. $^1$H NMR (400 MHz, DMSO-d$_6$) δ 7.93-7.88 (m, 1H), 7.79 (q, J=1.2 Hz, 1H), 3.83 (s, 3H), 3.20 (s, 2H), 1.49 (s, 6H).

1C. 7-Bromo-2,2-dimethyl-2,3-dihydrobenzofuran-5-carboxylic acid

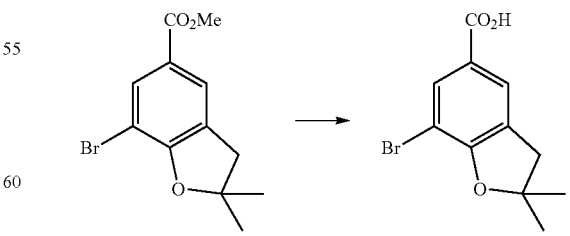

Methyl 7-bromo-2,2-dimethyl-2,3-dihydrobenzofuran-5-carboxylate (192 mg, 0.673 mmol) was dissolved in tetrahydrofuran-water (3:1.4 mL). Lithium hydroxide solution (1347 μl, 1.347 mmol, 1 N) was added. The reaction was warmed to 55° C. and stirred overnight. The reaction was cooled and neutralized with 1 N hydrochloric acid (1.35 mL). The reaction was concentrated under a stream of nitrogen to generate a colorless precipitate. The solid was filtered, rinsed well with water and then hexanes. Air drying then provided 7-bromo-2,2-dimethyl-2,3-dihydrobenzofuran-5-carboxylic acid (175 mg, 0.633 mmol, 94% yield) as a colorless solid. $^1$H NMR (400 MHz, DMSO-$d_6$) δ 12.80 (br. s., 1H), 7.87 (d, J=1.5 Hz, 1H), 7.76 (d, J=1.5 Hz, 1H), 3.19 (s, 2H), 1.49 (s, 6H).

1. 7-Bromo-N-((4,6-dimethyl-2-oxo-1,2-dihydropyridin-3-yl)methyl)-2,2-dimethyl-2,3-dihydrobenzofuran-5-carboxamide

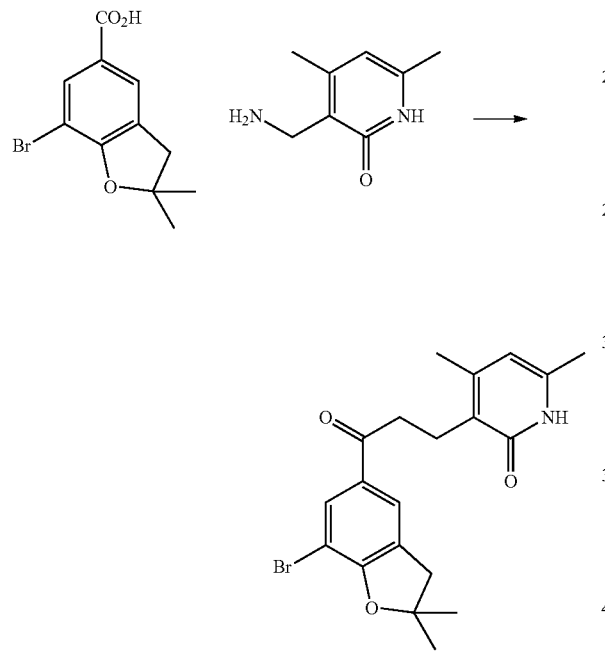

A reaction vial was charged with 7-bromo-2,2-dimethyl-2,3-dihydrobenzofuran-5-carboxylic acid (128 mg, 0.472 mmol). The starting material was dissolved in dimethylformamide (1.9 mL). Triethylamine (197 µl, 1.416 mmol) and 3-(aminomethyl)-4,6-dimethylpyridin-2(1H)-one hydrochloride (98 mg, 0.519 mmol) were then added. The reaction was initiated with the addition of BOP (251 mg, 0.567 mmol). The reaction was stirred for 2 hours. The reaction was quenched with 25% saturated sodium bicarbonate solution (4 mL). Stirring was continued for 15 minutes. The solid was filtered, rinsed with water and then hexanes. Air drying gave 7-bromo-N-((4,6-dimethyl-2-oxo-1,2-dihydropyridin-3-yl)methyl)-2,2-dimethyl-2,3-dihydrobenzofuran-5-carboxamide (166 mg, 0.401 mmol, 85% yield) as a colorless solid. $^1$H NMR (400 MHz, DMSO-$d_6$) δ 11.46 (br. s., 1H), 8.22 (t, J=4.6 Hz, 1H), 7.87 (d, J=1.5 Hz, 1H), 7.72 (d, J=1.5 Hz, 1H), 5.87 (s, 1H), 4.27 (d, J=4.8 Hz, 2H), 3.15 (s, 2H), 2.16 (s, 3H), 2.13 (s, 3H), 1.47 (s, 6H). MS(ES): m/z 405 [M+H]$^+$.

Example 2

N-((4,6-Dimethyl-2-oxo-1,2-dihydropyridin-3-yl)methyl)-2,2-dimethyl-2,3-dihydrobenzofuran-5-carboxamide

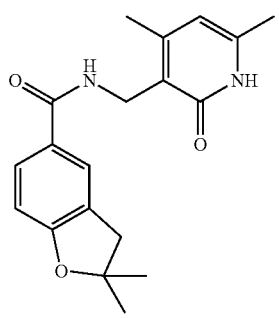 [SMILES: Cc1cc(C)c(CNC(=O)c2ccc3c(c2)CC(C)(C)O3)c(=O)[nH]1]

Example 2 was prepared using the methodology used in the synthesis of Example 1. $^1$H NMR (400 MHz, DMSO-$d_6$) δ 11.45 (br. s., 1H), 8.05 (br. s., 1H), 7.70 (s, 1H), 7.64 (dd, J=8.4, 2.0 Hz, 1H), 6.71 (d, J=8.4 Hz, 1H), 5.87 (s, 1H), 4.28 (d, J=4.8 Hz, 2H), 3.02 (s, 2H), 2.17 (s, 3H), 2.13 (s, 3H), 1.43 (s, 6H). MS(ES): m/z 327 [M+H]$^+$.

Example 3

7-Chloro-N-((4,6-dimethyl-2-oxo-1,2-dihydropyridin-3-yl)methyl)-2,2-dimethyl-2,3-dihydrobenzofuran-5-carboxamide

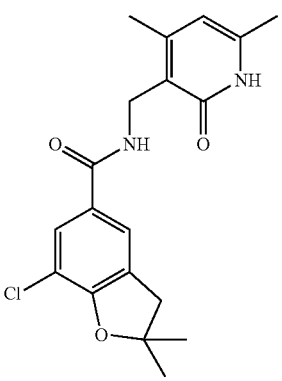 [SMILES: Cc1cc(C)c(CNC(=O)c2cc(Cl)c3c(c2)CC(C)(C)O3)c(=O)[nH]1]

Example 3 was prepared using the methodology used in the synthesis of Example 1. The final compound was purified by reverse phase HPLC using the following conditions: Column—Waters XBridge C18, 19×250 mm, 5-µm particles. Solvent—acetonitrile-water gradient containing 10 mM ammonium acetate. $^1$H NMR (500 MHz, DMSO-$d_6$) δ 11.48 (s, 1H), 8.23 (t, J=4.9 Hz, 1H), 7.74 (s, 1H), 7.68 (s, 1H), 5.87 (s, 1H), 4.26 (d, J=4.9 Hz, 2H), 3.12 (s, 2H), 2.15 (s, 3H), 2.12 (s, 3H). MS(ES): m/z 361 [M+H]$^+$.

Example 4

N-((4,6-Dimethyl-2-oxo-1,2-dihydropyridin-3-yl)methyl)-7-fluoro-2,2-dimethyl-2,3-dihydrobenzofuran-5-carboxamide

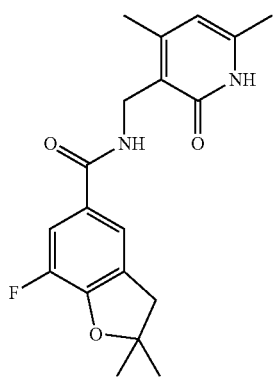 [SMILES: Cc1cc(C)c(CNC(=O)c2cc(F)c3c(c2)CC(C)(C)O3)c(=O)[nH]1]

Example 4 was prepared using the methodology used in the synthesis of Example 1. The final compound was purified by reverse phase HPLC using the following conditions: Column—Waters XBridge C18, 19×250 mm, 5-μm particles. Solvent—acetonitrile-water gradient containing 10 mM ammonium acetate. $^1$H NMR (500 MHz, DMSO-d$_6$) δ 11.48 (br. s., 1H), 8.20 (s, 1H), 7.66-7.46 (m, 2H), 5.87 (s, 1H), 4.27 (d, J=4.9 Hz, 2H), 3.09 (s, 2H), 2.16 (s, 3H), 2.12 (s, 3H), 1.47 (s, 6H). MS(ES): m/z 345 [M+H]$^+$.

Example 5

N-((4,6-Dimethyl-2-oxo-1,2-dihydropyridin-3-yl)methyl)-2,2-dimethyl-7-(trifluoromethyl)-2,3-dihydrobenzofuran-5-carboxamide

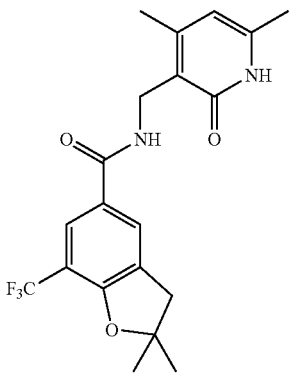 [SMILES: Cc1cc(C)c(CNC(=O)c2cc3c(c(C(F)(F)F)c2)OC(C)(C)C3)c(=O)[nH]1]

Example 5 was prepared using the methodology used in the synthesis of Example 1. The final compound was purified by reverse phase HPLC using the following conditions: Column—Waters XBridge C18, 19×250 mm, 5-μm particles. Solvent—acetonitrile-water gradient containing 10 mM ammonium acetate. $^1$H NMR (500 MHz, DMSO-d$_6$) δ 11.49 (br. s., 1H), 8.39 (s, 1H), 7.99 (s, 1H), 7.93 (s, 1H), 5.88 (s, 1H), 4.28 (d, J=4.3 Hz, 2H), 3.10 (s, 2H), 2.16 (s, 3H), 2.12 (s, 3H), 1.47 (s, 6H). MS(ES): m/z 396 [M+H]$^+$.

Example 6

N-((4,6-Dimethyl-2-oxo-1,2-dihydropyridin-3-yl)methyl)-2,2,7-trimethyl-2,3-dihydrobenzofuran-5-carboxamide

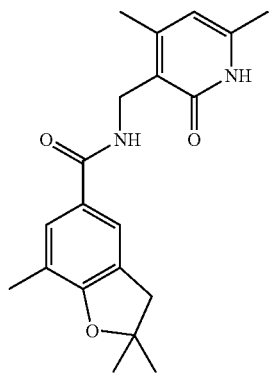

Example 6 was prepared using the methodology used in the synthesis of Example 1. The final compound was purified by reverse phase HPLC using the following conditions: Column—Waters XBridge C18, 19×250 mm, 5-μm particles. Solvent—acetonitrile-water gradient containing 10 mM ammonium acetate. $^1$H NMR (500 MHz, DMSO-d$_6$) δ 11.49 (br. s., 1H), 8.03 (br. s., 1H), 7.50 (s, 1H), 7.48 (s, 1H), 5.89 (s, 1H), 4.26 (d, J=4.9 Hz, 2H), 3.00 (s, 2H), 2.16 (s, 3H), 2.12 (s, 3H), 2.09 (s, 3H), 1.41 (s, 6H). MS(ES): m/z 341 [M+H]$^+$.

Example 7

7-Bromo-N-((4,6-dimethyl-2-oxo-1,2-dihydropyridin-3-yl)methyl)-2,2,4-trimethyl-2,3-dihydrobenzofuran-5-carboxamide

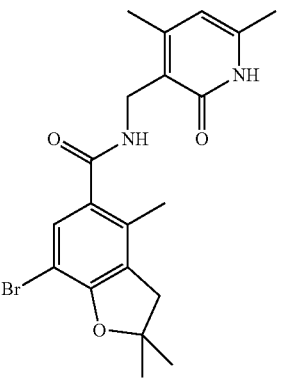 [SMILES: Cc1cc(C)c(CNC(=O)c2cc(Br)c3c(c2C)CC(C)(C)O3)c(=O)[nH]1]

7A. 7-Bromo-2,2,4-trimethyl-2,3-dihydrobenzofuran-5-carboxylic acid

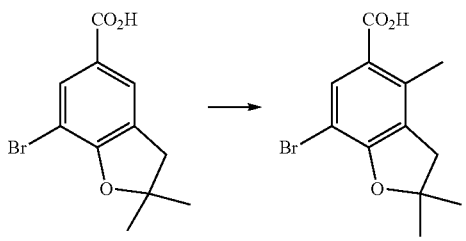 [SMILES: CC1(C)Cc2cc(C(=O)O)cc(Br)c2O1 ; Cc1c(C(=O)O)cc(Br)c2c1CC(C)(C)O2]

A reaction vial was charged with 7-bromo-2,2-dimethyl-2,3-dihydrobenzofuran-5-carboxylic acid (54.2 mg, 0.2 mmol, Intermediate 1C), palladium(II)acetate (4.5 mg, 0.02 mmol), silver carbonate (110 mg, 0.40 mmol), 1,4-benzoquinone (1.1 mg, 10 μmol), lithium carbonate (29.6 mg, 0.40 mmol), t-Boc-L-phenylalanine (10.6 mg, 0.04 mmol), potassium methyltrifluoroborate (73.2 mg, 0.60 mmol and a stirring bar. t-Butanol (2.0 mL) was added and the vial was evacuated and filled with nitrogen three times. The vial was sealed and stirred for 5 minutes. The reaction was then warmed to 90° C. for 12 hours. The reaction was cooled and quenched with 1 N hydrochloric acid (2 mL). The vial was sonicated and the contents passed 0.45 μm glass microfiber syringe filter. The filtrate was transferred to a separatory funnel and extracted twice with methylene chloride. The combined organic phases were dried over magnesium sulfate, filtered and evaporated. The crude product was purified by RP-HPLC (methanol-water gradient+0.1% TFA). Evaporation of the appropriate fractions gave 7-bromo-2,2,4-trimethyl-2,3-dihydrobenzofuran-5-carboxylic acid (18 mg, 0.063 mmol, 31.6% yield) as a colorless solid. $^1$H NMR (400 MHz, DMSO-d$_6$) δ 7.82 (s, 1H), 3.11 (s, 2H), 2.36 (s, 3H), 1.46 (s, 6H).

7. 7-Bromo-N-((4,6-dimethyl-2-oxo-1,2-dihydropyridin-3-yl)methyl)-2,2,4-trimethyl-2,3-dihydrobenzofuran-5-carboxamide

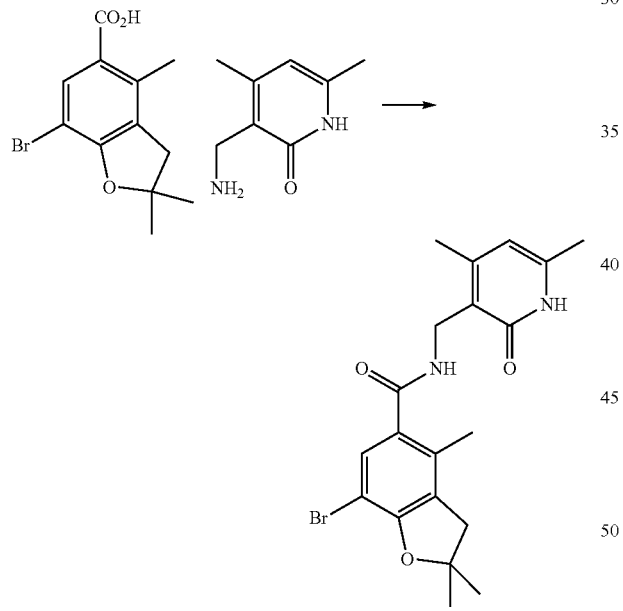

7-Bromo-2,2,4-trimethyl-2,3-dihydrobenzofuran-5-carboxylic acid (4.4 mg, 0.015 mmol) was dissolved in dry DMF (0.5 mL). 3-(Aminomethyl)-4,6-dimethylpyridin-2(1H)-one hydrochloride (3.20 mg, 0.017 mmol) and triethylamine (6.45 μl, 0.046 mmol) were added. The reaction was initiated with the addition of BOP (8.19 mg, 0.019 mmol). The reaction was stirred for an hour. The compound was purified by reverse phase HPLC using the following conditions: Column—Waters XBridge C18, 19×250 mm, 5-μm particles. Solvent—acetonitrile-water gradient containing 10 mM ammonium acetate. Evaporation of the appropriate fractions gave 7-bromo-N-((4,6-dimethyl-2-oxo-1,2-dihydropyridin-3-yl)methyl)-2,2,4-trimethyl-2,3-dihydrobenzofuran-5-carboxamide (4.5 mg, 10.30 μmol, 67%). $^1$H NMR (500 MHz, DMSO-d$_6$) δ 11.48 (br. s., 1H), 8.09 (br. s., 1H), 7.23 (br. s., 1H), 5.87 (br. s., 1H), 4.23 (br. s., 2H), 3.07 (br. s., 2H), 2.18 (br. s., 3H), 2.16 (br. s., 3H), 2.12 (br. s., 3H), 1.45 (s, 6H). MS(ES): m/z 419 [M+H]$^+$.

Example 8

N-((4,6-Dimethyl-2-oxo-1,2-dihydropyridin-3-yl)methyl)-2,2,4-trimethyl-2,3-dihydrobenzofuran-5-carboxamide

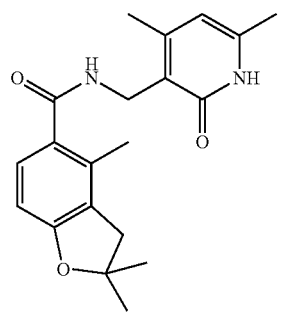 [SMILES: Cc1cc(C)c(CNC(=O)c2ccc3c(c2C)CC(C)(C)O3)c(=O)[nH]1]

Example 8 was prepared starting from the carboxylic acid intermediate prepared in Example 2. The introduction of the methyl group and formation of the amide were accomplished using the procedures described in Example 7. $^1$H NMR (400 MHz, CHLOROFORM-d) δ 7.18 (d, J=8.1 Hz, 1H), 6.71 (br. s., 1H), 6.60-6.54 (m, 2H), 4.60 (d, J=6.2 Hz, 2H), 2.96 (s, 2H), 2.65 (s, 3H), 2.50 (s, 3H), 2.30 (s, 3H), 1.51 (s, 6H). MS(ES): m/z 341 [M+H]$^+$.

Example 9

N-((4,6-Dimethyl-2-oxo-1,2-dihydropyridin-3-yl)methyl)-2,2,4,7-tetramethyl-2,3-dihydrobenzofuran-5-carboxamide

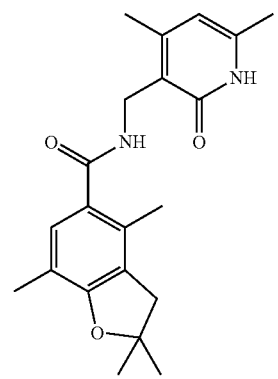

Example 9 was prepared starting from the carboxylic acid intermediate prepared in Example 6. The introduction of the methyl group and formation of the amide were accomplished using the procedures described in Example 7. $^1$H NMR (500 MHz, DMSO-d$_6$) δ 11.47 (br. s., 1H), 7.82 (br. s., 1H), 6.92 (s, 1H), 5.89 (s, 1H), 2.92 (s, 2H), 2.19 (s, 3H), 2.14 (s, 3H), 2.12 (s, 3H), 2.02 (s, 3H), 1.40 (s, 7H). MS(ES): m/z 355 [M+H]$^+$.

Example 10

N-((4,6-Dimethyl-2-oxo-1,2-dihydropyridin-3-yl)methyl)-2,2-dimethyl-7-(4-(morpholinomethyl)phenyl)-2,3-dihydrobenzofuran-5-carboxamide

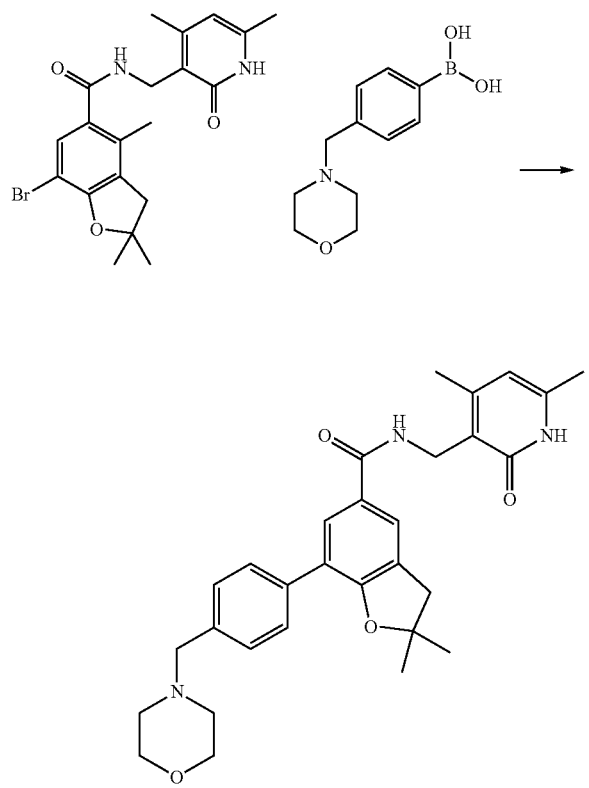 [SMILES: Cc1cc(C)c(CNC(=O)c2cc(Br)c3c(c2C)CC(C)(C)O3)c(=O)[nH]1 ; OB(O)c1ccc(CN2CCOCC2)cc1 ; Cc1cc(C)c(CNC(=O)c2cc3c(c(-c4ccc(CN5CCOCC5)cc4)c2)OC(C)(C)C3)c(=O)[nH]1]

A reaction vial was charged with 7-bromo-N-((4,6-dimethyl-2-oxo-1,2-dihydropyridin-3-yl)methyl)-2,2-dimethyl-2,3-dihydrobenzofuran-5-carboxamide (14.5 mg, 0.036 mmol, Intermediate 1C) and dimethylformamide (0.75 mL), sodium carbonate (71.6 µl, 0.072 mmol, 1M solution) and (4-(morpholinomethyl)phenyl)boronic acid (15.82 mg, 0.072 mmol) were added and the solution degassed with nitrogen for 15 minutes. Tetrakis(triphenylphosphine)palladium(0)(4.13 mg, 3.58 µmol) was added and the reaction was degassed for a few more minutes. The vial was sealed and heated to 100° C. for 3 hours. The reaction was then cooled and diluted with DMF (1.2 mL). The material was passed through a 0.45 µm glass microfiber syringe filter and purified by RP-HPLC using the following conditions: Column—Waters XBridge C18, 19×250 mm, 5-µm particles. Solvent—acetonitrile-water gradient containing 10 mM ammonium acetate. Evaporation of the appropriate fractions gave N-((4,6dimethyl-2-oxo-1,2-dihydropyridin-3-yl)methyl)-2,2-dimethyl-7-(4-(morpholinomethyl)phenyl)-2,3-dihydrobenzofuran-5-carboxamide (14.2 mg, 0.026 mmol, 73%). ¹H NMR (500 MHz, DMSO-d₆) δ 11.48 (br. s., 1H), 8.25 (s, 1H), 7.82 (s, 1H), 7.73-7.63 (m, 3H), 7.37 (d, J=8.5 Hz, 2H), 5.87 (s, 1H), 4.30 (d, J=4.9 Hz, 2H), 3.59 (d, J=4.3 Hz, 4H), 3.49 (s, 2H), 3.08 (s, 2H), 2.38 (br. s., 4H), 2.16 (s, 3H), 2.12 (s, 3H), 1.46 (s, 6H). MS(ES): m/z 502 [M+H]⁺.

Example 11

N-((4,6-Dimethyl-2-oxo-1,2-dihydropyridin-3-yl)methyl)-2,2-dimethyl-7-(6-(piperazin-1-yl)pyridin-3-yl)-2,3-dihydrobenzofuran-5-carboxamide

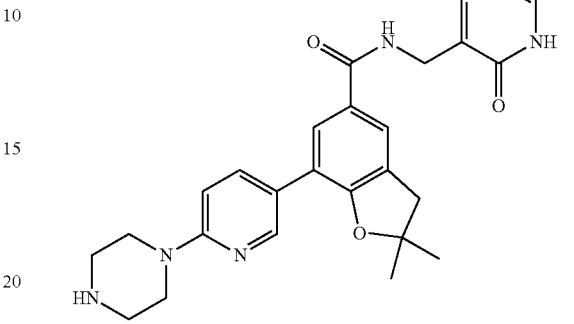

Example 11 was prepared from 1-(5-(4,4,5,5-tetramethyl-1,3,2-dioxaborolan-2-yl)pyridin-2-yl)piperazine and 7-bromo-N-((4,6-dimethyl-2-oxo-1,2-dihydropyridin-3-yl)methyl)-2,2-dimethyl-2,3-dihydrobenzofuran-5-carboxamide as described in Example 10. ¹H NMR (500 MHz, DMSO-d₆) δ 11.46 (s, 1H), 8.52 (d, J=1.8 Hz, 1H), 8.23 (s, 1H), 7.93-7.85 (m, 1H), 7.81 (s, 1H), 7.64 (s, 1H), 6.88 (d, J=8.5 Hz, 1H), 5.87 (s, 1H), 4.30 (d, J=4.9 Hz, 2H), 3.07 (s, 2H), 2.85-2.77 (m, 4H), 2.17 (s, 3H), 2.12 (s, 3H), 1.46 (s, 6H). MS(ES): m/z 488 [M+H]⁺.

Example 12

N-((4,6-Dimethyl-2-oxo-1,2-dihydropyridin-3-yl)methyl)-2,2-dimethyl-7-(6-morpholinopyridin-3-yl)-2,3-dihydrobenzofuran-5-carboxamide

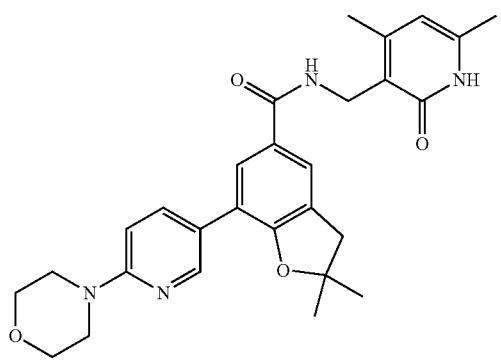 [SMILES: Cc1cc(C)c(CNC(=O)c2cc3c(c(-c4ccc(N5CCOCC5)nc4)c2)OC(C)(C)C3)c(=O)[nH]1]

Example 12 was prepared from 4-(5-(4,4,5,5-tetramethyl-1,3,2-dioxaborolan-2-yl)pyridin-2-yl)morpholine and 7-bromo-N-((4,6-dimethyl-2-oxo-1,2-dihydropyridin-3-yl)methyl)-2,2-dimethyl-2,3-dihydrobenzofuran-5-carboxamide as described in Example 10. ¹H NMR (500 MHz, DMSO-d₆) δ 11.49 (br. s., 1H), 8.54 (d, J=2.4 Hz, 1H), 8.24 (t, J=4.9 Hz, 1H), 7.92 (dd, J=8.5, 2.4 Hz, 1H), 7.82 (s, 1H), 7.65 (s, 1H), 6.92 (d, J=8.5 Hz, 1H), 5.87 (s, 1H), 4.30 (d, J=4.9 Hz, 2H), 3.76-3.67 (m, 4H), 3.55-3.46 (m, 4H), 3.07 (s, 2H), 2.17 (s, 3H), 2.12 (s, 3H), 1.46 (s, 6H). MS(ES): m/z 489 [M+H]⁺.

Example 13

N-((4,6-Dimethyl-2-oxo-1,2-dihydropyridin-3-yl)methyl)-2,2-dimethyl-7-(quinolin-3-yl)-2,3-dihydrobenzofuran-5-carboxamide

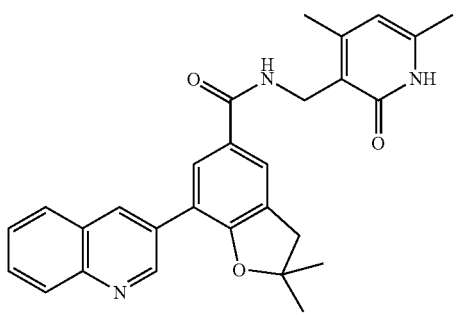 [SMILES: Cc1cc(C)c(CNC(=O)c2cc3c(c(-c4cnc5ccccc5c4)c2)OC(C)(C)C3)c(=O)[nH]1]

Example 13 was prepared from quinolin-3-ylboronic acid and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (400 MHz, METHANOL-$d_4$) δ 9.59 (d, J=1.5 Hz, 1H), 9.41 (s, 1H), 8.35 (d, J=8.4 Hz, 1H), 8.26 (d, J=8.6 Hz, 1H), 8.17 (br. s., 1H), 8.14 (s, 1H), 8.03-7.91 (m, 1H), 7.83 (s, 1H), 6.22 (s, 1H), 4.56 (s, 2H), 3.24 (s, 2H), 2.44 (s, 3H), 2.30 (s, 3H), 1.61 (s, 6H). MS(ES): m/z 454 [M+H]$^+$.

Example 14

N-((4,6-Dimethyl-2-oxo-1,2-dihydropyridin-3-yl)methyl)-7-(6-methoxypyridin-3-yl)-2,2-dimethyl-2,3-dihydrobenzofuran-5-carboxamide

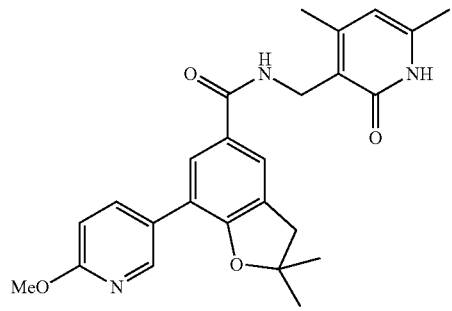 [SMILES: COc1ccc(-c2cc(C(=O)NCc3c(C)cc(C)[nH]c3=O)cc3c2OC(C)(C)C3)cn1]

Example 14 was prepared from (6-methoxypyridin-3-yl)boronic acid and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (400 MHz, DMSO-$d_6$) δ 11.47 (br. s., 1H), 8.56 (d, J=2.2 Hz, 1H), 8.23 (t, J=4.6 Hz, 1H), 8.05 (dd, J=8.7, 2.5 Hz, 1H), 7.86 (d, J=1.3 Hz, 1H), 7.71 (s, 1H), 6.92 (d, J=8.6 Hz, 1H), 5.87 (s, 1H), 4.31 (d, J=4.8 Hz, 2H), 3.90 (s, 3H), 3.10 (s, 2H), 2.18 (s, 3H), 2.13 (s, 3H), 1.48 (s, 6H). MS(ES): m/z 434 [M+H]$^+$.

Example 15

(E)-N-((4,6-Dimethyl-2-oxo-1,2-dihydropyridin-3-yl)methyl)-2,2-dimethyl-7-styryl-2,3-dihydrobenzofuran-5-carboxamide

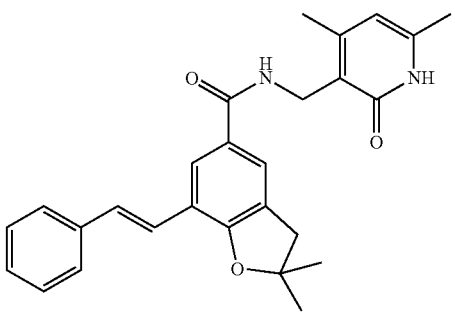 [SMILES: Cc1cc(C)c(CNC(=O)c2cc(/C=C/c3ccccc3)c3c(c2)CC(C)(C)O3)c(=O)[nH]1]

Example 15 was prepared from (E)-styrylboronic acid and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (400 MHz, DMSO-$d_6$) δ 11.46 (br. s., 1H), 8.14 (br. s., 1H), 7.94 (s, 1H), 7.64 (s, 1H), 7.57 (d, J=7.3 Hz, 2H), 7.42-7.38 (m, 2H), 7.36 (d, J=11.9 Hz, 1H), 7.32-7.24 (m, 1H), 7.15 (d, J=16.5 Hz, 1H), 5.88 (s, 1H), 4.32 (d, J=4.8 Hz, 2H), 3.07 (s, 2H), 2.19 (s, 3H), 2.14 (s, 3H), 1.51 (s, 6H). MS(ES): m/z 429 [M+H]$^+$.

Example 16

N-((4,6-Dimethyl-2-oxo-1,2-dihydropyridin-3-yl)methyl)-2,2-dimethyl-7-(4-(4-methylpiperazine-1-carbonyl)phenyl)-2,3-dihydrobenzofuran-5-carboxamide

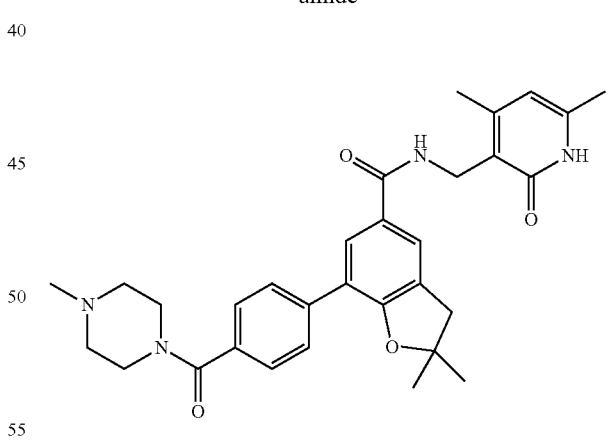

Example 16 was prepared from (4-methylpiperazin-1-yl)(4-(4,4,5,5-tetramethyl-1,3,2-dioxaborolan-2-yl)phenyl)methanone and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (500 MHz, DMSO-$d_6$) δ 11.49 (br. s., 1H), 8.29 (t, J=4.6 Hz, 1H), 7.87 (s, 1H), 7.79 (d, J=7.9 Hz, 2H), 7.72 (s, 1H), 7.45 (d, J=7.9 Hz, 2H), 5.88 (s, 1H), 4.31 (d, J=4.9 Hz, 2H), 3.10 (s, 2H), 2.45-2.25 (m, 4H), 2.20 (s, 3H), 2.17 (s, 3H), 2.12 (s, 3H), 1.47 (s, 6H). MS(ES): m/z 529 [M+H]$^+$.

Example 17 t-Butyl 4-(5-(5-(((4,6-dimethyl-2-oxo-1,2-dihydropyridin-3-yl)methyl)carbamoyl)-2,2-dimethyl-2,3-dihydrobenzofuran-7-yl)pyrimidin-2-yl)piperazine-1-carboxylate

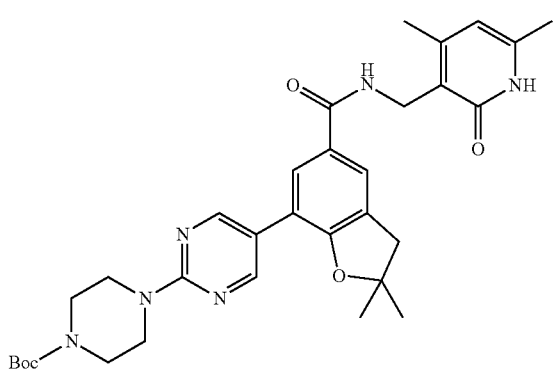 [SMILES: Cc1cc(C)c(CNC(=O)c2cc3c(c(-c4cnc(N5CCN(C(=O)OC(C)(C)C)CC5)nc4)c2)OC(C)(C)C3)c(=O)[nH]1]

Example 17 was prepared from tert-butyl 4-(5-(4,4,5,5-tetramethyl-1,3,2-dioxaborolan-2-yl)pyrimidin-2-yl)piperazine-1-carboxylate and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (500 MHz, DMSO-$d_6$) δ 11.50 (br. s., 1H), 8.76 (s, 2H), 8.21 (br. s., 1H), 7.86 (s, 1H), 7.68 (s, 1H), 5.87 (s, 1H), 4.30 (d, J=4.9 Hz, 2H), 3.83-3.72 (m, 4H), 3.42 (br. s., 4H), 3.08 (s, 2H), 2.17 (s, 3H), 2.12 (s, 3H), 1.46 (s, 6H), 1.44 (s, 9H). MS(ES): m/z 589 [M+H]$^+$.

Example 18

N-((4,6-Dimethyl-2-oxo-1,2-dihydropyridin-3-yl)methyl)-2,2-dimethyl-7-(4-(piperazin-1-yl)phenyl)-2,3-dihydrobenzofuran-5-carboxamide

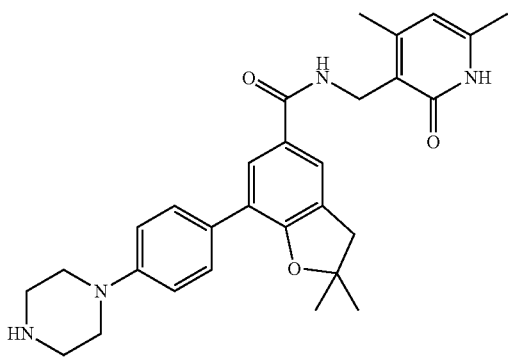 [SMILES: Cc1cc(C)c(CNC(=O)c2cc3c(c(-c4ccc(N5CCNCC5)cc4)c2)OC(C)(C)C3)c(=O)[nH]1]

Example 18 was prepared from 1-(4-(4,4,5,5-tetramethyl-1,3,2-dioxaborolan-2-yl)phenyl)piperazine and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (500 MHz, DMSO-$d_6$) δ 12.01-10.97 (m, 1H), 8.24 (t, J=4.9 Hz, 1H), 7.78 (s, 1H), 7.66-7.51 (m, 3H), 6.98 (d, J=9.2 Hz, 2H), 5.87 (s, 1H), 4.30 (d, J=4.9 Hz, 2H), 3.16-3.10 (m, 4H), 3.06 (s, 2H), 2.91-2.86 (m, 4H), 2.17 (s, 3H), 2.12 (s, 3H), 1.45 (s, 6H). MS(ES): m/z 487 [M+H]$^+$.

Example 19

N-((4,6-Dimethyl-2-oxo-1,2-dihydropyridin-3-yl)methyl)-2,2-dimethyl-7-(4-(piperidin-1-ylmethyl)phenyl)-2,3-dihydrobenzofuran-5-carboxamide

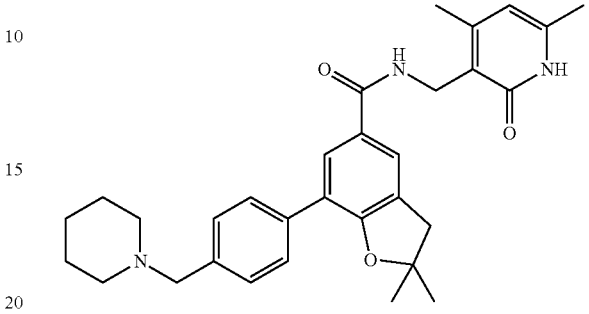

Example 19 was prepared from 1-(4-(4,4,5,5-tetramethyl-1,3,2-dioxaborolan-2-yl)benzyl)piperidine and 7-bromo-N-((4,6-dimethyl-2-oxo-1,2-dihydropyridin-3-yl)methyl)-2,2-dimethyl-2,3-dihydrobenzofuran-5-carboxamide as described in Example 10. $^1$H NMR (500 MHz, DMSO-$d_6$) δ 11.49 (br. s., 1H), 8.26 (t, J=4.6 Hz, 1H), 7.82 (s, 1H), 7.68 (s, 1H), 7.65 (d, J=8.5 Hz, 2H), 7.34 (d, J=8.5 Hz, 2H), 5.87 (s, 1H), 4.30 (d, J=4.9 Hz, 2H), 3.44 (br. s., 2H), 3.08 (s, 2H), 2.51 (s, 4H), 2.17 (s, 3H), 2.12 (s, 3H), 1.55-1.48 (m, 4H), 1.46 (s, 6H), 1.40 (br. s., 2H). MS(ES): m/z 500 [M+H]$^+$.

Example 20

N-((4,6-Dimethyl-2-oxo-1,2-dihydropyridin-3-yl)methyl)-2,2-dimethyl-7-(2-(piperazin-1-yl)pyrimidin-5-yl)-2,3-dihydrobenzofuran-5-carboxamide

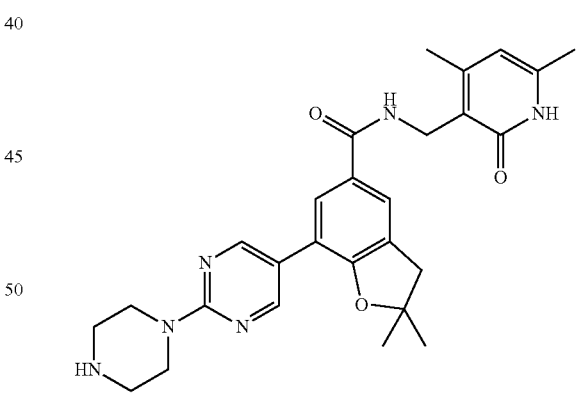

t-Butyl 4-(5-(5-(((4,6-dimethyl-2-oxo-1,2-dihydropyridin-3-yl)methyl)carbamoyl)-2,2-dimethyl-2,3-dihydrobenzofuran-7-yl)pyrimidin-2-yl)piperazine-1-carboxylate (11.3 mg, 0.019 mmol, Example 17) was dissolved in 4 N HCl in dioxane. The reaction was allowed to proceed for an hour when it was concentrated under a stream of nitrogen. Residual solvent was removed in vacuo to give N-((4,6-dimethyl-2-oxo-1,2-dihydropyridin-3-yl)methyl)-2,2-dimethyl-7-(2-(piperazin-1-yl)pyrimidin-5-yl)-2,3-dihydrobenzofuran-5-carboxamide (8.4 mg, 0.015 mmol) as a pale yellow hydrochloride salt (8.4 mg, 76%). $^1$H NMR (400 MHz, DMSO-$d_6$) δ 11.50 (br. s., 1H), 9.00 (br. s., 2H), 8.81

(s, 2H), 8.21 (br. s., 1H), 7.87 (s, 1H), 7.70 (s, 1H), 5.88 (s, 1H), 4.31 (d, J=4.6 Hz, 2H), 4.10-3.88 (m, 4H), 3.20 (br. s., 4H), 3.09 (s, 2H), 2.17 (s, 3H), 2.13 (s, 3H), 1.47 (s, 6H). MS(ES): m/z 489 [M+H]+.

Example 21

7-Benzyl-N-((4,6-dimethyl-2-oxo-1,2-dihydropyridin-3-yl)methyl)-2,2-dimethyl-2,3-dihydrobenzofuran-5-carboxamide

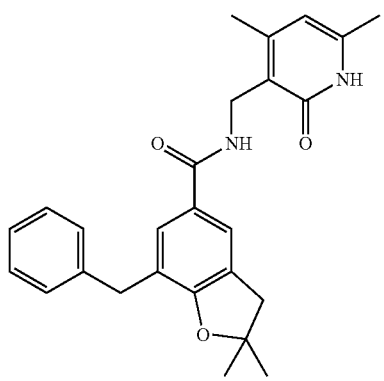 [SMILES: Cc1cc(C)c(CNC(=O)c2cc(Cc3ccccc3)c3c(c2)CC(C)(C)O3)c(=O)[nH]1]

21A. 7-Benzyl-2,2-dimethyl-2,3-dihydrobenzofuran-5-carboxylic acid

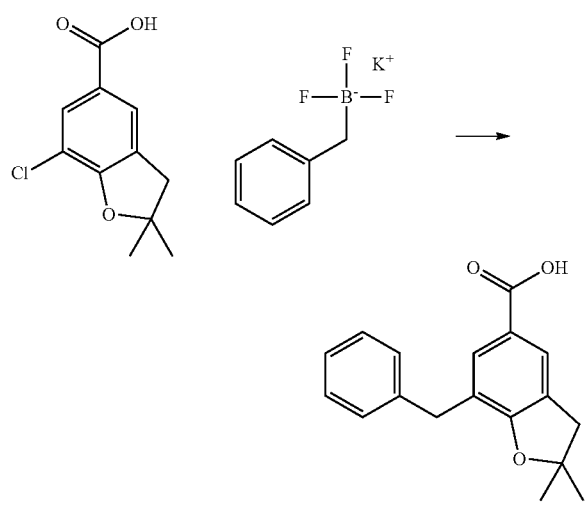

A reaction vial was charged with 7-chloro-2,2-dimethyl-2,3-dihydrobenzofuran-5-carboxylic acid (41 mg, 0.181 mmol., prepared in Example 3) and potassium benzyltrifluoroborate (71.6 mg, 0.362 mmol). The material was dissolved in dioxane (2 mL) and cesium carbonate solution (543 µl, 0.543 mmol) (1 M) was added. Nitrogen was bubbled through the stirred solution for 15 minutes. 2-(Dicyclohexylphosphino)-2',4',6'-tri-isopropylbiphenyl (XPhos) (17.25 mg, 0.036 mmol) and palladium (II) acetate (4.06 mg, 0.018 mmol) were then added. The vial was sealed and heated to 95° C. overnight. Some methanol was added and the reaction filtered. The filtrate was concentrated under a stream of nitrogen. The material was transferred to a reparatory funnel and acidified with 1 N hydrochloric acid. The material was extracted with ether. The organic layer was dried over magnesium sulfate, filtered and evaporated. The residue was dissolved in methanol and purified by RP-HPLC (methanol-water gradient+0.1% TFA). The product containing fraction was concentrated under a stream of nitrogen. The resultant colorless precipitate was filtered, rinsed with water and dried in a ChemDry oven at 40° C. for 15 minutes. 7-Benzyl-2,2-dimethyl-2,3-dihydrobenzofuran-5-carboxylic acid (4.7 mg, 0.016 mmol, 9% yield) was isolated as a colorless solid. $^1$H NMR (400 MHz, DMSO-$d_6$) δ 12.38 (br. s., 1H), 7.63 (s, 1H), 7.55 (s, 1H), 7.34-7.16 (m, 5H), 3.86 (s, 2H), 3.08 (s, 2H), 1.46 (s, 6H). MS(ES): m/z 283 [M+H]+.

21. 7-Benzyl-N-((4,6-dimethyl-2-oxo-1,2-dihydropyridin-3-yl)methyl)-2,2-dimethyl-2,3-dihydrobenzofuran-5-carboxamide

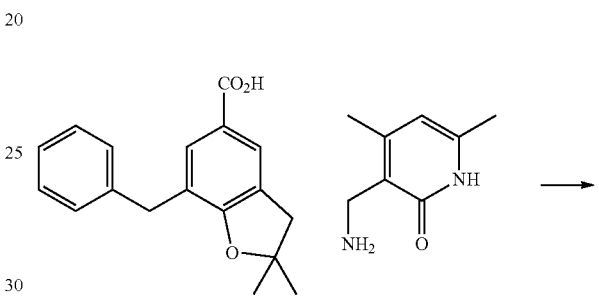

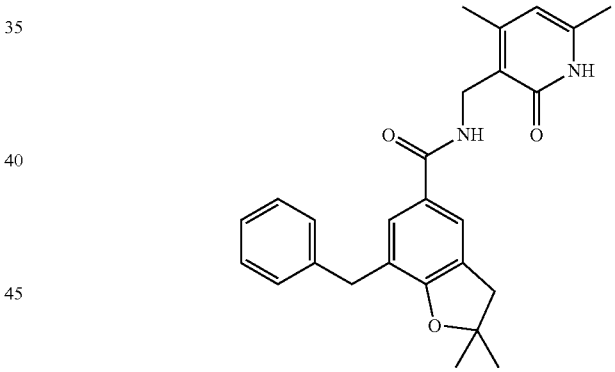

7-Benzyl-2,2-dimethyl-2,3-dihydrobenzofuran-5-carboxylic acid (3.5 mg, 0.012 mmol) was dissolved in dry DMF (0.5 mL). 3-(Aminomethyl)-4,6-dimethylpyridin-2(1H)-one hydrochloride (2.57 mg, 0.014 mmol) and triethylamine (5.18 µl, 0.037 mmol) were added. The reaction was initiated with the addition of BOP (6.58 mg, 0.015 mmol). Stirring was continued overnight. The reaction was quenched with half saturated sodium bicarbonate solution. Stirring was continued for half of an hour. The precipitate was filtered and rinsed well with water. The solid was dried in a ChemDry oven at 75° C. for half an hour. 7-Benzyl-N-((4,6-dimethyl-2-oxo-1,2-dihydropyridin-3-yl)methyl)-2,2-dimethyl-2,3-dihydrobenzofuran-5-carboxamide (4.8 mg, 0.011 mmol, 91% yield) was isolated as a colorless solid. $^1$H NMR (400 MHz, DMSO-$d_6$) δ 7.57 (s, 1H), 7.52 (s, 1H), 7.31-7.13 (m, 5H), 5.85 (s, 1H), 4.26 (d, J=4.8 Hz, 2H), 3.83 (s, 2H), 3.03 (s, 2H), 2.15 (s, 3H), 2.12 (s, 3H), 1.43 (s, 6H). MS(ES): m/z 417 [M+H]+.

Example 22

7-Cyano-N-((4,6-dimethyl-2-oxo-1,2-dihydropyridin-3-yl)methyl)-2,2-dimethyl-2,3-dihydrobenzofuran-5-carboxamide

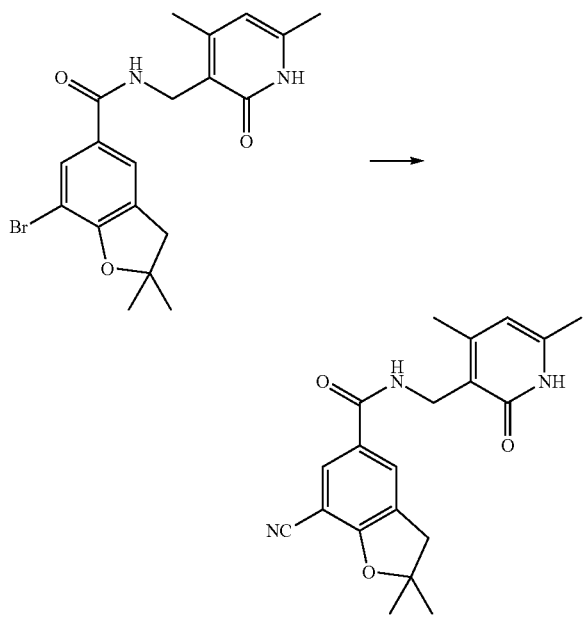

A reaction vial was charged with zinc cyanide (5.42 µl, 0.085 mmol), 7-bromo-N-((4,6-dimethyl-2-oxo-1,2-dihydropyridin-3-yl)methyl)-2,2-dimethyl-2,3-dihydrobenzofuran-5-carboxamide (17.3 mg, 0.043 mmol, Example 1), zinc (2.79 mg, 0.043 mmol) and DMF (0.75 mL). The reaction was degassed for ca. 15 minutes with a stream of nitrogen. Tetrakis(triphenylphosphine)palladium(0) (4.93 mg, 4.27 µmol) was then added. Bubbling with nitrogen was continued for a few minutes. The vial was sealed and heated to 90° C. for ca. 120 minutes. The reaction was then cooled and diluted with DMF (1 mL). The suspension was filtered and purified by RP-HPLC (methanol-water gradient+0.1% TFA). The product containing fraction was treated with half saturated sodium bicarbonate solution and concentrated under a stream of nitrogen. The resulting precipitate was filtered and rinsed well with water. Drying in the ChemDry oven at 75° C. for 0.5 hour gave 7-cyano-N-((4,6-dimethyl-2-oxo-1,2-dihydropyridin-3-yl)methyl)-2,2-dimethyl-2,3-dihydrobenzofuran-5-carboxamide (5.9 mg, 0.016 mmol, 37.4% yield) as a colorless solid. $^1$H NMR (400 MHz, DMSO-$d_6$) δ 11.47 (br. s., 1H), 8.28 (br. s., 1H), 8.04 (d, J=1.8 Hz, 1H), 8.00 (d, J=1.5 Hz, 1H), 5.88 (s, 1H), 4.29 (d, J=4.6 Hz, 2H), 3.14 (s, 2H), 2.17 (s, 3H), 2.13 (s, 3H), 1.51 (s, 6H). MS(ES): m/z 352 [M+H]$^+$.

Example 23

7-Chloro-2,2-dimethyl-N-((6-methyl-2-oxo-4-propyl-1,2-dihydropyridin-3-yl)methyl)-2,3-dihydrobenzofuran-5-carboxamide

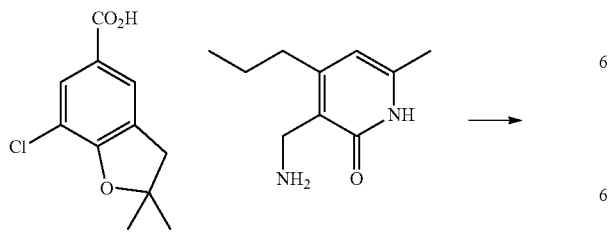

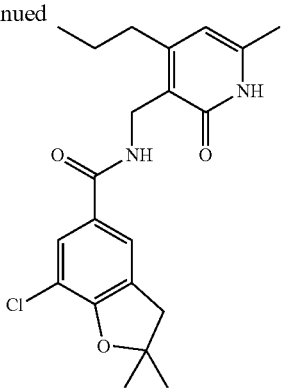

7-Chloro-2,2-dimethyl-2,3-dihydrobenzofuran-5-carboxylic acid (24.4 mg, 0.108 mmol, prepared in example 3) was dissolved in dry dimethylformamide (0.5 mL). 3-(Aminomethyl)-6-methyl-4-propylpyridin-2(1H)-one hydrochloride (28.0 mg, 0.129 mmol) and triethylamine (45.0 µl, 0.323 mmol) were added. The reaction was initiated with the addition of BOP (57.1 mg, 0.129 mmol). Stirring was continued overnight. The reaction was quenched with the addition of ca. 4 mL of half saturated sodium bicarbonate solution. The mixture was stirred for half an hour. The resulting precipitate was filtered and rinsed well with water. Drying in a ChemDry oven at 75° C. for half an hour provided 7-chloro-2,2-dimethyl-N-((6-methyl-2-oxo-4-propyl-1,2-dihydropyridin-3-yl)methyl)-2,3-dihydrobenzofuran-5-carboxamide (27 mg, 0.066 mmol, 61.3% yield) as an off white solid. $^1$H NMR (400 MHz, DMSO-$d_6$) δ 11.45 (br. s., 1H), 8.21 (br. s., 1H), 7.74 (s, 1H), 7.68 (s, 1H), 5.89 (s, 1H), 4.30 (d, J=4.6 Hz, 2H), 3.13 (s, 2H), 2.49-2.39 (m, 2H), 2.14 (s, 3H), 1.59-1.40 (m, 8H), 0.89 (t, J=7.3 Hz, 3H). MS(ES): m/z 389 [M+H]$^+$.

Example 24

7-Bromo-2,2-dimethyl-N-((6-methyl-2-oxo-4-propyl-1,2-dihydropyridin-3-yl)methyl)-2,3-dihydrobenzofuran-5-carboxamide

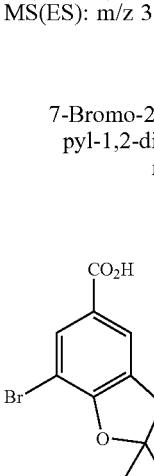
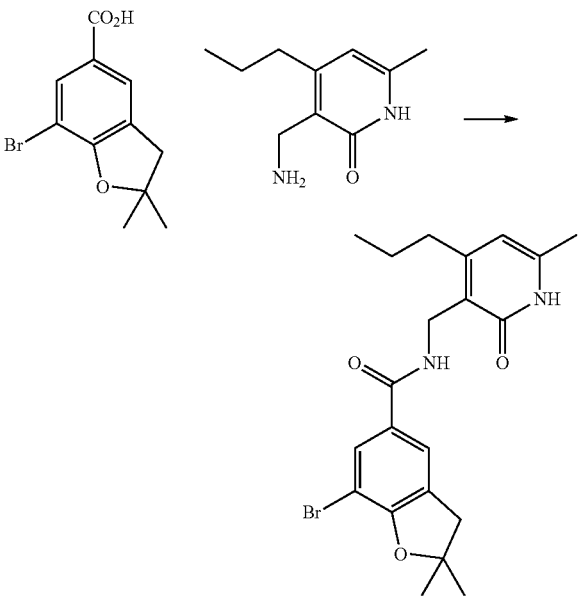

7-Bromo-2,2-dimethyl-2,3-dihydrobenzofuran-5-carboxylic acid (3.9 mg, 0.014 mmol, Intermediate 1C) was dissolved in dry dimethylformamide (0.5 mL). 3-(Aminomethyl)-6-methyl-4-propylpyridin-2(1H)-one hydrochloride (4.68 mg, 0.022 mmol) and triethylamine (6.02 µl, 0.043 mmol) were then added. The reaction was initiated with the addition of BOP (7.63 mg, 0.017 mmol). After ca. 2 hours, the reaction was diluted with methanol and purified by RP-HPLC (methanol-water gradient+0.1% TFA). The product containing fraction was evaporated. The resulting precipitate was filtered. As there was relatively little material, the filter paper was extracted with CDCl3 to generate the 1H-NMR spectrum. The sample was then evaporated to give 7-bromo-2,2-dimethyl-N-((6-methyl-2-oxo-4-propyl-1,2-dihydropyridin-3-yl)methyl)-2,3-dihydrobenzofuran-5-carboxamide (0.8 mg). $^1$H NMR (400 MHz, CHLOROFORM-d) δ 11.18-10.94 (m, 1H), 7.74 (s, 1H), 7.65 (br. s., 1H), 7.56 (s, 1H), 5.98 (s, 1H), 4.58 (d, J=5.5 Hz, 2H), 3.12 (s, 2H), 2.71 (t, J=7.7 Hz, 2H), 2.33 (s, 3H), 1.70-1.57 (m, 5H), 1.55 (s, 6H), 1.03 (t, J=7.2 Hz, 3H). MS(ES): m/z 433 [M+H]$^+$.

Example 25

N-((4,6-Dimethyl-2-oxo-1,2-dihydropyridin-3-yl)methyl)-7-(6-methoxypyridin-3-yl)-2,2,4-trimethyl-2,3-dihydrobenzofuran-5-carboxamide

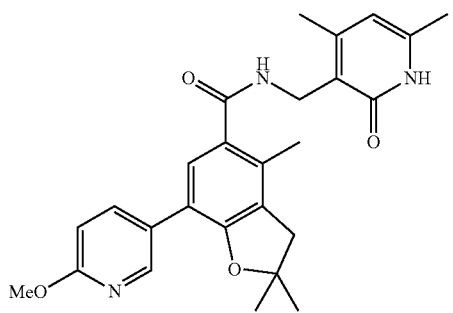 [SMILES: COc1ccc(-c2cc(C(=O)NCc3c(C)cc(C)[nH]c3=O)c(C)c3c2OC(C)(C)C3)cn1]

Example 25 was prepared from (6-methoxypyridin-3-yl)boronic acid and 7-bromo-N-((4,6-dimethyl-2-oxo-1,2-dihydropyridin-3-yl)methyl)-2,2,4-trimethyl-2,3-dihydrobenzofuran-5-carboxamide (Example 7) as described in Example 10. $^1$H NMR (500 MHz, DMSO-d$_6$) δ 11.49 (br. s., 1H), 8.48 (s, 1H), 8.08 (br. s., 1H), 7.98 (d, J=8.5 Hz, 1H), 7.28 (s, 1H), 6.89 (d, J=9.2 Hz, 1H), 5.88 (s, 1H), 4.27 (d, J=4.3 Hz, 2H), 3.87 (s, 3H), 3.00 (s, 2H), 2.23 (s, 3H), 2.20 (s, 3H), 2.11 (s, 3H), 1.45 (s, 6H). MS(ES): m/z 448 [M+H]$^+$.

Example 26

N-((4,6-Dimethyl-2-oxo-1,2-dihydropyridin-3-yl)methyl)-2,2,4-trimethyl-7-(6-(piperazin-1-yl)pyridin-3-yl)-2,3-dihydrobenzofuran-5-carboxamide

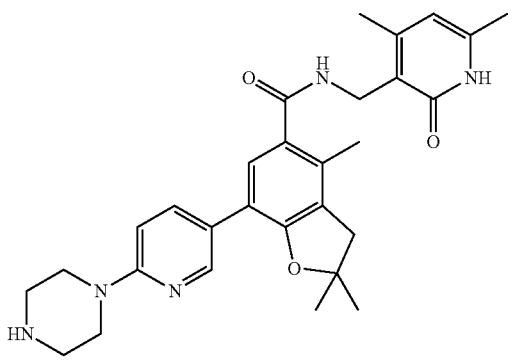 [SMILES: Cc1cc(C)c(CNC(=O)c2cc(-c3ccc(N4CCNCC4)nc3)c3c(c2C)CC(C)(C)O3)c(=O)[nH]1]

Example 26 was prepared from 1-(5-(4,4,5,5-tetramethyl-1,3,2-dioxaborolan-2-yl)pyridin-2-yl)piperazine and 7-bromo-N-((4,6-dimethyl-2-oxo-1,2-dihydropyridin-3-yl)methyl)-2,2,4-trimethyl-2,3-dihydrobenzofuran-5-carboxamide (Example 7) as described in Example 10. MS(ES): m/z 502 [M+H]$^+$.

Example 27

N-((4,6-Dimethyl-2-oxo-1,2-dihydropyridin-3-yl)methyl)-3-methyl-7-(6-morpholinopyridin-3-yl)-2,3-dihydrobenzofuran-5-carboxamide

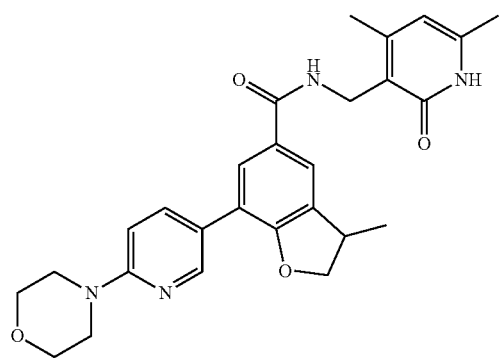 [SMILES: Cc1cc(C)c(CNC(=O)c2cc(-c3ccc(N4CCOCC4)nc3)c3c(c2)C(C)CO3)c(=O)[nH]1]

27A. Methyl 4-(allyloxy)-3-bromobenzoate

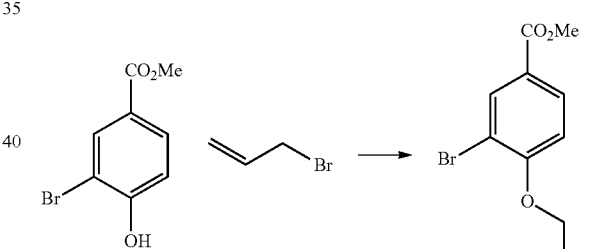

Methyl 3-bromo-4-hydroxybenzoate (1.03 g, 4.46 mmol) was dissolved in acetonitrile (10 mL) under nitrogen. Potassium carbonate (0.801 g, 5.80 mmol) was added and stirring continued for a few minutes. 3-Bromoprop-1-ene (0.463 ml, 5.35 mmol) was added and the reaction allowed to stir overnight. The reaction was then warmed to 60° C. After ca. 2 hours, reaction was complete by LCMS. The cooled reaction was transferred to a separatory funnel and diluted with ether. The diluted reaction was washed with water and brine. The ether layer was dried over magnesium sulfate, filtered and evaporated. The crude product was applied to an 80 g Isco silica gel column and eluted with 0-25% ethyl acetate in hexanes. Evaporation of the appropriate fractions provided methyl 4-(allyloxy)-3-bromobenzoate (1.11 g, 4.01 mmol, 90% yield) as a colorless solid. $^1$H NMR (400 MHz, DMSO-d$_6$) δ 8.11 (d, J=2.2 Hz, 1H), 7.96 (dd, J=8.7, 2.1 Hz, 1H), 7.25 (d, J=8.8 Hz, 1H), 6.08 (ddt, J=17.2, 10.5, 5.1 Hz, 1H), 5.49 (dq, J=17.2, 1.7 Hz, 1H), 5.33 (dq, J=10.6, 1.5 Hz, 1H), 4.78 (dt, J=5.0, 1.5 Hz, 2H), 3.85 (s, 3H). MS(ES): m/z 271 [M+H]$^+$.

27B. 3-Methyl-2,3-dihydrobenzofuran-5-carboxylic acid

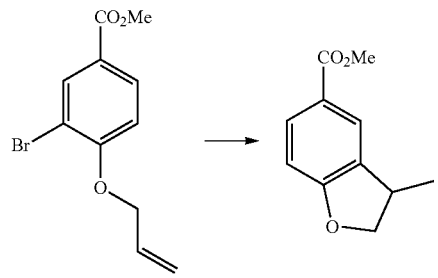

An oven dried flask was charged with methyl 4-(allyloxy)-3-bromobenzoate (523 mg, 1.929 mmol) under nitrogen. After the starting material was dissolved in dry toluene (5.0 mL), tri-N-butyltin hydride (618 μl, 2.315 mmol) and AIBN (20 mg, 0.122 mmol) were added. The flask was evacuated and purged with nitrogen three times. The reaction was then heated to 95° C. for 3 hours. The reaction was the cooled and evaporated. The residue was dissolved in tetrahydrofuran-water (3:1, 16 mL) and 1 N lithium hydroxide (5.0 mL) was added. Add a little methanol was introduced to add dissolution. The reaction was stirred overnight. Partial conversion to product was evident by LCMS. The reaction was then warmed to 55° C. for 6 hours. The cooled reaction was evaporated. Some water was added and the mixture transferred to a separatory funnel. The largely aqueous material was extracted twice with ether. The aqueous layer was then transferred to a small Erlenmeyer flask and neutralized with 1 N hydrochloric acid (5.0 mL). The resultant precipitate was filtered and rinsed well with water. After pumping down, 3-methyl-2,3-dihydrobenzofuran-5-carboxylic acid (255 mg, 1.378 mmol, 71.4% yield) was isolated as a colorless solid. $^1$H NMR (400 MHz, DMSO-$d_6$) δ 12.52 (d, J=4.0 Hz, 1H), 7.81 (s, 1H), 7.77 (dd, J=8.4, 1.8 Hz, 1H), 6.85 (d, J=8.4 Hz, 1H), 4.78 (t, J=9.0 Hz, 1H), 4.15 (dd, J=8.8, 7.3 Hz, 1H), 3.66-3.51 (m, 1H), 1.30 (d, J=6.8 Hz, 3H). MS(ES): m/z 179 [M+H]$^+$.

27C. 7-Bromo-3-methyl-2,3-dihydrobenzofuran-5-carboxylic acid

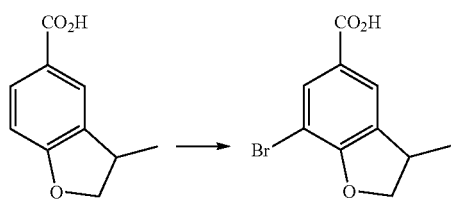

3-Methyl-2,3-dihydrobenzofuran-5-carboxylic acid (116 mg, 0.651 mmol) in glacial acetic acid (1.0 mL) was treated with bromine (67.1 μl, 1.302 mmol). After an hour, more bromine (30 uL) was added. One hour later, water was added and the resulting precipitate was filtered and rinsed with water. Drying for 0.5 hour in a ChemDry oven at 75° C. gave 7-bromo-3-methyl-2,3-dihydrobenzofuran-5-carboxylic acid (150 mg, 0.525 mmol, 81% yield) as an off-white solid. $^1$H NMR (400 MHz, DMSO-$d_6$) δ 12.87 (br. s., 1H), 7.89 (d, J=1.1 Hz, 1H), 7.79 (t, J=1.3 Hz, 1H), 4.88 (t, J=9.0 Hz, 1H), 4.27 (dd, J=8.9, 7.4 Hz, 1H), 3.81-3.63 (m, 1H), 1.32 (d, J=6.8 Hz, 3H).

27D. 7-Bromo-N-((4,6-dimethyl-2-oxo-1,2-dihydropyridin-3-yl)methyl)-3-methyl-2,3-dihydrobenzofuran-5-carboxamide

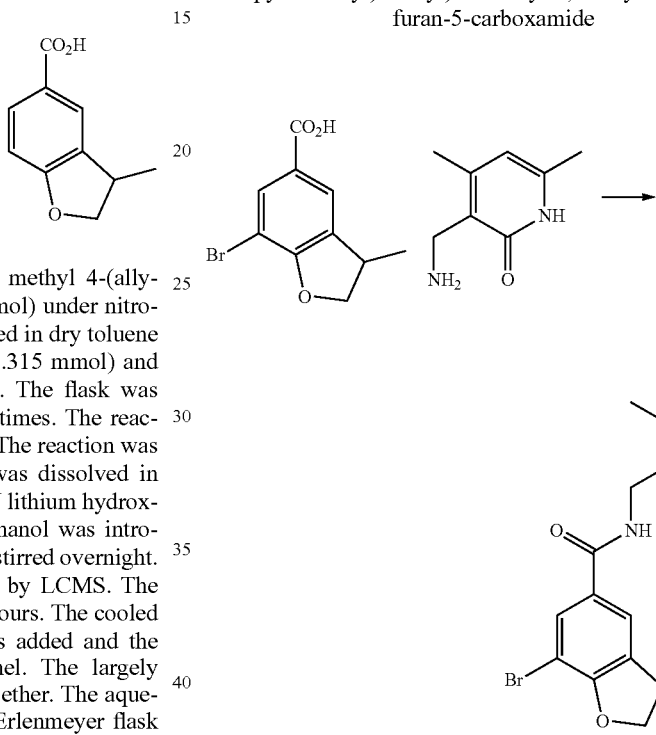

A reaction vial was charged with 7-bromo-3-methyl-2,3-dihydrobenzofuran-5-carboxylic acid (97.6 mg, 0.380 mmol). The starting material was dissolved in dimethylformamide (2.0 mL) and 3-(aminomethyl)-4,6-dimethylpyridin-2(1H)-one hydrochloride (79 mg, 0.418 mmol) was added. The reaction was then treated with triethylamine (159 μl, 1.139 mmol) and BOP (201 mg, 0.456 mmol). After stirring for 2 days, the reaction was quenched with one quarter saturated sodium bicarbonate solution (stir for an hour). The resulting precipitate was filtered, rinsed with one quarter saturated sodium bicarbonate then water. Drying in a ChemDry oven at 75° C. for 45 minutes provided 7-bromo-N-((4,6-dimethyl-2-oxo-1,2-dihydropyridin-3-yl)methyl)-3-methyl-2,3-dihydrobenzofuran-5-carboxamide (135 mg, 0.328 mmol, 86% yield) as a colorless solid. $^1$H NMR (400 MHz, DMSO-$d_6$) δ 11.47 (br. s., 1H), 8.26 (br. s., 1H), 7.89 (d, J=1.3 Hz, 1H), 7.77 (s, 1H), 5.88 (s, 1H), 4.83 (t, J=9.0 Hz, 1H), 4.28 (d, J=4.8 Hz, 2H), 4.25-4.15 (m, 1H), 3.75-3.60 (m, 1H), 2.17 (s, 3H), 2.13 (s, 3H), 1.30 (d, J=6.8 Hz, 3H).

27. N-((4,6-Dimethyl-2-oxo-1,2-dihydropyridin-3-yl)methyl)-3-methyl-7-(6-morpholinopyridin-3-yl)-2,3-dihydrobenzofuran-5-carboxamide

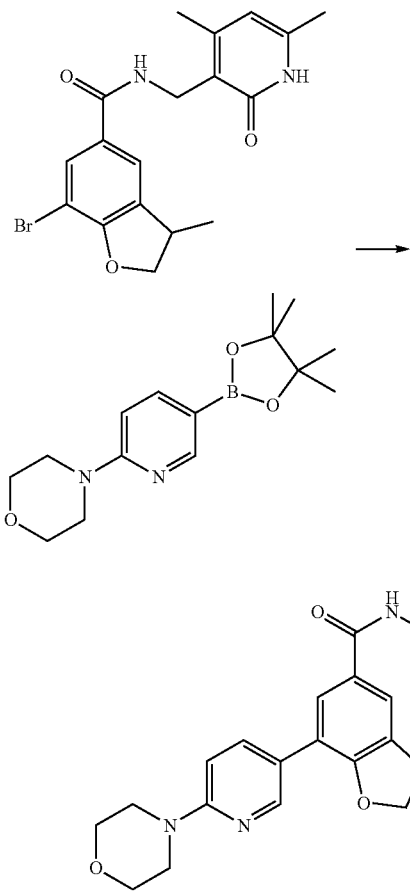

Example 27 was prepared from 4-(5-(4,4,5,5-tetramethyl-1,3,2-dioxaborolan-2-yl)pyridin-2-yl)morpholine and 7-bromo-N-((4,6-dimethyl-2-oxo-1,2-dihydropyridin-3-yl)methyl)-3-methyl-2,3-dihydrobenzofuran-5-carboxamide (Intermediate 27D) as described in Example 10. $^1$H NMR (500 MHz, DMSO-$d_6$) δ 11.50 (br. s., 1H), 8.53 (d, J=2.4 Hz, 1H), 8.29 (s, 1H), 8.00-7.90 (m, 1H), 7.85 (s, 1H), 7.69 (s, 1H), 6.91 (d, J=8.5 Hz, 1H), 5.88 (s, 1H), 4.80 (t, J=9.2 Hz, 1H), 4.30 (d, J=4.9 Hz, 2H), 4.15 (t, J=8.2 Hz, 2H), 3.72 (t, J=4.9 Hz, 4H), 3.66-3.54 (m, 1H), 3.52-3.45 (m, 4H), 2.18 (s, 3H), 2.12 (s, 3H), 1.31 (d, J=6.7 Hz, 3H). MS(ES): m/z 475 [M+H]$^+$.

Example 28

N-((4,6-Dimethyl-2-oxo-1,2-dihydropyridin-3-yl)methyl)-3-methyl-7-(4-(morpholinomethyl)phenyl)-2,3-dihydrobenzofuran-5-carboxamide

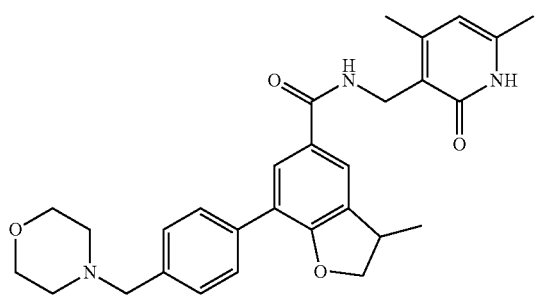 [SMILES: Cc1cc(C)c(CNC(=O)c2cc(-c3ccc(CN4CCOCC4)cc3)c3c(c2)C(C)CO3)c(=O)[nH]1]

Example 28 was prepared from (4-(morpholinomethyl)phenyl)boronic acid and 7-bromo-N-((4,6-dimethyl-2-oxo-1,2-dihydropyridin-3-yl)methyl)-3-methyl-2,3-dihydrobenzofuran-5-carboxamide (Intermediate 27D) as described in Example 10. $^1$H NMR (500 MHz, DMSO-$d_6$) δ 11.49 (br. s., 1H), 8.31 (br. s., 1H), 7.86 (s, 1H), 7.73 (s, 1H), 7.67 (d, J=7.9 Hz, 2H), 7.37 (d, J=7.9 Hz, 2H), 5.88 (s, 1H), 4.79 (t, J=8.9 Hz, 1H), 4.31 (d, J=4.9 Hz, 2H), 4.19-4.09 (m, 2H), 3.65-3.54 (m, 5H), 3.49 (s, 2H), 3.18 (d, J=4.9 Hz, 2H), 2.18 (s, 3H), 2.12 (s, 3H), 1.32 (d, J=6.7 Hz, 3H). MS(ES): m/z 488 [M+H]$^+$.

Example 29

N-((4,6-Dimethyl-2-oxo-1,2-dihydropyridin-3-yl)methyl)-3-methyl-7-(6-(piperazin-1-yl)pyridin-3-yl)-2,3-dihydrobenzofuran-5-carboxamide

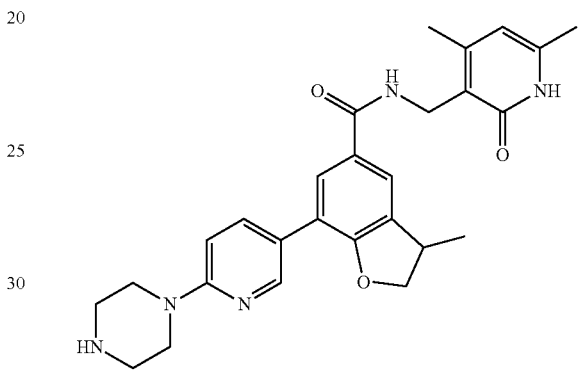

Example 29 was prepared from 1-(5-(4,4,5,5-tetramethyl-1,3,2-dioxaborolan-2-yl)pyridin-2-yl)piperazine and 7-bromo-N-((4,6-dimethyl-2-oxo-1,2-dihydropyridin-3-yl)methyl)-3-methyl-2,3-dihydrobenzofuran-5-carboxamide (Intermediate 27D) as described in Example 10. $^1$H NMR (500 MHz, DMSO-$d_6$) δ 11.50 (s, 1H), 8.51 (d, J=2.4 Hz, 1H), 8.28 (s, 1H), 7.90 (d, J=11.0 Hz, 1H), 7.84 (s, 1H), 7.68 (s, 1H), 6.87 (d, J=9.2 Hz, 1H), 5.88 (s, 1H), 4.79 (t, J=8.9 Hz, 1H), 4.30 (d, J=4.9 Hz, 2H), 4.18-4.10 (m, 3H), 3.18 (d, J=4.9 Hz, 7H), 2.80 (br. s., 4H), 2.18 (s, 3H), 2.12 (s, 3H), 1.31 (d, J=7.3 Hz, 3H). MS(ES): m/z 474 [M+H]$^+$.

Example 30

N-((4,6-Dimethyl-2-oxo-1,2-dihydropyridin-3-yl)methyl)-7-(6-methoxypyridin-3-yl)-3-methyl-2,3-dihydrobenzofuran-5-carboxamide

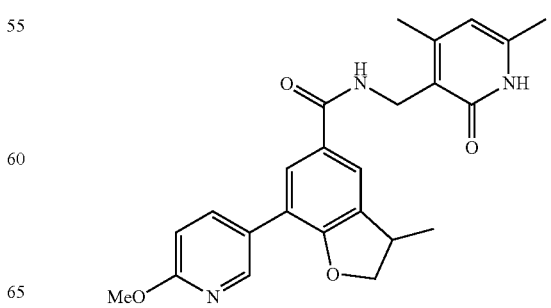

Example 30 was prepared from (6-methoxypyridin-3-yl)boronic acid and 7-bromo-N-((4,6-dimethyl-2-oxo-1,2-dihydropyridin-3-yl)methyl)-3-methyl-2,3-dihydrobenzofuran-5-carboxamide (Intermediate 27D) as described in Example 10. $^1$H NMR (500 MHz, DMSO-$d_6$) δ 11.51 (br. s., 1H), 8.53 (d, J=2.4 Hz, 1H), 8.31 (t, J=4.9 Hz, 1H), 8.05 (dd, J=8.5, 2.4 Hz, 1H), 7.87 (d, J=1.2 Hz, 1H), 7.74 (s, 1H), 6.91 (d, J=8.5 Hz, 1H), 5.89 (s, 1H), 4.81 (t, J=8.9 Hz, 1H), 4.31 (d, J=4.9 Hz, 2H), 4.17 (t, J=8.2 Hz, 1H), 3.70-3.56 (m, 1H), 2.18 (s, 3H), 2.13 (s, 3H), 1.32 (d, J=6.7 Hz, 3H). MS(ES): m/z 420 [M+H]$^+$.

Example 31

7-Bromo-N-((4,6-dimethyl-2-oxo-1,2-dihydropyridin-3-yl)methyl)-2-methyl-2,3-dihydrobenzofuran-5-carboxamide

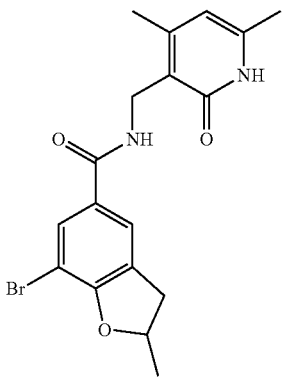 [SMILES: Cc1cc(C)c(CNC(=O)c2cc(Br)c3c(c2)CC(C)O3)c(=O)[nH]1]

31A. Methyl 2-methyl-2,3-dihydrobenzofuran-5-carboxylate

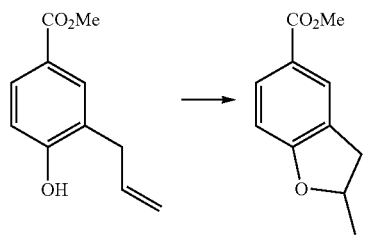

A flask was charged with silver trifluoromethanesulfonate (5.1 mg, 0.020 mmol) and DCE (1.0 mL) under nitrogen. t-Butyl chloride (8.4 µl, 0.077 mmol) was added and stirring continued for 5 minutes. Methyl 3-allyl-4-hydroxybenzoate (221 mg, 1.150 mmol) dissolved in DCE (3.0 mL) was added and the flask sealed with a caplug. The reaction was then warmed to 50° C. and stirred for 4 days. LCMS suggested that the reaction was about half complete. The reaction was cooled and additional silver trifluoromethanesulfonate (5.1 mg, 0.020 mmol) and t-butyl chloride (8.4 µl, 0.077 mmol) were added. The reaction was then heated at 50° C. for another day. The reaction was then cooled, filtered, and diluted with methanol. The crude compound was then purified by RP-HPLC (methanol-water gradient+0.1% TFA). The product containing fractions were evaporated and azeotroped dry with ethanol. Removal of residual solid in vacuo gave methyl 2-methyl-2,3-dihydrobenzofuran-5-carboxylate (104 mg, 0.541 mmol, 47.1% yield) as a colorless film. $^1$H NMR (400 MHz, DMSO-$d_6$) δ 7.81 (s, 1H), 7.77 (dd, J=8.4, 1.8 Hz, 1H), 6.83 (d, J=8.4 Hz, 1H), 5.19-4.88 (m, 1H), 3.81 (s, 3H), 3.39 (dd, J=16.0, 8.9 Hz, 1H), 2.84 (dd, J=16.1, 7.5 Hz, 1H), 1.42 (d, J=6.2 Hz, 3H).

31B. 2-Methyl-2,3-dihydrobenzofuran-5-carboxylic acid

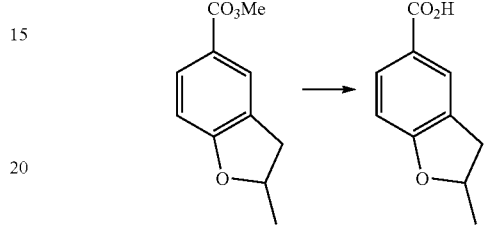

Methyl 2-methyl-2,3-dihydrobenzofuran-5-carboxylate (105 mg, 0.546 mmol) was dissolved in tetrahydrofuran-water (3:1, 8 mL). A solution of lithium hydroxide (1639 µl, 1.639 mmol, 1 N) was then added. A little methanol was added until the reaction became homogeneous. The reaction was allowed to stir for 2 days. The reaction was quenched with 1N hydrochloric acid (1.64 mL) and concentrated under a stream of nitrogen. The resultant solid was filtered and rinsed with water. Drying in a ChemDry oven at 75° C. for 0.5 hour provided 2-methyl-2,3-dihydrobenzofuran-5-carboxylic acid (81 mg, 0.455 mmol, 83% yield) as a colorless solid. $^1$H NMR (400 MHz, DMSO-$d_6$) δ 12.46 (br. s., 1H), 7.78 (d, J=1.1 Hz, 1H), 7.77-7.72 (m, 1H), 6.80 (d, J=8.4 Hz, 1H), 5.14-4.87 (m, 1H), 3.38 (dd, J=16.0, 8.9 Hz, 1H), 2.83 (dd, J=15.8, 7.5 Hz, 1H), 1.41 (d, J=6.2 Hz, 3H).

31C. 7-Bromo-2-methyl-2,3-dihydrobenzofuran-5-carboxylic acid

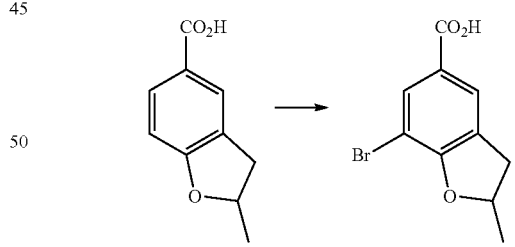

2-Methyl-2,3-dihydrobenzofuran-5-carboxylic acid (79.6 mg, 0.447 mmol) was dissolved in glacial acetic acid (1.0 mL). Bromine (69.0 µl, 1.340 mmol) was added and stirring was continued for 1.5 hours. Water was added and the resultant solid was filtered and rinsed with lots of water. Drying in a ChemDry oven at 75° C. for an hour gave 7-bromo-2-methyl-2,3-dihydrobenzofuran-5-carboxylic acid (98.2 mg, 0.374 mmol, 84% yield) as a cream color solid. $^1$H NMR (400 MHz, DMSO-$d_6$) δ 12.81 (br. s., 1H), 7.87 (d, J=1.3 Hz, 1H), 7.76 (d, J=1.3 Hz, 1H), 5.20-5.06 (m, 1H), 3.51 (dd, J=16.1, 9.0 Hz, 1H), 2.97 (dd, J=16.2, 7.6 Hz, 1H), 1.46 (d, J=6.2 Hz, 3H).

31. 7-Bromo-N-((4,6-dimethyl-2-oxo-1,2-dihydro-pyridin-3-yl)methyl)-2-methyl-2,3-dihydrobenzo-furan-5-carboxamide

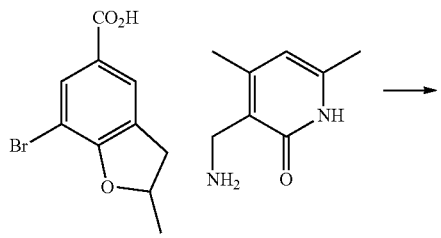

7-Bromo-2-methyl-2,3-dihydrobenzofuran-5-carboxylic acid (91 mg, 0.354 mmol) was dissolved in dry dimethylformamide (0.25 mL). 3-(Aminomethyl)-4,6-dimethylpyridin-2(1H)-one hydrochloride (73.5 mg, 0.389 mmol) and triethylamine (148 μl, 1.062 mmol) were added. The reaction was initiated with the addition of BOP (188 mg, 0.425 mmol). The reaction was stirred overnight and then quenched with half saturated sodium bicarbonate solution. After stirring for 15 minutes, the precipitate was filtered and rinsed well with water. Drying in a ChemDry oven at 75° C. for 2 hours provided 7-bromo-N-((4,6-dimethyl-2-oxo-1,2-dihydropyridin-3-yl)methyl)-2-methyl-2,3-dihydrobenzofuran-5-carboxamide (109 mg, 0.273 mmol, 77% yield) as a colorless solid. $^1$H NMR (400 MHz, DMSO-d$_6$) δ 11.45 (br. s., 1H), 8.24 (br. s., 1H), 7.87 (d, J=1.5 Hz, 1H), 7.72 (d, J=1.5 Hz, 1H), 5.87 (s, 1H), 5.17-5.00 (m, 1H), 4.27 (d, J=4.8 Hz, 2H), 3.47 (dd, J=16.0, 8.9 Hz, 1H), 2.93 (dd, J=15.8, 7.7 Hz, 1H), 2.16 (s, 3H), 2.13 (s, 3H), 1.44 (d, J=6.2 Hz, 3H). MS(ES): m/z 391 [M+H]$^+$.

Example 32

N-((4,6-Dimethyl-2-oxo-1,2-dihydropyridin-3-yl)methyl)-7-(6-methoxypyridin-3-yl)-2-methyl-2,3-dihydrobenzofuran-5-carboxamide

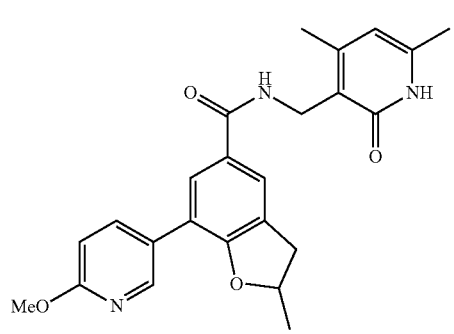 [SMILES: COc1ccc(-c2cc(C(=O)NCc3c(C)cc(C)[nH]c3=O)cc3c2OC(C)C3)cn1]

Example 32 was prepared from (6-methoxypyridin-3-yl) boronic acid and 7-bromo-N-((4,6-dimethyl-2-oxo-1,2-dihydropyridin-3-yl)methyl)-2-methyl-2,3-dihydrobenzofuran-5-carboxamide (Example 31) as described in Example 10. $^1$H NMR (500 MHz, DMSO-d$_6$) δ 11.49 (br. s., 1H), 8.54 (d, J=1.8 Hz, 1H), 8.32-8.24 (m, 1H), 8.05 (dd, J=8.5, 2.4 Hz, 1H), 7.85 (s, 1H), 7.71 (s, 1H), 6.91 (d, J=8.5 Hz, 1H), 5.87 (s, 1H), 5.15-4.96 (m, 1H), 4.30 (d, J=4.9 Hz, 2H), 3.89 (s, 3H), 3.47-3.38 (m, 1H), 2.89-2.80 (m, 1H), 2.17 (s, 3H), 2.12 (s, 3H), 1.43 (d, J=6.1 Hz, 3H). MS(ES): m/z 420 [M+H]$^+$.

Example 33

N-((4,6-Dimethyl-2-oxo-1,2-dihydropyridin-3-yl)methyl)-2-methyl-7-(6-morpholinopyridin-3-yl)-2,3-dihydrobenzofuran-5-carboxamide

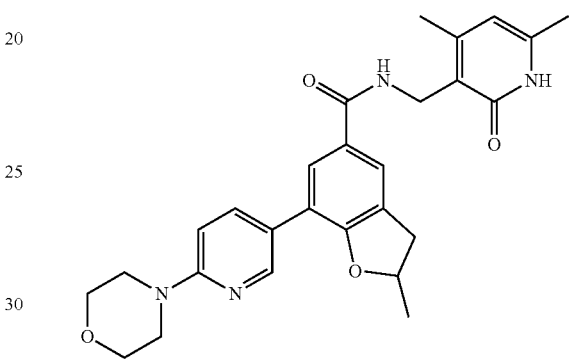

Example 33 was prepared from 4-(5-(4,4,5,5-tetramethyl-1,3,2-dioxaborolan-2-yl)pyridin-2-yl)morpholine and 7-bromo-N-((4,6-dimethyl-2-oxo-1,2-dihydropyridin-3-yl)methyl)-2-methyl-2,3-dihydrobenzofuran-5-carboxamide (Example 31) as described in Example 10. $^1$H NMR (500 MHz, DMSO-d$_6$) δ 11.51 (br. s., 1H), 8.51 (s, 1H), 8.31-8.20 (m, 1H), 8.05 (d, J=7.9 Hz, 1H), 7.85 (s, 1H), 7.68 (s, 1H), 7.06 (d, J=9.2 Hz, 1H), 5.88 (s, 1H), 5.24-4.90 (m, 1H), 4.30 (d, J=4.3 Hz, 2H), 3.80-3.66 (m, 4H), 2.86 (dd, J=15.9, 7.3 Hz, 1H), 2.17 (s, 3H), 2.12 (s, 3H), 1.42 (d, J=6.1 Hz, 3H). MS(ES): m/z 475 [M+H]$^+$.

Example 34

N-((4,6-Dimethyl-2-oxo-1,2-dihydropyridin-3-yl)methyl)-2-methyl-7-(6-(piperazin-1-yl)pyridin-3-yl)-2,3-dihydrobenzofuran-5-carboxamide

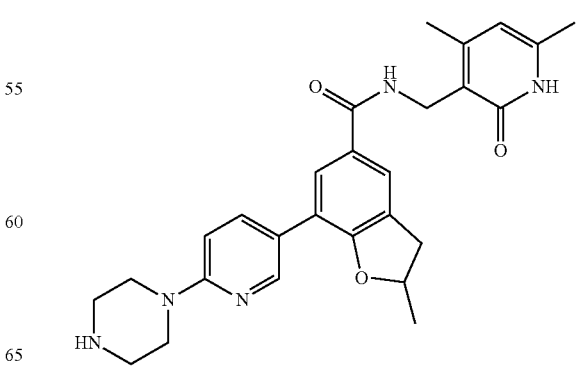

Example 34 was prepared from 1-(5-(4,4,5,5-tetramethyl-1,3,2-dioxaborolan-2-yl)pyridin-2-yl)piperazine and 7-bromo-N-((4,6-dimethyl-2-oxo-1,2-dihydropyridin-3-yl)methyl)-2-methyl-2,3-dihydrobenzofuran-5-carboxamide (Example 31) as described in Example 10. $^1$H NMR (500 MHz, DMSO-d$_6$) δ 11.50 (br. s., 1H), 8.86 (br. s., 2H), 8.57 (d, J=1.8 Hz, 1H), 8.26 (br. s., 1H), 8.04-7.94 (m, 1H), 7.83 (s, 1H), 7.68 (s, 1H), 7.07-6.95 (m, 1H), 5.88 (s, 1H), 5.11-4.94 (m, 1H), 4.30 (d, J=4.9 Hz, 2H), 3.84-3.72 (m, 4H), 3.39 (dd, J=15.6, 8.9 Hz, 1H), 3.22 (br. s., 4H), 2.86 (dd, J=15.9, 7.3 Hz, 1H), 2.17 (s, 3H), 2.12 (s, 3H), 1.42 (d, J=6.1 Hz, 3H). MS(ES): m/z 474 [M+H]$^+$.

Example 35

N-((4,6-Dimethyl-2-oxo-1,2-dihydropyridin-3-yl)methyl)-2-methyl-7-(4-(morpholinomethyl)phenyl)-2,3-dihydrobenzofuran-5-carboxamide

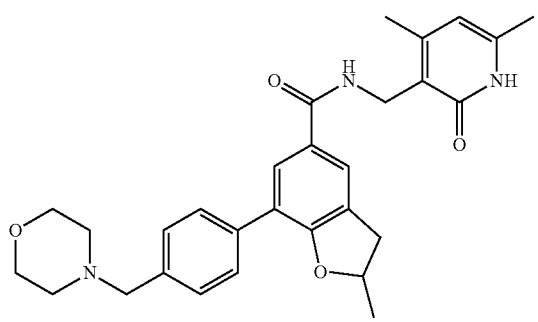 [SMILES: Cc1cc(C)c(CNC(=O)c2cc3c(c(-c4ccc(CN5CCOCC5)cc4)c2)OC(C)C3)c(=O)[nH]1]

Example 35 was prepared from (4-(morpholinomethyl)phenyl)boronic acid and 7-bromo-N-((4,6-dimethyl-2-oxo-1,2-dihydropyridin-3-yl)methyl)-2-methyl-2,3-dihydrobenzofuran-5-carboxamide (Example 31) as described in Example 10. MS(ES): m/z 488 [M+H]$^+$.

Example 36

N-((4,6-Dimethyl-2-oxo-1,2-dihydropyridin-3-yl)methyl)-7-(6-methoxypyridin-3-yl)-2,3-dihydrobenzofuran-5-carboxamide

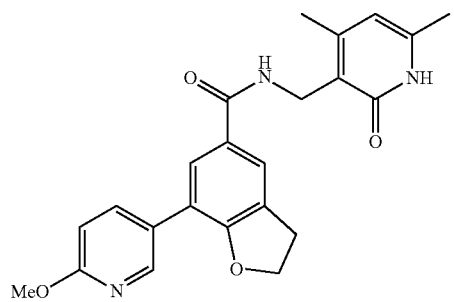 [SMILES: COc1ccc(-c2cc(C(=O)NCc3c(C)cc(C)[nH]c3=O)cc3c2OCC3)cn1]

36A. 7-Bromo-2,3-dihydrobenzofuran-5-carboxylic acid

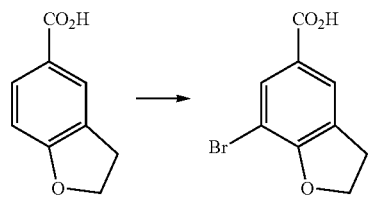 [SMILES: O=C(O)c1ccc2c(c1)CCO2 ; O=C(O)c1cc(Br)c2c(c1)CCO2]

To a suspension of 2,3-dihydrobenzofuran-5-carboxylic acid (625 mg, 3.81 mmol) in glacial acetic acid (10 mL) was added bromine (294 µl, 5.71 mmol) dropwise. More bromine (0.1 mL) was added after 2 hours as LCMS suggested only partial conversion. The reaction was stirred for another 2 hours when it was diluted with water (ca. 20 mL). The resultant precipitate was filtered and rinsed extensively with water. Residual solvent was removed in vacuo to give 7-bromo-2,3-dihydrobenzofuran-5-carboxylic acid (917 mg, 3.66 mmol, 96% yield) as an off white solid. $^1$H NMR (400 MHz, DMSO-d$_6$) δ 12.83 (br. s., 1H), 7.87 (d, J=1.5 Hz, 1H), 7.79 (d, J=1.5 Hz, 1H), 4.74 (t, J=8.8 Hz, 2H), 3.37 (t, J=8.8 Hz, 2H).

36B. 7-Bromo-N-((4,6-dimethyl-2-oxo-1,2-dihydropyridin-3-yl)methyl)-2,3-dihydrobenzofuran-5-carboxamide

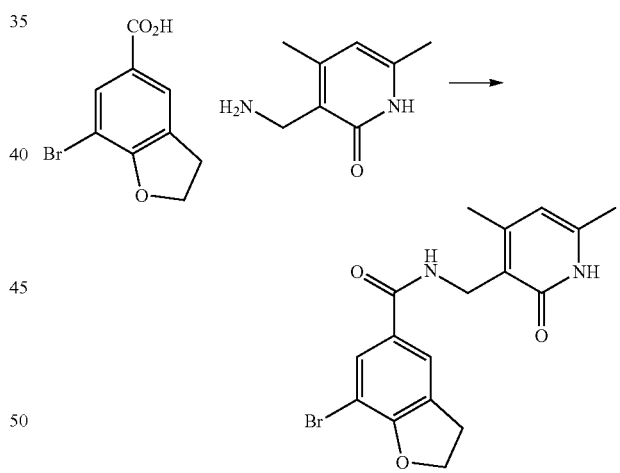

A reaction vial was charged with 7-bromo-2,3-dihydrobenzofuran-5-carboxylic acid (202 mg, 0.831 mmol). The starting material was dissolved in dimethylformamide (4.0 mL). The reaction was initiated with the sequential addition of triethylamine (348 µl, 2.493 mmol), 3-(aminomethyl)-4,6-dimethylpyridin-2(1H)-one hydrochloride (172 mg, 0.914 mmol) and BOP (441 mg, 0.997 mmol). After stirring for 4 hours, the reaction was quenched with 25% saturated sodium bicarbonate solution. The resultant precipitate was filtered and rinsed with water. Drying of the precipitate in a ChemDry oven at 75° C. for 0.5 hour provide the title compound (197 mg, 0.512 mmol, 62%) as a colorless solid. $^1$H NMR (500 MHz, DMSO-d$_6$) δ 11.45 (br. s., 1H), 8.24 (t, J=4.7 Hz, 1H), 7.86 (d, J=1.7 Hz, 1H), 7.74 (d, J=1.4 Hz, 1H), 5.86 (s, 1H), 4.68 (t, J=8.9 Hz, 2H), 4.27 (d, J=5.0 Hz, 2H), 3.32 (t, J=8.9 Hz, 3H), 2.16 (s, 3H), 2.12 (s, 3H). MS(ES): m/z 377 [M+H]+.

36. N-((4,6-Dimethyl-2-oxo-1,2-dihydropyridin-3-yl)methyl)-7-(6-methoxypyridin-3-yl)-2,3-dihydrobenzofuran-5-carboxamide

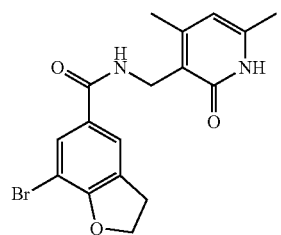
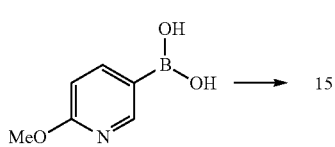
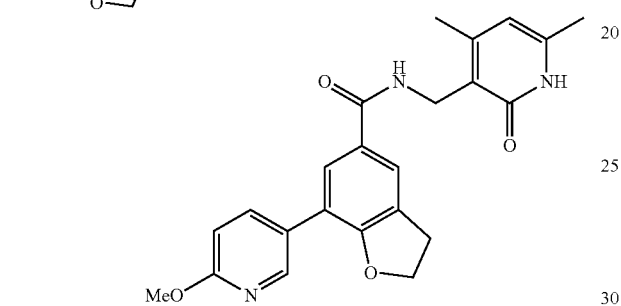

Example 36 was prepared from (6-methoxypyridin-3-yl)boronic acid and 7-bromo-N-((4,6-dimethyl-2-oxo-1,2-dihydropyridin-3-yl)methyl)-2,3-dihydrobenzofuran-5-carboxamide as described in Example 10. ¹H NMR (500 MHz, DMSO-d₆) δ 11.49 (br. s., 1H), 8.52 (d, J=2.4 Hz, 1H), 8.28 (t, J=4.9 Hz, 1H), 8.05 (dd, J=8.5, 2.4 Hz, 1H), 7.85 (s, 1H), 7.74 (s, 1H), 6.91 (d, J=8.5 Hz, 1H), 5.88 (s, 1H), 4.66 (t, J=8.9 Hz, 2H), 4.30 (d, J=4.3 Hz, 2H), 3.89 (s, 3H), 3.27 (t, J=8.5 Hz, 2H), 2.18 (s, 3H), 2.12 (s, 3H). MS(ES): m/z 406 [M+H]+.

Example 37

N-((4,6-Dimethyl-2-oxo-1,2-dihydropyridin-3-yl)methyl)-7-(6-morpholinopyridin-3-yl)-2,3-dihydrobenzofuran-5-carboxamide

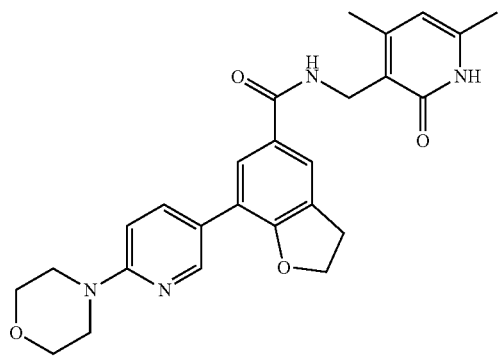 [SMILES: Cc1cc(C)c(CNC(=O)c2cc3c(c(-c4ccc(N5CCOCC5)nc4)c2)OCC3)c(=O)[nH]1]

Example 37 was prepared from 4-(5-(4,4,5,5-tetramethyl-1,3,2-dioxaborolan-2-yl)pyridin-2-yl)morpholine and 7-bromo-N-((4,6-dimethyl-2-oxo-1,2-dihydropyridin-3-yl)methyl)-2,3-dihydrobenzofuran-5-carboxamide as described in Example 10. ¹H NMR (500 MHz, DMSO-d₆) δ 11.49 (br. s., 1H), 8.54 (d, J=1.8 Hz, 1H), 8.31-8.21 (m, 1H), 7.94 (dd, J=9.2, 2.4 Hz, 1H), 7.83 (s, 1H), 7.69 (s, 1H), 6.91 (d, J=9.2 Hz, 1H), 5.88 (s, 1H), 4.64 (t, J=8.9 Hz, 2H), 4.30 (d, J=4.9 Hz, 2H), 3.77-3.66 (m, 4H), 3.56-3.46 (m, 4H), 3.25 (t, J=8.9 Hz, 2H), 2.17 (s, 3H), 2.12 (s, 3H). MS(ES): m/z 461 [M+H]+.

Example 38

N-((4,6-Dimethyl-2-oxo-1,2-dihydropyridin-3-yl)methyl)-7-(6-(piperazin-1-yl)pyridin-3-yl)-2,3-dihydrobenzofuran-5-carboxamide

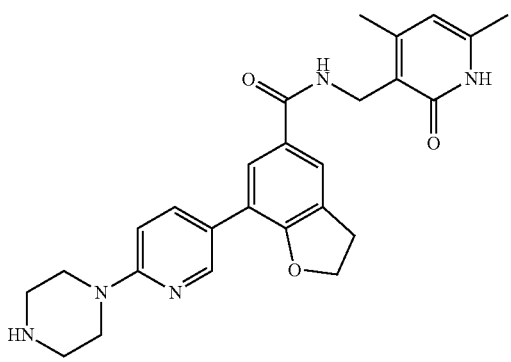 [SMILES: Cc1cc(C)c(CNC(=O)c2cc3c(c(-c4ccc(N5CCNCC5)nc4)c2)OCC3)c(=O)[nH]1]

Example 38 was prepared from 1-(5-(4,4,5,5-tetramethyl-1,3,2-dioxaborolan-2-yl)pyridin-2-yl)piperazine and 7-bromo-N-((4,6-dimethyl-2-oxo-1,2-dihydropyridin-3-yl)methyl)-2,3-dihydrobenzofuran-5-carboxamide as described in Example 10. ¹H NMR (500 MHz, DMSO-d₆) δ 11.46 (br. s., 1H), 8.51 (d, J=2.4 Hz, 1H), 8.26 (t, J=4.9 Hz, 1H), 7.90 (dd, J=9.2, 2.4 Hz, 1H), 7.82 (s, 1H), 7.68 (s, 1H), 6.87 (d, J=8.5 Hz, 1H), 5.88 (s, 1H), 4.64 (t, J=8.9 Hz, 2H), 4.30 (d, J=4.9 Hz, 2H), 3.25 (t, J=8.9 Hz, 3H), 2.85-2.77 (m, 4H), 2.17 (s, 3H), 2.12 (s, 3H). MS(ES): m/z 460 [M+H]+.

Example 39

N-((4,6-Dimethyl-2-oxo-1,2-dihydropyridin-3-yl)methyl)-7-(6-methoxypyridin-3-yl)-3,3-dimethyl-2,3-dihydrobenzofuran-5-carboxamide

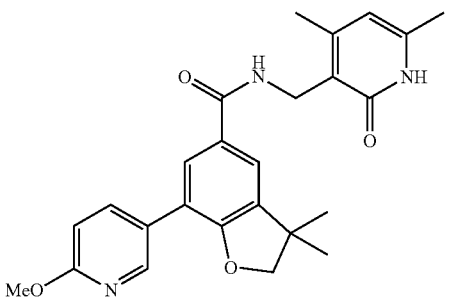 [SMILES: COc1ccc(-c2cc(C(=O)NCc3c(C)cc(C)[nH]c3=O)cc3c2OCC3(C)C)cn1]

39A. 3,3-Dimethyl-2,3-dihydrobenzofuran-5-carboxylic acid

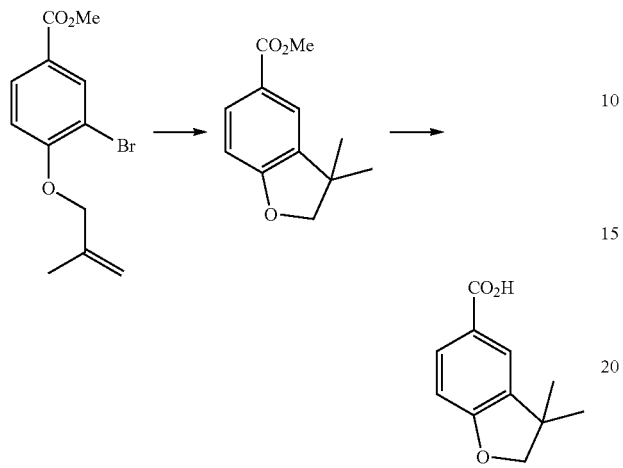

An oven dried flask was charged with methyl 3-bromo-4-((2-methylallyl)oxy)benzoate (270 mg, 0.947 mmol, Intermediate 1A) and tri-n-butyltin hydride (379 μl, 1.420 mmol) in toluene (5.0 mL). Nitrogen was bubbled through the reaction for 15 minutes. AIBN (25 mg, 0.152 mmol) was added and degassing continued for another 15 minutes. The flask was equipped with a three way valve and a nitrogen balloon. The flask was evacuated and flushed with nitrogen. The reaction was then heated to 100° C. for 1.5 hours. LCMS analysis suggests mostly starting material is present. Additional reagents were added and the reaction was heated overnight. LCMS analysis failed to show any conversion to product and 1H-NMR of the tin reagent showed no hydride resonance. A new bottle of tri-n-butyltin hydride was obtained. AIBN (25 mg, 0.152 mmol) and tri-n-butyltin hydride (379 μl, 1.420 mmol) were added and the flask was evacuated and flushed with nitrogen three times. The reaction was then warmed to 90° C. for 1.5 hours, The cooled reaction was the evaporated. The residue was dissolved in tetrahydofuran-water (3:1, 8 mL). A solution of lithium hydroxide (5.0 mL, 1 N) was added and the reaction stirred overnight. Volatiles were the evaporated. Water was added and the suspension passed through a syringe filter. The filtrate was transferred to a reparatory funnel. and washed twice with ether. The aqueous phase was acidified with 1 N hydrochloric acid, generating a nice solid. The solid was filtered, rinsed with water, and air dried to give 3,3-dimethyl-2,3-dihydrobenzofuran-5-carboxylic acid (96 mg). $^{1}$H NMR (400 MHz, DMSO-d$_6$) δ 12.54 (br. s., 1H), 7.80-7.74 (m, 2H), 6.86 (d, J=9.0 Hz, 1H), 4.33 (s, 2H), 1.33 (s, 6H).

39B. 7-Bromo-3,3-dimethyl-2,3-dihydrobenzofuran-5-carboxylic acid

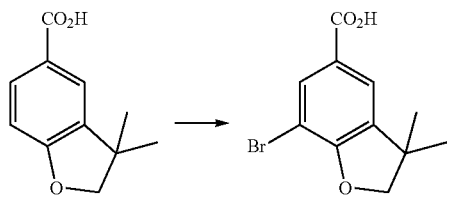

A solution of 3,3-dimethyl-2,3-dihydrobenzofuran-5-carboxylic acid (16.8 mg, 0.087 mmol) in glacial acetic acid (0.5 mL) was treated with bromine (5.40 μl, 0.105 mmol) and allowed to stir overnight. Additional bromine (20 uL) was added to drive the reaction to completion. The reaction was then diluted with water and a few drops of 10% sodium thiosulfate were added. The resultant solid was filtered and rinsed with water. The material was rinsed into a flask and azeotroped with ethanol to give 7-bromo-3,3-dimethyl-2,3-dihydrobenzofuran-5-carboxylic acid (26 mg) as a pale yellow solid. The weight is a bit high, presumably from byproducts derived from the thiosulfate. $^{1}$H NMR (400 MHz, DMSO-d$_6$) δ 12.90 (br. s., 1H), 7.90 (d, J=1.5 Hz, 1H), 7.78 (d, J=1.5 Hz, 1H), 4.45 (s, 2H), 1.35 (s, 6H).

39C. 7-Bromo-N-((4,6-dimethyl-2-oxo-1,2-dihydropyridin-3-yl)methyl)-3,3-dimethyl-2,3-dihydrobenzofuran-5-carboxamide

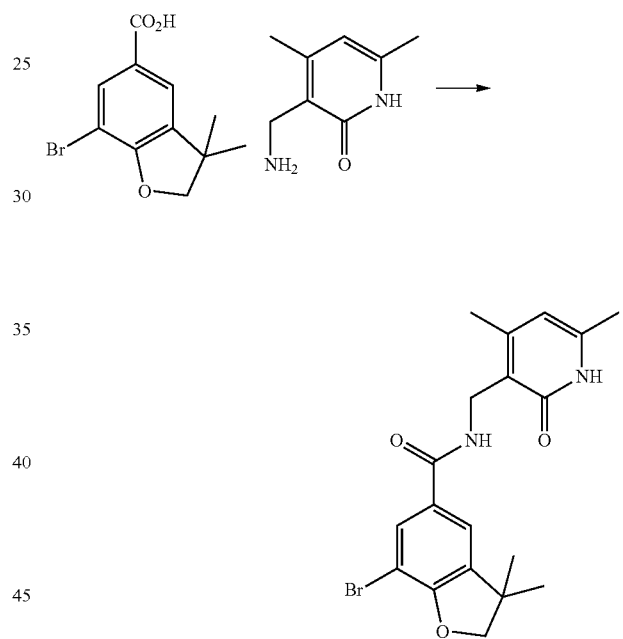

A solution of 7-bromo-3,3-dimethyl-2,3-dihydrobenzofuran-5-carboxylic acid (26 mg, 0.096 mmol) in dimethylformamide (2.0 mL) was treated sequentially with triethylamine (40.1 μl, 0.288 mmol),3-(aminomethyl)-4,6-dimethylpyridin-2(1H)-one, hydrochloride (21.71 mg, 0.115 mmol) and BOP (55.1 mg, 0.125 mmol). After 2 hours, the reaction was diluted with methanol and purified by RP-HPLC (methanol-water gradient+0.1% TFA). The product containing fractions were treated with half saturated sodium bicarbonate solution and concentrated to mostly water. The resultant colorless precipitate was filtered, rinsed with water and air dried to give 7-bromo-N-((4,6-dimethyl-2-oxo-1,2-dihydropyridin-3-yl)methyl)-3,3-dimethyl-2,3-dihydrobenzofuran-5-carboxamide (20.1 mg, 0.049 mmol, 50.7% yield). $^{1}$H NMR (400 MHz, DMSO-d$_6$) δ 11.45 (br. s., 1H), 8.25 (t, J=4.7 Hz, 1H), 7.88 (d, J=1.5 Hz, 1H), 7.74 (d, J=1.8 Hz, 1H), 5.85 (s, 1H), 4.37 (s, 2H), 4.26 (d, J=4.8 Hz, 2H), 2.15 (s, 3H), 2.11 (s, 3H), 1.31 (s, 6H).

39. N-((4,6-Dimethyl-2-oxo-1,2-dihydropyridin-3-yl)methyl)-7-(6-methoxypyridin-3-yl)-3,3-dimethyl-2,3-dihydrobenzofuran-5-carboxamide

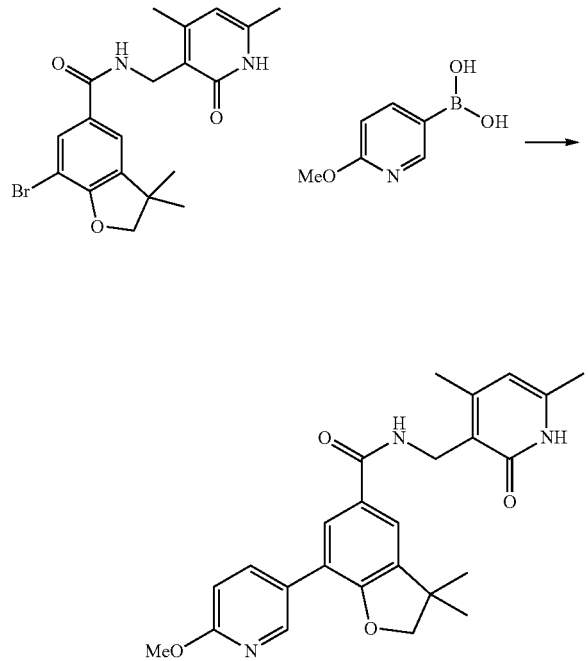

Example 39 was prepared from (6-methoxypyridin-3-yl) boronic acid and 7-bromo-N-((4,6-dimethyl-2-oxo-1,2-dihydropyridin-3-yl)methyl)-3,3-dimethyl-2,3-dihydrobenzofuran-5-carboxamide as described in Example 10. $^1$H NMR (400 MHz, DMSO-$d_6$) δ 11.48 (br. s., 1H), 8.55 (d, J=2.2 Hz, 1H), 8.29 (br. s., 1H), 8.07 (dd, J=8.6, 2.4 Hz, 1H), 7.89 (d, J=1.8 Hz, 1H), 7.74 (d, J=1.8 Hz, 1H), 6.92 (d, J=8.6 Hz, 1H), 5.88 (s, 1H), 4.37 (s, 2H), 4.32 (d, J=4.8 Hz, 2H), 3.91 (s, 3H), 2.20 (s, 3H), 2.13 (s, 3H), 1.36 (s, 6H). MS(ES): m/z 461 [M+H]$^+$.

Example 40

(2S,3R)-7-Bromo-N-((4,6-dimethyl-2-oxo-1,2-dihydropyridin-3-yl)methyl)-2,3-dimethyl-2,3-dihydrobenzofuran-5-carboxamide

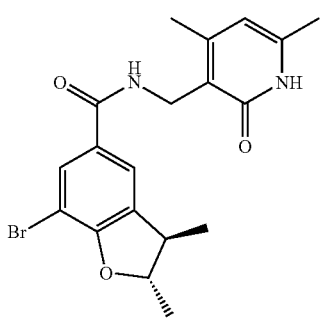 [SMILES: Cc1cc(C)c(CNC(=O)c2cc(Br)c3c(c2)[C@@H](C)[C@H](C)O3)c(=O)[nH]1]

40A. (E)-Methyl 3-bromo-4-(but-2-en-1-yloxy)benzoate

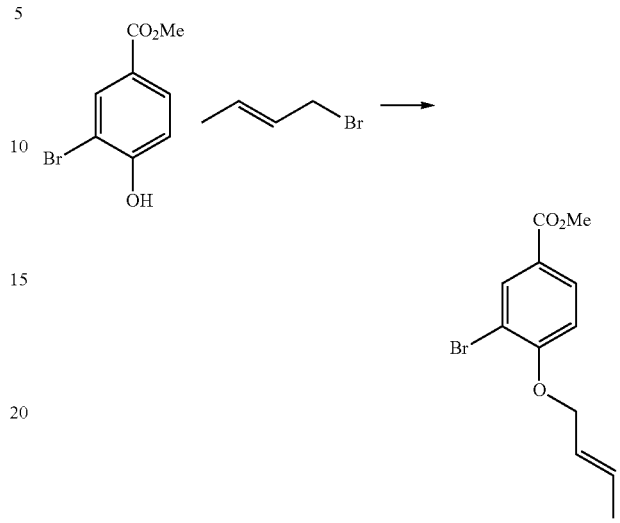

Methyl 3-bromo-4-hydroxybenzoate (460 mg, 1.991 mmol) was dissolved in acetonitrile (4.0 mL) under nitrogen. Potassium carbonate (358 mg, 2.59 mmol) was added and stirring continued for a few minutes. (E)-1-Bromobut-2-ene (246 µl, 2.389 mmol) was introduced and the reaction was stirred overnight. The reaction was transferred to a separatory funnel and diluted with ether. The organic layer was washed with water and brine. The ether layer was dried over magnesium sulfate, filtered and evaporated. The crude product was applied to a 40 g Isco silica gel column and eluted with 0-20% ethyl acetate in hexanes. Evaporation of the appropriate fractions gave (E)-methyl 3-bromo-4-(but-2-en-1-yloxy)benzoate (500 mg, 1.754 mmol, 88% yield) as a colorless viscous oil. $^1$H NMR (400 MHz, DMSO-$d_6$) δ 8.10 (d, J=2.2 Hz, 1H), 7.94 (dd, J=8.6, 2.2 Hz, 1H), 7.25 (d, J=8.6 Hz, 1H), 6.03-5.87 (m, 1H), 5.80-5.67 (m, 1H), 4.69 (d, J=5.9 Hz, 2H), 3.84 (s, 3H), 1.74 (dd, J=6.5, 1.4 Hz, 3H).

40B. rac-Methyl 3-bromo-5-(but-3-en-2-yl)-4-hydroxybenzoate

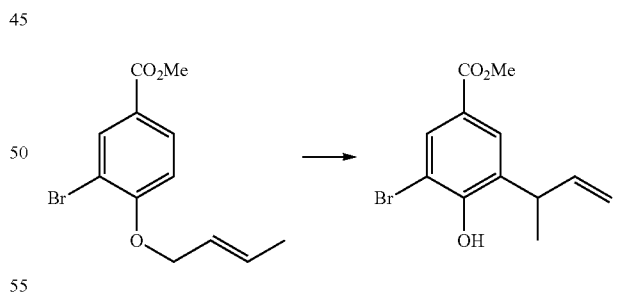

(E)-Methyl 3-bromo-4-(but-2-en-1-yloxy)benzoate (440 mg, 1.543 mmol) was dissolved in Dowtherm (3 mL) and heated to 200° C. for ca. 3 hours. The cooled reaction was applied to a 120 g Isco silica gel column and eluted with 0-25% ethyl acetate in hexanes. Evaporation of the appropriate fractions gave methyl 3-bromo-5-(but-3-en-2-yl)-4-hydroxybenzoate (186 mg, 0.652 mmol, 42.3% yield). $^1$H NMR (400 MHz, DMSO-$d_6$) δ 10.01 (br. s., 1H), 7.91 (d, J=2.2 Hz, 1H), 7.64 (d, J=2.2 Hz, 1H), 6.01 (ddd, J=17.0, 10.7, 5.9 Hz, 1H), 5.10 (quip, J=1.7 Hz, 1H), 5.06 (dt, J=9.9, 1.5 Hz, 1H), 3.96-3.86 (m, 1H), 3.79 (s, 3H), 1.25 (d, J=6.8 Hz, 3H).

40C. rac-(2S,3R)-Methyl 7-bromo-2,3-dimethyl-2,3-dihydrobenzofuran-5-carboxylate

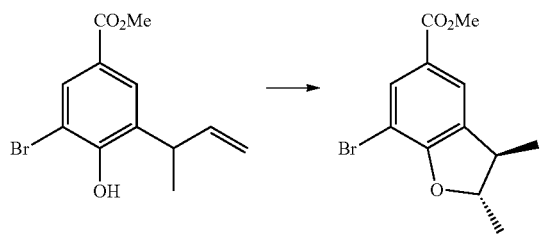 [SMILES: C=CC(C)c1cc(C(=O)OC)cc(Br)c1O ; COC(=O)c1cc(Br)c2c(c1)[C@@H](C)[C@H](C)O2]

Methyl 3-bromo-5-(but-3-en-2-yl)-4-hydroxybenzoate (184 mg, 0.645 mmol) was suspended in formic acid (4.0 mL) and heated to 110° C. As no conversion is evident by LCMS, the react was cooled and triflic acid (10 uL) was added. As no product was formed at room temperature, the reaction was warmed to 80° C. and stirred overnight. The reaction was transferred to a separatory funnel and dilute with ether. The solution was washed successively with saturated sodium bicarbonate solution, water, and brine. The crude product was isolated by drying over magnesium sulfate, filtration and evaporation. The material was applied to 3 0.5 mm silica gel plates and eluted with 9:1 hexanes-ethyl acetate (2 developments). Impure product was isolated by extracting a fast moving band (60 mg). This material was further purified by RP-HPLC (methanol-water gradient+ 0.1% TFA). The product containing fraction was treated with half saturated sodium bicarbonate solution and concentrated. The product was extracted with ether. Drying over magnesium sulfate, filtration and evaporation gave 20 mg of somewhat purer material. $^1$H NMR (400 MHz, CHLOROFORM-d) δ 8.06 (d, J=1.5 Hz, 1H), 7.78 (d, J=1.1 Hz, 1H), 5.17-5.06 (m, 1H), 3.91 (s, 3H), 3.58 (quin, J=7.5 Hz, 1H), 1.46 (d, J=6.8 Hz, 3H), 1.25 (d, J=7.3 Hz, 3H).

40D rac-(2S,3R)-7-Bromo-2,3-dimethyl-2,3-dihydrobenzofuran-5-carboxylic acid

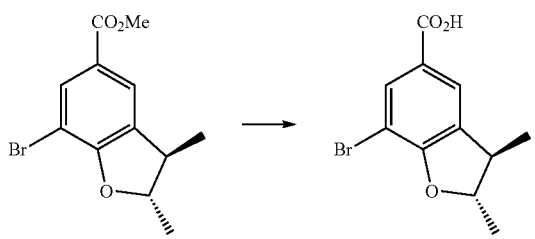 [SMILES: COC(=O)c1cc(Br)c2c(c1)[C@@H](C)[C@H](C)O2 ; C[C@@H]1Oc2c(Br)cc(C(=O)O)cc2[C@H]1C]

A solution of rac-(2R,3S)-Methyl 7-bromo-2,3-dimethyl-2,3-dihydrobenzofuran-5-carboxylate (20 mg, 0.070 mmol) in tetrahydrofuran-water (4 mL, 3:1) was treated with lithium hydroxide (421 μl, 0.421 mmol, 1 N). A little methanol was added to make the reaction homogeneous. Stirring was continued overnight. The reaction was neutralized with 1 N hydrochloric acid (0.42 mL) and concentrated under a stream of nitrogen. The resulting precipitate was filtered, rinsed with water and air dried to give rac-(2R,3S)-7-bromo-2,3-dimethyl-2,3-dihydrobenzofuran-5-carboxylic acid (12.2 mg, 0.043 mmol, 60.9% yield) as a pale yellow solid. $^1$H NMR (400 MHz, DMSO-$d_6$) δ 12.84 (br. s., 1H), 7.87 (d, J=1.3 Hz, 1H), 7.77 (s, 1H), 5.20-5.03 (m, 1H), 1.36 (d, J=6.6 Hz, 3H), 1.17 (d, J=7.0 Hz, 3H).

40. rac-(2S,3R)-7-bromo-N-((4,6-dimethyl-2-oxo-1,2-dihydropyridin-3-yl)methyl)-2,3-dimethyl-2,3-dihydrobenzofuran-5-carboxamide

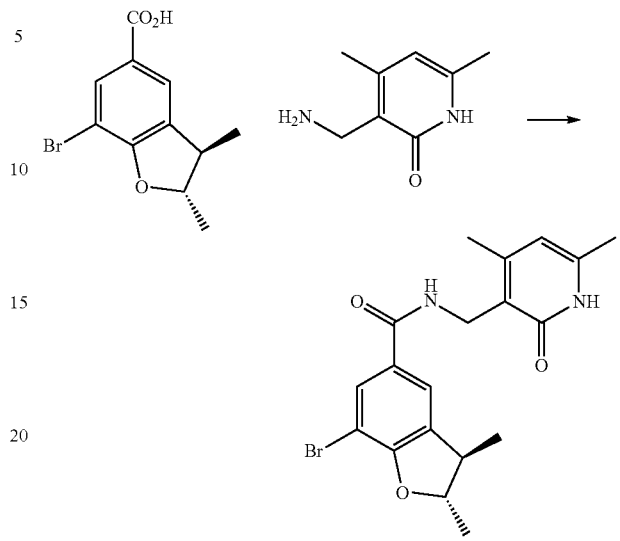

A reaction vial was charged with rac-(2R,3S)-7-bromo-2,3-dimethyl-2,3-dihydrobenzofuran-5-carboxylic acid (9 mg, 0.033 mmol) in dimethylformamide (0.5 mL). Reaction was initiated with the sequential addition of triethylamine (13.88 μl, 0.100 mmol, 3-(aminomethyl)-4,6-dimethylpyridin-2(1H)-one hydrochloride (6.89 mg, 0.037 mmol) and BOP (17.62 mg, 0.040 mmol). After 1 hour, the reaction was quenched with 25% saturated sodium bicarbonate solution (2 mL). The resulting solid was filtered, rinsed with water, and then hexanes. Air drying gave rac-(2R,3S)-7-bromo-N-((4,6-dimethyl-2-oxo-1,2-dihydropyridin-3-yl)methyl)-2,3-dimethyl-2,3-dihydrobenzofuran-5-carboxamide (8.9 mg, 0.021 mmol, 62.8% yield) as a colorless solid. $^1$H NMR (400 MHz, DMSO-$d_6$) δ 11.46 (br. s., 1H), 8.24 (br. s., 1H), 7.87 (s, 1H), 7.74 (s, 1H), 5.87 (s, 1H), 5.14-5.01 (m, 1H), 4.28 (d, J=4.8 Hz, 2H), 3.67-3.52 (m, 1H), 2.17 (s, 3H), 2.13 (s, 3H), 1.33 (d, J=6.6 Hz, 3H), 1.16 (d, J=7.0 Hz, 3H). MS(ES): m/z 405 [M+H]$^+$.

Example 41

N-((4,6-Dimethyl-2-oxo-1,2-dihydropyridin-3-yl)methyl)-2,2-dimethylchroman-6-carboxamide

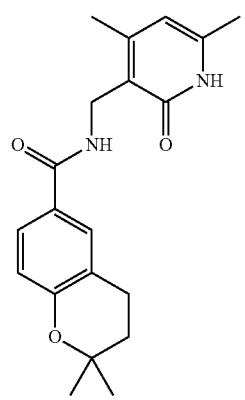 [SMILES: Cc1cc(C)c(CNC(=O)c2ccc3c(c2)CCC(C)(C)O3)c(=O)[nH]1]

41A. Methyl 2,2-dimethylchroman-6-carboxylate

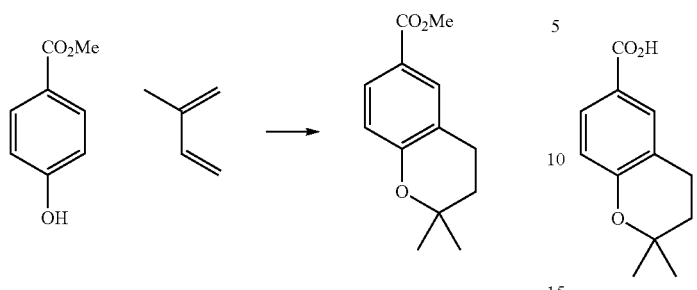

41. N-((4,6-Dimethyl-2-oxo-1,2-dihydropyridin-3-yl)methyl)-2,2-dimethylchroman-6-carboxamide

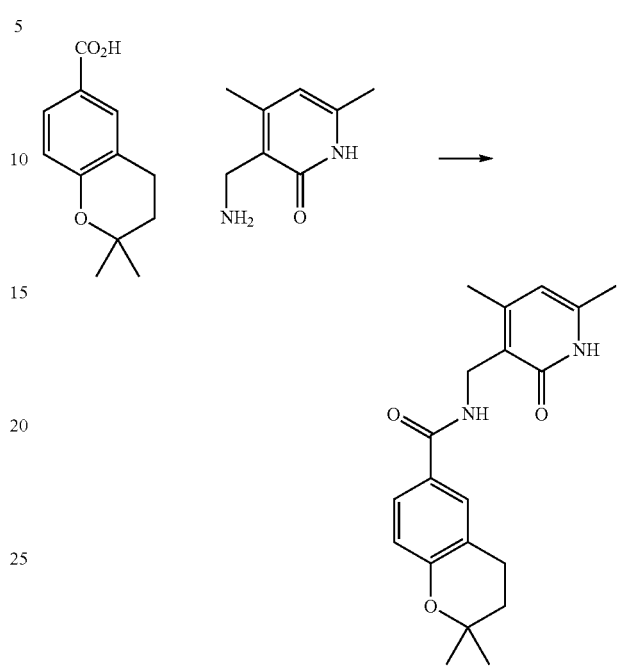

A flask was charged with silver trifluoromethanesulfonate (5.13 mg, 0.020 mmol) under nitrogen. DCE (10 mL) was added and the reaction warmed to 80° C. After 2.5 hours, the reaction was cooled and methyl 4-hydroxybenzoate (152 mg, 0.999 mmol) and isoprene (150 µl, 1.499 mmol) were added. As no reaction was evident by LCMS, triflic acid (50 uL) was added and stirring continued for 2 hours. The reaction was then transferred to a reparatory funnel and washed with saturated sodium bicarbonate solution. The organic layer was dried over sodium sulfate, filtered and evaporated. The crude product was applied to a 40 g Isco silica gel column and eluted with 0-25% ethyl acetate in hexanes. Evaporation of the product containing fractions gave methyl 2,2-dimethylchroman-6-carboxylate (45.7 mg, 0.203 mmol, 20.35% yield) as a slightly yellow solid. $^1$H NMR (400 MHz, DMSO-$d_6$) δ 7.75 (d, J=2.2 Hz, 1H), 7.68 (dd, J=8.6, 2.2 Hz, 1H), 6.80 (d, J=8.6 Hz, 1H), 3.81 (s, 3H), 2.81 (t, J=6.8 Hz, 2H), 1.81 (t, J=6.7 Hz, 2H), 1.32 (s, 6H).

Amide bond formation for Example 41 was conducted as in Example 1. The final compound was purified by reverse phase HPLC using the following conditions: Column—Waters XBridge C18, 19×250 mm, 5-µm particles. Solvent—acetonitrile-water gradient containing 10 mM ammonium acetate. $^1$H NMR (500 MHz, DMSO-$d_6$) δ 11.47 (br. s., 1H), 8.15-8.03 (m, 1H), 7.64 (s, 1H), 7.56 (d, J=8.5 Hz, 1H), 6.70 (d, J=8.5 Hz, 1H), 5.87 (s, 1H), 4.27 (d, J=4.9 Hz, 2H), 2.81-2.70 (m, 2H), 2.16 (s, 3H), 2.12 (s, 3H), 1.78 (t, J=6.7 Hz, 2H), 1.28 (s, 6H). MS(ES): m/z 341 [M+H]$^+$.

41B. 2,2-Dimethylchroman-6-carboxylic acid

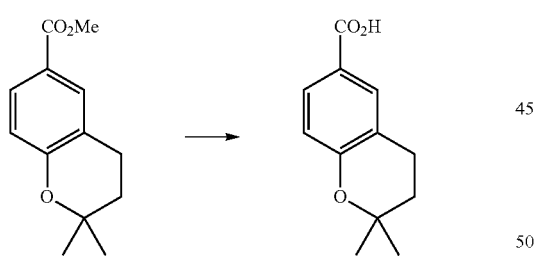

A solution of methyl 2,2-dimethylchroman-6-carboxylate (42 mg, 0.191 mmol) in tetrahydrofuran-water (3:1, 2.0 mL) was treated with lithium hydroxide (572 µl, 0.572 mmol, 1 N). Methanol was added until the solution became homogeneous. The reaction was then warmed to 55° C. and stirred for ca. 2 hours. The cooled reaction was treated with 1 N hydrochloric acid (573 µL) and concentrated under a stream of nitrogen. The resultant precipitate was filtered and rinsed with water. Drying in ChemDry oven at 75° C. for 0.5 hour gave 2,2-dimethylchroman-6-carboxylic acid (30.0 mg, 0.141 mmol, 73.8% yield) as a pale yellow solid. $^1$H NMR (400 MHz, DMSO-$d_6$) δ 12.46 (br. s., 1H), 7.72 (d, J=2.0 Hz, 1H), 7.65 (dd, J=8.5, 2.1 Hz, 1H), 6.78 (d, J=8.6 Hz, 1H), 2.80 (t, J=6.7 Hz, 2H), 1.81 (t, J=6.7 Hz, 2H), 1.31 (s, 6H).

Example 42

8-Bromo-N-((4,6-dimethyl-2-oxo-1,2-dihydropyridin-3-yl)methyl)-2,2-dimethylchroman-6-carboxamide

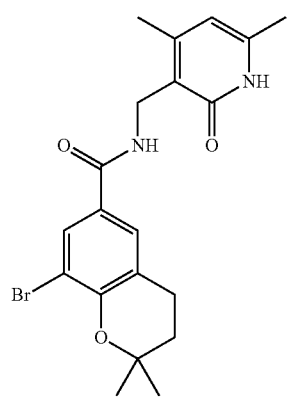 [SMILES: Cc1cc(C)c(CNC(=O)c2cc(Br)c3c(c2)CCC(C)(C)O3)c(=O)[nH]1]

42A. 8-Bromo-2,2-dimethylchroman-6-carboxylic acid

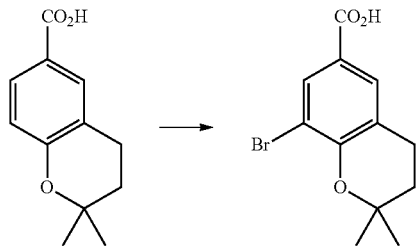 [SMILES: CC1(C)CCc2cc(C(=O)O)ccc2O1 ; CC1(C)CCc2cc(C(=O)O)cc(Br)c2O1]

A solution of 2,2-dimethylchroman-6-carboxylic acid (19.5 mg, 0.095 mmol) in glacial acetic acid (1.0 mL) was treated with bromine (14.61 μl, 0.284 mmol). After stirring for 2 hours, water was added. The resultant precipitate was filtered, rinsed with water, and dried in a ChemDry oven at 75° C. for 0.5 hour to give 8-bromo-2,2-dimethylchroman-6-carboxylic acid (16.4 mg, 0.056 mmol, 59.3% yield) as an off white solid. $^1$H NMR (400 MHz, DMSO-$d_6$) δ 12.81 (br. s., 1H), 7.89 (d, J=2.2 Hz, 1H), 7.72 (d, J=2.0 Hz, 1H), 2.85 (t, J=6.6 Hz, 2H), 1.84 (t, J=6.7 Hz, 2H), 1.35 (s, 6H).

42. 8-Bromo-N-((4,6-dimethyl-2-oxo-1,2-dihydropyridin-3-yl)methyl)-2,2-dimethylchroman-6-carboxamide

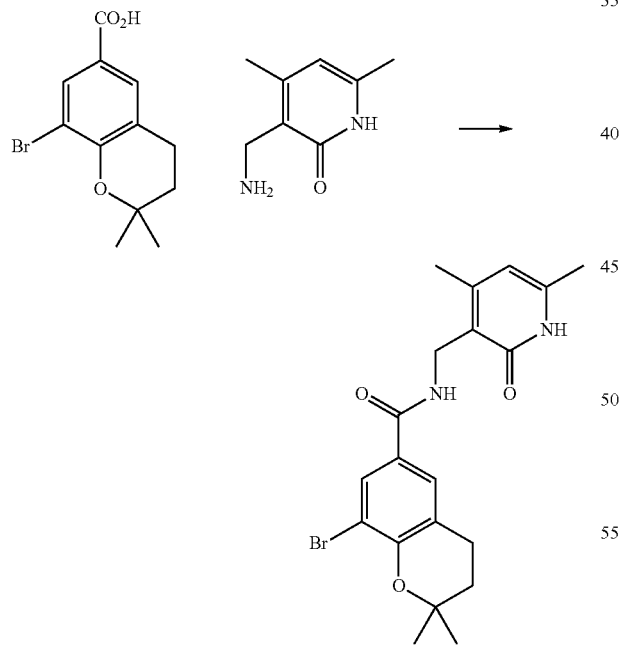

Amide bond formation for Example 42 was conducted as in Example 21. $^1$H NMR (400 MHz, DMSO-$d_6$) δ 11.46 (br. s., 1H), 8.23 (br. s., 1H), 7.91 (d, J=2.2 Hz, 1H), 7.68 (d, J=2.0 Hz, 1H), 5.87 (s, 1H), 4.28 (d, J=4.8 Hz, 2H), 2.81 (t, J=6.6 Hz, 2H), 2.16 (s, 3H), 2.13 (s, 3H), 1.82 (t, J=6.7 Hz, 2H), 1.33 (s, 6H). MS(ES): m/z 419 [M+H]$^+$.

Example 43

N-((4,6-Dimethyl-2-oxo-1,2-dihydropyridin-3-yl)methyl)-8-(6-methoxypyridin-3-yl)-2,2-dimethyl-chroman-6-carboxamide

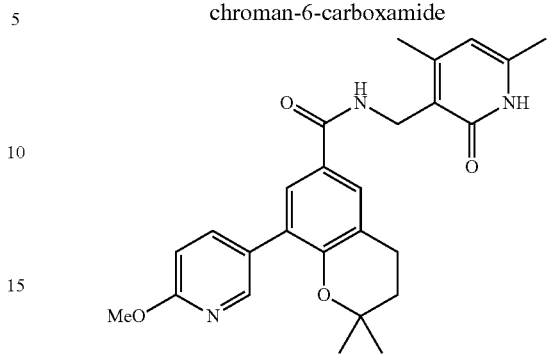

Example 43 was prepared from (6-methoxypyridin-3-yl) boronic acid and 8-bromo-N-((4,6-dimethyl-2-oxo-1,2-dihydropyridin-3-yl)methyl)-2,2-dimethylchroman-6-carboxamide (Example 42) as described in Example 10. $^1$H NMR (500 MHz, DMSO-$d_6$) δ 11.48 (s, 1H), 8.33 (d, J=1.8 Hz, 1H), 8.22 (t, J=4.9 Hz, 1H), 7.87 (dd, J=8.5, 2.4 Hz, 1H), 7.66 (s, 2H), 6.87 (d, J=8.5 Hz, 1H), 5.87 (s, 1H), 4.29 (d, J=4.9 Hz, 2H), 3.89 (s, 3H), 2.83 (t, J=6.4 Hz, 2H), 2.16 (s, 3H), 2.12 (s, 3H), 1.81 (t, J=6.7 Hz, 2H), 1.29 (s, 6H). MS(ES): m/z 448 [M+H]$^+$.

Example 44

9-Bromo-N-((4,6-dimethyl-2-oxo-1,2-dihydropyridin-3-yl)methyl)-4-methyl-2,5-dihydrobenzo[b]oxepine-7-carboxamide

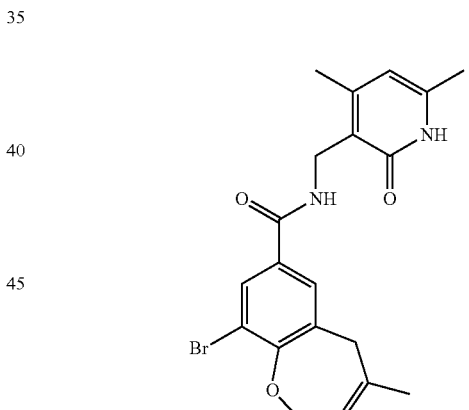

44A. Methyl 4-(allyloxy)-3-bromo-5-(2-methylallyl)benzoate

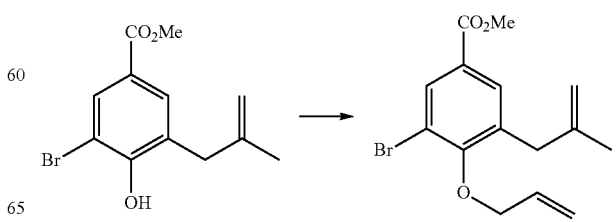

A solution of methyl 3-bromo-4-hydroxy-5-(2-methylallyl)benzoate (863 mg, 3.03 mmol, from Intermediate 1B) in acetonitrile (10 mL) was treated with potassium carbonate (837 mg, 6.05 mmol) for 5 minutes. Allyl bromide (393 µl, 4.54 mmol) was then added and the reaction stirred overnight. Water was then added and the reaction transferred to a separatory funnel. The material was extracted with ether. The organic layer was then washed with water then brine. Drying over magnesium sulfate, filtration and evaporation then provided the crude product. This material was applied to an 80 g Isco silica gel column and eluted with 0-25% ethyl acetate in hexanes. Evaporation of product containing fractions gave methyl 4-(allyloxy)-3-bromo-5-(2-methylallyl)benzoate as a colorless liquid. The material contains some impurities, but the quality is sufficient for the next transformation.

44B. Methyl 9-bromo-4-methyl-2,5-dihydrobenzo[b]oxepine-7-carboxylate

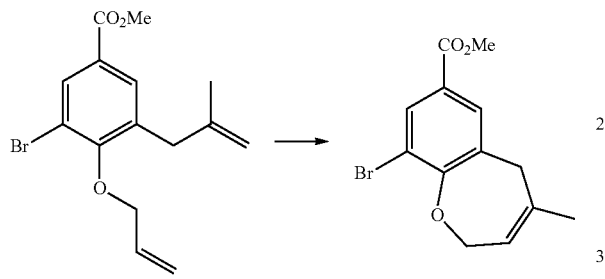

A flask was charged with methyl 4-(allyloxy)-3-bromo-5-(2-methylallyl)benzoate (630 mg, 1.937 mmol) and DCE (50 ml). The solution was degassed 5× with a vacuum/nitrogen flush. The Grubbs II catalyst (50 mg, 0.059 mmol) was added and the vessel was flushed again. The reaction was then warmed to 55° C. for 2 hours. The cooled reaction was transferred to the rotary evaporator and concentrated with no heating. The material was then applied to an 80 g Isco silica gel column in ethyl acetate and eluted with 0-50% ethyl acetate in hexanes. Evaporation of the product containing fractions gave methyl 9-bromo-4-methyl-2,5-dihydrobenzo[b]oxepine-7-carboxylate (205 mg, 34%).

$^1$H NMR (400 MHz, DMSO-$d_6$) δ 7.96 (d, J=2.2 Hz, 1H), 7.75 (d, J=2.2 Hz, 1H), 5.41 (d, J=1.5 Hz, 1H), 4.71-4.64 (m, 2H), 3.82 (s, 3H), 3.56 (s, 2H), 1.83 (d, J=1.3 Hz, 3H). $^{13}$C NMR (101 MHz, DMSO-$d_6$) δ 164.7, 158.0, 137.4, 133.5, 132.0, 130.1, 125.0, 120.1, 114.9, 68.3, 52.3, 36.0, 25.0. MS(ES): m/z 297 [M+H]$^+$.

44C. 9-Bromo-4-methyl-2,5-dihydrobenzo[b]oxepine-7-carboxylic acid

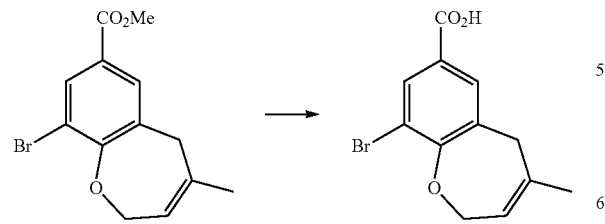

A solution of methyl 9-bromo-4-methyl-2,5-dihydrobenzo[b]oxepine-7-carboxylate (99.4 mg, 0.335 mmol) in tetrahydrofuran-water (3:1, 4 mL) was prepared under nitrogen. A 1N solution of lithium hydroxide (502 µl, 0.502 mmol) and enough methanol to make the reaction homogeneous were then added. The reaction was stirred overnight. The reaction was quenched with 1 N hydrochloric acid (502 uL) and concentrated under a stream of nitrogen. The resulting solid was filtered and rinsed with water. Drying in a ChemDry oven at 75° C. for 0.5 hour gave 9-bromo-4-methyl-2,5-dihydrobenzo[b]oxepine-7-carboxylic acid (88.2 mg, 0.290 mmol, 87% yield) as an off white solid. $^1$H NMR (400 MHz, DMSO-$d_6$) δ 13.05 (br. s., 1H), 7.96 (d, J=2.0 Hz, 1H), 7.75 (d, J=2.0 Hz, 1H), 5.41 (br. s., 1H), 4.67 (br. s., 2H), 3.56 (s, 2H), 1.85 (s, 3H). MS(ES): m/z 283 [M+H]$^+$.

44. 9-Bromo-N-((4,6-dimethyl-2-oxo-1,2-dihydropyridin-3-yl)methyl)-4-methyl-2,5-dihydrobenzo[b]oxepine-7-carboxamide

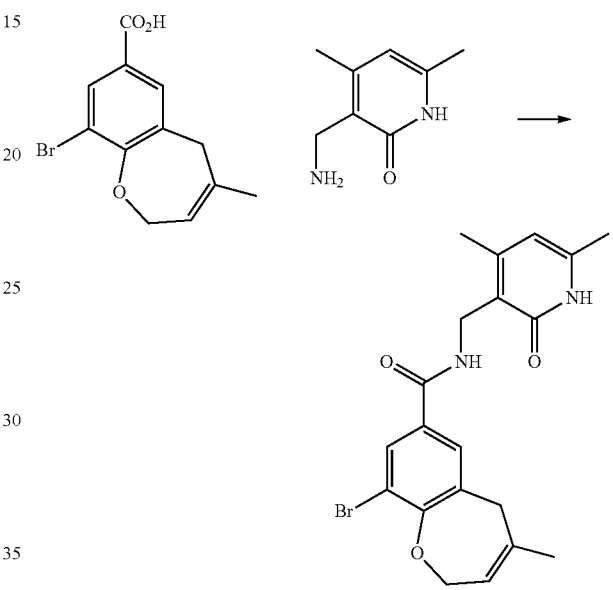

Amide bond formation for Example 44 was conducted as in Example 21. $^1$H NMR (400 MHz, DMSO-$d_6$) δ 11.44 (br. s., 1H), 8.38 (br. s., 1H), 7.97 (d, J=2.0 Hz, 1H), 7.68 (d, J=1.8 Hz, 1H), 5.87 (s, 1H), 5.36 (br. s., 1H), 4.61 (d, J=1.8 Hz, 2H), 4.29 (d, J=4.6 Hz, 2H), 3.49 (s, 2H), 2.16 (s, 3H), 2.13 (s, 3H), 1.84 (s, 3H). MS(ES): m/z 417 [M+H]$^+$.

Example 45

9-Bromo-N-((4,6-dimethyl-2-oxo-1,2-dihydropyridin-3-yl)methyl)-4-methyl-2,3,4,5-tetrahydrobenzo[b]oxepine-7-carboxamide

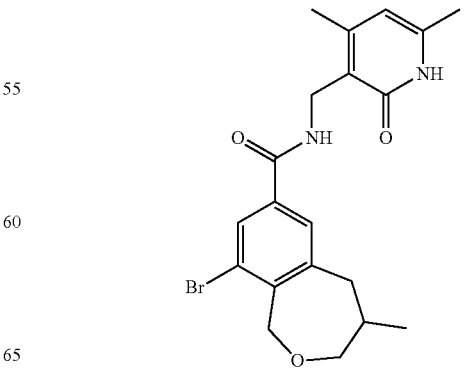

45A. Methyl 9-bromo-4-methyl-2,3,4,5-tetrahydrobenzo[b]oxepine-7-carboxylate

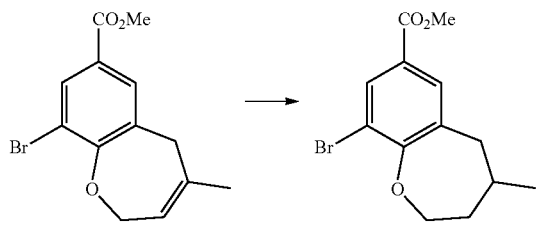 [SMILES: COC(=O)c1cc(Br)c2c(c1)CC(C)=CCO2 ; COC(=O)c1cc(Br)c2c(c1)CC(C)CCO2]

A Parr bottle was charged with methyl 9-bromo-4-methyl-2,5-dihydrobenzo[b]oxepine-7-carboxylate (51 mg, 0.172 mmol, Intermediate 44B) in ethyl acetate (4 mL). Palladium on carbon (9.5 mg, 8.93 µmol) was added and the bottle pressurized to 45 psi with hydrogen. After 45 minutes, the reaction was filtered through celite, evaporated and pumped down overnight. The crude material was applied to a 24 g Isco silica gel column and eluted with 0-25% ethyl acetate in hexanes. Evaporation of the appropriate fractions gave methyl 9-bromo-4-methyl-2,3,4,5-tetrahydrobenzo[b]oxepine-7-carboxylate (20 mg) as a pale yellow solid. $^1$H NMR (400 MHz, CHLOROFORM-d) δ 8.09 (d, J=2.0 Hz, 1H), 7.76 (d, J=1.8 Hz, 1H), 4.45-4.34 (m, 1H), 3.90 (s, 1H), 3.85-3.74 (m, 1H), 2.84-2.67 (m, 2H), 2.07-1.92 (m, 1H), 1.90-1.71 (m, 2H), 1.05 (d, J=6.4 Hz, 3H).

45B. 9-Bromo-4-methyl-2,3,4,5-tetrahydrobenzo[b]oxepine-7-carboxylic acid

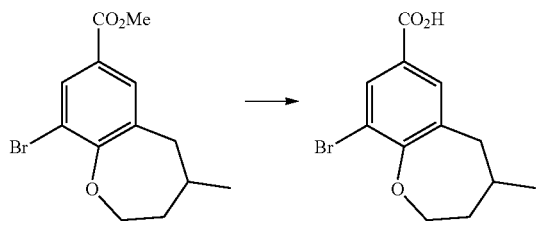 [SMILES: COC(=O)c1cc(Br)c2c(c1)CC(C)CCO2 ; CC1CCOc2c(Br)cc(C(=O)O)cc2C1]

Intermediate 45B was prepared using the chemistry described for Intermediate 44C. $^1$H NMR (400 MHz, DMSO-d$_6$) δ 13.03 (br. s., 1H), 7.92 (d, J=1.8 Hz, 1H), 7.74 (s, 1H), 4.38-4.27 (m, 1H), 3.77 (t, J=10.1 Hz, 1H), 2.89-2.65 (m, 2H), 1.94 (d, J=15.0 Hz, 1H), 1.86-1.58 (m, 2H), 0.99 (d, J=6.4 Hz, 3H). MS(ES): m/z 285 [M+H]$^+$.

45. 9-Bromo-N-((4,6-dimethyl-2-oxo-1,2-dihydropyridin-3-yl)methyl)-4-methyl-2,3,4,5-tetrahydrobenzo[b]oxepine-7-carboxamide

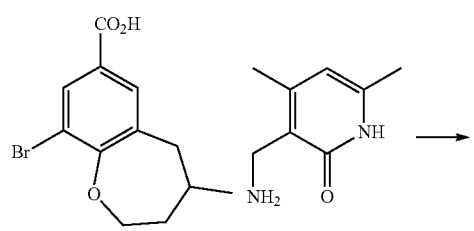

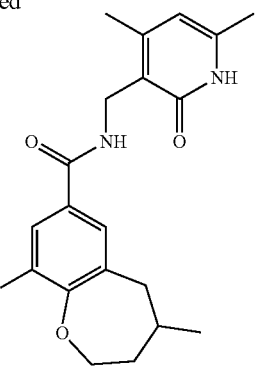

Amide bond formation for Example 45 was conducted as in Example 21. $^1$H NMR (400 MHz, DMSO-d$_6$) δ 11.45 (br. s., 1H), 8.33 (br. s., 1H), 7.93 (d, J=2.0 Hz, 1H), 7.68 (d, J=2.0 Hz, 1H), 5.85 (s, 1H), 4.40-4.19 (m, 3H), 3.70 (t, J=9.9 Hz, 1H), 2.75-2.62 (m, 2H), 2.14 (s, 3H), 2.11 (s, 3H), 1.92 (d, J=13.6 Hz, 1H), 1.82-1.55 (m, 2H), 0.98 (d, J=6.4 Hz, 3H). MS(ES): m/z 419 [M+H]$^+$.

Example 46

N-((4,6-Dimethyl-2-oxo-1,2-dihydropyridin-3-yl)methyl)-9-(6-methoxypyridin-3-yl)-4-methyl-2,3,4,5-tetrahydrobenzo[b]oxepine-7-carboxamide

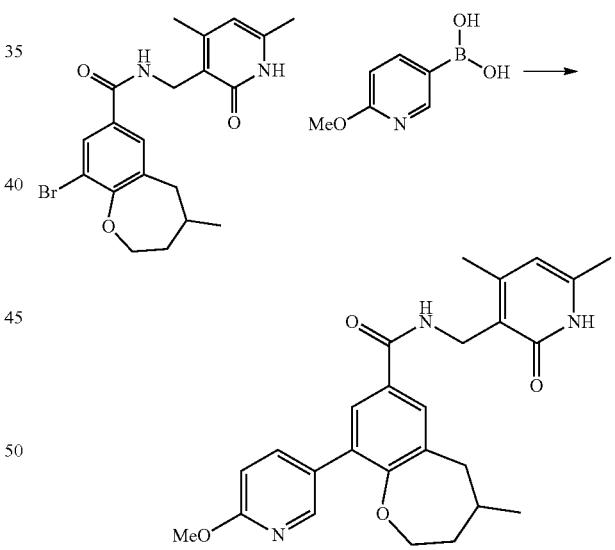

Example 46 was prepared from (6-methoxypyridin-3-yl)boronic acid and 9-bromo-N-((4,6-dimethyl-2-oxo-1,2-dihydropyridin-3-yl)methyl)-4-methyl-2,3,4,5-tetrahydrobenzo[b]oxepine-7-carboxamide (Example 45) as described in Example 10. $^1$H NMR (500 MHz, DMSO-d$_6$) δ 11.49 (br. s., 1H), 8.31 (br. s., 1H), 8.27 (d, J=2.0 Hz, 1H), 7.82 (dd, J=8.4, 2.4 Hz, 1H), 7.71 (s, 2H), 6.88 (d, J=8.8 Hz, 1H), 5.87 (s, 1H), 4.30 (d, J=4.7 Hz, 2H), 4.18 (d, J=12.1 Hz, 1H), 3.89 (s, 3H), 3.69 (t, J=11.1 Hz, 1H), 2.79-2.65 (m, 2H), 2.16 (s, 3H), 2.12 (s, 3H), 1.90 (d, J=12.8 Hz, 1H), 1.78 (br. s., 1H), 1.72-1.59 (m, 1H), 1.02 (d, J=6.4 Hz, 3H). MS(ES): m/z 448 [M+H]$^+$.

Example 47

N-((4,6-Dimethyl-2-oxo-1,2-dihydropyridin-3-yl)methyl)-2-methyl-2,3-dihydrobenzo[b]oxepine-7-carboxamide

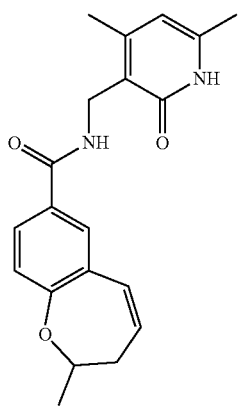 [SMILES: Cc1cc(C)c(CNC(=O)c2ccc3c(c2)C=CCC(C)O3)c(=O)[nH]1]

47A. (E)-Ethyl 3-(3-methylbut-2-en-1-yl)-4-(pent-3-en-2-yloxy)benzoate

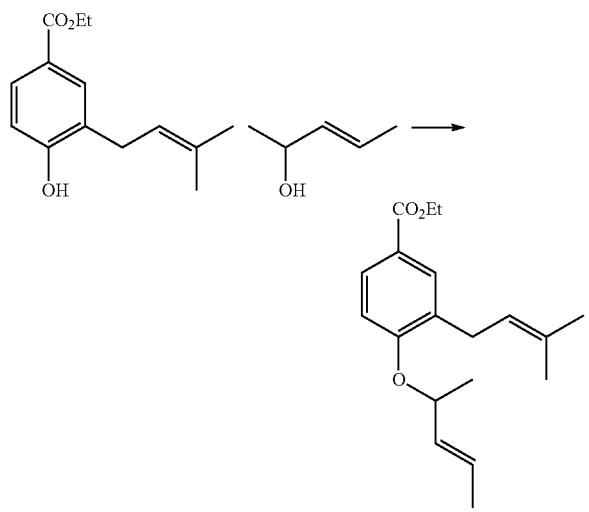

To a solution of ethyl 4-hydroxy-3-(3-methylbut-2-en-1-yl)benzoate (500 mg, 2.134 mmol) in dry THF (5.0 mL) under nitrogen was added (E)-pent-3-en-2-ol (327 μl, 3.20 mmol) and triphenylphosphine (840 mg, 3.20 mmol). The reaction was stirred until everything dissolved. DIAD (622 μl, 3.20 mmol) was then added and the reaction stirred overnight. The solvent was evaporated and the residue applied to an 80 g Isco silica gel column in THF. The product was eluted with 0-25% ethyl acetate in hexanes. Evaporation of the appropriate fractions gave (E)-ethyl 3-(3-methylbut-2-en-1-yl)-4-(pent-3-en-2-yloxy)benzoate (570 mg, 1.885 mmol, 88% yield) as a colorless liquid. Material is not completely clean, but the desired product is the major component by 1H-NMR. $^1$H NMR (400 MHz, DMSO-$d_6$) δ 7.75 (dd, J=8.6, 2.3 Hz, 1H), 7.70 (d, J=2.2 Hz, 1H), 7.04 (d, J=8.7 Hz, 1H), 5.80-5.69 (m, 1H), 5.55-5.47 (m, 1H), 5.23 (ddd, J=7.4, 6.1, 1.3 Hz, 1H), 5.02 (quin, J=6.3 Hz, 1H), 4.26 (q, J=7.1 Hz, 2H), 3.27 (d, J=7.3 Hz, 2H), 1.69 (s, 6H), 1.67-1.62 (m, 4H), 1.37 (d, J=6.2 Hz, 3H), 1.29 (t, J=7.1 Hz, 3H), 1.33-1.25 (m, 3H).

47B. Ethyl 2-methyl-2,3-dihydrobenzo[b]oxepine-7-carboxylate

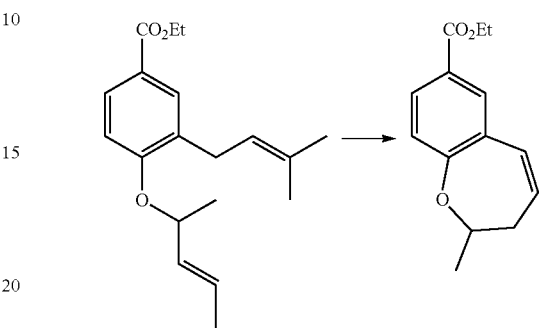

A flask was charged with (E)-ethyl 3-(3-methylbut-2-en-1-yl)-4-(pent-3-en-2-yloxy)benzoate (540 mg, 1.786 mmol) and DCE (100 ml). Nitrogen was bubbled through the solution for 0.5 hours. The solution was degassed 3× with a vacuum/nitrogen flush. The GrubbsII catalyst (76 mg, 0.089 mmol) was then added and the vessel was flushed again. The reaction was then warmed to 78° C. and stirred overnight. The cooled reaction was treated with a solution of potassium isocyanidoacetate (77 mg, 0.623 mmol) in water (2.0 mL). After stirring for an hour, the volatiles were removed and the residue dissolved in ethyl acetate. The solution was applied to a 40 g Isco silica gel column and eluted with 0-30% ethyl acetate in hexanes. Evaporation of the appropriate fractions gave ethyl 2-methyl-2,3-dihydrobenzo[b]oxepine-7-carboxylate (341 mg, 82%). Olefin isomerization appears to have occurred during the metathesis reaction. $^1$H NMR (400 MHz, DMSO-d6) δ 7.83 (d, J=2.2 Hz, 1H), 7.71 (dd, J=8.3, 2.2 Hz, 1H), 6.99 (d, J=8.3 Hz, 1H), 6.43 (d, J=11.9 Hz, 1H), 5.96 (dt, J=11.8, 4.6 Hz, 1H), 4.28 (q, J=7.1 Hz, 3H), 4.21-4.12 (m, 1H), 2.63-2.57 (m, 2H), 1.39 (d, J=6.4 Hz, 3H), 1.30 (t, J=7.1 Hz, 3H). MS(ES): m/z 233 [M+H]$^+$.

47C. 2-Methyl-2,3-dihydrobenzo[b]oxepine-7-carboxylic acid

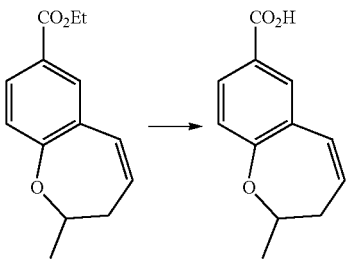 [SMILES: CCOC(=O)c1ccc2c(c1)C=CCC(C)O2 ; CC1CC=Cc2cc(C(=O)O)ccc2O1]

Intermediate 47C was prepared using the chemistry described for Intermediate 44C. $^1$H NMR (500 MHz, DMSO-$d_6$) δ 12.72 (s, 1H), 7.83 (d, J=1.9 Hz, 1H), 7.70 (dd, J=8.5, 2.1 Hz, 1H), 6.98 (d, J=8.3 Hz, 1H), 6.43 (d, J=11.9 Hz, 1H), 5.96 (dt, J=11.7, 4.7 Hz, 1H), 4.21-4.12 (m, 1H), 2.61 (td, J=4.6, 1.4 Hz, 2H), 1.40 (d, J=6.4 Hz, 3H). MS(ES): m/z 205 [M+H]$^+$.

47. N-((4,6-Dimethyl-2-oxo-1,2-dihydropyridin-3-yl)methyl)-2-methyl-2,3-dihydrobenzo[b]oxepine-7-carboxamide

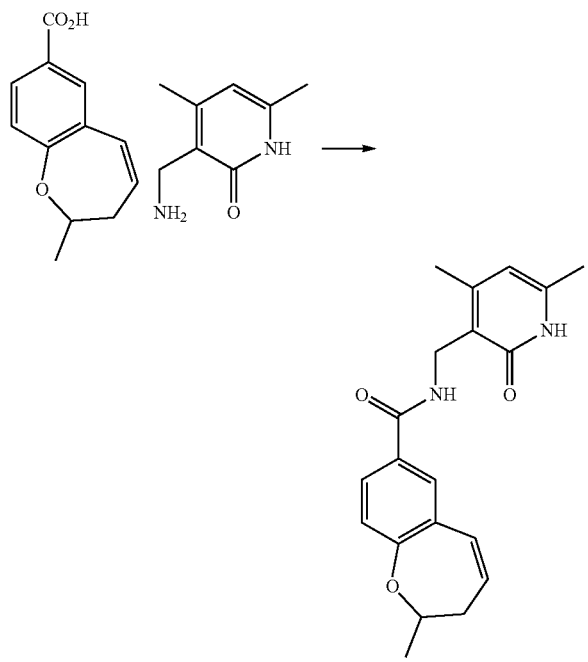

Amide bond formation for Example 47 was conducted as in Example 7. $^1$H NMR (500 MHz, DMSO-$d_6$) δ 11.50 (br. s., 1H), 8.22 (br. s., 1H), 7.74 (d, J=1.8 Hz, 1H), 7.62 (dd, J=8.5, 1.8 Hz, 1H), 6.91 (d, J=8.5 Hz, 1H), 6.35 (d, J=12.2 Hz, 1H), 5.93 (dt, J=11.6, 4.6 Hz, 1H), 5.88 (s, 1H), 4.28 (d, J=4.3 Hz, 2H), 4.18-4.05 (m, 1H), 2.59 (br. s., 2H), 2.17 (s, 3H), 2.12 (s, 3H), 1.38 (d, J=6.7 Hz, 3H). MS(ES): m/z 339 [M+H]$^+$.

Example 48

N-((4,6-Dimethyl-2-oxo-1,2-dihydropyridin-3-yl)methyl)-2-methyl-2,3,4,5-tetrahydrobenzo[b]oxepine-7-carboxamide

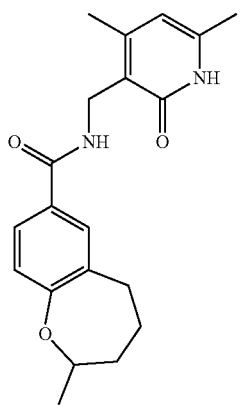 [SMILES: Cc1cc(C)c(CNC(=O)c2ccc3c(c2)CCCC(C)O3)c(=O)[nH]1]

A Parr bottle was charged with 2-methyl-2,3-dihydrobenzo[b]oxepine-7-carboxylic acid (9.21 mg, 0.045 mmol, Intermediate 47C) in ethanol (10 mL). Palladium on carbon (48 mg, 0.045 mmol) was added and the bottle was pressurized to 45 psi of hydrogen. The reaction was allowed to proceed for 2.5 hours. The reaction was then diluted with ethyl acetate and filtered through celite. Evaporation gave 2-methyl-2,3,4,5-tetrahydrobenzo[b]oxepine-7-carboxylic acid. This material was dissolved in dry dimethylformamide (0.5 mL). 3-(Aminomethyl)-4,6-dimethylpyridin-2(1H)-one hydrochloride (15.50 mg, 0.082 mmol) and triethylamine (31.2 μl, 0.224 mmol) were added. The reaction was initiated with the addition of BOP (39.6 mg, 0.090 mmol). After stirring for an hour, the reaction was diluted with dimethylformamide (1.5 mL). The crude material was purified via preparative LC/MS with the following conditions: Column: Waters XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-90% B over 20 minutes, then a 5-minute hold at 100% B; Flow: 20 mL/min. Fractions containing the desired product were combined and dried via centrifugal evaporation. The yield of the product was 15.1 mg. $^1$H NMR (500 MHz, DMSO-$d_6$) δ 11.49 (br. s., 1H), 8.19 (t, J=4.6 Hz, 1H), 7.66 (s, 1H), 7.60 (dd, J=8.5, 1.8 Hz, 1H), 6.92 (d, J=7.9 Hz, 1H), 5.87 (s, 1H), 4.28 (d, J=4.9 Hz, 2H), 3.77 (dd, J=10.1, 5.8 Hz, 1H), 2.74 (d, J=5.5 Hz, 2H), 2.17 (s, 3H), 2.12 (s, 3H), 1.99-1.83 (m, 2H), 1.76-1.63 (m, 1H), 1.53-1.38 (m, 1H), 1.31 (d, J=6.1 Hz, 3H). MS(ES): m/z 341 [M+H]$^+$.

Example 49

9-Bromo-N-((4,6-dimethyl-2-oxo-1,2-dihydropyridin-3-yl)methyl)-2-methyl-2,3,4,5-tetrahydrobenzo[b]oxepine-7-carboxamide

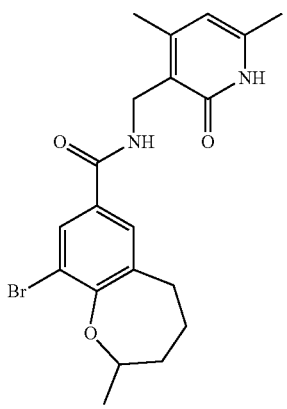 [SMILES: Cc1cc(C)c(CNC(=O)c2cc(Br)c3c(c2)CCCC(C)O3)c(=O)[nH]1]

49A. 9-Bromo-2-methyl-2,3,4,5-tetrahydrobenzo[b]oxepine-7-carboxylic acid

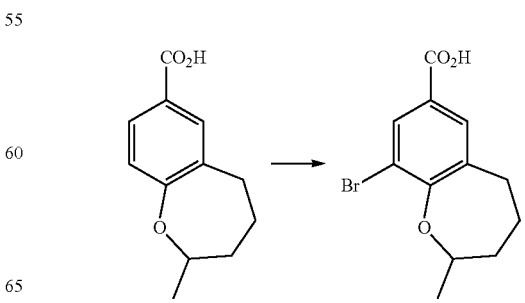

2-Methyl-2,3,4,5-tetrahydrobenzo[b]oxepine-7-carboxylic acid (202 mg, 0.979 mmol, an intermediate in the preparation of Example 48) was dissolved in glacial acetic acid (4.0 mL). Bromine (76 μl, 1.469 mmol) was added and stirring continued for 3 days. The reaction was diluted with water and the resulting solid was filtered and rinsed with water. As this material is not a nice solid, the filter paper was rinsed with ethanol and the washes evaporated. The residue was crystallized from hot ethyl acetate to give the desired product (76 mg). $^1$H NMR (400 MHz, DMSO-$d_6$) δ 13.03 (br. s., 1H), 7.93 (d, J=2.1 Hz, 1H), 7.75 (d, J=2.0 Hz, 1H), 3.92-3.77 (m, 1H), 2.94-2.75 (m, 2H), 1.98-1.85 (m, 2H), 1.84-1.69 (m, 1H), 1.55-1.45 (m, 1H), 1.43 (d, J=6.2 Hz, 3H). MS(ES): m/z 285 [M+H]$^+$.

49. 9-Bromo-N-((4,6-dimethyl-2-oxo-1,2-dihydropyridin-3-yl)methyl)-2-methyl-2,3,4,5-tetrahydrobenzo[b]oxepine-7-carboxamide

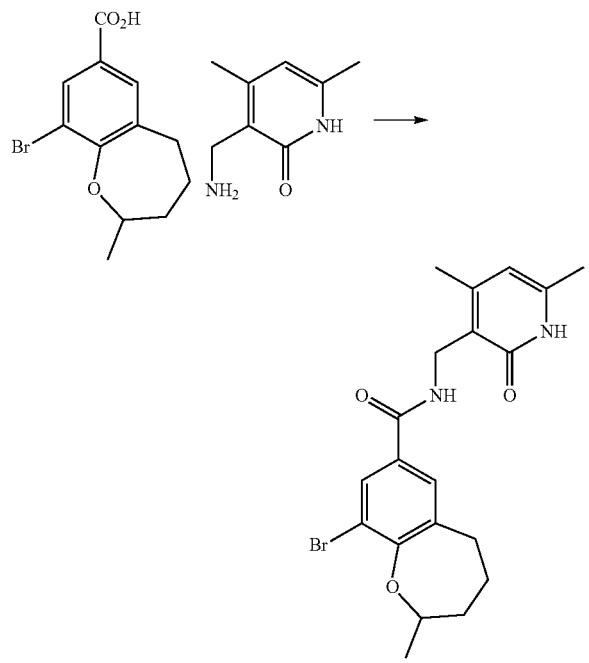

Amide bond formation for Example 49 was accomplished as in Example 21. $^1$H NMR (400 MHz, DMSO-$d_6$) δ 11.46 (s, 1H), 8.32 (t, J=4.7 Hz, 1H), 7.93 (d, J=2.1 Hz, 1H), 7.68 (d, J=2.1 Hz, 1H), 5.86 (s, 1H), 4.27 (d, J=4.9 Hz, 2H), 3.85-3.70 (m, 1H), 2.87-2.72 (m, 2H), 2.15 (s, 3H), 2.12 (s, 3H), 2.01-1.86 (m, 1H), 1.82-1.67 (m, 1H), 1.50-1.43 (m, 1H), 1.41 (d, J=6.4 Hz, 3H). MS(ES): m/z 419 [M+H]$^+$.

Example 50

N-((4,6-Dimethyl-2-oxo-1,2-dihydropyridin-3-yl)methyl)-2-methyl-9-(4-(morpholinomethyl)phenyl)-2,3,4,5-tetrahydrobenzo[b]oxepine-7-carboxamide

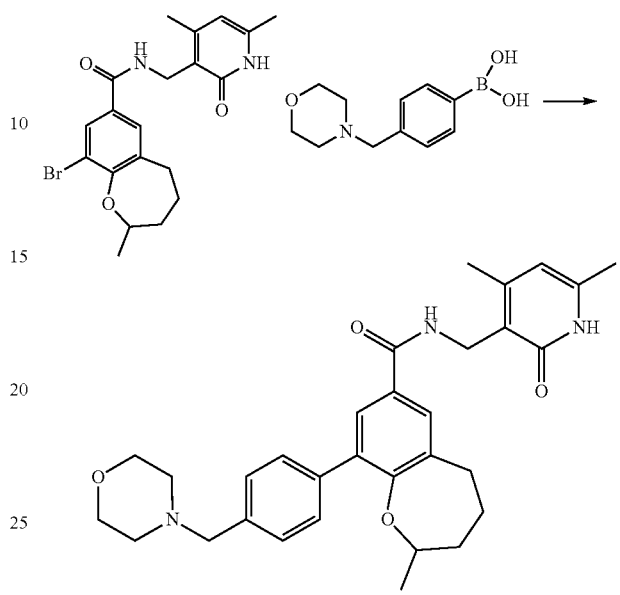

Example 50 was prepared from (4-(morpholinomethyl)phenyl)boronic acid and 9-bromo-N-((4,6-dimethyl-2-oxo-1,2-dihydropyridin-3-yl)methyl)-2-methyl-2,3,4,5-tetrahydrobenzo[b]oxepine-7-carboxamide (Example 49) as described in Example 10.

$^1$H NMR (500 MHz, DMSO-$d_6$) δ 11.48 (br. s., 1H), 8.31 (t, J=4.9 Hz, 1H), 7.96 (s, 1H), 7.66 (d, J=6.1 Hz, 2H), 7.44-7.38 (m, 2H), 7.37-7.33 (m, 2H), 5.87 (s, 1H), 4.29 (d, J=4.9 Hz, 2H), 3.69 (dd, J=9.8, 6.1 Hz, 1H), 3.59 (t, J=4.3 Hz, 4H), 3.51 (s, 2H), 2.86-2.75 (m, 2H), 2.51 (br. s., 4H), 2.16 (s, 3H), 2.11 (s, 3H), 1.96-1.82 (m, 2H), 1.74-1.62 (m, 1H), 1.50-1.36 (m, 1H), 1.07 (d, J=6.1 Hz, 3H). MS(ES): m/z 516 [M+H]$^+$.

Example 51

N-((4,6-Dimethyl-2-oxo-1,2-dihydropyridin-3-yl)methyl)-2-methyl-9-(6-(piperazin-1-yl)pyridin-3-yl)-2,3,4,5-tetrahydrobenzo[b]oxepine-7-carboxamide

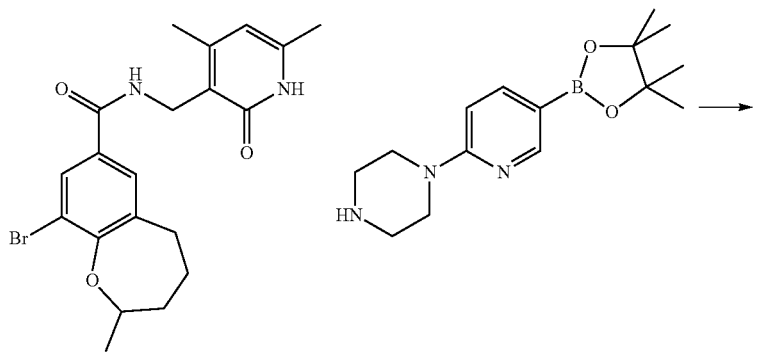

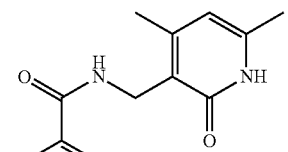

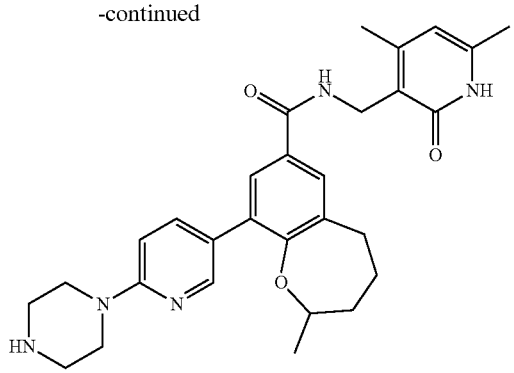

Example 51 was prepared from 1-(5-(4,4,5,5-tetramethyl-1,3,2-dioxaborolan-2-yl)pyridin-2-yl)piperazine and 9-bromo-N-((4,6-dimethyl-2-oxo-1,2-dihydropyridin-3-yl)methyl)-2-methyl-2,3,4,5-tetrahydrobenzo[b]oxepine-7-carboxamide (Example 49) as described in Example 10.

$^1$H NMR (500 MHz, DMSO-d$_6$) δ 11.84-11.02 (m, 1H), 8.30 (t, J=4.6 Hz, 1H), 8.24 (d, J=1.8 Hz, 1H), 7.96 (s, 1H), 7.69 (dd, J=9.2, 2.4 Hz, 1H), 7.66 (d, J=1.8 Hz, 1H), 7.63 (s, 1H), 6.87 (d, J=9.2 Hz, 1H), 5.87 (s, 1H), 4.29 (d, J=4.9 Hz, 2H), 3.69 (dd, J=10.1, 6.4 Hz, 2H), 2.88-2.83 (m, 4H), 2.83-2.75 (m, 2H), 2.16 (s, 3H), 2.12 (s, 3H), 1.91 (s, 2H), 1.78-1.63 (m, 1H), 1.50-1.34 (m, 1H), 1.14 (d, J=6.1 Hz, 3H). MS(ES): m/z 502 [M+H]$^+$.

Example 52

N-((4,6-Dimethyl-2-oxo-1,2-dihydropyridin-3-yl)methyl)-9-(6-methoxypyridin-3-yl)-2-methyl-2,3,4,5-tetrahydrobenzo[b]oxepine-7-carboxamide

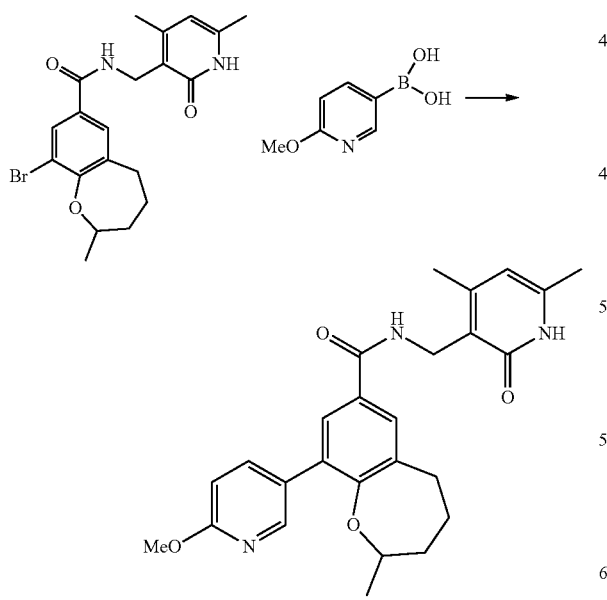

Example 52 was prepared from (6-methoxypyridin-3-yl)boronic acid and 9-bromo-N-((4,6-dimethyl-2-oxo-1,2-dihydropyridin-3-yl)methyl)-2-methyl-2,3,4,5-tetrahydrobenzo[b]oxepine-7-carboxamide (Example 49) as described in Example 10. $^1$H NMR (500 MHz, DMSO-d$_6$)

δ 11.49 (br. s., 1H), 8.31 (t, J=4.6 Hz, 1H), 8.25 (d, J=1.8 Hz, 1H), 7.82 (dd, J=8.5, 2.4 Hz, 1H), 7.69 (s, 2H), 6.89 (d, J=8.5 Hz, 1H), 5.87 (s, 1H), 4.29 (d, J=4.9 Hz, 2H), 3.96-3.84 (m, 3H), 3.71 (dd, J=9.8, 6.1 Hz, 1H), 2.87-2.76 (m, 2H), 2.16 (s, 3H), 2.12 (s, 3H), 2.00-1.84 (m, 2H), 1.77-1.63 (m, 1H), 1.43 (d, J=11.6 Hz, 1H), 1.10 (d, J=6.1 Hz, 3H). MS(ES): m/z 448 [M+H]$^+$.

Example 53

9-Bromo-N-((4,6-dimethyl-2-oxo-1,2-dihydropyridin-3-yl)methyl)-3-methyl-2,3,4,5-tetrahydrobenzo[b]oxepine-7-carboxamide 53A. Ethyl 4-((2-methylallyl)oxy)-3-(3-methylbut-2-en-1-yl)benzoate

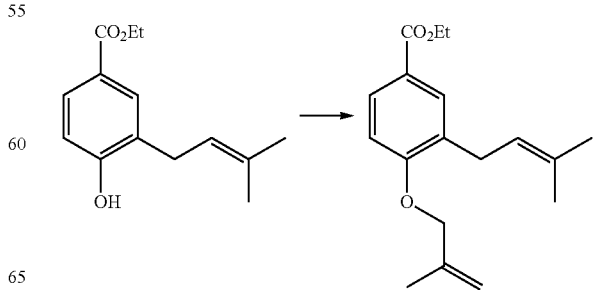

Ethyl 4-hydroxy-3-(3-methylbut-2-en-1-yl)benzoate (1.09 g, 4.65 mmol) was dissolved in acetonitrile (10 mL) under nitrogen. Potassium carbonate (0.772 g, 5.58 mmol) was added and stirring continued for 5 minutes. 1-Bromo-3-methyl-2-butene (0.518 ml, 4.65 mmol) was then added and the reaction warmed to 55° C. After stirring overnight, the reaction was quenched with water and transferred to a separatory funnel. The material was extracted with ether and the organic layer washed with brine. Drying over magnesium sulfate, filtration and evaporation provided the crude product. The crude material was applied to an 80 g Isco silica gel column and eluted with 0-30% ethyl acetate in hexanes. Evaporation of the appropriate fractions gave ethyl 4-((2-methylallyl)oxy)-3-(3-methylbut-2-en-1-yl)benzoate (0.86 g, 2.92 mmol, 62.8% yield) as a colorless liquid. $^1$H NMR (400 MHz, DMSO-$d_6$) δ 7.80 (dd, J=8.6, 2.2 Hz, 1H), 7.73 (d, J=2.2 Hz, 1H), 7.06 (d, J=8.6 Hz, 1H), 5.33-5.22 (m, 1H), 5.10 (s, 1H), 5.00 (s, 1H), 4.59 (s, 2H), 4.28 (q, J=7.1 Hz, 2H), 3.37-3.30 (m, 2H), 1.81 (s, 3H), 1.71 (s, 3H), 1.69 (s, 3H). MS(ES): m/z 289 [M+H]$^+$.

53B. Ethyl 3-methyl-2,5-dihydrobenzo[b]oxepine-7-carboxylate

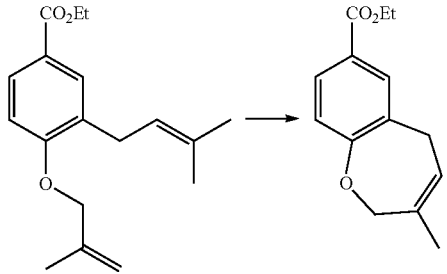 [SMILES: C=C(C)COc1ccc(C(=O)OCC)cc1CC=C(C)C ; CCOC(=O)c1ccc2c(c1)CC=C(C)CO2]

A flask was charged with ethyl 4-((2-methylallyl)oxy)-3-(3-methylbut-2-en-1-yl)benzoate (223 mg, 0.773 mmol) and DCE (50 ml). The solution was degassed with a stream of nitrogen for 15 minutes. The Grubbs II catalyst (32.8 mg, 0.039 mmol) was added and a nitrogen inlet was attached. The reaction was then warmed to 55° C. for 2 hours. The reaction was then concentrated on the rotary evaporator with no heating. The residue was applied to a 40 g Isco silica gel column in ethyl acetate and eluted with 0-50% ethyl acetate in hexanes. Evaporation of the appropriate fractions gave ethyl 3-methyl-2,5-dihydrobenzo[b]oxepine-7-carboxylate (149 mg, 83%). $^1$H NMR (400 MHz, DMSO-$d_6$) δ 7.81 (dd, J=8.4, 2.2 Hz, 1H), 7.76 (d, J=2.2 Hz, 1H), 7.12 (d, J=8.4 Hz, 1H), 5.67 (ddd, J=7.0, 4.0, 1.5 Hz, 1H), 4.50 (s, 2H), 4.30 (q, J=7.0 Hz, 2H), 3.45 (d, J=4.4 Hz, 2H), 1.57 (s, 3H), 1.32 (t, J=7.2 Hz, 3H).

53C. Ethyl 3-methyl-2,3,4,5-tetrahydrobenzo[b]oxepine-7-carboxylate

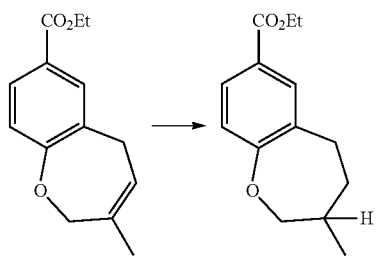 [SMILES: CCOC(=O)c1ccc2c(c1)CC=C(C)CO2 ; CCOC(=O)c1ccc2c(c1)CCC(C)CO2]

A Parr bottle was charged with ethyl 3-methyl-2,5-dihydrobenzo[b]oxepine-7-carboxylate (85 mg, 0.366 mmol) in ethanol (10 mL). The catalyst, 10% Pd/C (27 mg) was added and the bottle pressurized to 40 psi $H_2$. After reacting for an hour, the reaction was diluted with ethyl acetate and filtered through a pad of magnesium sulfate. The solvent was evaporated and the residue suspended in ether. Filtration and evaporation gave the crude product. This material was purified by RP-HPLC (methanol-water gradient+0.1% TFA). The product containing fraction was evaporated and azeotroped with ethanol. Ethyl 3-methyl-2,3,4,5-tetrahydrobenzo[b]oxepine-7-carboxylate (48 mg, 0.205 mmol, 56.0% yield) was obtained as a colorless film. $^1$H NMR (400 MHz, CHLOROFORM-d) δ 7.92-7.81 (m, 2H), 7.01 (d, J=7.9 Hz, 1H), 4.37 (q, J=7.1 Hz, 2H), 4.25 (ddd, J=12.0, 3.4, 1.3 Hz, 1H), 3.45 (dd, J=11.9, 9.2 Hz, 1H), 2.96-2.80 (m, 2H), 2.17 (qtd, J=9.9, 6.8, 3.7 Hz, 1H), 2.05-1.92 (m, 1H), 1.41 (t, J=7.2 Hz, 3H), 1.32 (dtd, J=13.5, 10.1, 3.3 Hz, 1H), 0.97 (d, J=7.0 Hz, 3H).

53D. 3-Methyl-2,3,4,5-tetrahydrobenzo[b]oxepine-7-carboxylic acid

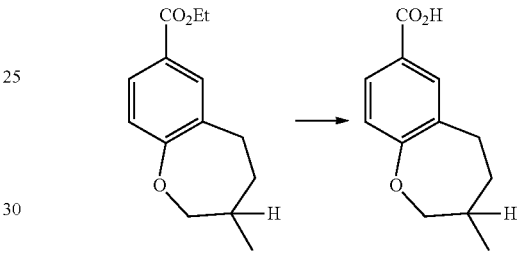

To a solution of ethyl 3-methyl-2,3,4,5-tetrahydrobenzo[b]oxepine-7-carboxylate (48 mg, 0.205 mmol) in tetrahydrofuran-water (3:1, 4 mL) was added lithium hydroxide (615 μl, 0.615 mmol, 1 N). A little methanol was added until the reaction became homogeneous. The reaction was warmed to 55° C. for an hour then stirred at room temperature overnight. The reaction was quenched with 1 N hydrochloric acid (615 μL) and concentrated under a stream of nitrogen. The resulting solid was filtered, rinsed with water and then dried in a ChemDry oven at 76° C. for 0.5 hour. 3-Methyl-2,3,4,5-tetrahydrobenzo[b]oxepine-7-carboxylic acid (32.7 mg, 0.155 mmol, 76% yield) was isolated as a colorless solid. $^1$H NMR (400 MHz, DMSO-$d_6$) δ 12.67 (br. s., 1H), 7.78 (d, J=2.2 Hz, 1H), 7.72 (dd, J=8.1, 2.2 Hz, 1H), 7.00 (d, J=8.1 Hz, 1H), 4.21 (dd, J=12.0, 2.5 Hz, 1H), 3.44 (dd, J=12.0, 8.9 Hz, 1H), 2.90-2.74 (m, 2H), 2.17-2.02 (m, 1H), 2.00-1.88 (m, 1H), 1.33-1.20 (m, 1H), 0.92 (d, J=7.0 Hz, 3H).

53E. 9-Bromo-3-methyl-2,3,4,5-tetrahydrobenzo[b]oxepine-7-carboxylic acid

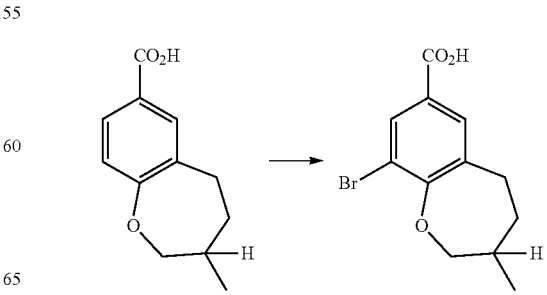

3-Methyl-2,3,4,5-tetrahydrobenzo[b]oxepine-7-carboxylic acid (25 mg, 0.121 mmol) was dissolved in glacial acetic acid. Bromine (12.49 µl, 0.242 mmol) was added and the reaction stirred overnight. More bromine (20 uL) was then added and stirring continued for 2 hours, Water was added to induce precipitation. The solid was filtered, rinsed with water and dried in a ChemDry oven at 75° C. for an hour. 9-Bromo-3-methyl-2,3,4,5-tetrahydrobenzo[b]oxepine-7-carboxylic acid (24 mg, 0.077 mmol, 63.7% yield) was isolated as an off-white solid. $^1$H NMR (400 MHz, DMSO-$d_6$) δ 13.02 (br. s., 1H), 7.92 (d, J=2.2 Hz, 1H), 7.75 (d, J=2.2 Hz, 1H), 4.25 (dd, J=11.9, 2.4 Hz, 1H), 3.42 (dd, J=11.9, 9.2 Hz, 1H), 2.95-2.76 (m, 2H), 1.90 (t, J=6.7 Hz, 1H), 1.31-1.17 (m, 1H), 0.89 (d, J=6.8 Hz, 3H). MS(ES): m/z 285 [M+H]$^+$.

53. 9-Bromo-N-((4,6-dimethyl-2-oxo-1,2-dihydropyridin-3-yl)methyl)-3-methyl-2,3,4,5-tetrahydrobenzo[b]oxepine-7-carboxamide

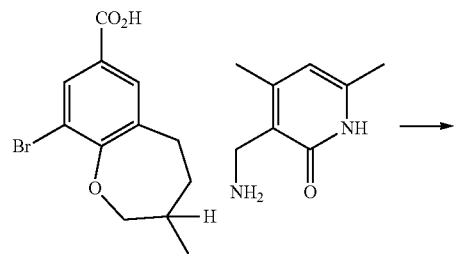

9-Bromo-3-methyl-2,3,4,5-tetrahydrobenzo[b]oxepine-7-carboxylic acid (22 mg, 0.077 mmol) was dissolved in dry dimethylformamide (0.5 mL). 3-(Aminomethyl)-4,6-dimethylpyridin-2(1H)-one hydrochloride (16.01 mg, 0.085 mmol) and triethylamine (32.3 µl, 0.231 mmol) were added. The reaction was initiated with the addition of BOP (40.9 mg, 0.093 mmol). After an hour, the reaction was diluted with methanol and purified by RP-HPLC (methanol-water gradient+0.1% TFA). The product containing fraction was concentrated and azeotroped dry with ethanol. Pumping down in vacuo then gave 9-bromo-N-((4,6-dimethyl-2-oxo-1,2-dihydropyridin-3-yl)methyl)-3-methyl-2,3,4,5-tetrahydrobenzo[b]oxepine-7-carboxamide (22.5 mg). $^1$H NMR (400 MHz, DMSO-$d_6$) δ 11.47 (br. s., 1H), 8.33 (br. s., 1H), 7.95 (d, J=2.0 Hz, 1H), 7.71 (d, J=2.0 Hz, 1H), 5.87 (s, 1H), 4.28 (d, J=4.6 Hz, 2H), 4.24 (dd, J=11.9, 2.6 Hz, 1H), 3.38 (dd, J=11.8, 9.4 Hz, 1H), 2.83 (t, J=4.7 Hz, 2H), 2.16 (s, 3H), 2.13 (s, 3H), 1.91 (dd, J=9.1, 4.3 Hz, 1H), 1.34-1.15 (m, 2H), 0.90 (d, J=6.8 Hz, 3H). MS(ES): m/z 419 [M+H]$^+$.

Example 54

N-((4,6-dimethyl-2-oxo-1,2-dihydropyridin-3-yl)methyl)-9-(6-methoxypyridin-3-yl)-3-methyl-2,3,4,5-tetrahydrobenzo[b]oxepine-7-carboxamide

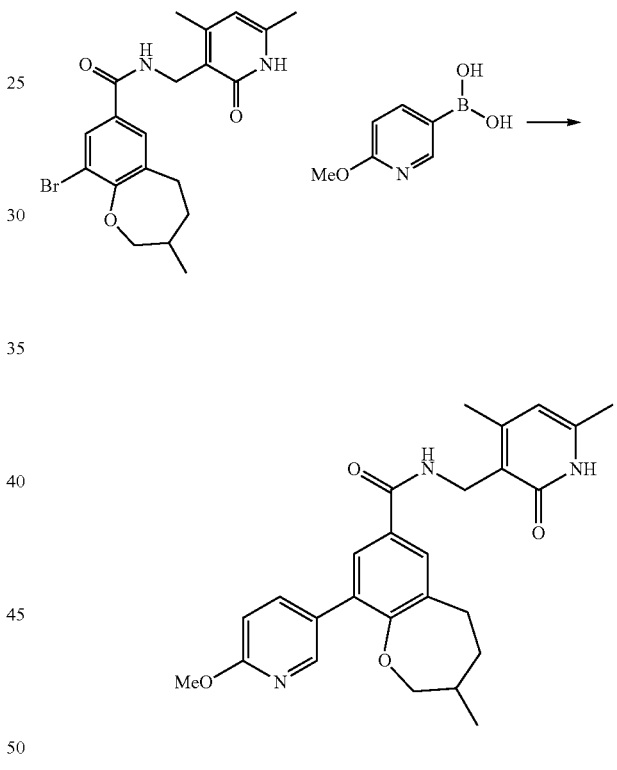

Example 54 was prepared from (6-methoxypyridin-3-yl) boronic acid and 9-bromo-N-((4,6-dimethyl-2-oxo-1,2-dihydropyridin-3-yl)methyl)-3-methyl-2,3,4,5-tetrahydrobenzo[b]oxepine-7-carboxamide (Example 53) as described in Example 10. $^1$H NMR (500 MHz, DMSO-$d_6$) δ 11.49 (br. s., 1H), 8.32 (br. s., 1H), 8.27 (d, J=2.0 Hz, 1H), 7.82 (dd, J=8.4, 2.4 Hz, 1H), 7.71 (s, 2H), 6.89 (d, J=8.4 Hz, 1H), 5.87 (s, 1H), 4.29 (d, J=4.4 Hz, 2H), 4.10 (d, J=9.8 Hz, 1H), 3.94-3.85 (m, 4H), 2.83 (br. s., 2H), 2.16 (s, 3H), 2.12 (s, 3H), 2.07 (br. s., 1H), 1.98-1.81 (m, 1H), 1.24 (d, J=9.8 Hz, 1H), 0.87 (d, J=6.7 Hz, 3H). MS(ES): m/z 448 [M+H]$^+$.

Example 55

N-((4,6-Dimethyl-2-oxo-1,2-dihydropyridin-3-yl)methyl)-3-methyl-9-(6-(piperazin-1-yl)pyridin-3-yl)-2,3,4,5-tetrahydrobenzo[b]oxepine-7-carboxamide

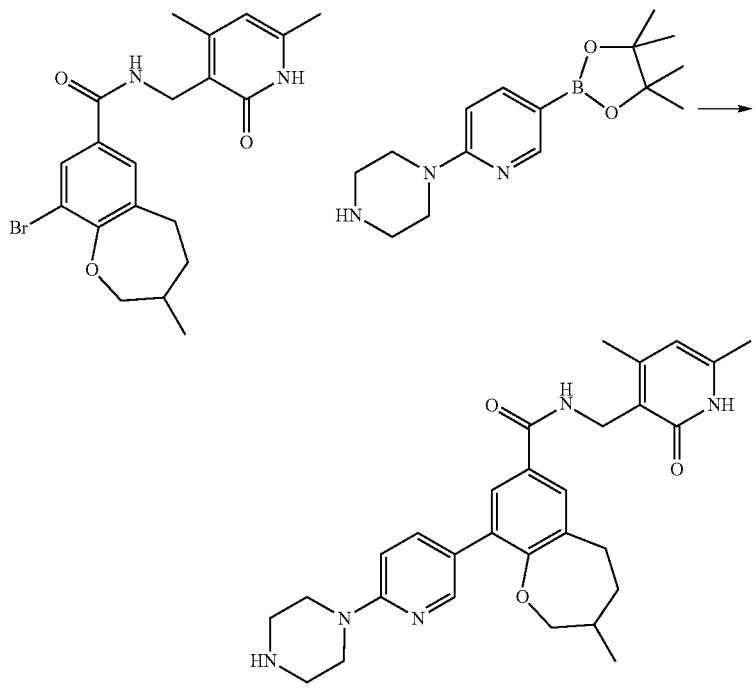

Example 55 was prepared from 1-(5-(4,4,5,5-tetramethyl-1,3,2-dioxaborolan-2-yl)pyridin-2-yl)piperazine and 9-bromo-N-((4,6-dimethyl-2-oxo-1,2-dihydropyridin-3-yl)methyl)-3-methyl-2,3,4,5-tetrahydrobenzo[b]oxepine-7-carboxamide (Example 53) as described in Example 10. $^1$H NMR (500 MHz, DMSO-$d_6$) δ 11.47 (s, 1H), 8.31 (t, J=4.9 Hz, 1H), 8.24 (d, J=1.8 Hz, 1H), 7.73-7.57 (m, 3H), 6.86 (d, J=8.5 Hz, 1H), 5.87 (s, 1H), 4.29 (d, J=4.9 Hz, 2H), 4.09 (d, J=9.8 Hz, 1H), 2.86-2.78 (m, 6H), 2.16 (s, 3H), 2.12 (s, 3H), 2.06 (br. s., 1H), 1.22 (d, J=8.5 Hz, 1H), 0.87 (d, J=6.7 Hz, 3H). MS(ES): m/z 502 [M+H]$^+$.

Example 56

N-((4,6-Dimethyl-2-oxo-1,2-dihydropyridin-3-yl)methyl)-7-(6-methoxypyridin-3-yl)-2-methyl-2-vinyl-2,3-dihydrobenzofuran-5-carboxamide

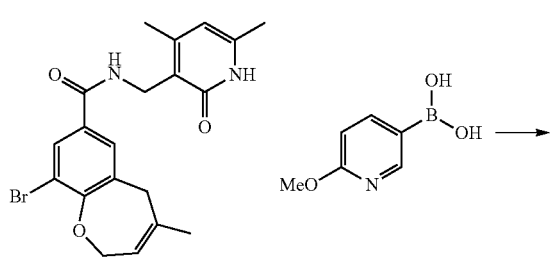

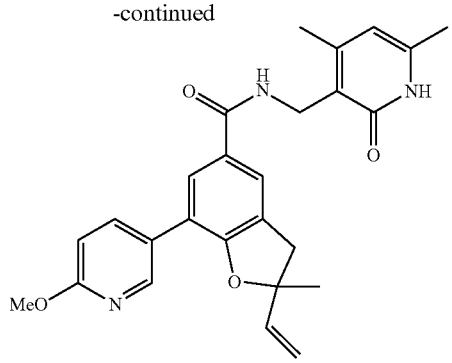

A reaction vial was charged with (6-methoxypyridin-3-yl)boronic acid (12.53 mg, 0.082 mmol), 9-bromo-N-((4,6-dimethyl-2-oxo-1,2-dihydropyridin-3-yl)methyl)-4-methyl-2,5-dihydrobenzo[b]oxepine-7-carboxamide (17.1 mg, 0.041 mmol, Example 44) and dimethylformamide (0.75 mL). Nitrogen was bubbled through the solution for 15 minutes. Sodium carbonate solution (82 µl, 0.082 mmol, 1 M) and tetrakis(triphenylphosphine)palladium(0) (4.74 mg, 4.10 µmol) were then added. Bubbling with nitrogen was continued for a few minutes. The vial was then sealed and heated to 95° C. After ca. 180 minutes, the reaction was cooled, diluted with methanol, and filtered. The crude material was purified by RP-HPLC (methanol-water gradient+ 0.1% TFA). The product containing fraction was treated with with half saturated sodium bicarbonate solution and concentrated on the rotary evaporator. The resulting precipitate was filtered, rinsed with water and dried in a ChemDry oven at 75° C. N-((4,6-Dimethyl-2-oxo-1,2-dihydropyridin-3-yl)methyl)-7-(6-methoxypyridin-3-yl)-2-methyl-2-vinyl-2,3-dihydrobenzofuran-5-carboxamide (5.5 mg, 0.012 mmol, 29.5% yield) was obtained as a colorless solid. $^1$H NMR (400 MHz, DMSO-$d_6$) δ 11.46 (br. s., 1H), 8.59 (d, J=2.4 Hz, 1H), 8.25 (br. s., 1H), 8.08 (dd, J=8.6, 2.6 Hz, 1H), 7.88 (s, 1H), 7.71 (s, 1H), 6.94 (d, J=8.6 Hz, 1H), 6.14 (dd, J=17.2, 10.8 Hz, 1H), 5.87 (s, 1H), 5.26 (d, J=17.4 Hz, 1H), 5.12 (d, J=10.3 Hz, 1H), 4.32 (d, J=4.4 Hz, 2H), 3.91 (s, 3H), 3.27 (d, J=15.6 Hz, 1H), 3.18 (d, J=15.2 Hz, 1H), 2.18 (s, 3H), 2.13 (s, 3H), 1.56 (s, 3H). MS(ES): m/z 446 [M+H]$^+$.

Example 57

7-Bromo-N-((4,6-dimethyl-2-oxo-1,2-dihydropyridin-3-yl)methyl)-2-methyl-2-vinyl-2,3-dihydrobenzofuran-5-carboxamide

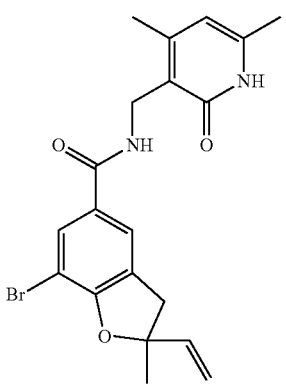 [SMILES: C=CC1(C)Cc2cc(C(=O)NCc3c(C)cc(C)[nH]c3=O)cc(Br)c2O1]

57A. Methyl 7-bromo-2-methyl-2-vinyl-2,3-dihydrobenzofuran-5-carboxylate

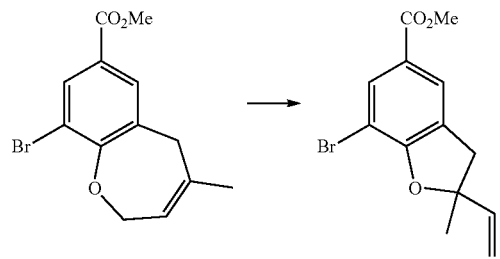 [SMILES: COC(=O)c1cc(Br)c2c(c1)CC(C)=CCO2 ; C=CC1(C)Cc2cc(C(=O)OC)cc(Br)c2O1]

A reaction vial was charged with methyl 9-bromo-4-methyl-2,5-dihydrobenzo[b]oxepine-7-carboxylate (21.1 mg, 0.071 mmol, Intermediate 44B) and dimethylformamide (1.0 mL). Nitrogen was bubbled through the solution for 15 minutes. Tetrakis(triphenylphosphine)palladium(0) (4.10 mg, 3.55 μmol) was added and the vial was sealed. The reaction was warmed to 50° C. and stirred overnight. The cooled reaction was applied to a 12 g Isco silica gel column and eluted with 0-30% ethyl acetate in hexanes. The product containing fractions were evaporated and then lyophilized from frozen benzene to give methyl 7-bromo-2-methyl-2-vinyl-2,3-dihydrobenzofuran-5-carboxylate (18 mg, 0.061 mmol, 85% yield) as a colorless solid. $^1$H NMR (400 MHz, CHLOROFORM-d) δ 8.05 (d, J=0.7 Hz, 1H), 7.76 (d, J=0.9 Hz, 1H), 6.04 (dd, J=17.2, 10.8 Hz, 1H), 5.34 (d, J=17.2 Hz, 1H), 5.15 (d, J=10.8 Hz, 1H), 3.88 (s, 3H), 3.35-3.25 (m, 1H), 3.22-3.12 (m, 1H), 1.64 (s, 3H). MS(ES): m/z 297 [M+H]$^+$.

57B. 7-Bromo-2-methyl-2-vinyl-2,3-dihydrobenzofuran-5-carboxylic acid

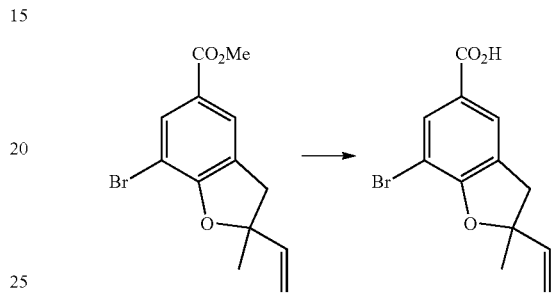

Methyl 7-bromo-2-methyl-2-vinyl-2,3-dihydrobenzofuran-5-carboxylate (16 mg, 0.054 mmol) was dissolved in tetrahydrofuran-water (2:1, 3 mL). A solution of lithium hydroxide (162 μl, 0.162 mmol, 1 N) was added and the reaction allowed to stir overnight. As LCMS analysis suggested that the reaction was not quite complete, the reaction was heated briefly with a heat gun. After cooling, the reaction was quenched with 1 N hydrochloric acid (182 mL) and concentrated under a stream of nitrogen. The resulting solid was filtered, rinsed with water and dried in a ChemDry oven at 75° C. for 0.5 hour. 7-Bromo-2-methyl-2-vinyl-2,3-dihydrobenzofuran-5-carboxylic acid (12.7 mg, 0.045 mmol, 83% yield) was isolated as a colorless solid. $^1$H NMR (400 MHz, DMSO-$d_6$) δ 12.84 (br. s., 1H), 7.87 (d, J=1.5 Hz, 1H), 7.75 (d, J=1.3 Hz, 1H), 6.10 (dd, J=17.2, 10.8 Hz, 1H), 5.28 (dd, J=17.2, 1.1 Hz, 1H), 5.13 (dd, J=10.8, 1.1 Hz, 1H), 1.58 (s, 3H) (benzylic CH$_2$ is obscured). MS(ES): m/z 283 [M+H]$^+$.

57. 7-Bromo-N-((4,6-dimethyl-2-oxo-1,2-dihydropyridin-3-yl)methyl)-2-methyl-2-vinyl-2,3-dihydrobenzofuran-5-carboxamide

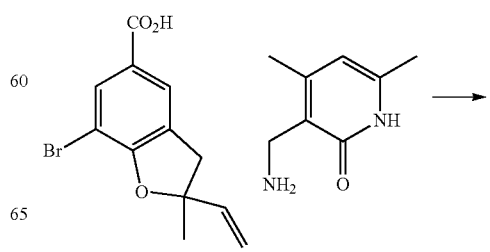

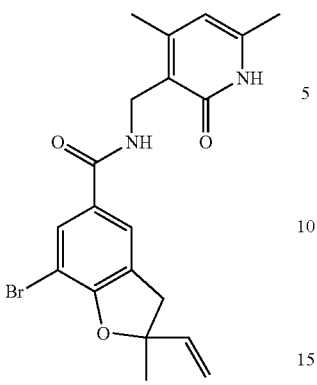

7-Bromo-2-methyl-2-vinyl-2,3-dihydrobenzofuran-5-carboxylic acid (12 mg, 0.042 mmol) was dissolved in dry dimethylformamide (0.5 mL). 3-(Aminomethyl)-4,6-dimethylpyridin-2(1H)-one, hydrochloride (8.80 mg, 0.047 mmol) and triethylamine (17.72 µl, 0.127 mmol) were added. The reaction was initiated with the addition of BOP (22.50 mg, 0.051 mmol). After stirring for an hour, the reaction was diluted with dimethylformamide (1.5 mL) and purified by RP-HPLC (methanol-water gradient+0.1% TFA). The product containing fraction was treated with half saturated sodium bicarbonate solution and concentrated partly on the rotary evaporator. The resulting solid was filtered, rinsed well with water and dried in a ChemDry oven at 40° C. for an hour. 7-Bromo-N-((4,6-dimethyl-2-oxo-1,2-dihydropyridin-3-yl)methyl)-2-methyl-2-vinyl-2,3-dihydrobenzofuran-5-carboxamide (8.6 mg, 0.019 mmol, 43.8% yield) was isolated as a colorless solid. $^1$H NMR (400 MHz, DMSO-$d_6$) δ 11.46 (br. s., 1H), 8.23 (t, J=4.8 Hz, 1H), 7.88 (s, 1H), 7.70 (s, 1H), 6.08 (dd, J=17.2, 10.8 Hz, 1H), 5.86 (s, 1H), 5.26 (dd, J=17.2, 1.0 Hz, 1H), 5.11 (dd, J=10.7, 1.0 Hz, 1H), 4.26 (d, J=4.8 Hz, 2H), 3.30-3.17 (m, 2H), 2.15 (s, 3H), 2.12 (s, 3H), 1.56 (s, 3H). MS(ES): m/z 417 [M+H]$^+$.

Example 58

N-((4,6-Dimethyl-2-oxo-1,2-dihydropyridin-3-yl)methyl)-2-methyl-7-(4-(morpholinomethyl)phenyl)-2-vinyl-2,3-dihydrobenzofuran-5-carboxamide

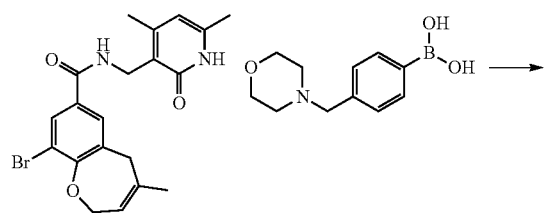

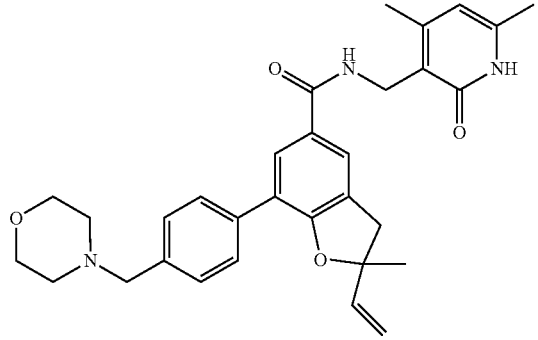

Example 58 was prepared from 9-bromo-N-((4,6-dimethyl-2-oxo-1,2-dihydropyridin-3-yl)methyl)-4-methyl-2,5-dihydrobenzo[b]oxepine-7-carboxamide (Example 44) and (4-(morpholinomethyl)phenyl)boronic acid in 33% yield using the procedures of Example 56. $^1$H NMR (400 MHz, DMSO-$d_6$) δ 11.46 (br. s., 1H), 8.25 (br. s., 1H), 7.85 (s, 1H), 7.71 (d, J=8.1 Hz, 3H), 7.39 (d, J=7.9 Hz, 2H), 6.13 (dd, J=17.5, 10.9 Hz, 1H), 5.87 (s, 1H), 5.27 (d, J=17.4 Hz, 1H), 5.12 (d, J=11.0 Hz, 1H), 4.31 (d, J=4.4 Hz, 2H), 3.60 (br. s., 4H), 3.51 (s, 2H), 3.22-3.08 (m, 1H), 2.39 (br. s., 4H), 2.17 (s, 3H), 2.13 (s, 3H), 1.55 (s, 3H). MS(ES): m/z 514 [M+H]$^+$.

Example 59

N-((4,6-Dimethyl-2-oxo-1,2-dihydropyridin-3-yl)methyl)-2-methyl-7-(6-(piperazin-1-yl)pyridin-3-yl)-2-vinyl-2,3-dihydrobenzofuran-5-carboxamide

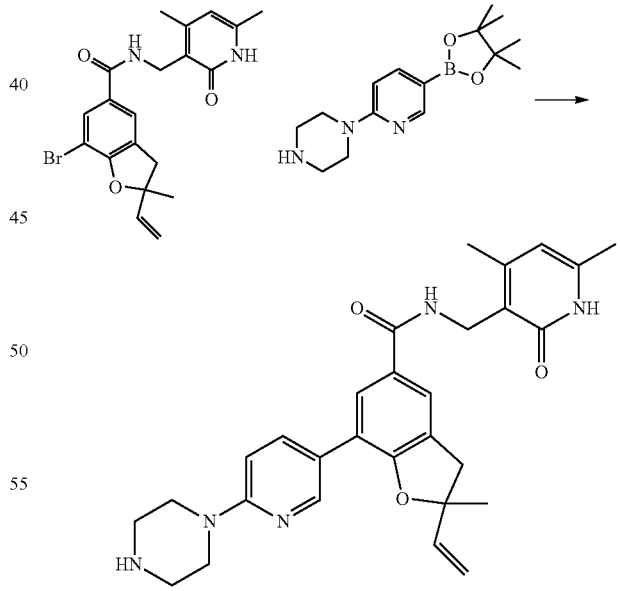

A reaction vial was charged with 1-(5-(4,4,5,5-tetramethyl-1,3,2-dioxaborolan-2-yl)pyridin-2-yl)piperazine (46.4 mg, 0.161 mmol), 7-bromo-N-((4,6-dimethyl-2-oxo-1,2-dihydropyridin-3-yl)methyl)-2-methyl-2-vinyl-2,3-dihydrobenzofuran-5-carboxamide (33.5 mg, 0.080 mmol) and dimethylformamide (1.0 mL). A solution of sodium carbonate (161 µl, 0.161 mmol, 1 M) was added and the reaction degassed for ca. 15 minutes with nitrogen. Tetrakis(triphenylphosphine)palladium(0) (9.28 mg, 8.03 μmol) was added and degassing continued for a couple of minutes. The vial was then sealed and heated to 100° C. for ca. 90 minutes. The cooled reaction was diluted with methanol, filtered and purified by RP-HPLC (methanol-water gradient+0.1% TFA). The product containing fraction was treated with half-saturated sodium bicarbonate solution and concentrated under a stream of nitrogen. The resulting precipitate was filtered and rinsed with water. The filter paper was rinsed with methanol and the filtrate evaporated to give N-((4,6-dimethyl-2-oxo-1,2-dihydropyridin-3-yl)methyl)-2-methyl-7-(6-(piperazin-1-yl)pyridin-3-yl)-2-vinyl-2,3-dihydrobenzofuran-5-carboxamide (16 mg, 0.031 mmol, 39.1% yield) as an off white solid. $^1$H NMR (500 MHz, DMSO-d$_6$) δ 11.46 (s, 1H), 8.55 (d, J=2.1 Hz, 1H), 8.23 (br. s., 1H), 7.91 (dd, J=8.9, 2.2 Hz, 1H), 7.83 (s, 1H), 7.63 (br. s., 1H), 6.88 (d, J=9.0 Hz, 1H), 6.11 (dd, J=17.2, 10.7 Hz, 1H), 5.86 (s, 1H), 5.24 (d, J=17.2 Hz, 1H), 5.10 (d, J=10.7 Hz, 1H), 4.30 (d, J=4.4 Hz, 3H), 3.51-3.41 (m, 4H), 3.23 (d, J=15.9 Hz, 1H), 3.14 (d, J=16.6 Hz, 1H), 2.79 (d, J=4.6 Hz, 4H), 2.17 (s, 3H), 2.12 (s, 3H), 1.54 (s, 3H). MS(ES): m/z 500 [M+H]$^+$.

Example 60 t-Butyl 4-(5-(5-(((4,6-dimethyl-2-oxo-1,2-dihydropyridin-3-yl)methyl)carbamoyl)-2-methyl-2-vinyl-2,3-dihydrobenzofuran-7-yl)pyrimidin-2-yl)piperazine-1-carboxylate A reaction vial was charged with tert-butyl 4-(5-(4,4,5,5-tetramethyl-1,3,2-dioxaborolan-2-yl)pyrimidin-2-yl)piperazine-1-carboxylate (16.09 mg, 0.041 mmol), 7-bromo-N-((4,6-dimethyl-2-oxo-1,2-dihydropyridin-3-yl)methyl)-2-methyl-2-vinyl-2,3-dihydrobenzofuran-5-carboxamide (8.6 mg, 0.021 mmol) and dimethylformamide (0.5 mL). A solution of sodium carbonate (87 μl, 0.087 mmol, 1 M) was added and the reaction degassed for ca. 15 minutes with a stream of nitrogen. Tetrakis(triphenyl phosphine)palladium (0) (2.381 mg, 2.061 μmol) was then added and degassing continued for a few minutes. The vial was sealed and heated to 100° C. for ca. 120 minutes. The cooled reactions was diluted with DMF (1.5 mL) and filtered. The crude material was purified via preparative LC/MS with the following conditions: Column: Waters XBridge C18, 19×250 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-75% B over 25 minutes, then a 10-minute hold at 100% B; Flow: 20 mL/min. Fractions containing the desired product were combined and dried via centrifugal evaporation. The yield of the product was 3.5 mg (27%). $^1$H NMR (500 MHz, DMSO-d$_6$) δ 11.52 (br. s., 1H), 8.79 (s, 2H), 8.31-8.19 (m, 1H), 7.88 (s, 1H), 7.67 (s, 1H), 6.11 (dd, J=17.4, 10.7 Hz, 1H), 5.88 (s, 1H), 5.23 (d, J=17.1 Hz, 1H), 5.10 (d, J=10.4 Hz, 1H), 4.30 (d, J=4.9 Hz, 2H), 3.83-3.74

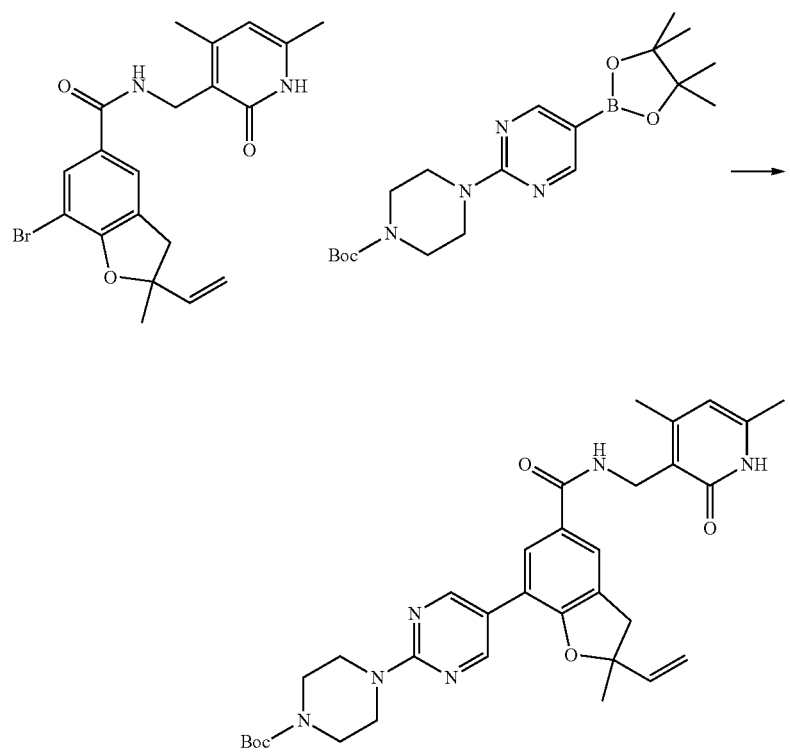

(m, 4H), 3.42 (br. s., 4H), 3.29-3.21 (m, 1H), 3.19-3.11 (m, 1H), 2.17 (s, 3H), 2.12 (s, 3H), 1.54 (s, 3H), 1.43 (s, 9H). MS(ES): m/z 601 [M+H]+.

Example 61

N-((4,6-Dimethyl-2-oxo-1,2-dihydropyridin-3-yl)methyl)-2-ethyl-7-(6-methoxypyridin-3-yl)-2-methyl-2,3-dihydrobenzofuran-5-carboxamide

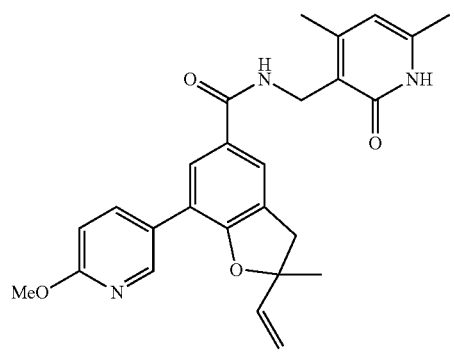

N-((4,6-Dimethyl-2-oxo-1,2-dihydropyridin-3-yl)methyl)-7-(6-methoxypyridin-3-yl)-2-methyl-2-vinyl-2,3-dihydrobenzofuran-5-carboxamide (5 mg, 0.011 mmol, Example 56) was dissolved in ethanol (4 mL) in a Parr bottle. Palladium on carbon (11.94 mg, 0.011 mmol) was added and the bottle was pressurized with 48 psi of hydrogen for 2 hours. The reaction was filtered through Celite, rinsed with ethyl acetate and evaporated to give N-((4,6-dimethyl-2-oxo-1,2-dihydropyridin-3-yl)methyl)-2-ethyl-7-(6-methoxypyridin-3-yl)-2-methyl-2,3-dihydrobenzofuran-5-carboxamide (4.8 mg, 10.19 μmol, 91% yield) as a colorless film. $^1$H NMR (400 MHz, METHANOL-d$_4$) δ 8.56 (d, J=2.2 Hz, 1H), 8.07 (dd, J=8.6, 2.4 Hz, 1H), 7.82 (d, J=1.1 Hz, 1H), 7.65 (s, 1H), 6.88 (d, J=8.6 Hz, 1H), 6.13 (s, 1H), 4.52 (s, 2H), 3.97 (s, 3H), 3.27-3.17 (m, 1H), 3.11-2.96 (m, 1H), 2.40 (s, 3H), 2.27 (s, 3H), 1.85 (q, J=7.3 Hz, 2H), 1.48 (s, 3H), 1.01 (t, J=7.4 Hz, 3H). MS(ES): m/z 448 [M+H]+.

Example 62

N-((4,6-Dimethyl-2-oxo-1,2-dihydropyridin-3-yl)methyl)-2-ethyl-2-methyl-7-(6-(piperazin-1-yl)pyridin-3-yl)-2,3-dihydrobenzofuran-5-carboxamide

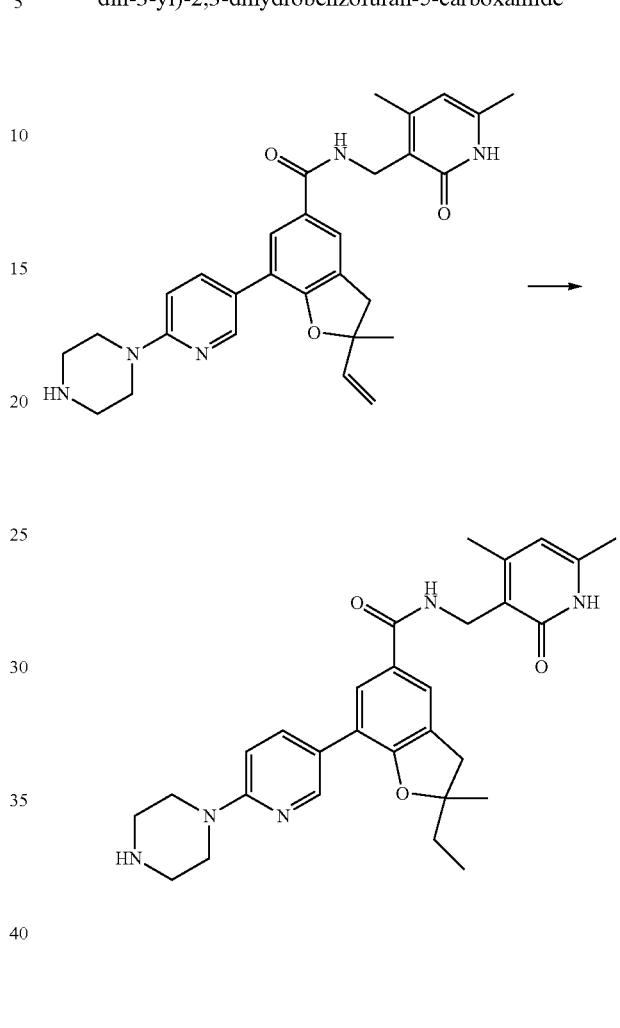

A Parr bottle was charged with N-((4,6-dimethyl-2-oxo-1,2-dihydropyridin-3-yl)methyl)-2-methyl-7-(6-(piperazin-1-yl)pyridin-3-yl)-2-vinyl-2,3-dihydrobenzofuran-5-carboxamide (20 mg, 0.040 mmol, Example 59) in ethanol (4 mL). Palladium on carbon (20 mg, 0.019 mmol) was added and the bottle pressurize to 48 psi with hydrogen for 1.5 hours. A couple drops of triethylamine were added and the reaction filtered through celite. Around 20 mg of a yellow film were isolated. The crude product was purified by RP-HPLC (methanol-water gradient+0.1% TFA). The product containing fraction was treated with half saturated sodium bicarbonate solution and concentrated. The resulting solid was filtered and air dried to give N-((4,6-dimethyl-2-oxo-1,2-dihydropyridin-3-yl)methyl)-2-ethyl-2-methyl-7-(6-(piperazin-1-yl)pyridin-3-yl)-2,3-dihydrobenzofuran-5-carboxamide (0.6 mg). $^1$H NMR (500 MHz, DMSO-d$_6$) δ 11.46 (br. s., 1H), 8.57-8.47 (m, 1H), 8.20 (t, J=4.9 Hz, 1H), 7.89 (dd, J=8.9, 2.5 Hz, 1H), 7.80 (d, J=1.7 Hz, 1H), 7.63 (s, 1H), 6.87 (d, J=8.6 Hz, 1H), 5.87 (s, 1H), 4.30 (d, J=4.7 Hz, 2H), 3.52-3.39 (m, 4H), 3.13 (d, J=16.1 Hz, 1H), 3.03-2.93 (m, 1H), 2.83-2.75 (m, 4H), 2.17 (s, 3H), 2.12 (s, 3H), 1.75 (q, J=7.2 Hz, 2H), 1.40 (s, 3H), 0.92 (t, J=7.5 Hz, 3H). MS(ES): m/z 502 [M+H]+.

Example 63

N-((4,6-Dimethyl-2-oxo-1,2-dihydropyridin-3-yl)methyl)-2-ethyl-2-methyl-7-(p-tolyl)-2,3-dihydrobenzofuran-5-carboxamide

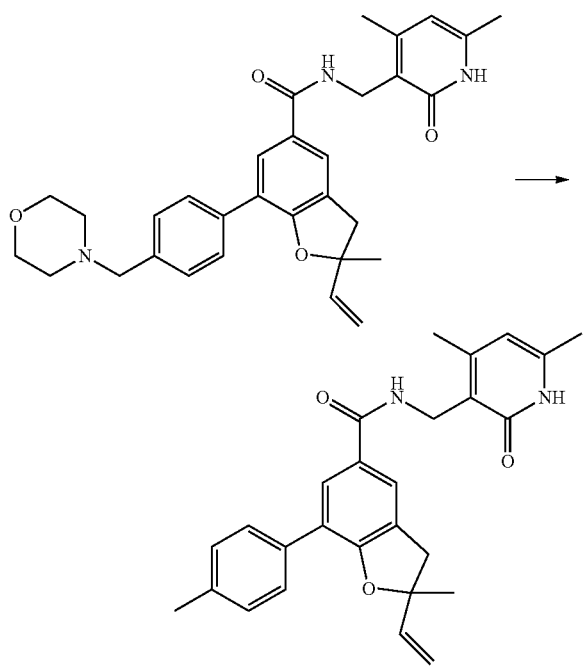

N-((4,6-Dimethyl-2-oxo-1,2-dihydropyridin-3-yl)methyl)-2-ethyl-2-methyl-7-(p-tolyl)-2,3-dihydrobenzofuran-5-carboxamide was prepared in 52% yield using the chemistry described for Example 62. $^1$H NMR (400 MHz, CHLOROFORM-d) δ 11.48 (br. s., 1H), 7.72 (d, J=1.5 Hz, 1H), 7.60 (d, J=8.1 Hz, 3H), 7.55 (s, 1H), 7.19 (d, J=7.9 Hz, 2H), 5.89 (s, 1H), 4.56 (d, J=5.7 Hz, 2H), 3.15-3.04 (m, 1H), 2.97-2.79 (m, 1H), 2.39 (s, 3H), 2.37 (s, 3H), 2.16 (s, 3H), 1.79 (q, J=7.5 Hz, 2H), 1.43 (s, 3H), 0.97 (t, J=7.4 Hz, 3H). MS(ES): m/z 431 [M+H]$^+$.

Example 64 rac-(3aS,8bS)-5-Bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide

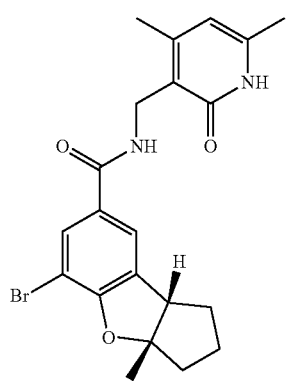 [SMILES: Cc1cc(C)c(CNC(=O)c2cc(Br)c3c(c2)[C@@H]2CCC[C@]2(C)O3)c(=O)[nH]1]

64A. Methyl 3-bromo-4-(cyclopent-1-en-1-ylmethoxy)benzoate

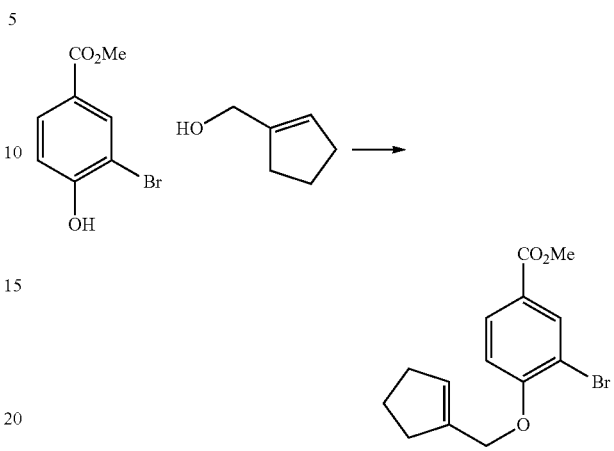

A solution of methyl 3-bromo-4-hydroxybenzoate (1.2 g, 5.19 mmol), cyclopent-1-en-1-ylmethanol (0.824 g, 8.40 mmol) and triphenylphosphine (2.64 g, 10.08 mmol) in THF (15 mL) under nitrogen was prepared. The solution was cooled in an ice bath and DIAD (1.960 ml, 10.08 mmol) was added. The cooling bath was removed and the reaction stirred overnight. The reaction was concentrated partly, applied to an 120 g Isco silica gel column and eluted with 0-30% ethyl acetate in hexanes. Evaporation of the appropriate fractions gave methyl 3-bromo-4-(cyclopent-1-en-1-ylmethoxy)benzoate (1.31 g, 4.13 mmol, 49.1% yield) as a pale pink solid. $^1$H NMR (400 MHz, DMSO-d$_6$) δ 8.09 (d, J=2.2 Hz, 1H), 7.93 (dd, J=8.7, 2.1 Hz, 1H), 7.25 (d, J=8.8 Hz, 1H), 5.80 (d, J=1.7 Hz, 1H), 4.81 (s, 2H), 3.83 (s, 3H), 2.44-2.26 (m, 4H), 1.98-1.80 (m, 2H). MS(ES): m/z 311 [M+H]$^+$.

64B. rac-(3aS,8bS)-Methyl 5-bromo-3a-methyl-2,3,3a,8b-tetrahydro-1H-cyclopenta[b]benzofuran-7-carboxylate

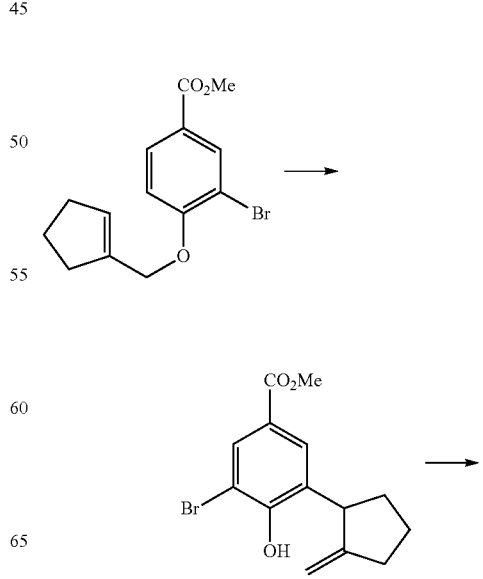

-continued

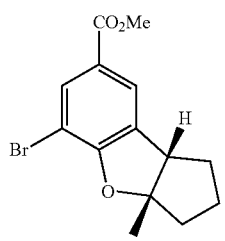

Methyl 3-bromo-4-(cyclopent-1-en-1-ylmethoxy)benzoate (767 mg, 2.465 mmol) was dissolved in Dowtherm (2.0 mL) in a reaction vial. The vial was flushed with nitrogen for 10 minutes, sealed and heated for 2 hours. LCMS looks like ca. 2:1 product/starting material. The cooled reaction was applied to an 80 g Isco silica gel column and eluted with 0-50% ethyl acetate in hexanes. Evaporation of the appropriate fractions gave the partially purified intermediate. This material was dissolved in formic acid and heated to 100° C. for an hour. The cooled reaction was diluted with ether and transferred to a separatory funnel. The acid was carefully neutralized with saturated sodium bicarbonate solution. The organic layer was dried over magnesium sulfate, filtered and evaporated. The crude product was purified on an Isco silica gel column using an ethyl acetate-hexanes gradient to give rac-(3aS,8bS)-Methyl 5-bromo-3a-methyl-2,3,3a,8b-tetrahydro-1H-cyclopenta[b]benzofuran-7-carboxylate (512 mg, 60%). $^1$H NMR (500 MHz, CHLOROFORM-d) δ 8.04 (d, J=1.7 Hz, 1H), 7.79-7.70 (m, 1H), 3.90 (s, 3H), 3.50 (d, J=8.4 Hz, 1H), 2.30-2.23 (m, 1H), 2.15-2.03 (m, 1H), 1.89-1.80 (m, 1H), 1.78-1.66 (m, 2H), 1.62 (s, 3H), 1.61-1.56 (m, 1H). MS(ES): m/z 311 [M+H]$^+$.

64C. rac-(3aS,8bS)-5-Bromo-3a-methyl-2,3,3a,8b-tetrahydro-1H-cyclopenta[b]benzofuran-7-carboxylic acid

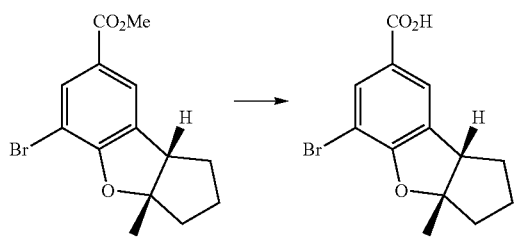 [SMILES: COC(=O)c1cc(Br)c2c(c1)[C@@H]1CCC[C@]1(C)O2 ; C[C@]12CCC[C@H]1c1cc(C(=O)O)cc(Br)c1O2]

A solution of rac-(3aR,8bR)-methyl 5-bromo-3a-methyl-2,3,3a,8b-tetrahydro-1H-cyclopenta[b]benzofuran-7-carboxylate (500 mg, 1.607 mmol) in THF (6 mL), water (2 mL) and methanol (1 mL) was prepared under nitrogen. Lithium hydroxide (3214 µl, 3.21 mmol) (1 M) was added and the reaction warmed to 55° C. After stirring for ca. 1.5 hour the reaction was cooled and neutralized with 1 N hydrochloric acid (3.21 mL). Concentration under a stream of nitrogen generated a solid that was filtered and rinsed with water. Drying in a ChemDry oven at 70° C. for an hour gave rac-(3aR,8bR)-5-bromo-3a-methyl-2,3,3a,8b-tetrahydro-1H-cyclopenta[b]benzofuran-7-carboxylic acid (423 mg, 1.424 mmol, 89% yield) as a tan solid. $^1$H NMR (400 MHz, DMSO-d$_6$) δ 12.80 (br. s., 1H), 7.85 (d, J=1.6 Hz, 1H), 7.77-7.68 (m, 1H), 3.58 (d, J=8.2 Hz, 1H), 2.15-2.00 (m, 2H), 1.81-1.61 (m, 3H), 1.54 (s, 3H), 1.45-1.27 (m, 1H). MS(ES): m/z 297 [M+H]$^+$.

64. rac-(3aS,8bS)-5-Bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide

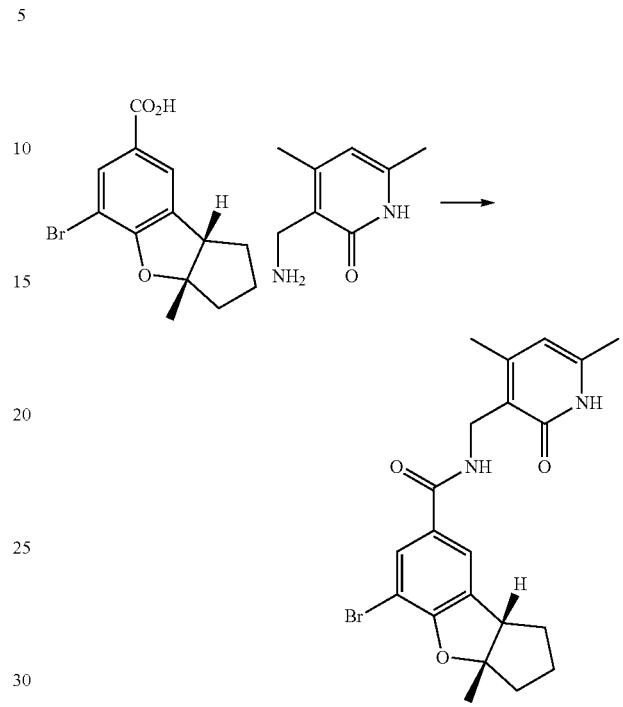

rac-(3aS,8bS)-5-Bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide was prepared from rac-(3aR,8bR)-5-bromo-3a-methyl-2,3,3a,8b-tetrahydro-1H-cyclopenta[b]benzofuran-7-carboxylic acid and 3-(aminomethyl)-4,6-dimethylpyridin-2(1H)-one hydrochloride in 94% yield using the procedure described for Example 6. $^1$H NMR (500 MHz, DMSO-d$_6$) δ 11.49 (br. s., 1H), 8.23 (br. s., 1H), 7.85 (s, 1H), 7.68 (s, 1H), 5.88 (s, 1H), 4.26 (d, J=4.4 Hz, 2H), 3.54 (d, J=8.8 Hz, 1H), 2.16 (s, 3H), 2.12 (s, 3H), 2.09-1.97 (m, 2H), 1.80-1.63 (m, 3H), 1.51 (s, 3H), 1.36 (dt, J=11.7, 5.8 Hz, 1H). MS(ES): m/z 431 [M+H]$^+$.

Example 65 rac-(3aS,8bS)—N-((4,6-Dimethyl-2-oxo-1,2-dihydropyridin-3-yl)methyl)-3a-methyl-5-(6-(piperazin-1-yl)pyridin-3-yl)-2,3,3a,8b-tetrahydro-1H-cyclopenta[b]benzofuran-7-carboxamide

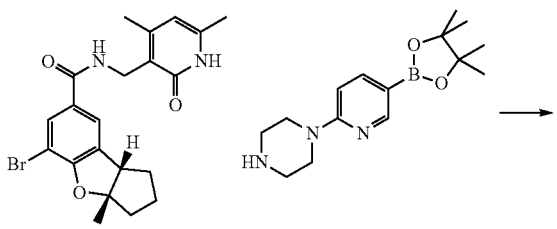

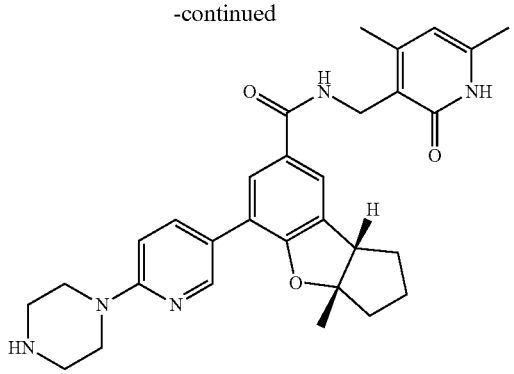

Example 65 was prepared from rac-(3aR,8bR)-5-bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide (Example 64) and 1-(5-(4,4,5,5-tetramethyl-1,3,2-dioxaborolan-2-yl)pyridin-2-yl)piperazine in 60% yield using the procedures of Example 10. MS(ES): m/z 514 [M+H]⁺.

Example 66 rac-(3aS,8bS)—N-((4,6-Dimethyl-2-oxo-1,2-dihydropyridin-3-yl)methyl)-5-(6-methoxypyridin-3-yl)-3a-methyl-2,3,3a,8b-tetrahydro-1H-cyclopenta[b]benzofuran-7-carboxamide

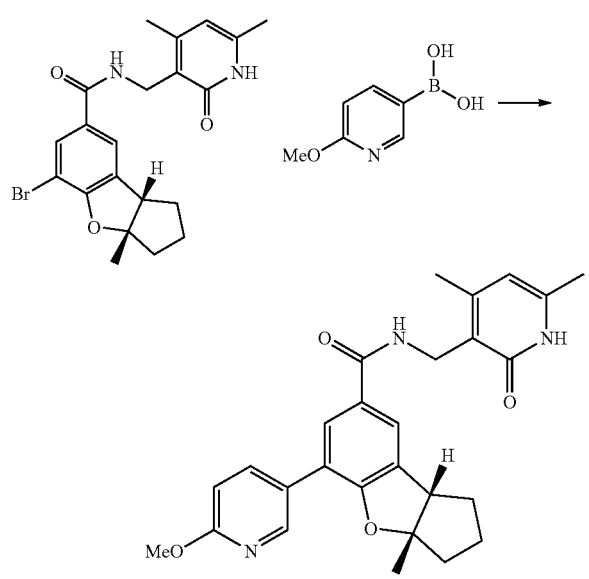

Example 66 was prepared from rac-(3aR,8bR)-5-bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide (Example 64) and (6-methoxypyridin-3-yl)boronic acid in 72% yield using the procedures of Example 10. ¹H NMR (500 MHz, DMSO-d₆) δ 11.49 (br. s., 1H), 8.54 (d, J=2.0 Hz, 1H), 8.31-8.19 (m, 1H), 8.04 (dd, J=8.8, 2.4 Hz, 1H), 7.83 (s, 1H), 7.67 (s, 1H), 6.91 (d, J=8.4 Hz, 1H), 5.88 (s, 1H), 4.30 (d, J=3.4 Hz, 2H), 3.89 (s, 3H), 3.47 (d, J=8.4 Hz, 1H), 2.17 (s, 3H), 2.12 (s, 3H), 2.06 (dd, J=13.0, 5.9 Hz, 2H), 1.77-1.59 (m, 3H), 1.52 (s, 3H), 1.47-1.32 (m, 1H). MS(ES): m/z 460 [M+H]⁺.

Example 67 rac-(3aS,8bS)—N-((4,6-Dimethyl-2-oxo-1,2-dihydropyridin-3-yl)methyl)-3a-methyl-5-(4-(piperidin-1-ylmethyl)phenyl)-2,3,3a,8b-tetrahydro-1H-cyclopenta[b]benzofuran-7-carboxamide

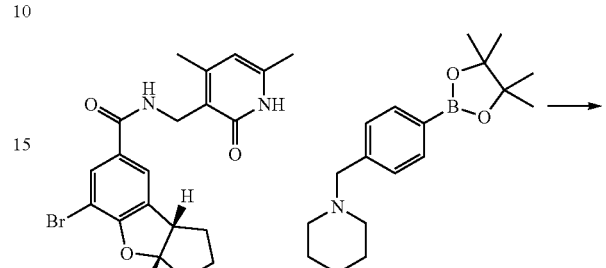

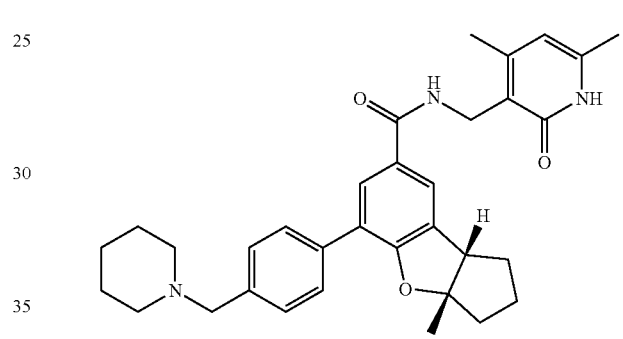

Example 67 was prepared from rac-(3aR,8bR)-5-bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide (Example 64) and 1-(4-(4,4,5,5-tetramethyl-1,3,2-dioxaborolan-2-yl)benzyl)piperidine in 82% yield using the procedures of Example 10. MS(ES): m/z 526 [M+H]⁺.

Example 68 rac-(3aS,8bS)—N-((4,6-Dimethyl-2-oxo-1,2-dihydropyridin-3-yl)methyl)-3a-methyl-5-(4-(piperazin-1-yl)phenyl)-2,3,3a,8b-tetrahydro-1H-cyclopenta[b]benzofuran-7-carboxamide

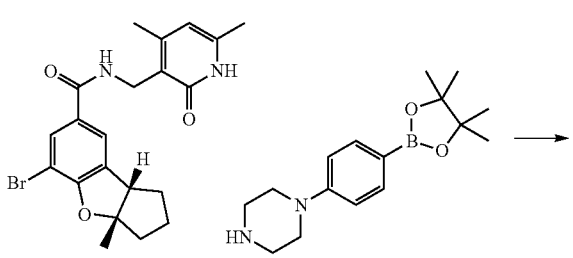

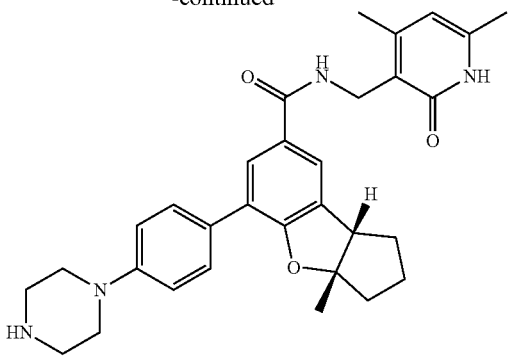

Example 68 was prepared from rac-(3aR,8bR)-5-bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide (Example 64) and 1-(4-(4,4,5,5-tetramethyl-1,3,2-dioxaborolan-2-yl)phenyl)piperazine in 68% yield using the procedures of Example 10. MS(ES): m/z 513 [M+H]$^+$.

Example 69 rac-(3aS,8bS)-5-Bromo-N-((4,6-dimethyl-2-oxo-1,2-dihydropyridin-3-yl)methyl)-3a,6-dimethyl-2, 3,3a,8b-tetrahydro-1H-cyclopenta[b]benzofuran-7-carboxamide

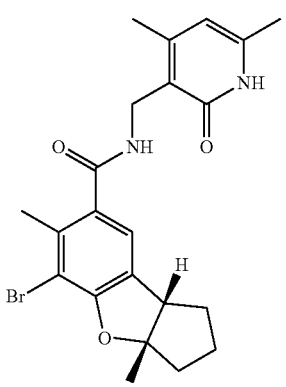 [SMILES: Cc1cc(C)c(CNC(=O)c2cc3c(c(Br)c2C)O[C@@]2(C)CCC[C@@H]32)c(=O)[nH]1]

69A. rac-(3aS,8bS)-5-Bromo-3a,6-dimethyl-2,3,3a,8b-tetrahydro-1H-cyclopenta[b]benzofuran-7-carboxylic acid

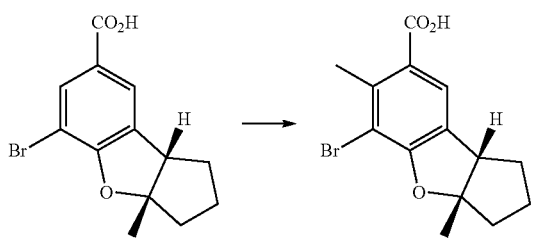 [SMILES: C[C@]12CCC[C@H]1c1cc(C(=O)O)cc(Br)c1O2 ; Cc1c(C(=O)O)cc2c(c1Br)O[C@@]1(C)CCC[C@@H]21]

A reaction vial was charged with rac-(3aR,8bR)-5-bromo-3a-methyl-2,3,3a,8b-tetrahydro-1H-cyclopenta[b]benzofuran-7-carboxylic acid (50 mg, 0.168 mmol), palladium(II) acetate (3.8 mg, 0.017 mmol), silver carbonate (93 mg, 0.337 mmol), 1,4-benzoquinone (0.9 mg, 8.41 μmol), lithium carbonate (24.9 mg, 0.337 mmol), t-Boc-L-Phe (8.9 mg, 0.034 mmol), potassium methyltrifluoroborate (61.6 mg, 0.505 mmol) and a stirring bar. t-Butanol (2.0 mL) was added and the vial was evacuated and filled with nitrogen three times. The sealed vial was stirred for 5 minutes then warmed to 90° C. for 12 hours. The cooled reaction was quenched with 1 N hydrochloric acid (3 mL). After sonication, the suspension was passed through a syringe filter and evaporated. The material was then dissolved in methanol, filtered and purified by RP-HPLC (methanol-water gradient+0.1% TFA). The product containing fractions were evaporated and azeotroped with acetonitrile. The material was dissolved in benzene, frozen and lyophilized to give 8 mg of a tan solid. $^1$H NMR (500 MHz, CHLOROFORM-d) δ7.38 (s, 1H), 3.49 (dd, J=9.1, 2.5 Hz, 1H), 2.52 (s, 3H), 2.32-2.24 (m, 1H), 2.17-2.05 (m, 1H), 1.84-1.70 (m, 4H). MS(ES): m/z 311 [M+H]$^+$.

69. rac-(3aS,8bS)-5-Bromo-N-((4,6-dimethyl-2-oxo-1,2-dihydropyridin-3-yl)methyl)-3a,6-dimethyl-2,3,3a,8b-tetrahydro-1H-cyclopenta[b]benzofuran-7-carboxamide

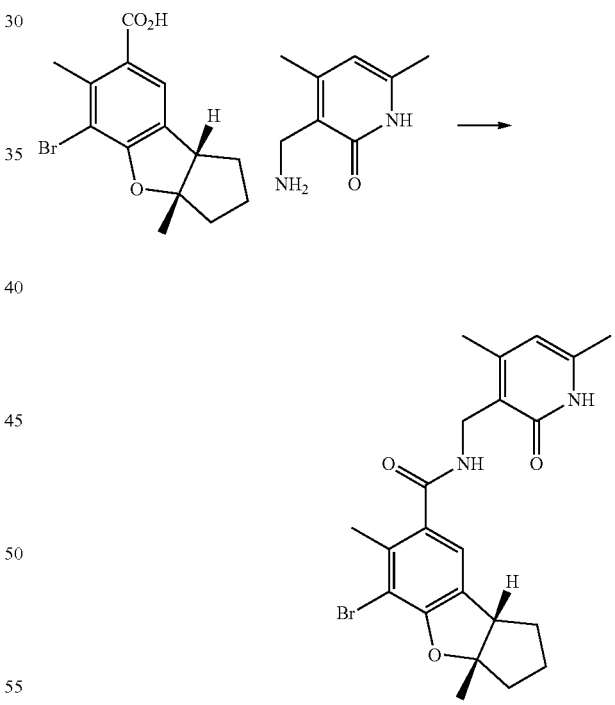

Example 69 was prepared from rac-(3aS,8bS)-5-bromo-3a,6-dimethyl-2,3,3a,8b-tetrahydro-1H-cyclopenta[b]benzofuran-7-carboxylic acid (Intermediate 69A) and 3-(aminomethyl)-4,6-dimethylpyridin-2(1H)-one hydrochloride in 59% yield using the procedures of Example 7. $^1$H NMR (500 MHz, DMSO-d$_6$) δ 8.08 (br. s., 1H), 7.22 (s, 1H), 5.87 (s, 1H), 4.22 (d, J=4.7 Hz, 2H), 3.17 (d, J=5.0 Hz, 1H), 2.19 (s, 3H), 2.18 (s, 3H), 2.12 (s, 3H), 2.04 (d, J=9.1 Hz, 2H), 1.79-1.60 (m, 3H), 1.47 (s, 3H), 1.41 (d, J=5.7 Hz, 1H). MS(ES): m/z 445 [M+H]$^+$.

Example 70

7-Bromo-N-((4,6-dimethyl-2-oxo-1,2-dihydropyridin-3-yl)methyl)-3H-spiro[benzofuran-2,1'-cyclopentane]-5-carboxamide

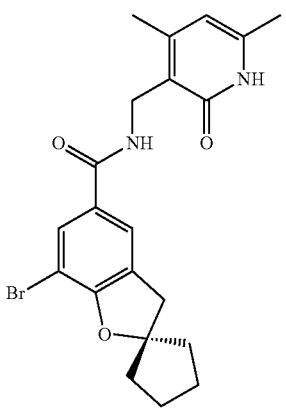

70A. Methyl 3-bromo-4-(2-oxocyclopentyl)oxy)benzoate

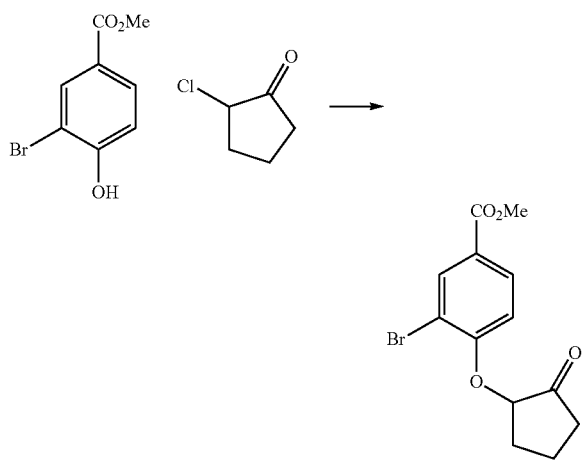

A flask was charged with methyl 3-bromo-4-hydroxybenzoate (1.48 g, 6.41 mmol) under nitrogen. The starting material was dissolved in dimethylformamide (12 mL) and potassium carbonate (1.771 g, 12.81 mmol) was added. The suspension was stirred for 5 minutes and 2-chlorocyclopentanone (0.833 ml, 8.33 mmol) was added. The reaction was then warmed to 60° C. and stirred for 1.5 hours. The cooled reaction was transferred to a separatory funnel and partitioned between ether and water. The organic layer was rinsed with water then brine. Drying over magnesium sulfate, filtration and evaporation provided the crude product. The crude product was applied to an 80 g Isco silica gel column and eluted with 0-50% ethyl acetate in hexanes. As the material was not sufficiently pure, it was applied to a 120 g Isco silica gel column and eluted with methylene chloride. Evaporation of the appropriate fractions gave methyl 3-bromo-4-((2-oxocyclopentyl)oxy)benzoate (0.81 g, 2.53 mmol, 39.6% yield) as a colorless viscous oil.

$^1$H NMR (400 MHz, DMSO-$d_6$) δ 8.09 (d, J=2.2 Hz, 1H), 7.91 (dd, J=8.7, 2.2 Hz, 1H), 7.32 (d, J=8.9 Hz, 1H), 5.22 (t, J=9.1 Hz, 1H), 3.84 (s, 3H), 2.49-2.39 (m, 1H), 2.39-2.23 (m, 2H), 2.10-1.97 (m, 1H), 1.97-1.82 (m, 2H). MS(ES): m/z 313 [M+H]$^+$.

70B. Methyl 3-bromo-4-(2-methylenecyclopentyl)oxy)benzoate

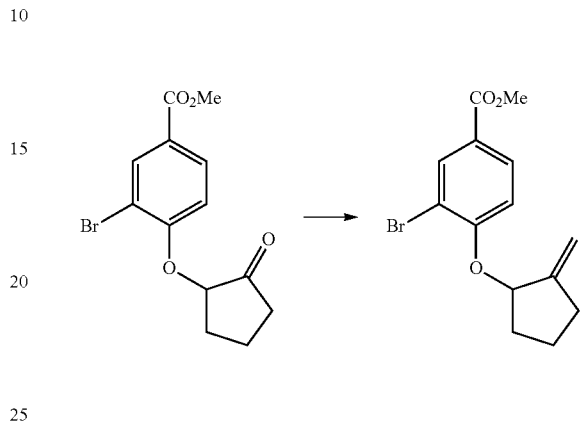

A 100 mL flask with stir bar was oven dried and cooled under vacuum. The flask was charged with methyltriphenylphosphonium bromide (1.109 g, 3.10 mmol) and dry THF (8 mL). Potassium tert-butoxide (0.348 g, 3.10 mmol) was added and stirring continued for 2 hours. Methyl 3-bromo-4-((2-oxocyclopentyl)oxy)benzoate (0.81 g, 2.59 mmol) dissolved in THF (3 mL) was then added. The reaction was then stirred overnight. The reaction was transferred to a separatory funnel and partioned between water and ether. The organic layer was washed with brine. Drying over magnesium sulfate, filtration and evaporation provided the crude product. This material was applied to a 40 g Isco silica gel column and eluted with 0-50% ethyl acetate in hexanes. Evaporation of the appropriate fractions gave methyl 3-bromo-4-((2-methylenecyclopentyl)oxy)benzoate (396 mg, 1.209 mmol, 46.7% yield) as a colorless oil. $^1$H NMR (400 MHz, DMSO-$d_6$) δ 8.09 (d, J=2.2 Hz, 1H), 7.93 (dd, J=8.7, 2.2 Hz, 1H), 7.44-7.29 (m, 1H), 5.25 (t, J=4.4 Hz, 1H), 5.22-5.17 (m, 1H), 5.12 (s, 1H), 3.84 (s, 3H), 2.49-2.41 (m, 1H), 2.39-2.26 (m, 1H), 2.17-2.04 (m, 1H), 1.93-1.82 (m, 1H), 1.81-1.66 (m, 2H).

70C. Methyl 7-bromo-3H-spiro[benzofuran-2,1'-cyclopentane]-5-carboxylate

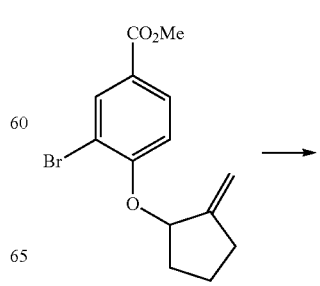

-continued

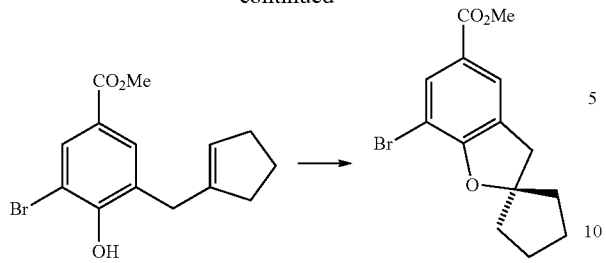

Methyl 3-bromo-4-((2-methylenecyclopentyl)oxy)benzoate (390 mg, 1.253 mmol) was dissolved in Dowtherm (2.0 mL) under nitrogen. The vial was warmed to 180° C. for an hour. The cooled reaction was applied to a 40 g Isco silica gel column and eluted with 0-50% ethyl acetate in hexanes. Evaporation of the appropriate fractions gave the desired intermediate (621 mg). This material looked excellent by 1H-NMR except for the presence of some Dowtherm. $^1$H NMR (400 MHz, DMSO-$d_6$) δ 9.95 (s, 1H), 7.92 (d, J=2.2 Hz, 1H), 7.65 (d, J=2.1 Hz, 1H), 5.37-5.09 (m, 1H), 3.81 (s, 3H), 3.32 (s, 2H), 2.31-2.21 (m, 2H), 2.19 (t, J=6.7 Hz, 2H), 1.88-1.73 (m, 2H). This material was suspended in formic acid (5 mL) under nitrogen and warmed to 100° C. for 1 hour. The cooled reaction was transferred to a separatory funnel and diluted with ether. The formic acid was carefully neutralized with saturated sodium bicarbonate solution. The organic layer was washed with brine. Drying over magnesium sulfate, filtration and evaporation gave the crude product. This material was applied to a 40 g Isco silica gel column and eluted with 0-30% ethyl acetate in hexanes. Evaporation of the appropriate fractions gave methyl 7-bromo-3H-spiro[benzofuran-2,1'-cyclopentane]-5-carboxylate (330 mg, 1.039 mmol, 83% yield) as a colorless solid. $^1$H NMR (400 MHz, DMSO-$d_6$) δ 7.86 (d, J=1.5 Hz, 1H), 7.76 (d, J=1.5 Hz, 1H), 3.80 (s, 3H), 3.34 (s, 2H), 2.08-1.93 (m, 2H), 1.89-1.60 (m, 6H).

70D. 7-Bromo-3H-spiro[benzofuran-2,1'-cyclopentane]-5-carboxylic acid

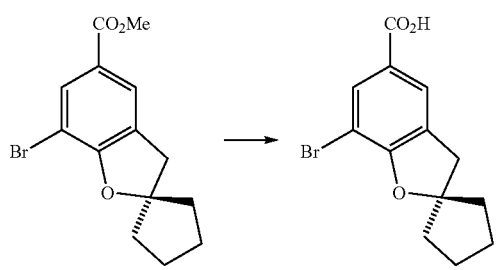

A solution of methyl 7-bromo-3H-spiro[benzofuran-2,1'-cyclopentane]-5-carboxylate (320 mg, 1.028 mmol) in tetrahydrofuran (6 mL)-methanol (2 mL)-water (2 mL) was prepared under nitrogen. A solution of lithium hydroxide (2057 μl, 2.057 mmol, 1 N) was added and stirring continued overnight. The reaction was quenched with 1 N hydrochloric acid (2.06 mL) and concentrated under a stream of nitrogen. The resulting solid was filtered, rinsed with water and then a little hexanes. Drying in the ChemDry oven at 70° C. for an hour gave 7-bromo-3H-spiro[benzofuran-2,1'-cyclopentane]-5-carboxylic acid (287 mg, 0.918 mmol, 89% yield) as a colorless solid. $^1$H NMR (400 MHz, DMSO-$d_6$) δ 12.80 (s, 1H), 7.92-7.80 (m, 1H), 7.75 (d, J=1.5 Hz, 1H), 3.35 (s, 2H), 2.10-1.96 (m, 2H), 1.91-1.64 (m, 6H). MS(ES): m/z 297 [M+H]$^+$.

70. 7-Bromo-N-((4,6-dimethyl-2-oxo-1,2-dihydropyridin-3-yl)methyl)-3H-spiro[benzofuran-2,1'-cyclopentane]-5-carboxamide

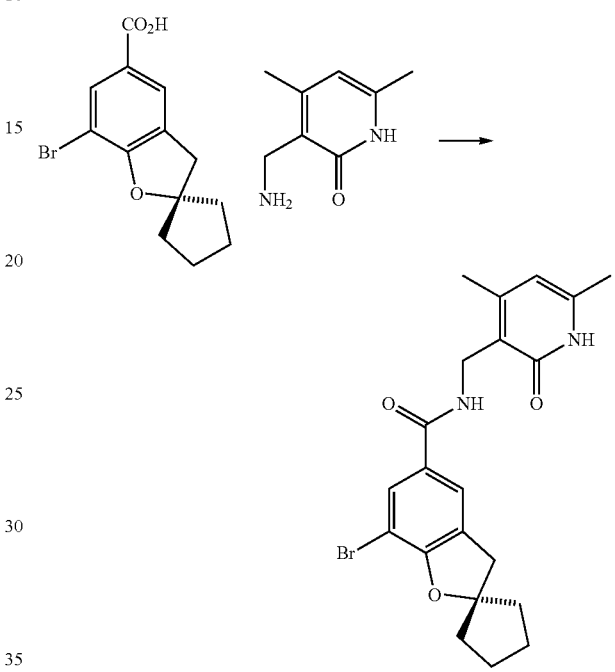

Example 70 was prepared from 7-bromo-3H-spiro[benzofuran-2,1'-cyclopentane]-5-carboxylic acid and 3-(aminomethyl)-4,6-dimethylpyridin-2(1H)-one hydrochloride in 36% yield using the procedures of Example 7. $^1$H NMR (500 MHz, DMSO-$d_6$) δ 11.48 (br. s., 1H), 8.24 (br. s., 1H), 7.85 (s, 1H), 7.70 (s, 1H), 5.87 (s, 1H), 4.26 (d, J=4.7 Hz, 2H), 3.31 (s, 2H), 2.15 (s, 3H), 2.12 (s, 3H), 1.99 (br. s., 2H), 1.87-1.64 (m, 6H). MS(ES): m/z 431 [M+H]$^+$.

Example 71

N-((4,6-Dimethyl-2-oxo-1,2-dihydropyridin-3-yl)methyl)-7-(6-methoxypyridin-3-yl)-3H-spiro[benzofuran-2,1'-cyclopentane]-5-carboxamide

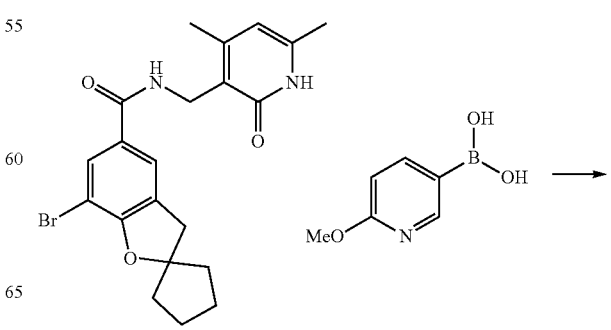

-continued

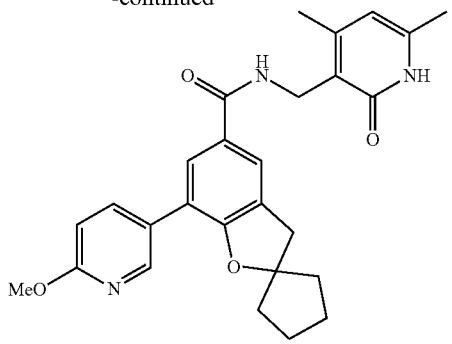

Example 71 was prepared from 7-bromo-N-((4,6-dimethyl-2-oxo-1,2-dihydropyridin-3-yl)methyl)-3H-spiro[benzofuran-2,1'-cyclopentane]-5-carboxamide (Example 70) and (6-methoxypyridin-3-yl)boronic acid in 70% yield using the procedures of Example 10. $^1$H NMR (500 MHz, DMSO-$d_6$) δ 11.49 (br. s., 1H), 8.55 (d, J=2.0 Hz, 1H), 8.26 (br. s., 1H), 8.05 (dd, J=8.6, 2.2 Hz, 1H), 7.85 (s, 1H), 7.69 (s, 1H), 6.91 (d, J=8.8 Hz, 1H), 5.88 (s, 1H), 4.30 (d, J=4.7 Hz, 2H), 3.89 (s, 3H), 3.25 (s, 2H), 2.17 (s, 3H), 2.12 (s, 3H), 2.01 (br. s., 2H), 1.86-1.62 (m, 6H), 1.86-1.62 (m, 6H). MS(ES): m/z 460 [M+H]$^+$.

Example 72

N-((4,6-Dimethyl-2-oxo-1,2-dihydropyridin-3-yl)methyl)-7-(6-(piperazin-1-yl)pyridin-3-yl)-3H-spiro[benzofuran-2,1'-cyclopentane]-5-carboxamide

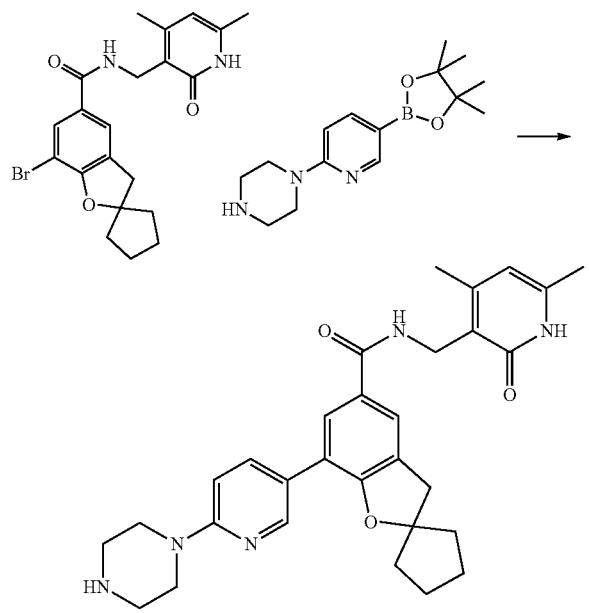

Example 72 was prepared from 7-bromo-N-((4,6-dimethyl-2-oxo-1,2-dihydropyridin-3-yl)methyl)-3H-spiro[benzofuran-2,1'-cyclopentane]-5-carboxamide (Example 70) and 1-(4-(4,4,5,5-tetramethyl-1,3,2-dioxaborolan-2-yl)phenyl)piperazine in 34% yield using the procedures of Example 10. $^1$H NMR (500 MHz, DMSO-$d_6$) δ 8.51 (d, J=2.0 Hz, 1H), 8.24 (t, J=4.7 Hz, 1H), 7.88 (dd, J=8.9, 2.2 Hz, 1H), 7.80 (s, 1H), 7.62 (s, 1H), 6.87 (d, J=9.1 Hz, 1H), 6.92-6.82 (m, 1H), 5.86 (s, 1H), 4.29 (d, J=4.7 Hz, 2H), 3.22 (s, 2H), 2.80 (br. s., 4H), 2.16 (s, 3H), 2.11 (s, 3H), 1.99 (br. s., 2H), 1.83-1.65 (m, 7H). MS(ES): m/z 514 [M+H]$^+$.

Example 73 tert-Butyl 4-(5-(5-(((4,6-dimethyl-2-oxo-1,2-dihydropyridin-3-yl)methyl)carbamoyl)-3H-spiro[benzofuran-2,1'-cyclopentan]-7-yl)pyrimidin-2-yl)piperazine-1-carboxylate

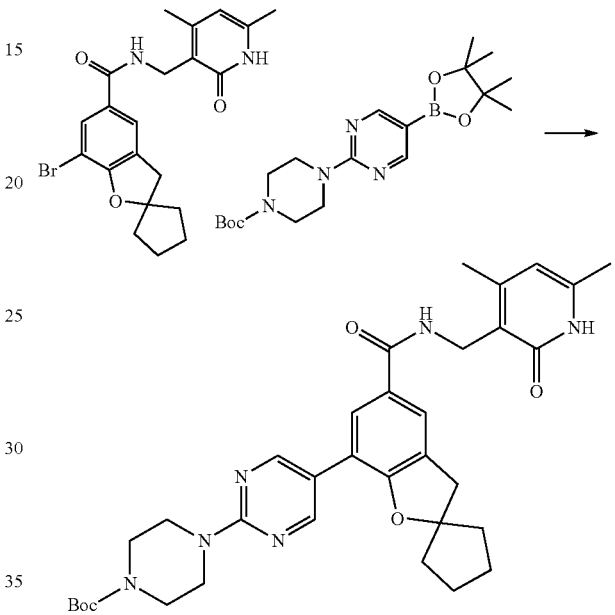

Example 73 was prepared from 7-bromo-N-((4,6-dimethyl-2-oxo-1,2-dihydropyridin-3-yl)methyl)-3H-spiro[benzofuran-2,1'-cyclopentane]-5-carboxamide (Example 70) and tert-butyl 4-(5-(4,4,5,5-tetramethyl-1,3,2-dioxaborolan-2-yl)pyrimidin-2-yl)piperazine-1-carboxylate in 32% yield using the procedures of Example 10. $^1$H NMR (500 MHz, DMSO-$d_6$) δ 11.50 (br. s., 1H), 8.76 (s, 2H), 8.23 (br. s., 1H), 7.85 (s, 1H), 7.67 (s, 1H), 5.88 (s, 1H), 4.30 (d, J=4.0 Hz, 2H), 3.77 (br. s., 4H), 3.24 (s, 2H), 2.51 (br. s., 4H), 2.17 (s, 3H), 2.12 (s, 3H), 2.01 (d, J=5.0 Hz, 2H), 1.77 (d, J=9.1 Hz, 6H), 1.43 (s, 9H). MS(ES): m/z 615 [M+H]$^+$.

Example 74

N-((4,6-Dimethyl-2-oxo-1,2-dihydropyridin-3-yl)methyl)-7-(4-(piperidin-1-ylmethyl)phenyl)-3H-spiro[benzofuran-2,1'-cyclopentane]-5-carboxamide

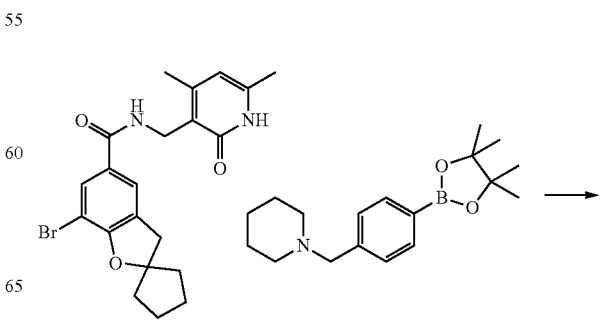

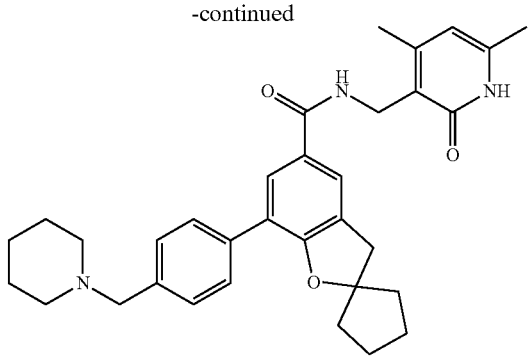

Example 74 was prepared from 7-bromo-N-((4,6-dimethyl-2-oxo-1,2-dihydropyridin-3-yl)methyl)-3H-spiro[benzofuran-2,1'-cyclopentane]-5-carboxamide (Example 70) and 1-(4-(4,4,5,5-tetramethyl-1,3,2-dioxaborolan-2-yl)benzyl)piperidine in 49% yield using the procedures of Example 10. $^1$H NMR (500 MHz, DMSO-d$_6$) δ 8.26 (t, J=4.5 Hz, 1H), 7.82 (s, 1H), 7.66 (d, J=8.4 Hz, 3H), 7.33 (d, J=8.1 Hz, 2H), 5.86 (s, 1H), 4.29 (d, J=4.7 Hz, 2H), 3.23 (s, 2H), 2.32 (br. s., 4H), 2.15 (s, 3H), 2.11 (s, 3H), 1.99 (br. s., 2H), 1.87 (s, 2H), 1.83-1.67 (m, 6H), 1.54-1.44 (m, 4H), 1.38 (br. s., 2H). MS(ES): m/z 526 [M+H]$^+$.

Example 75

7-Bromo-N-((4,6-dimethyl-2-oxo-1,2-dihydropyridin-3-yl)methyl)-2H-spiro[benzofuran-3,1'-cyclopentane]-5-carboxamide

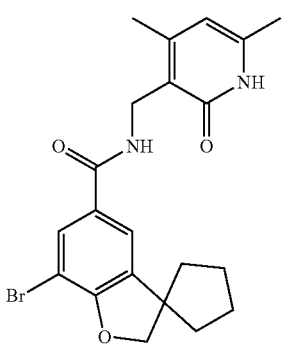 [SMILES: Cc1cc(C)c(CNC(=O)c2cc(Br)c3c(c2)C2(CCCC2)CO3)c(=O)[nH]1]

75A. 2H-Spiro[benzofuran-3,1'-cyclopentane]-5-carboxylic acid

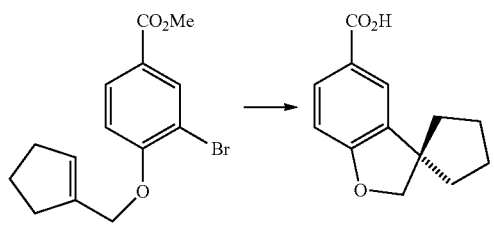

A flask and stir bar were oven dried and cooled under vacuum. The flask was charged with methyl 3-bromo-4-(cyclopent-1-en-1-ylmethoxy)benzoate (456 mg, 1.465 mmol, Intermediate 64A), tri-n-butyltin hydride (587 μl, 2.198 mmol) and AIBN (24.06 mg, 0.147 mmol) in toluene (5.0 mL). The reaction was subjected to three cycles of vacuum/nitrogen and finally one cycle of vacuum/argon. The flask was heated to 90° C. for an hour. The cooled reaction was the evaporated and dissolved in tetrahydrofuran-water (3:1, 8 mL). A solution of lithium hydroxide (5.0 mL, 1 N) and a little methanol to aid dissolution were then added. The reaction was stirred overnight. As the reaction was incomplete, it was warmed to 55° C. for ca. 5 hours. The cooled reaction was passed through a syringe filter and transferred to a separatory funnel. The aqueous layer was extracted twice with ether. The aqueous layer was the acidified with 1 N hydrochloric acid (5 mL). The resulting solid was filtered, rinsed with water and a little hexanes. Drying in the ChemDry oven at 70° C. for 0.5 hour gave 2H-spiro[benzofuran-3,1'-cyclopentane]-5-carboxylic acid (274.5 mg, 1.170 mmol, 80% yield) as a colorless solid. $^1$H NMR (400 MHz, DMSO-d$_6$) δ 12.55 (s, 1H), 7.82-7.71 (m, 2H), 6.92-6.73 (m, 1H), 4.40 (s, 2H), 1.95-1.77 (m, 6H), 1.75-1.61 (m, 2H). $^{13}$C NMR (101 MHz, DMSO-d$_6$) δ 167.5, 163.7, 136.3, 131.1, 124.8, 124.0, 109.4, 85.3, 52.3, 40.2, 25.1. MS(ES): m/z 219 [M+H]$^+$.

75B. 7-Bromo-2H-spiro[benzofuran-3,1'-cyclopentane]-5-carboxylic acid

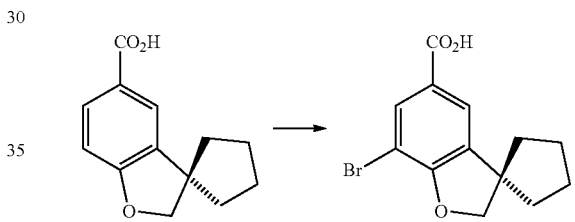

To a suspension of 2H-spiro[benzofuran-3,1'-cyclopentane]-5-carboxylic acid (166 mg, 0.761 mmol) in glacial acetic acid (1 mL) was added bromine (58.8 μl, 1.141 mmol). After ca. 6 hours, another portion of bromine (58.8 μl, 1.141 mmol) was added. After 2 hours the reaction was diluted with water. The resulting solid was filtered and rinsed well with water and hexanes. Air-drying gave 7-bromo-2H-spiro[benzofuran-3,1'-cyclopentane]-5-carboxylic acid (210 mg, 0.671 mmol, 88% yield) as an off white solid. $^1$H NMR (500 MHz, DMSO-d$_6$) δ 12.88 (br. s., 1H), 7.88 (d, J=1.7 Hz, 1H), 7.73 (d, J=1.5 Hz, 1H), 4.51 (s, 2H), 1.97-1.76 (m, 6H), 1.73-1.56 (m, 2H). MS(ES): m/z 297 [M+H]$^+$.

75. 7-Bromo-N-((4,6-dimethyl-2-oxo-1,2-dihydropyridin-3-yl)methyl)-2H-spiro[benzofuran-3,1'-cyclopentane]-5-carboxamide

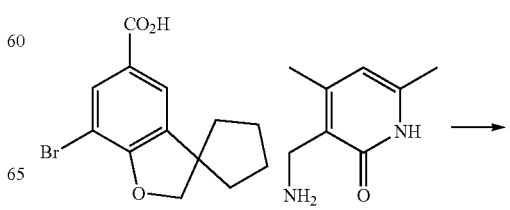

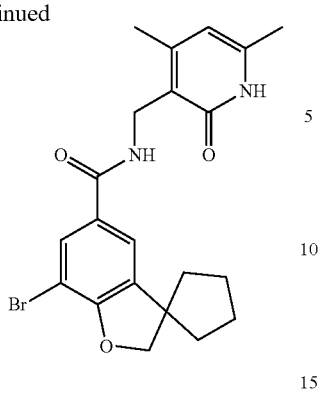

Example 75 was prepared from 7-bromo-2H-spiro[benzofuran-3,1'-cyclopentane]-5-carboxylic acid and 3-(aminomethyl)-4,6-dimethylpyridin-2(1H)-one hydrochloride in 83% yield using the procedures of Example 7. $^1$H NMR (500 MHz, DMSO-$d_6$) δ 11.58 (br. s., 1H), 8.39 (br. s., 1H), 7.94 (s, 1H), 7.79 (s, 1H), 5.96 (s, 1H), 4.53 (s, 2H), 4.34 (d, J=4.7 Hz, 2H), 2.24 (s, 3H), 2.19 (s, 3H), 1.89 (d, J=11.8 Hz, 6H), 1.74 (br. s., 2H). MS(ES): m/z 431 [M+H]$^+$.

Example 76

N-((4,6-Dimethyl-2-oxo-1,2-dihydropyridin-3-yl)methyl)-7-(6-methoxypyridin-3-yl)-2H-spiro[benzofuran-3,1'-cyclopentane]-5-carboxamide

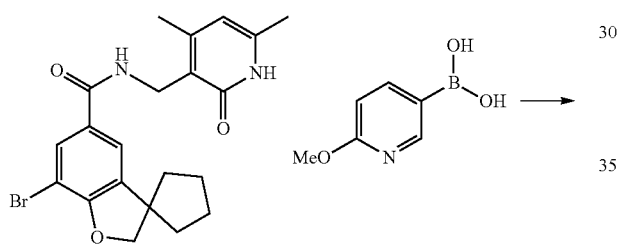

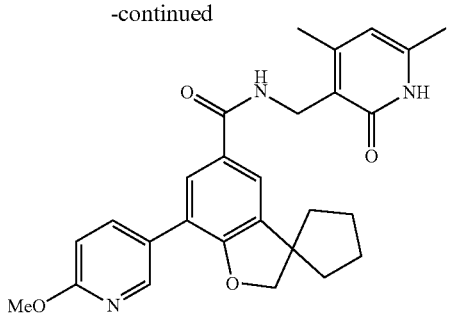

Example 76 was prepared from 7-bromo-N-((4,6-dimethyl-2-oxo-1,2-dihydropyridin-3-yl)methyl)-2H-spiro[benzofuran-3,1'-cyclopentane]-5-carboxamide (Example 75) and (6-methoxypyridin-3-yl)boronic acid in 49% yield using the procedures of Example 10. $^1$H NMR (500 MHz, DMSO-$d_6$) δ 11.51 (br. s., 1H), 8.53 (d, J=1.7 Hz, 1H), 8.33 (br. s., 1H), 8.05 (dd, J=8.6, 2.2 Hz, 1H), 7.87 (s, 1H), 7.71 (s, 1H), 6.91 (d, J=8.8 Hz, 1H), 5.88 (s, 1H), 4.43 (s, 2H), 4.30 (d, J=4.4 Hz, 2H), 3.89 (s, 3H), 2.18 (s, 3H), 2.12 (s, 3H), 1.86 (br. s., 6H), 1.70 (br. s., 2H). MS(ES): m/z 460 [M+H]$^+$.

Example 77

N-((4,6-Dimethyl-2-oxo-1,2-dihydropyridin-3-yl)methyl)-7-(6-(piperazin-1-yl)pyridin-3-yl)-2H-spiro[benzofuran-3,1'-cyclopentane]-5-carboxamide

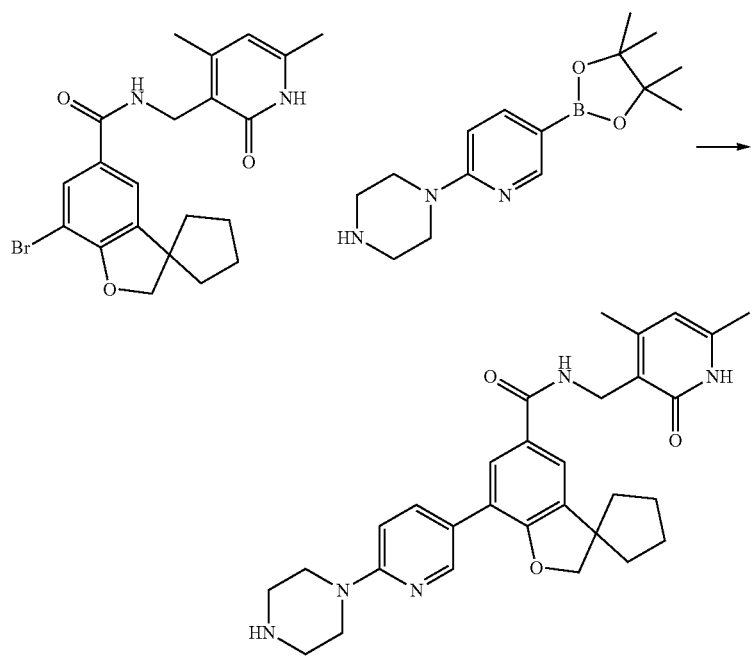

Example 77 was prepared from 7-bromo-N-((4,6-dimethyl-2-oxo-1,2-dihydropyridin-3-yl)methyl)-2H-spiro[benzofuran-3,1'-cyclopentane]-5-carboxamide (Example 75) and 1-(5-(4,4,5,5-tetramethyl-1,3,2-dioxaborolan-2-yl)pyridin-2-yl)piperazine in 59% yield using the procedures of Example 10. MS(ES): m/z 514 [M+H]$^+$.

Example 78

N-((4,6-Dimethyl-2-oxo-1,2-dihydropyridin-3-yl)methyl)-7-(4-(piperidin-1-ylmethyl)phenyl)-2H-spiro[benzofuran-3,1'-cyclopentane]-5-carboxamide

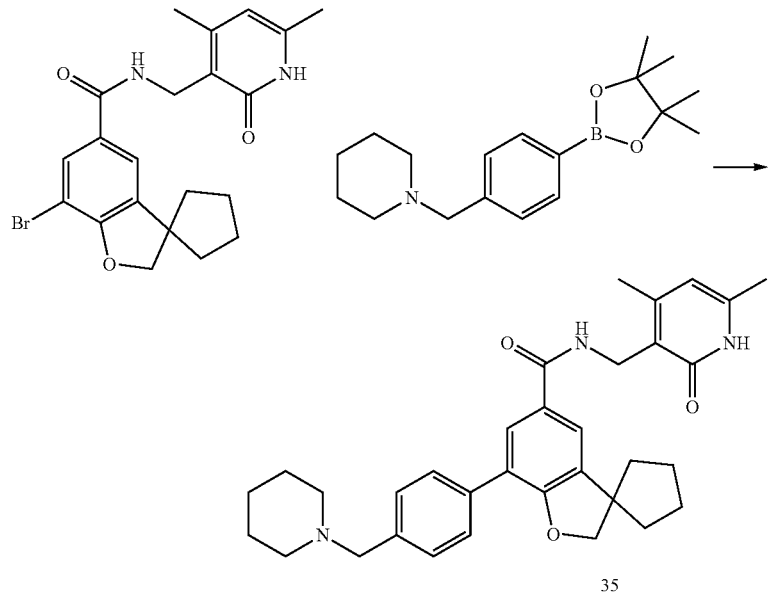

Example 78 was prepared from 7-bromo-N-((4,6-dimethyl-2-oxo-1,2-dihydropyridin-3-yl)methyl)-2H-spiro[benzofuran-3,1'-cyclopentane]-5-carboxamide (Example 75) and 1-(4-(4,4,5,5-tetramethyl-1,3,2-dioxaborolan-2-yl)benzyl)piperidine in 67% yield using the procedures of Example 10. MS(ES): m/z 526 [M+H]$^+$.

Example 79

7-Bromo-N-((4,6-dimethyl-2-oxo-1,2-dihydropyridin-3-yl)methyl)-2-isopropyl-2,3-dihydrobenzofuran-5-carboxamide

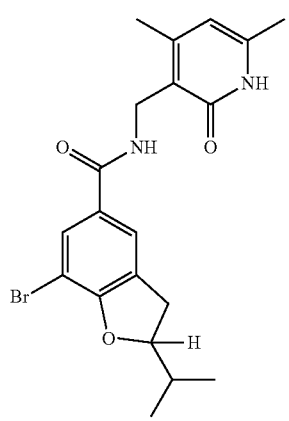 [SMILES: Cc1cc(C)c(CNC(=O)c2cc(Br)c3c(c2)CC(C(C)C)O3)c(=O)[nH]1]

79A. Ethyl 2-(prop-1-en-2-yl)-2,3-dihydrobenzofuran-5-carboxylate

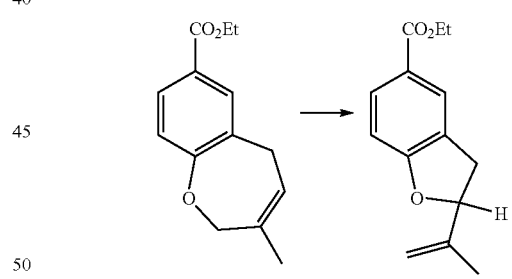

A vial was charged with ethyl 3-methyl-2,5-dihydrobenzo[b]oxepine-7-carboxylate (190 mg, 0.818 mmol, Intermediate 53B) in dimethylformamide (3.0 mL). The solution was subjected to vacuum for 10 minutes and then flushed with argon. Tetrakis(triphenylphosphine)palladium(0) (47.3 mg, 0.041 mmol) was added and the flask evacuated and sealed under argon. The reaction was then warmed to 55° C. for two hours. The cooled reaction was purified by RP-HPLC (methanol-water gradient+0.1% TFA). Evaporation of the product containing peaks and azeotroping with ethanol gave ethyl 2-(prop-1-en-2-yl)-2,3-dihydrobenzofuran-5-carboxylate (79 mg, 42%). $^1$H NMR (400 MHz, DMSO-d$_6$) δ 7.87-7.72 (m, 2H), 6.90 (d, J=8.4 Hz, 1H), 5.45-5.28 (m, 1H), 5.08 (s, 1H), 4.93 (s, 1H), 4.28 (q, J=7.2 Hz, 2H), 3.45

(dd, J=16.1, 9.7 Hz, 1H), 3.07 (dd, J=16.1, 7.7 Hz, 1H), 1.72 (s, 3H), 1.31 (t, J=7.0 Hz, 3H).

79B. Ethyl 2-isopropyl-2,3-dihydrobenzofuran-5-carboxylate

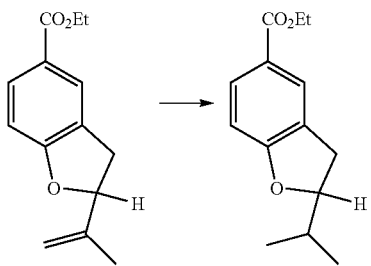 [SMILES: C=C(C)C1Cc2cc(C(=O)OCC)ccc2O1 ; CCOC(=O)c1ccc2c(c1)CC(C(C)C)O2]

A Parr bottle was charged with ethyl 2-(prop-1-en-2-yl)-2,3-dihydrobenzofuran-5-carboxylate (109 mg, 0.469 mmol) in ethanol (6 mL). Palladium on carbon (20 mg, 0.019 mmol) was added and the bottle was pressurized to ca. 48 psi with hydrogen for 2 hours. The reaction was then filtered through Celite and evaporated. The crude product was purified on an Isco column, eluted with 0-30% ethyl acetate in hexanes to give ethyl 2-isopropyl-2,3-dihydrobenzofuran-5-carboxylate (52 mg, 0.222 mmol, 47.3% yield) as a colorless oil. $^1$H NMR (400 MHz, CHLOROFORM-d) δ 7.95-7.84 (m, 2H), 6.78 (d, J=8.1 Hz, 1H), 4.62 (td, J=8.7, 6.8 Hz, 1H), 4.36 (q, J=7.2 Hz, 2H), 3.23 (dd, J=15.7, 9.1 Hz, 1H), 2.98 (dd, J=15.7, 8.3 Hz, 1H), 2.00 (dsxt, J=13.5, 6.7 Hz, 1H), 1.40 (t, J=7.2 Hz, 3H), 1.06 (d, J=6.8 Hz, 3H), 1.00 (d, J=6.6 Hz, 3H).

79C. 2-Isopropyl-2,3-dihydrobenzofuran-5-carboxylic acid

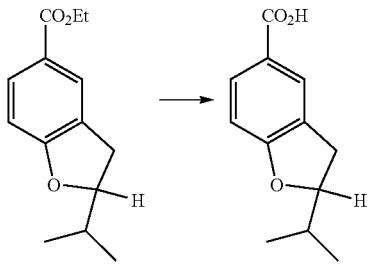 [SMILES: CCOC(=O)c1ccc2c(c1)CC(C(C)C)O2 ; CC(C)C1Cc2cc(C(=O)O)ccc2O1]

A solution of ethyl 2-isopropyl-2,3-dihydrobenzofuran-5-carboxylate (52 mg, 0.222 mmol) in tetrahydrofuran-water (3:1, 4 mL) was prepared. A solution of lithium hydroxide (666 µl, 0.666 mmol, 1 M) and enough methanol to make the reaction homogeneous were added. The flask was sealed and warmed to 55° C. The cooled reaction was quenched with 1 N hydrochloric acid. Concentration under a stream of nitrogen generated a precipitate which was filtered and rinsed with water. Drying in a ChemDry oven at 75° C. for an hour gave 2-isopropyl-2,3-dihydrobenzofuran-5-carboxylic acid (39.6 mg, 0.188 mmol, 85% yield) as a colorless solid. $^1$H NMR (400 MHz, DMSO-d$_6$) δ 12.47 (br. s., 1H), 7.77 (s, 1H), 7.74 (d, J=8.1 Hz, 1H), 6.81 (d, J=8.1 Hz, 1H), 4.72-4.59 (m, 1H), 3.25 (dd, J=16.4, 9.4 Hz, 2H), 2.97 (dd, J=16.1, 8.4 Hz, 1H), 1.94 (dq, J=13.4, 6.7 Hz, 1H), 0.98 (d, J=6.6 Hz, 3H), 0.93 (d, J=6.8 Hz, 3H). MS(ES): m/z 207 [M+H]$^+$.

79D. 7-Bromo-2-isopropyl-2,3-dihydrobenzofuran-5-carboxylic acid

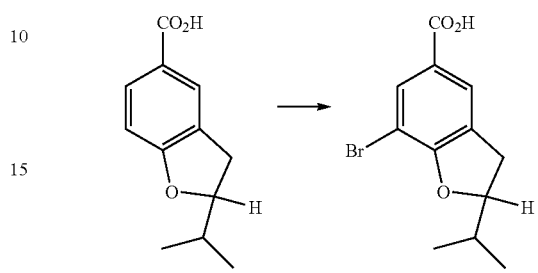

2-Isopropyl-2,3-dihydrobenzofuran-5-carboxylic acid (29.3 mg, 0.142 mmol) was suspended in glacial acetic acid (0.5 mL). Bromine (14.64 µl, 0.284 mmol) was added and stirring continued for 5 hours. Additional bromine (14.64 µl, 0.284 mmol) was added and the reaction continued for 0.5 hour. Water was then added and the resulting precitiate was filter and rinsed well with water. Drying in a ChemDry oven at 75° C. for 0.5 hour gave 7-bromo-2-isopropyl-2,3-dihydrobenzofuran-5-carboxylic acid (24 mg, 58%) as a colorless solid. $^1$H NMR (400 MHz, DMSO-d$_6$) δ 12.79 (br. s., 1H), 7.86 (s, 1H), 7.75 (s, 1H), 4.84-4.71 (m, 1H), 3.40 (dd, J=16.3, 9.2 Hz, 1H), 3.11 (dd, J=16.2, 8.0 Hz, 1H), 1.98 (dq, J=13.2, 6.7 Hz, 1H), 0.98 (d, J=6.6 Hz, 3H), 0.93 (d, J=6.6 Hz, 3H). MS(ES): m/z 285 [M+H]$^+$.

79. 7-Bromo-N-((4,6-dimethyl-2-oxo-1,2-dihydropyridin-3-yl)methyl)-2-isopropyl-2,3-dihydrobenzofuran-5-carboxamide

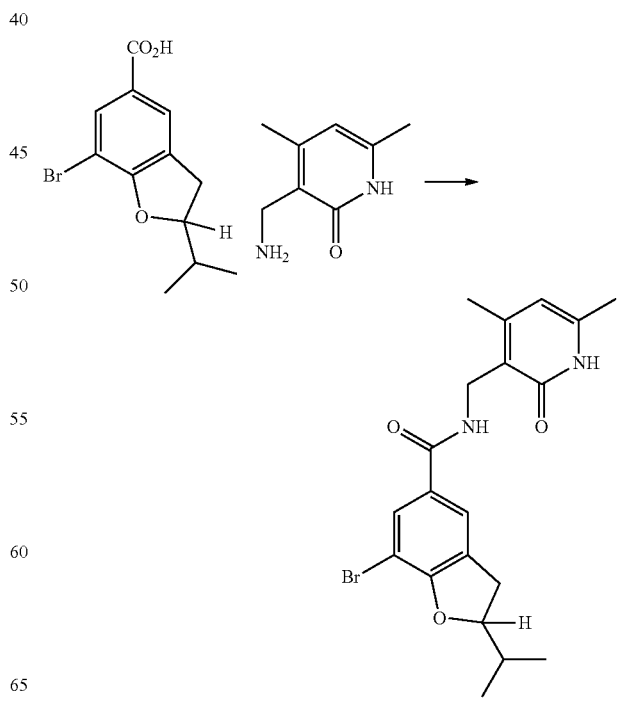

7-Bromo-2-isopropyl-2,3-dihydrobenzofuran-5-carboxylic acid (21 mg, 0.074 mmol) was dissolved in dry DMF (0.5 mL). 3-(Aminomethyl)-4,6-dimethylpyridin-2(1H)-one hydrochloride (15.28 mg, 0.081 mmol) and triethylamine (30.8 μl, 0.221 mmol) were added. The reaction was initiated with the addition of BOP (39.1 mg, 0.088 mmol). After stirring overnight, the reaction was treated with half saturated sodium bicarbonate (ca. 3 mL). The reaction was stirred for 15 minutes, and the resulting solid was filtered and rinsed with water. Drying in a ChemDry oven at 75° C. for an hour gave 7-bromo-N-((4,6-dimethyl-2-oxo-1,2-dihydropyridin-3-yl)methyl)-2-isopropyl-2,3-dihydrobenzofuran-5-carboxamide (10.3 mg, 32%) as an off-white solid. $^1$H NMR (400 MHz, DMSO-$d_6$) δ 11.45 (br. s., 1H), 8.22 (br. s., 1H), 7.86 (s, 1H), 7.70 (s, 1H), 5.87 (s, 1H), 4.73 (q, J=8.1 Hz, 1H), 4.27 (d, J=4.8 Hz, 2H), 3.45-3.34 (m, 1H), 3.07 (dd, J=16.2, 7.8 Hz, 1H), 2.16 (s, 3H), 2.13 (s, 3H), 2.02-1.85 (m, 1H), 0.97 (d, J=6.6 Hz, 3H), 0.92 (d, J=6.6 Hz, 3H). MS(ES): m/z 419 [M+H]$^+$.

Example 80

N-((4,6-Dimethyl-2-oxo-1,2-dihydropyridin-3-yl)methyl)-2-isopropyl-7-(6-(piperazin-1-yl)pyridin-3-yl)-2,3-dihydrobenzofuran-5-carboxamide

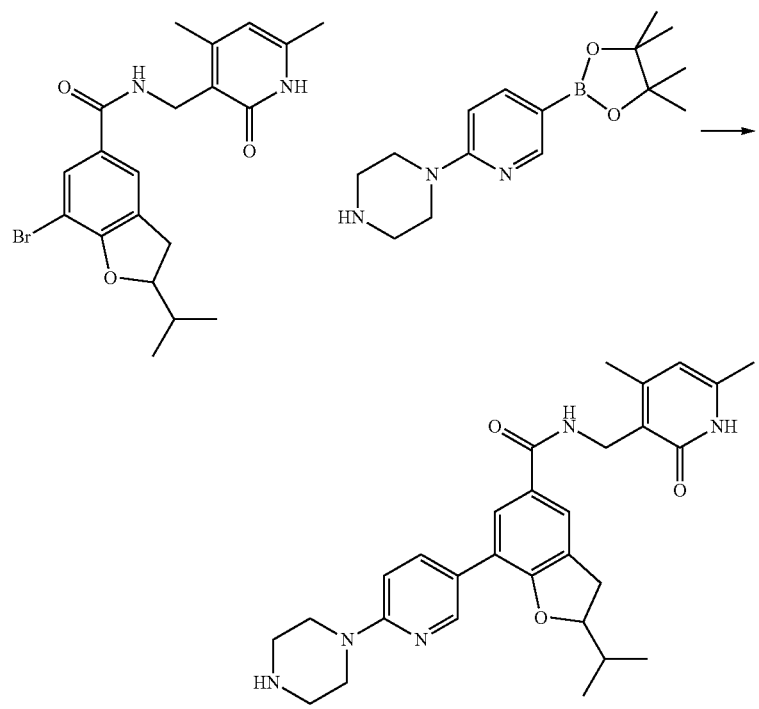

Example 80 was prepared from 7-bromo-N-((4,6-dimethyl-2-oxo-1,2-dihydropyridin-3-yl)methyl)-2-isopropyl-2,3-dihydrobenzofuran-5-carboxamide (Example 79) and 1-(5-(4,4,5,5-tetramethyl-1,3,2-dioxaborolan-2-yl)pyridin-2-yl)piperazine in 57% yield using the procedures of Example 10. $^1$H NMR (500 MHz, DMSO-$d_6$) δ 8.58 (d, J=1.7 Hz, 1H), 8.26 (br. s., 1H), 8.01-7.94 (m, 2H), 7.83 (s, 1H), 7.65 (s, 1H), 6.96 (d, J=9.1 Hz, 1H), 5.87 (s, 1H), 4.65 (q, J=8.1 Hz, 1H), 4.30 (d, J=4.4 Hz, 2H), 3.27 (dd, J=16.0, 9.3 Hz, 1H), 3.06-2.96 (m, 4H), 2.17 (s, 3H), 2.12 (s, 3H), 2.01-1.92 (m, 1H), 0.98 (d, J=6.4 Hz, 3H), 0.94 (d, J=6.4 Hz, 3H). MS(ES): m/z 502 [M+H]$^+$ Example 81

9-Bromo-N-((4,6-dimethyl-2-oxo-1,2-dihydropyridin-3-yl)methyl)-3,4-dimethyl-2,5-dihydrobenzo[b]oxepine-7-carboxamide

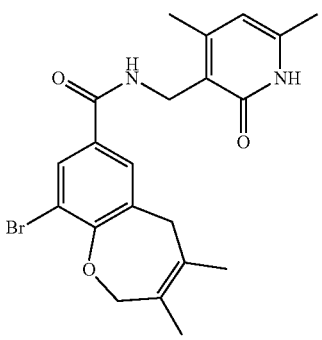 [SMILES: CC1=C(C)Cc2cc(C(=O)NCc3c(C)cc(C)[nH]c3=O)cc(Br)c2OC1]

81A. Methyl 3-bromo-5-(2-methylallyl)-4-((2-methylallyl)oxy)benzoate

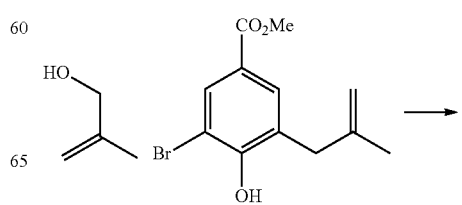

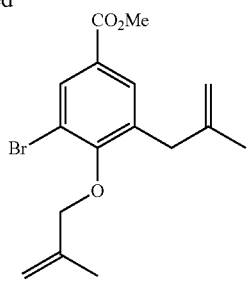

A solution of methyl 3-bromo-4-hydroxy-5-(2-methylallyl)benzoate (0.2 g, 0.701 mmol) and 2-methylprop-2-en-1-ol (0.101 g, 1.403 mmol) and triphenylphosphine (0.239 g, 0.912 mmol) in THF (2 mL) was cooled to 0° C. and treated with DIAD (0.177 mL, 0.912 mmol), dropwise over 1 min. The reaction was stirred for 20 min. then chromatographed on silica gel (gradient elution with ether-hexanes). Concentration of the appropriate fractions afforded methyl 3-bromo-5-(2-methylallyl)-4-((2-methylallyl)oxy)benzoate (0.22 g, 0.616 mmol, 88% yield) as a pale yellow oil. $^1$H NMR (400 MHz, DMSO-$d_6$) δ 8.02 (d, J=2.0 Hz, 1H), 7.78 (d, J=2.0 Hz, 1H), 5.14 (s, 1H), 5.01 (s, 1H), 4.86 (s, 1H), 4.61 (s, 1H), 4.34 (s, 2H), 3.84 (s, 3H), 3.41 (s, 2H), 1.84 (s, 3H), 1.67 (s, 3H).

81B. Methyl 9-bromo-3,4-dimethyl-2,5-dihydrobenzo[b]oxepine-7-carboxylate

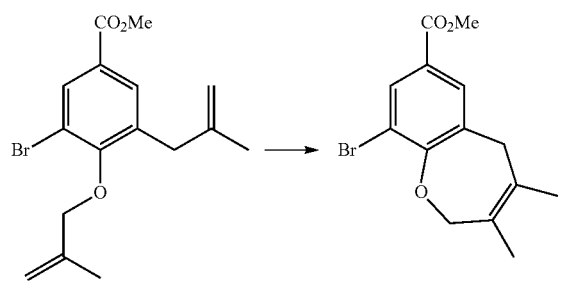 [SMILES: C=C(C)COc1c(Br)cc(C(=O)OC)cc1CC(=C)C ; COC(=O)c1cc(Br)c2c(c1)CC(C)=C(C)CO2]

Methyl 3-bromo-5-(2-methylallyl)-4-((2-methylallyl)oxy)benzoate (0.1 g, 0.295 mmol) in ClCH$_2$CH$_2$Cl (29.5 ml) was degassed and treated with GrubbsII (0.013 g, 0.015 mmol). This solution was placed under nitrogen and heated at 55° C. for 1 h. The reaction was treated with 10 mg of potassium isocyanoacetate in 50 microliters of water and concentrated under a stream of nitrogen. The residue was purified by prep. HPLC (Axia Luna 30×100 mm column, MeOH-water-TFA gradient). Concentration of the appropriate fraction afforded methyl 9-bromo-3,4-dimethyl-2,5-dihydrobenzo[b]oxepine-7-carboxylate (0.05 g, 0.153 mmol, 51.8% yield) as colorless needles, mp. 93-94° C. $^1$H NMR (400 MHz, CDCl$_3$) δ 8.08 (d, J=2.2 Hz, 1H), 7.68 (d, J=2.2 Hz, 1H), 4.67 (s, 2H), 3.89 (s, 3H), 3.53 (s, 2H), 1.84 (s, 3H), 1.64 (s, 3H). MS(ES): m/z 313 [M+H]$^+$.

81C. 9-Bromo-3,4-dimethyl-2,5-dihydrobenzo[b]oxepine-7-carboxylic acid

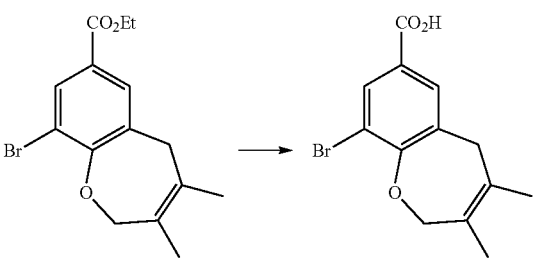 [SMILES: CCOC(=O)c1cc(Br)c2c(c1)CC(C)=C(C)CO2 ; CC1=C(C)Cc2cc(C(=O)O)cc(Br)c2OC1]

A solution of methyl 9-bromo-3,4-dimethyl-2,5-dihydrobenzo[b]oxepine-7-carboxylate (0.047 g, 0.151 mmol) in THF (2 mL) was treated with lithium hydroxide (0.018 g, 0.755 mmol) in water (1 mL). Methanol, 0.3 mL, was added to give a single phase, and the resulting solution was warmed to 60° C. with stirring for 30 min. The reaction was cooled to RT under a stream of nitrogen, and the reaction was then diluted with 2 mL of water, treated with decolorizing carbon and filtered. This gave a solution which was brought to pH1 with 1M aq. HCl. A precipitate formed which was filtered, rinsed with water, and air-dried to afford 9-bromo-3,4-dimethyl-2,5-dihydrobenzo[b]oxepine-7-carboxylic acid (0.042 g, 89% yield) as a pewter-colored solid, mp. 213-216° C. $^1$H NMR (400 MHz, DMSO-$d_6$) δ 7.90 (d, J=2.0 Hz, 1H), 7.67 (d, J=2.0 Hz, 1H), 4.69 (s, 2H), 3.58 (s, 2H), 1.79 (s, 3H), 1.61 (s, 3H). MS(ES): m/z 299 [M+H]$^+$.

81. 9-Bromo-N-((4,6-dimethyl-2-oxo-1,2-dihydropyridin-3-yl)methyl)-3,4-dimethyl-2,5-dihydrobenzo[b]oxepine-7-carboxamide

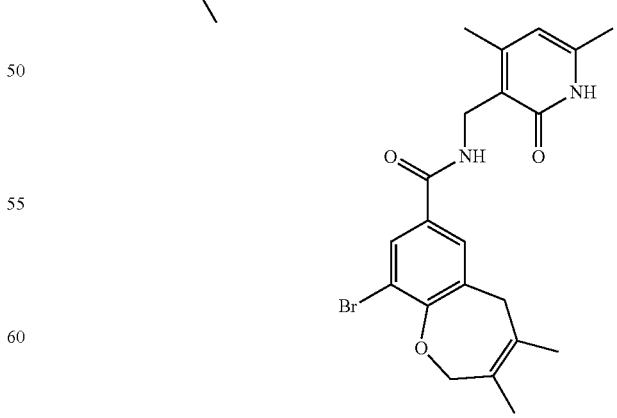

A solution of 9-bromo-3,4-dimethyl-2,5-dihydrobenzo[b]oxepine-7-carboxylic acid (0.035 g, 0.118 mmol) and 3-(aminomethyl)-4,6-dimethylpyridin-2(1H)-one, HCl (0.029 g, 0.153 mmol) in DMF was treated with triethylamine (0.049 ml, 0.353 mmol) followed by BOP (0.063 g, 0.141 mmol). The reaction was stirred 1.5 h at RT then treated with dilute aq. sodium bicarbonate (~6 mL) with rapid stirring. After a few minutes the mixture was filtered, rinsed with water, and air-dried to afford 9-bromo-N-((4,6-dimethyl-2-oxo-1,2-dihydropyridin-3-yl)methyl)-3,4-dimethyl-2,5-dihydrobenzo[b]oxepine-7-carboxamide (0.046 g, 86% yield) as a stone-colored solid, mp. 249-251° C. $^1$H NMR (400 MHz, DMSO-$d_6$) δ 11.43-11.47 (br.s, 1H), 8.27 (t, J=4.5 Hz, 1H), 7.92 (d, J=2.2 Hz, 1H), 7.62 (d, J=2.0 Hz, 1H), 5.85 (s, 1H), 4.60 (s, 2H), 4.25 (d, J=4.8 Hz, 2H), 3.51 (s, 2H), 2.14 (s, 3H), 2.11 (s, 3H), 1.78 (s, 3H), 1.57 (s, 3H). MS(ES): m/z 433 [M+H]$^+$.

Example 82

7-Bromo-N-((4,6-dimethyl-2-oxo-1,2-dihydropyridin-3-yl)methyl)-2-methyl-2-(prop-1-en-2-yl)-2,3-dihydrobenzofuran-5-carboxamide μmol) in degassed DMF (0.3 mL) was placed under nitrogen and heated at 60° C. for 1 h. The reaction was then purified by prep. HPLC (Axia Luna 21×100 mm column, MeOH-water-TFA gradient. Concentration of the appropriate fraction and lyophilization afforded 7-bromo-N-((4,6-dimethyl-2-oxo-1,2-dihydropyridin-3-yl)methyl)-2-methyl-2-(prop-1-en-2-yl)-2,3-dihydrobenzofuran-5-carboxamide, TFA (0.004 g, 50.1% yield) as a white powder. $^1$H NMR (400 MHz, MeOH-$d_4$) δ 7.81 (s, 1H), 7.59 (s, 1H), 6.14 (s, 1H), 5.10 (s, 1H), 4.87 (s, 1H), 4.46 (s, 2H), 3.38 (d, J=16.1 Hz, 1H), 3.20 (d, J=15.9 Hz, 1H), 2.36 (s, 3H), 2.25 (s, 3H), 1.83 (s, 3H), 1.59 (s, 3H). MS(ES): m/z 433 [M+H]$^+$.

Example 83

N-((4,6-dimethyl-2-oxo-1,2-dihydropyridin-3-yl)methyl)-7-(6-methoxypyridin-3-yl)-2-methyl-2-(prop-1-en-2-yl)-2,3-dihydrobenzofuran-5-carboxamide

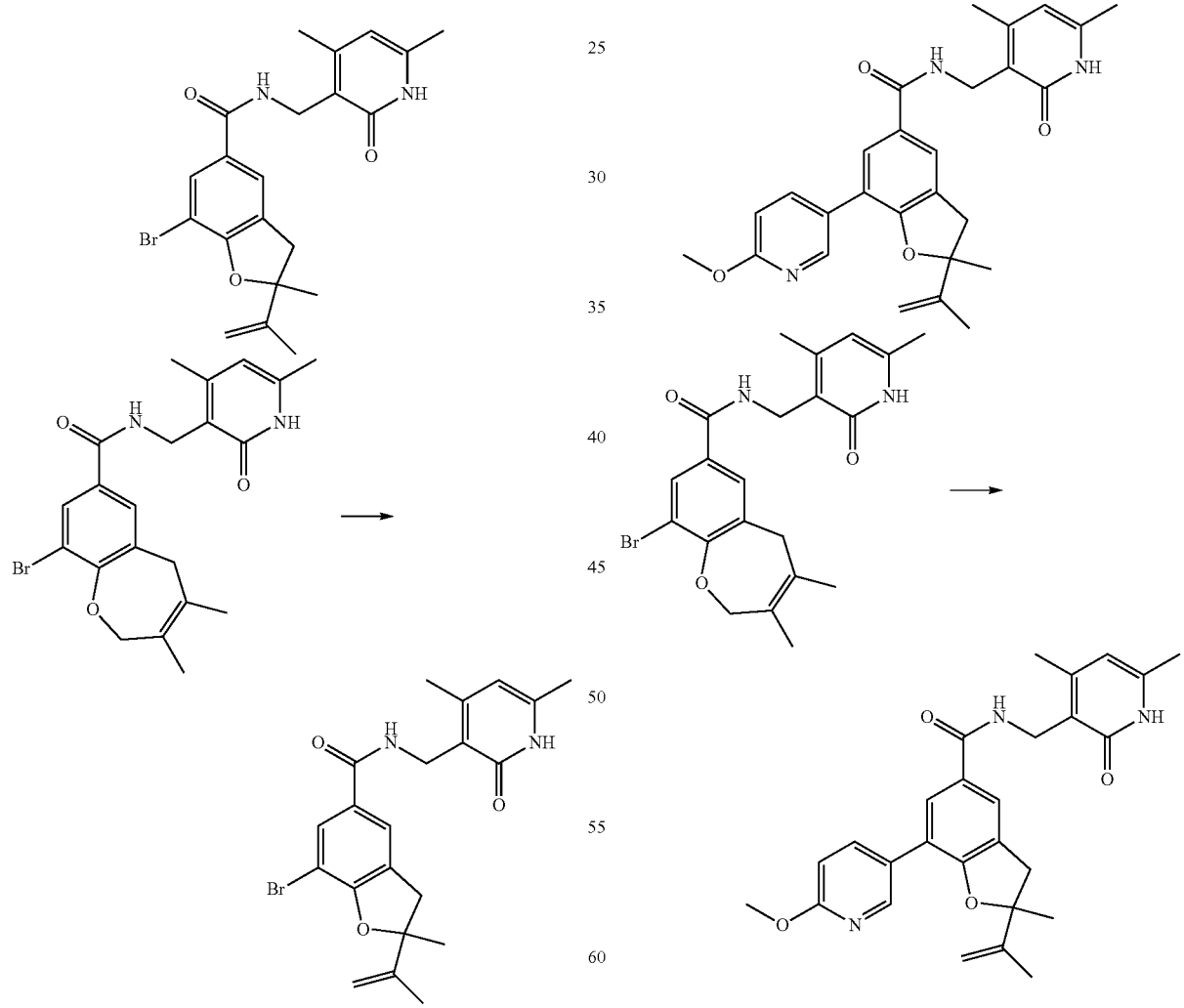

A suspension of 9-bromo-N-((4,6-dimethyl-2-hydropyridin-3-yl)methyl)-3,4-dimethyl-2,5-dihydrobenzo[b]oxepine-7-carboxamide (0.006 g, 0.014 mmol) and tetrakis(triphenylphosphine)palladium(0) (1.607 mg, 1.391

A suspension of (6-methoxypyridin-3-yl)boronic acid (0.016 g, 0.102 mmol) and 9-bromo-N-((4,6-dimethyl-2-oxo-1,2-dihydropyridin-3-yl)methyl)-3,4-dimethyl-2,5-dihydrobenzo[b]oxepine-7-carboxamide (0.022 g, 0.051 mmol) and tetrakis(triphenylphosphine)palladium(0) (5.89 mg, 5.10 μmol) in degassed DMF (1 mL) was treated with aq. potassium carbonate (0.102 mL, 0.153 mmol) and placed under nitrogen. This mixture was heated at 90° C. for 2 h then cooled to 60° C. and quenched with glacial HOAc. After stirring a few minutes at 60° C. the mixture was cooled to RT, filtered, and purified by prep. HPLC (Axia Luna 30×100 mm column, MeOH-water-TFA gradient). Concentration of the appropriate fraction and lyophilization afforded N-((4,6-dimethyl-2-oxo-1,2-dihydropyridin-3-yl)methyl)-7-(6-methoxypyridin-3-yl)-2-methyl-2-(prop-1-en-2-yl)-2,3-dihydrobenzofuran-5-carboxamide, TFA (0.025 g, 84% yield) as a white powder. $^1$H NMR (400 MHz, DMSO-d$_6$) δ 11.45-11.55 (br.s, 1H), 8.59 (d, J=2.5 Hz, 1H), 8.27 (t, J=4.8 Hz, 1H), 8.08 (dd, J=8.7, 2.6 Hz, 1H), 7.88 (d, J=1.7 Hz, 1H), 7.70 (d, J=1.6 Hz, 1H), 6.94 (d, J=8.7 Hz, 1H), 5.88 (s, 1H), 5.03 (s, 1H), 4.87 (t, J=1.4 Hz, 1H), 4.31 (d, J=4.7 Hz, 2H), 3.90 (s, 3H), 3.31 (d, J=16.3 Hz, 1H), 3.15 (d, J=16.3 Hz, 1H), 2.17 (s, 3H), 2.12 (s, 3H), 1.81 (s, 3H), 1.54 (s, 3H). MS(ES): m/z 460 [M+H]$^+$.

Example 84

N-((4,6-Dimethyl-2-oxo-1,2-dihydropyridin-3-yl)methyl)-2-isopropyl-7-(6-methoxypyridin-3-yl)-2-methyl-2,3-dihydrobenzofuran-5-carboxamide, HCl A solution of N-((4,6-dimethyl-2-oxo-1,2-dihydropyridin-3-yl)methyl)-7-(6-methoxypyridin-3-yl)-2-methyl-2-(prop-1-en-2-yl)-2,3-dihydrobenzofuran-5-carboxamide, TFA (0.014 g, 0.024 mmol) in EtOH (1 mL) was treated with palladium on carbon (2.60 mg, 0.024 mmol) and placed under an atmosphere of hydrogen. The reaction was stirred for 18 h then diluted with dichloromethane and treated with a little MgSO$_4$ (as a filter aid). The solids were removed by filtration, and the organic phase was concentrated under reduced pressure. It was then re-dissolved in EtOAc and treated with 0.2 mL of 4M HCl/dioxane and stripped. The residue was azeotroped from EtOAc twice to afford N-((4,6-dimethyl-2-oxo-1,2-dihydropyridin-3-yl)methyl)-2-isopropyl-7-(6-methoxypyridin-3-yl)-2-methyl-2,3-dihydrobenzofuran-5-carboxamide, HCl (0.012 g, 94% yield) as a foam. $^1$H NMR (400 MHz, DMSO-d$_6$) δ 11.55-11.75 (br.s, 1H), 8.58 (s, 1H), 8.31 (t, J=4.4 Hz, 1H), 8.07 (d, J=8.6 Hz, 1H), 7.86 (s, 1H), 7.69 (s, 1H), 6.93 (d, J=8.7 Hz, 1H), 5.92 (s, 1H), 4.30-4.32 (br.s, 2H), 3.89 (s, 3H), 3.21 (d, J=16.0 Hz, 1H), 2.92 (d, J=16.4 Hz, 1H), 2.19 (s, 3H), 2.19 (s, 3H), 1.95-2.05 (m, 1H), 1.33 (s, 3H), 0.97 (d, J=6.6 Hz, 3H), 0.92 (d, J=6.7 Hz, 3H). MS(ES): m/z 462 [M+H]$^+$.

Example 85

N-((4,6-Dimethyl-2-oxo-1,2-dihydropyridin-3-yl)methyl)-2-methyl-7-(6-(piperazin-1-yl)pyridin-3-yl)-2-(prop-1-en-2-yl)-2,3-dihydrobenzofuran-5-carboxamide, 2 TFA

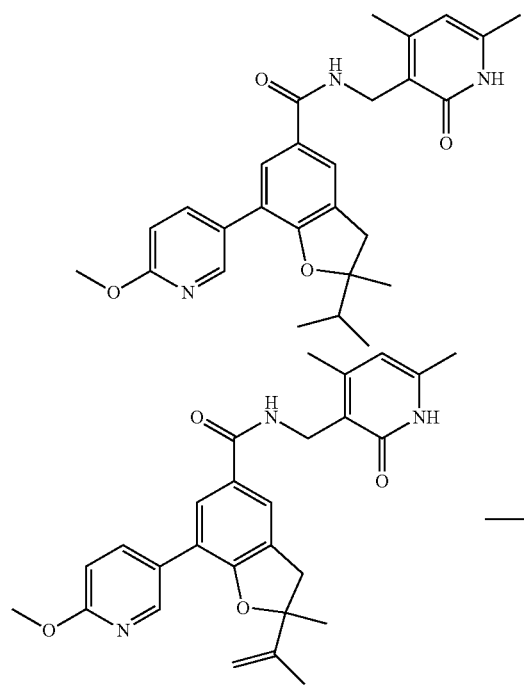

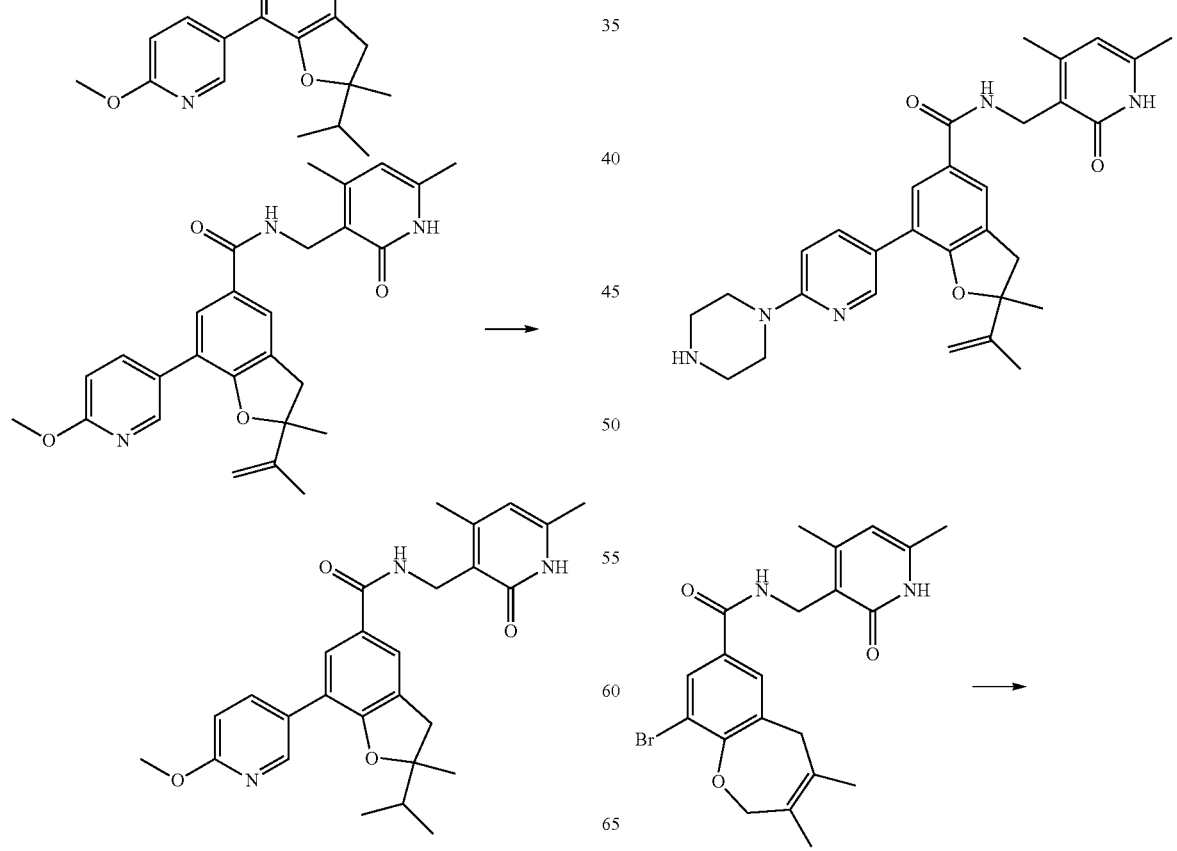

137

-continued

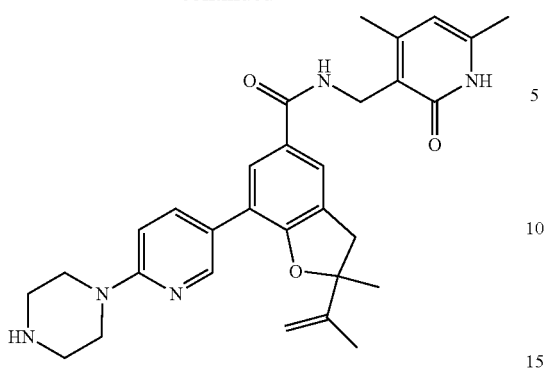

The title compound was prepared from 9-bromo-N-((4,6-dimethyl-2-oxo-1,2-dihydropyridin-3-yl)methyl)-3,4-dimethyl-2,5-dihydrobenzo[b]oxepine-7-carboxamide and (6-(piperazin-1-yl)pyridin-3-yl)boronic acid in 66% yield using the procedure for the preparation of 83 from 81. ¹H NMR (400 MHz, DMSO-d₆) δ 11.41-11.50 (br.s, 1H), 8.69-8.77 (br. s, 3H), 8.60 (d, J=2.4 Hz, 1H), 8.22 (t, J=4.9 Hz, 1H), 8.00 (dd, J=8.8, 2.6 Hz, 1H), 7.84 (d, J=1.5 Hz, 1H), 7.65 (d, J=0.9 Hz, 1H), 7.03 (d, J=9.0 Hz, 1H), 5.85 (s, 1H), 5.01 (s, 1H), 4.85 (s, 1H), 4.29 (d, J=4.8 Hz, 2H), 3.76 (t, J=5.2 Hz, 4H), 3.28 (d, J=16.3 Hz, 1H), 3.17-3.23 (m, 4H), 3.12 (d, J=16.3 Hz, 1H), 2.16 (s, 3H), 2.11 (s, 3H), 1.79 (s, 3H), 1.51 (s, 3H). MS(ES): m/z 514 [M+H]⁺.

Example 86

9-Bromo-3,4-dimethyl-N-((6-methyl-2-oxo-4-propyl-1,2-dihydropyridin-3-yl)methyl)-2,5-dihydrobenzo[b]oxepine-7-carboxamide

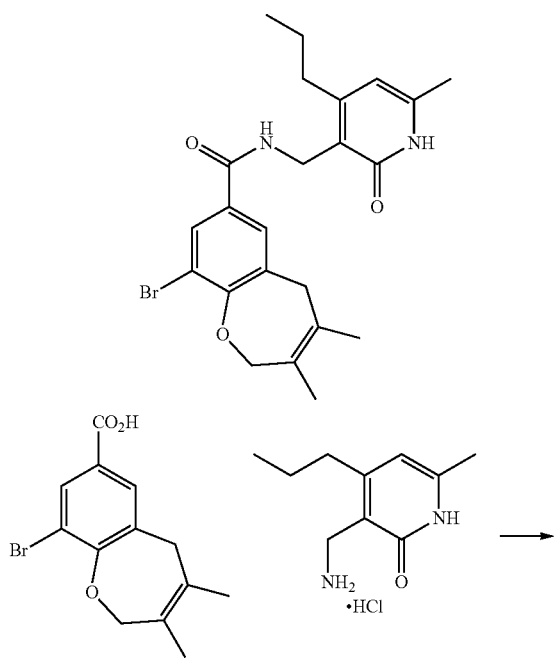

138

-continued

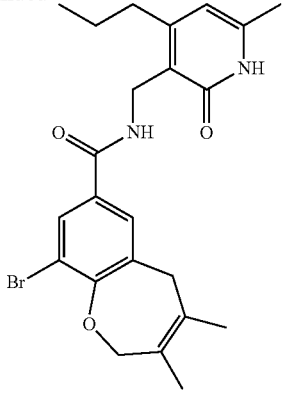

The title compound was prepared from 9-bromo-3,4-dimethyl-2,5-dihydrobenzo[b]oxepine-7-carboxylic acid and 3-(aminomethyl)-6-methyl-4-propylpyridin-2(1H)-one, HCl in 90% yield using the procedure for the preparation of 81 from 81C. mp. 183-186° C. ¹H NMR (400 MHz, DMSO-d₆) δ 11.43-11.48 (br.s, 1H), 8.27 (t, J=4.6 Hz, 1H), 7.91 (d, J=2.0 Hz, 1H), 7.61 (d, J=2.0 Hz, 1H), 5.87 (s, 1H), 4.61 (s, 2H), 4.28 (d, J=4.6 Hz, 2H), 3.50 (s, 2H), 2.41-2.47 (m, 2H), 2.11 (s, 3H), 1.78 (s, 3H), 1.57 (s, 3H), 1.42-1.52 (m, 2H), 0.86 (t, J=7.4 Hz, 3H). MS(ES): m/z 461 [M+H]⁺.

Example 87

2-Methyl-N-((6-methyl-2-oxo-4-propyl-1,2-dihydropyridin-3-yl)methyl)-7-(6-(piperazin-1-yl)pyridin-3-yl)-2-(prop-1-en-2-yl)-2,3-dihydrobenzofuran-5-carboxamide, 2 TFA

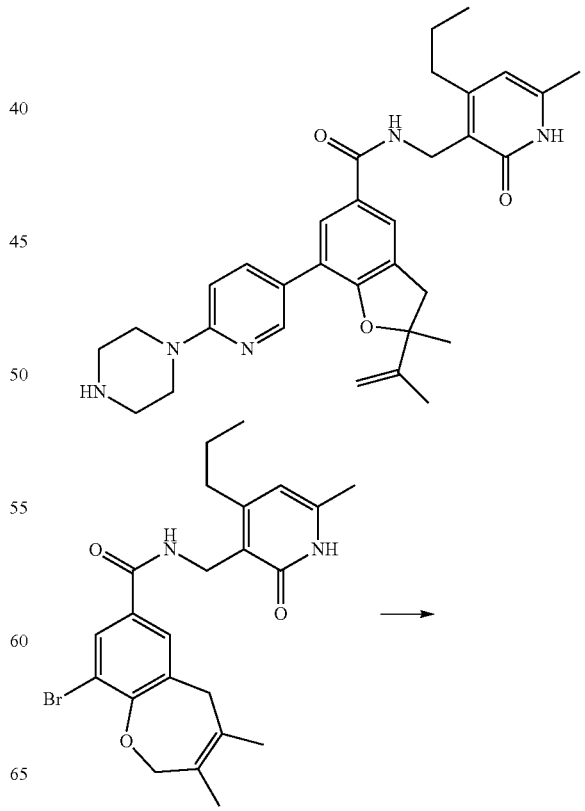

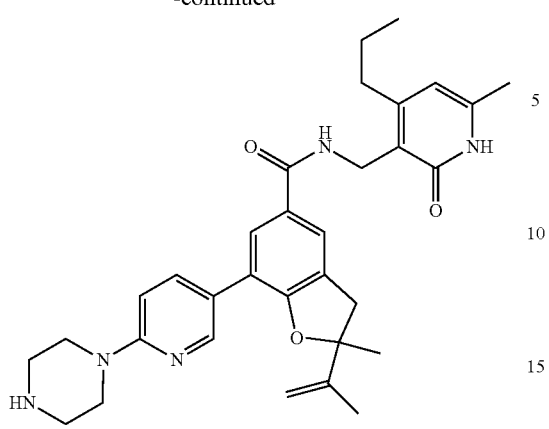

The title compound was prepared from 9-bromo-3,4-dimethyl-N-((6-methyl-2-oxo-4-propyl-1,2-dihydropyridin-3-yl)methyl)-2,5-dihydrobenzo[b]oxepine-7-carboxamide and (6-(piperazin-1-yl)pyridin-3-yl)boronic acid in 82% yield using the procedure for the preparation of 83 from 81. $^1$H NMR (400 MHz, DMSO-$d_6$) δ 11.41-11.50 (br.s, 1H), 8.69-8.79 (br. s, 3H), 8.59 (d, J=2.4 Hz, 1H), 8.23 (t, J=4.5 Hz, 1H), 8.00 (dd, J=8.8, 2.6 Hz, 1H), 7.83 (d, J=1.3 Hz, 1H), 7.64 (d, J=0.9 Hz, 1H), 7.03 (d, J=9.0 Hz, 1H), 5.88 (s, 1H), 5.01 (s, 1H), 4.85 (s, 1H), 4.31 (d, J=4.6 Hz, 2H), 3.76 (t, J=5.2 Hz, 4H), 3.29 (d, J=15.6 Hz, 1H), 3.17-3.24 (m, 4H), 3.12 (d, J=15.9 Hz, 1H), 2.43-2.48 (m, 2H), 2.12 (s, 3H), 1.79 (s, 3H), 1.45-1.53 (m, 5H), 0.86 (t, J=7.3 Hz, 3H). MS(ES): m/z 542 [M+H]$^+$.

Example 88

2-isopropyl-2-methyl-N-((6-methyl-2-oxo-4-propyl-1,2-dihydropyridin-3-yl)methyl)-7-(6-(piperazin-1-yl)pyridin-3-yl)-2,3-dihydrobenzofuran-5-carboxamide, 2 HCl

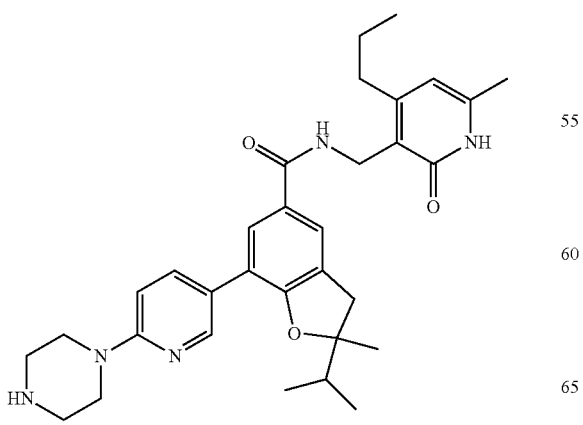

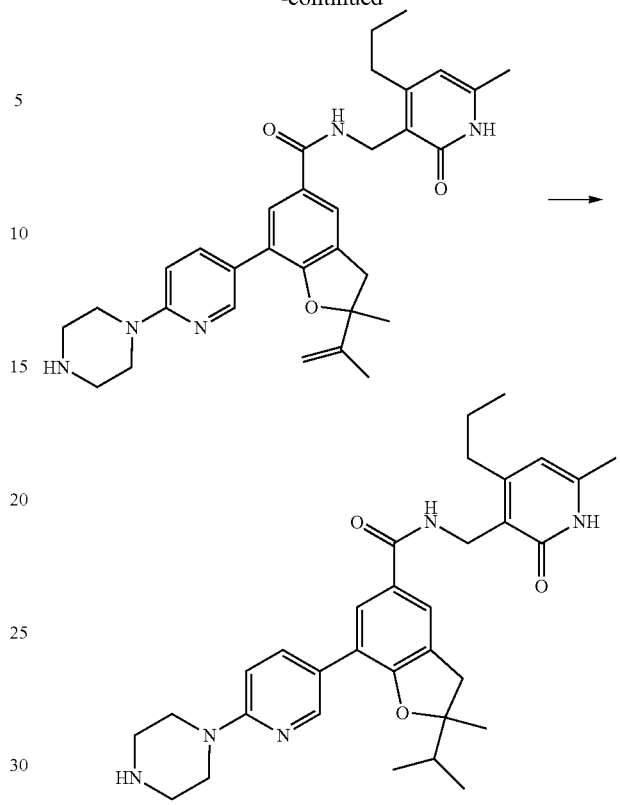

The title compound was prepared from 2-methyl-N-((6-methyl-2-oxo-4-propyl-1,2-dihydropyridin-3-yl)methyl)-7-(6-(piperazin-1-yl)pyridin-3-yl)-2-(prop-1-en-2-yl)-2,3-dihydrobenzofuran-5-carboxamide, 2 TFA in 81% yield using the procedure for the preparation of 84 from 83. $^1$H NMR (400 MHz, DMSO-$d_6$) δ 11.54 (br. s., 1H), 9.22 (br. s., 2H), 8.55 (d, J=2.4 Hz, 1H), 8.27 (br. s., 1H), 8.09 (d, J=9.5 Hz, 1H), 7.83 (s, 1H), 7.65 (s, 1H), 7.14 (d, J=8.8 Hz, 1H), 5.90 (s, 1H), 4.31 (d, J=4.6 Hz, 2H), 3.84 (br. s., 4H), 3.27-3.12 (m, 5H), 2.90 (d, J=16.5 Hz, 1H), 2.12 (s, 3H), 2.04-1.92 (m, 1H), 1.60-1.41 (m, 2H), 1.31 (s, 3H), 0.96 (d, J=6.6 Hz, 3H), 0.91 (d, J=6.8 Hz, 3H), 0.87 (t, J=7.4 Hz, 3H) MS(ES): m/z 544 [M+H]$^+$.

Example 89

9-Bromo-N-((4,6-dimethyl-2-oxo-1,2-dihydropyridin-3-yl)methyl)-3,4-dimethyl-2,5-dihydrobenzo[b]oxepine-7-carboxamide

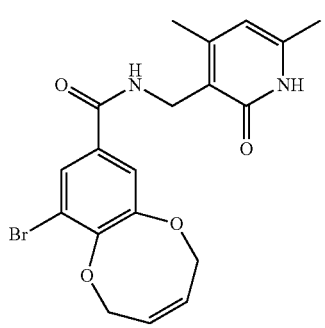 [SMILES: Cc1cc(C)c(CNC(=O)c2cc(Br)c3c(c2)OC/C=C\CO3)c(=O)[nH]1]

89A. Ethyl 3-bromo-4,5-dihydroxybenzoate
98946-052-01

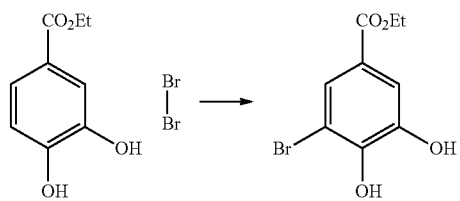

A solution of ethyl 3,4-dihydroxybenzoate (1.822 g, 10 mmol) in HOAc (12 ml) was cooled to ~10° C. and treated with dibromine (0.717 ml, 14.00 mmol). The reaction was warmed to RT over 10 min., during which time a precipitate formed. The reaction was re-cooled to ~10° C., filtered, and the filtrate was rinsed with glacial HOAc, and air-dried to afford ~2 g of a light tan solid. This crude product was suspended in 10 mL of glacial HOAc and warmed to 80° C. It was then slowly cooled to RT and filtered. The filtrate was rinsed with glacial HOAc and air-dried to afford 1.2 g (46%) of ethyl 3-bromo-4,5-dihydroxybenzoate as a light tan solid. Recrystallization of a small sample affords material which melts at 167-169° C. $^1$H NMR (400 MHz, DMSO-$d_6$) δ 10.08-10.25 (br. s, 2H), 7.52 (d, J=2.0 Hz, 1H), 7.37 (d, J=2.2 Hz, 1H), 4.24 (q, J=7.1 Hz, 2H), 1.28 (t, J=7.1 Hz, 3H). MS(ES): m/z 263 [M+H]$^+$.

89B. Ethyl 3,4-bis(allyloxy)-5-bromobenzoate

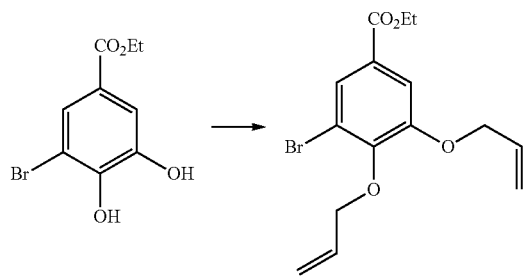 [SMILES: CCOC(=O)c1cc(O)c(O)c(Br)c1 ; C=CCOc1cc(C(=O)OCC)cc(Br)c1OCC=C]

A solution of ethyl 3-bromo-4,5-dihydroxybenzoate (0.522 g, 2 mmol) in DMF (5 mL) was treated with potassium carbonate (0.691 g, 5.00 mmol) followed by allyl bromide (0.433 mL, 5.00 mmol). The resulting mixture was stirred 2 h at 60° C. then cooled and transferred into rapidly-stirred aq. HOAc. 1:1 ether-hexanes was added, and the phases were separated. The org. phase was washed with sat. aq. sodium bicarbonate, dried, and stripped to afford ethyl 3,4-bis(allyloxy)-5-bromobenzoate (0.7 g, 97% yield) as a honey-colored oil. $^1$H NMR (400 MHz, DMSO-$d_6$) δ 7.72 (d, J=2.0 Hz, 1H), 7.54 (d, J=2.0 Hz, 1H), 6.00-6.12 (m, 2H), 5.20-5.47 (m, 4H), 4.69-4.73 (m, 2H), 4.60-4.64 (m, 2H), 4.30 (q, J=7.1 Hz, 2H), 1.31 (t, J=7.0 Hz, 3H). MS(ES): m/z 343 [M+H]$^+$.

89C. (Z)-ethyl 10-bromo-2,5-dihydrobenzo[b][1,4]dioxocine-8-carboxylate

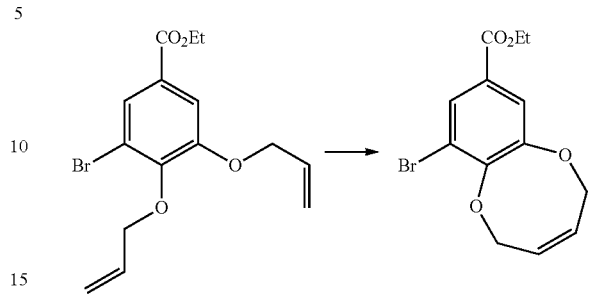

In each of two 40 mL vials, a solution of ethyl 3,4-bis (allyloxy)-5-bromobenzoate (0.11 g, 0.322 mmol) in ClCH$_2$CH$_2$Cl (32.2 ml) was degassed and treated with GrubbsII (0.016 g, 0.019 mmol). The reaction was stirred 1 h at 55° C. then concentrated under a stream of nitrogen. The residue was purified by prep. HPLC (Axia Luna 30×100 mm column, MeOH-water-TFA gradient, one injection for each reaction). The appropriate fractions for both runs were pooled and concentrated. Just prior to dryness the product was transferred (ethanol) into another flask and partially concentrated. Needles formed and were filtered, rinsed with 1:1 EtOH-water, and air-dried to afford (Z)-ethyl 10-bromo-2,5-dihydrobenzo[b][1,4]dioxocine-8-carboxylate (0.158 g, 77% yield) as a colorless solid, mp. 85-86° C. $^1$H NMR (400 MHz, DMSO-$d_6$) δ 7.84 (d, J=2.1 Hz, 1H), 7.61 (d, J=2.1 Hz, 1H), 5.91-6.05 (m, 2H), 5.11 (d, J=6.6 Hz, 2H), 4.89-4.92 (m, 2H), 4.29 (q, J=7.1 Hz, 2H), 1.31 (t, J=7.1 Hz, 3H). MS(ES): m/z 315 [M+H]$^+$.

89D. (Z)-10-Bromo-2,5-dihydrobenzo[b][1,4]dioxocine-8-carboxylic acid

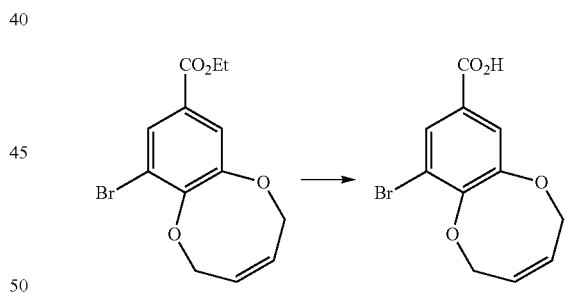

A solution of (Z)-ethyl 10-bromo-2,5-dihydrobenzo[b][1,4]dioxocine-8-carboxylate (0.09 g, 0.287 mmol) in THF (2 mL) was treated with lithium hydroxide (0.034 g, 1.437 mmol) in water (2 mL). MeOH, 1 mL, was added to give a single phase, and the reaction was stirred 1 h at RT. Most of the THF was removed under a stream of nitrogen, and the resulting cloudy solution was diluted up to 5 mL with water and filtered through an Acrodisc submicron filter. This alkaline solution was treated with 1M aq. HCl with rapid stirring until precipitation was then complete. The resulting suspension was rapidly stirred for 3-4 min. longer then filtered. The precipitate was rinsed with water and air-dried to afford (Z)-10-bromo-2,5-dihydrobenzo[b][1,4]dioxocine-8-carboxylic acid (0.076 g, 91% yield) as a colorless solid, mp. 207-209° C. $^1$H NMR (400 MHz, DMSO-$d_6$) δ 13.08-13.13 (br. s, 1H), 7.81 (d, J=2.1 Hz, 1H), 7.58 (d, J=2.1 Hz, 1H), 5.92-6.05 (m, 2H), 5.09 (d, J=6.4 Hz, 2H), 4.89-4.92 (m, 2H). MS(ES): m/z 326 [M+H+CH₃CN]⁺.

89. 9-Bromo-N-((4,6-dimethyl-2-oxo-1,2-dihydropyridin-3-yl)methyl)-3,4-dimethyl-2,5-dihydrobenzo[b]oxepine-7-carboxamide

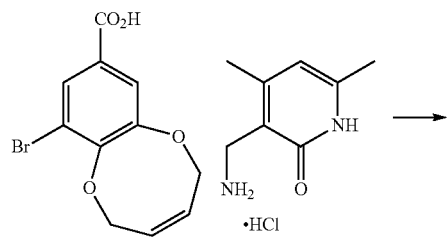

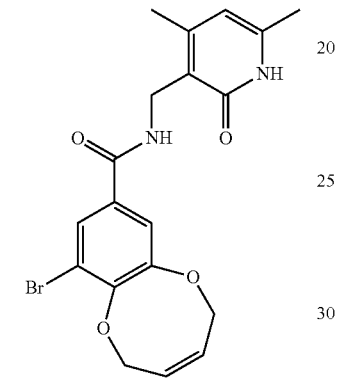

This intermediate was prepared in 92% yield from (Z)-10-bromo-2,5-dihydrobenzo[b][1,4]dioxocine-8-carboxylic acid using the procedure for the conversion of 81C into 81. Colorless solid, mp. 247-249° C. ¹H NMR (400 MHz, DMSO-d₆) δ 11.43-11.47 (br.s, 1H), 8.33 (t, J=4.6 Hz, 1H), 7.81 (d, J=2.0 Hz, 1H), 7.55 (d, J=2.2 Hz, 1H), 5.88-6.01 (m, 2H), 5.85 (s, 1H), 5.02 (d, J=5.9 Hz, 2H), 4.87 (d, J=4.0 Hz, 2H), 4.25 (d, J=4.8 Hz, 2H), 2.13 (s, 3H), 2.10 (s, 3H). MS(ES): m/z 421 [M+H]⁺.

Example 90

8-Bromo-N-((4,6-dimethyl-2-oxo-1,2-dihydropyridin-3-yl)methyl)-2-vinyl-2,3-dihydrobenzo[b][1,4]dioxine-6-carboxamide

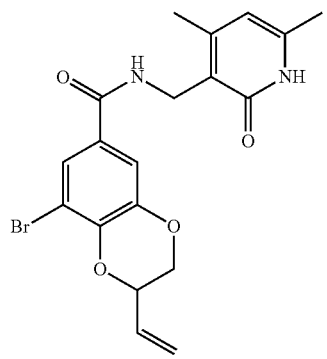

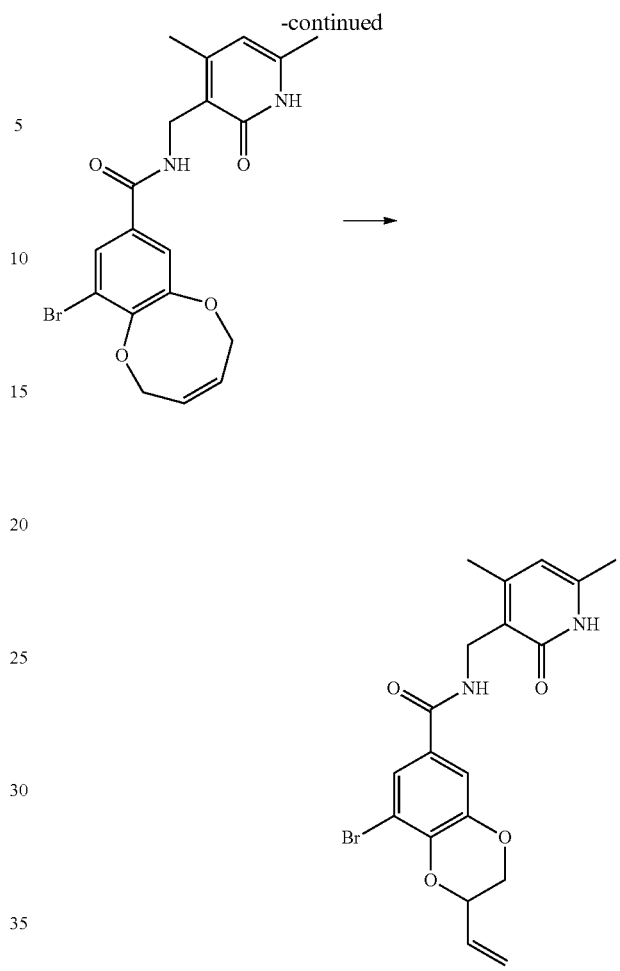

A solution of (Z)-10-bromo-N-((4,6-dimethyl-2-oxo-1,2-dihydropyridin-3-yl)methyl)-2,5-dihydrobenzo[b][1,4]dioxocine-8-carboxamide (0.01 g, 0.024 mmol) in degassed DMF (0.8 mL) was treated with tetrakis(triphenylphosphine)palladium(0) (5.51 mg, 4.77 μmol) and placed under nitrogen. The reaction was stirred for 2 h at 60° C. then purified by prep. HPLC (Axia Luna 21×100 mm column, MeOH-water-TFA gradient). Concentration of the appropriate fraction afforded 8-bromo-N-((4,6-dimethyl-2-oxo-1,2-dihydropyridin-3-yl)methyl)-2-vinyl-2,3-dihydrobenzo[b][1,4]dioxine-6-carboxamide (4 mg, 38%) as a white powder. ¹H NMR (400 MHz, CDCl₃) δ 7.61 (t, J=5.7 Hz, 1H), 7.57 (d, J=2.0 Hz, 1H), 7.31 (d, J=2.0 Hz, 1H), 5.87-5.96 (m, 2H), 5.53-5.59 (m, 1H), 5.40-5.44 (m, 1H), 4.73-4.78 (m, 1H), 4.52 (d, J=5.9 Hz, 2H), 4.28 (dd, J=11.2, 2.6 Hz, 1H), 3.93 (dd, J=11.7, 7.3 Hz, 1H), 2.38 (s, 3H), 2.28 (s, 3H). MS(ES): m/z 421 [M+H]⁺.

Example 91

8-Bromo-N-((4,6-dimethyl-2-oxo-1,2-dihydropyridin-3-yl)methyl)-2-ethyl-2,3-dihydrobenzo[b][1,4]dioxine-6-carboxamide

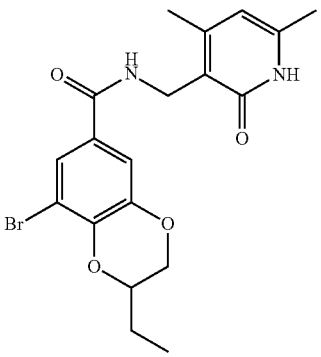 [SMILES: CCC1COc2cc(C(=O)NCc3c(C)cc(C)[nH]c3=O)cc(Br)c2O1]

91A. Ethyl 8-bromo-2-vinyl-2,3-dihydrobenzo[b][1,4]dioxine-6-carboxylate

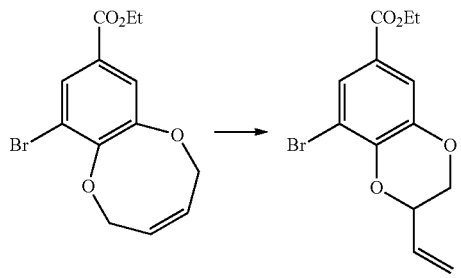 [SMILES: CCOC(=O)c1cc(Br)c2c(c1)OC/C=C\CO2 ; C=CC1COc2cc(C(=O)OCC)cc(Br)c2O1]

A solution of (Z)-ethyl 10-bromo-2,5-dihydrobenzo[b][1,4]dioxocine-8-carboxylate (0.15 g, 0.479 mmol) in DMF (2 mL) was degassed and treated with tetrakis(triphenylphosphine)palladium(0) (0.028 g, 0.024 mmol). The reaction was placed under nitrogen and heated at 55° C. for 30 min. The reaction was purified by prep. HPLC (Axia Luna 30×100 mm column, MeOH-water-TFA gradient, two injections). The appropriate fractions (second of two large peaks to elute) were pooled and concentrated to afford ethyl 8-bromo-2-vinyl-2,3-dihydrobenzo[b][1,4]dioxine-6-carboxylate (0.094 g, 61.4% yield) as an off-white solid, mp. 105-107° C. $^1$H NMR (400 MHz, DMSO-$d_6$) δ 7.69 (d, J=2.0 Hz, 1H), 7.40 (d, J=2.0 Hz, 1H), 5.97 (ddd, J=17.3, 10.7, 5.2 Hz, 1H), 5.46 (dt, J=17.3, 1.5 Hz, 1H), 5.38 (dt, J=10.8, 1.4 Hz, 1H), 5.01-4.94 (m, 1H), 4.40 (dd, J=11.7, 2.6 Hz, 1H), 4.27 (q, J=7.1 Hz, 2H), 4.06 (dd, J=11.8, 6.7 Hz, 1H), 1.29 (t, J=7.2 Hz, 3H). MS(ES): m/z 315 [M+H]$^+$.

91B. Ethyl 8-bromo-2-ethyl-2,3-dihydrobenzo[b][1,4]dioxine-6-carboxylate

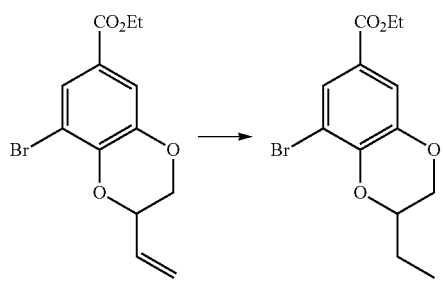 [SMILES: C=CC1COc2cc(C(=O)OCC)cc(Br)c2O1 ; CCOC(=O)c1cc(Br)c2c(c1)OCC(CC)O2]

A solution of ethyl 8-bromo-2-vinyl-2,3-dihydrobenzo[b][1,4]dioxine-6-carboxylate (0.084 g, 0.268 mmol) in ethyl acetate (4 mL) was treated with palladium on carbon (0.029 g, 0.268 mmol) and placed under an atmosphere of H$_2$. This mixture was stirred for 6 h at RT then filtered and stripped to afford ethyl 8-bromo-2-ethyl-2,3-dihydrobenzo[b][1,4]dioxine-6-carboxylate (0.084 g, 94% yield) as an off-white solid, mp. 78-80° C. $^1$H NMR (400 MHz, DMSO-$d_6$) δ 7.67 (d, J=2.0 Hz, 1H), 7.39 (d, J=2.0 Hz, 1H), 4.40 (dd, J=11.7, 2.4 Hz, 1H), 4.23-4.30 (m, 3H), 3.98 (dd, J=11.7, 7.3 Hz, 1H), 1.61-1.71 (m, 2H), 1.29 (t, J=7.0 Hz, 3H), 1.03 (t, J=7.5 Hz, 3H). MS(ES): m/z 317 [M+H]$^+$.

91C. 8-bromo-2-ethyl-2,3-dihydrobenzo[b][1,4]dioxine-6-carboxylic acid

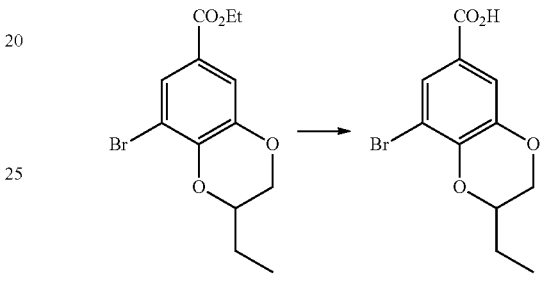

A solution of ethyl 8-bromo-2-ethyl-2,3-dihydrobenzo[b][1,4]dioxine-6-carboxylate (0.08 g, 0.254 mmol) in THF (5 mL) was treated with lithium hydroxide (0.061 g, 2.54 mmol) in 2 mL of water. The resulting biphasic mixture was treated with 2 mL of MeOH to give a single phase, and the reaction was warmed to reflux. The reaction was then cooled to RT and stirred for 6 h. Most of the THF was removed under a stream of nitrogen, and the residue was diluted with 5 mL of water, treated with a bit of decolorizing charcoal, and filtered (water rinse). The filtrate was brought to pH 2 with conc. HCl, and the resulting precipitate was filtered, rinsed with water, and air-dried to afford 8-bromo-2-ethyl-2,3-dihydrobenzo[b][1,4]dioxine-6-carboxylic acid (0.065 g, 85% yield) as a white, papery solid. $^1$H NMR (400 MHz, DMSO-$d_6$) δ 12.92-13.02 (br. s, 1H), 7.65 (d, J=2.0 Hz, 1H), 7.37 (d, J=1.8 Hz, 1H), 4.38 (dd, J=11.4, 2.4 Hz, 1H), 4.22-4.29 (m, 1H), 3.97 (dd, J=11.7, 7.0 Hz, 1H), 1.61-1.70 (m, 2H), 1.03 (t, J=7.5 Hz, 3H). MS(ES): m/z 330 [M+H+CH$_3$CN]$^+$.

91. 8-bromo-N-((4,6-dimethyl-2-oxo-1,2-dihydropyridin-3-yl)methyl)-2-ethyl-2,3-dihydrobenzo[b][1,4]dioxine-6-carboxamide

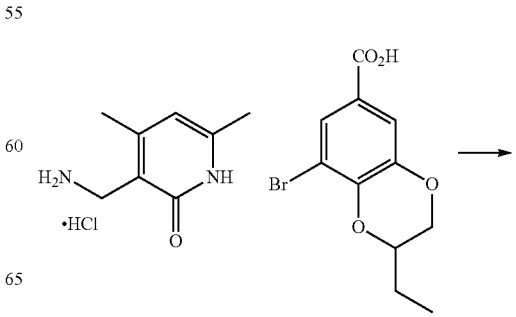

147

-continued

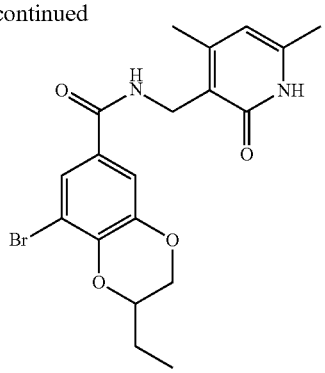

The title compound was prepared from 8-bromo-2-ethyl-2,3-dihydrobenzo[b][1,4]dioxine-6-carboxylic acid and 3-(aminomethyl)-4,6-dimethylpyridin-2(1H)-one, HCl in 96% yield using the procedure for the preparation of 81 from 81C. Stone colored solid, mp. 229-232° C. $^1$H NMR (400 MHz, DMSO-d$_6$) δ 11.44-11.47 (br. s, 1H), 8.32 (t, J=4.6 Hz, 1H), 7.69 (d, J=2.1 Hz, 1H), 7.41 (d, J=2.0 Hz, 1H), 5.86 (s, 1H), 4.37 (dd, J=11.6, 2.3 Hz, 1H), 4.19-4.27 (m, 3H), 3.96 (dd, J=11.6, 7.2 Hz, 1H), 2.15 (s, 3H), 2.12 (s, 3H), 1.61-1.70 (m, 2H), 1.02 (t, J=7.5 Hz, 3H). MS(ES): m/z 423 [M+H]$^+$.

Example 92

N-((4,6-Dimethyl-2-oxo-1,2-dihydropyridin-3-yl)methyl)-2-ethyl-8-(6-(piperazin-1-yl)pyridin-3-yl)-2,3-dihydrobenzo[b][1,4]dioxine-6-carboxamide, 2 TFA

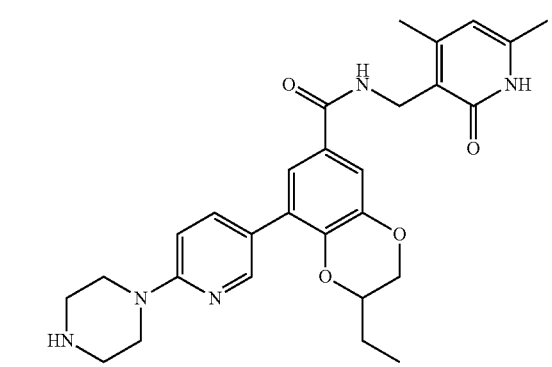

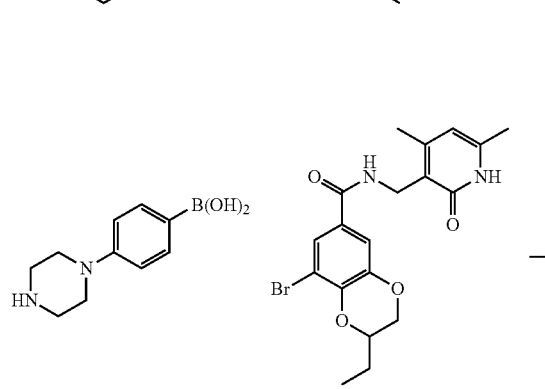

148

-continued

The title compound was prepared from 8-bromo-N-((4,6-dimethyl-2-oxo-1,2-dihydropyridin-3-yl)methyl)-2-ethyl-2,3-dihydrobenzo[b][1,4]dioxine-6-carboxamide and (6-(piperazin-1-yl)pyridin-3-yl)boronic acid in 88% yield using the procedure for the preparation of 83 from 81. $^1$H NMR (400 MHz, DMSO-d$_6$) δ 11.42-11.48 (br.s, 1H), 8.71-8.79 (br. s, 3H), 8.38 (d, J=2.2 Hz, 1H), 8.28 (t, J=4.8 Hz, 1H), 7.85 (dd, J=8.8, 2.4 Hz, 1H), 7.42 (d, J=2.2 Hz, 1H), 7.35 (d, J=2.0 Hz, 1H), 6.99 (d, J=8.8 Hz, 1H), 5.85 (s, 1H), 4.35 (dd, J=11.2, 2.0 Hz, 1H), 4.27 (d, J=4.6 Hz, 2H), 4.09-4.16 (m, 1H), 3.91 (dd, J=11.2, 7.9 Hz, 1H), 3.72-3.78 (m, 4H), 3.17-3.24 (m, 4H), 2.15 (s, 3H), 2.10 (s, 3H), 1.51-1.67 (m, 2H), 0.96 (t, J=7.5 Hz 3H). MS(ES): m/z 504 [M+H]$^+$.

Example 93

2-Isopropyl-7-(6-(4-isopropylpiperazin-1-yl)pyridin-3-yl)-2-methyl-N-((6-methyl-2-oxo-4-propyl-1,2-dihydropyridin-3-yl)methyl)-2,3-dihydrobenzofuran-5-carboxamide

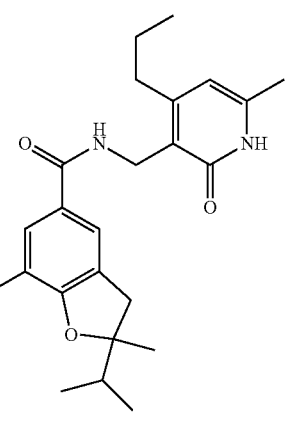

149
-continued

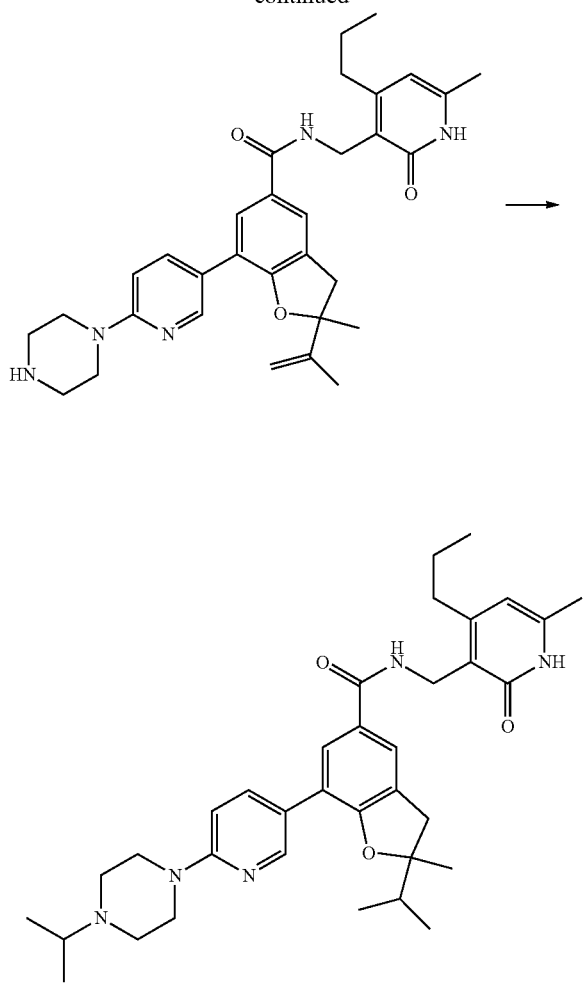

A solution of 2-isopropyl-2-methyl-N-((6-methyl-2-oxo-4-propyl-1,2-dihydropyridin-3-yl)methyl)-7-(6-(piperazin-1-yl)pyridin-3-yl)-2,3-dihydrobenzofuran-5-carboxamide (Example 88, 0.007 g, 0.013 mmol) in MeOH (1 mL) was treated with potassium acetate (0.025 g, 0.257 mmol) followed by acetic acid (7.37 µl, 0.129 mmol) then acetone (0.095 mL, 1.287 mmol). This solution was stirred 5 min. then treated with sodium cyanoborohydride (0.129 mL, 0.129 mmol) in THF. The reaction was stirred ON at RT then quenched with 0.3 mL of conc. aq. ammonia, diluted with water, and ext. with 9:1 chloroform-ethanol. The org. ext. was dried and stripped, and the residue was lyophilized from benzene to afford 2-isopropyl-7-(6-(4-isopropylpiperazin-1-yl)pyridin-3-yl)-2-methyl-N-((6-methyl-2-oxo-4-propyl-1,2-dihydropyridin-3-yl)methyl)-2,3-dihydrobenzofuran-5-carboxamide (0.004 g, 50% yield) as a white powder. $^1$H NMR (400 MHz, DMSO-d$_6$) δ 11.45 (br. s., 1H), 8.52 (d, J=2.2 Hz, 1H), 8.19 (t, J=4.8 Hz, 1H), 7.89 (dd, J=8.9, 2.3 Hz, 1H), 7.78 (d, J=1.3 Hz, 1H), 7.60 (s, 1H), 6.89 (d, J=9.0 Hz, 1H), 5.87 (s, 1H), 4.31 (d, J=4.8 Hz, 2H), 3.50 (br. s., 4H), 3.18 (d, J=16.1 Hz, 1H), 2.88 (d, J=16.1 Hz, 1H), 2.65-2.72 (m, 1H), 2.42-2.57 (integration, multiplicity obscured by solvent), 2.11 (s, 3H), 1.93-2.02 (m, 1H), 1.44-1.55 (m, 2H), 1.31 (s, 3H), 1.00 (d, J=6.4 Hz, 6H), 0.96 (d, J=6.8 Hz, 3H), 0.90 (d, J=6.8 Hz, 3H), 0.86 (t, J=7.3 Hz, 3H). MS(ES): m/z 586.7 [M+H]$^+$.

150
Example 94

2-Methyl-N-((6-methyl-2-oxo-4-propyl-1,2-dihydropyridin-3-yl)methyl)-7-(2-(piperazin-1-yl)pyrimidin-5-yl)-2-(prop-1-en-2-yl)-2,3-dihydrobenzofuran-5-carboxamide, 2 HCl

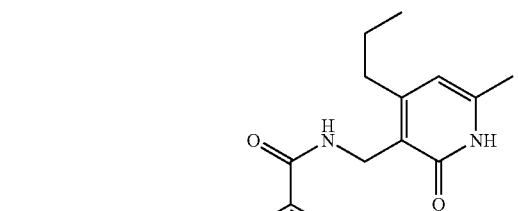

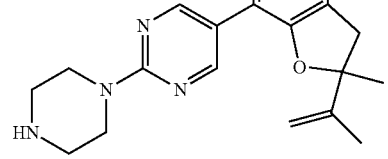

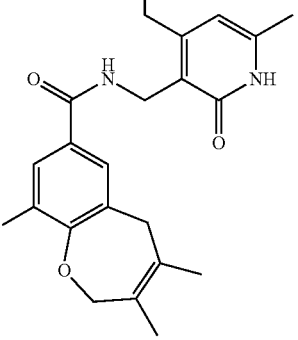

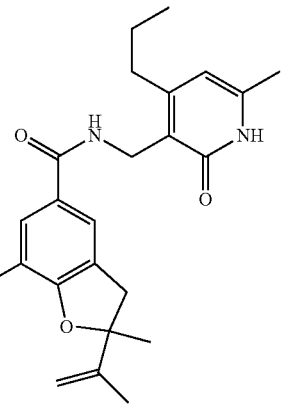

A suspension of tetrakis(triphenylphosphine)palladium(0) (2.7 mg, 2.4 µmol) and tert-butyl 4-(5-(4,4,5,5-tetramethyl-1,3,2-dioxaborolan-2-yl)pyrimidin-2-yl)piperazine-1-carboxylate (0.018 g, 0.046 mmol) and 9-bromo-N-((4,6-dimethyl-2-oxo-1,2-dihydropyridin-3-yl)methyl)-3,4-dimethyl-2,5-dihydrobenzo[b]oxepine-7-carboxamide (Example 86, 0.01 g, 0.023 mmol) in degassed DMF (1 mL) was treated with aq. potassium carbonate (0.046 mL, 0.070 mmol) and placed under nitrogen. This mixture was heated at 95° C. for 1 h. The reaction was cooled to 60° C., quenched with glacial HOAc, and purified by prep. HPLC (Axia Luna 30×100 mm column, gradient elution with MeOH-water-TFA). Concentration of the appropriate fraction afforded a glass. This was stirred for 30 min. with 4M HCl in dioxane (~1 mL) then concentrated and lyophilized from benzene to afford 2-methyl-N-((6-methyl-2-oxo-4-propyl-1,2-dihydropyridin-3-yl)methyl)-7-(2-(piperazin-1-yl)pyrimidin-5-yl)-2-(prop-1-en-2-yl)-2,3-dihydrobenzofuran-5-carboxamide, 2 HCl (0.01 g, 69% yield) as a white powder. $^1$H NMR (400 MHz, DMSO-d$_6$) δ 11.52 (br.s, 1H), 9.09 (br. s, 2H), 8.83 (s, 2H), 8.23 (t, J=4.6 Hz, 1H), 7.88 (d, J=1.5 Hz, 1H), 7.68 (s, 1H), 5.90 (s, 1H), 5.00 (s, 1H), 4.85 (s, integration obscured by broad water signal), 4.31 (d, J=4.6 Hz, 2H), 4.01 (t, J=5.2 Hz, 4H), 3.30 (d, J=16.3 Hz, 1H), 3.21-3.11 (m, 5H), 2.51-2.45 (multiplicity, integration obscured by solvent), 2.12 (s, 3H), 1.79 (s, 3H), 1.54-1.44 (m, 5H), 0.87 (t, J=7.4 Hz, 3H). LCMS: 543 (M+H)$^+$.

Biological Assay

EZH2 Histone Methyl Transferase Assay

The effectiveness of compounds of the present invention as inhibitors of histone methyl transferases can be readily tested by assays known to those skilled in the art. For example, in vitro histone methyl transferase assays may be conducted with a relevant purified histone methyl transferase and an appropriate synthetic substrate to determine the inhibitory activity of the compounds. Assays for inhibition of EZH2 by the instant compounds were performed in 384-well plates with reaction mixtures containing 350 nM of histone peptide substrate (ATKAAR-K(Me2)-SAPATG-GVKKPHRYRPG-GK(Biotin), 500 nM S-[methyl-$^3$H]adenosyl-L-methionine (55-85 Ci/mmol), 50 mM Tris-HCl (pH 9.0), 50 mM NaCl, 1 mM dithiothreitol, Tween-20 at 0.01% and fatty-acid free bovine serum albumin at 0.01%, and recombinant EZH2-641F complex (EZH2 Y641F/EED/SUZ12/RbAp48/AEBP2) at 5 nM (>98% purity, BPS Bioscience) or 15 nM (50% purity, in-house). Reaction mixtures were incubated at room temperature for 3 hours, and the reactions were terminated by 0.005% poly-L-lysine solution in 20 mM Tris-HCl (pH 7.5) and 150 mM NaCl. Reaction products were captured by binding to strepavidin-conjugated imaging beads. Incorporation of radioactive methyl group into the histone peptide substrate was determined in Leadseeker (GE Healthcare) by means of scintillation proximity assay. Dose response curves were generated to determine the concentration required to inhibit 50% of methyl transferase activity (EC$_{50}$). Compounds were dissolved at 10 mM in dimethylsulfoxide (DMSO) and evaluated at eleven concentrations. EC$_{50}$ values were derived by non-linear regression analysis.

Results:

Results of the assays are shown in the Table below. Compounds with an IC$_{50}$>1 μM are shown with (+), compounds with an IC$_{50}$ between 0.5-1.0 μM are shown with (++) and those with an IC$_{50}$<0.5 μM are shown with (+++).

| Ex. No. | EZH2 Activity (IC$_{50}$) |
| --- | --- |
| 1 | +++ |
| 2 | + |
| 3 | + |
| 4 | + |
| 5 | + |
| 6 | + |
| 7 | ++ |
| 8 | + |
| 9 | + |
| 10 | + |
| 11 | +++ |
| 12 | +++ |
| 13 | + |
| 14 | ++ |
| 15 | + |
| 16 | + |
| 17 | +++ |
| 18 | +++ |
| 19 | + |
| 20 | +++ |
| 21 | + |
| 22 | + |
| 23 | + |
| 24 | + |
| 25 | ++ |
| 26 | +++ |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | + |
| 55 | + |
| 56 | + |
| 57 | + |
| 58 | + |
| 59 | +++ |
| 60 | + |
| 61 | + |
| 62 | +++ |
| 63 | + |
| 64 | + |
| 65 | +++ |
| 66 | ++ |
| 67 | ++ |
| 68 | ++ |
| 69 | +++ |
| 70 | + |
| 71 | + |
| 72 | +++ |
| 73 | + |
| 74 | + |
| 75 | + |
| 76 | + |
| 77 | + |
| 78 | + |
| 79 | + |
| 80 | + |
| 81 | + |

| Ex. No. | EZH2 Activity (IC$_{50}$) |
|---|---|
| 82 | + |
| 83 | ++ |
| 84 | + |
| 85 | +++ |
| 86 | + |
| 87 | +++ |
| 88 | +++ |
| 89 | + |
| 90 | + |
| 91 | + |
| 92 | + |
| 93 | +++ |
| 94 | +++ |

We claim:

1. A compound of formula (I)

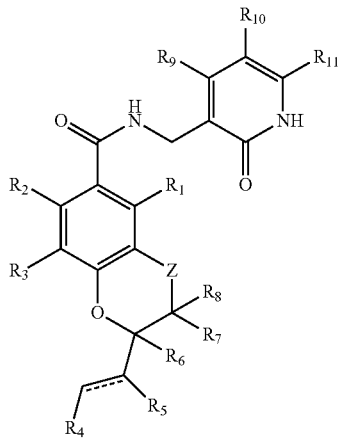

wherein
the dotted line represents an optional double bond;
Z is O, CH$_2$ or a direct bond;
R$_1$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_2$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_3$ is hydrogen, halogen, —CN, —CONR$_{12}$R$_{13}$, optionally substituted C$_6$-C$_{10}$ mono or bicyclic aryl, optionally substituted C$_6$-C$_{10}$ mono or bicyclic heteroaryl, optionally substituted C$_1$-C$_6$ alkyl C$_6$aryl or optionally substituted C$_1$-C$_6$ alkyl C$_5$-C$_8$ heteroaryl, wherein the optional substituents are halogen, C$_1$-C$_6$ alkyl, C$_1$-C$_6$ alkoxy, —CONR$_{12}$R$_{13}$ or heterocyclo;
R$_4$, R$_5$, R$_6$, R$_7$ and R$_8$ are independently one or more hydrogen, flourine, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo; or
R$_6$ and R$_7$ may be taken together to form a fused C$_3$-C$_8$ cycloalkyl group, or
R$_4$ and R$_6$ may be taken together to form a spiro C$_4$-C$_8$ cycloalkyl group; or
R$_7$ and R$_8$ may be taken together to form a spiro C$_3$-C$_8$ cycloalkyl group;
R$_9$, R$_{10}$ and R$_{11}$ are independently hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_{12}$ and R$_{13}$ are independently hydrogen, C$_1$-C$_6$ alkyl, or
R$_{12}$ and R$_{13}$ are taken together with the nitrogen atom to which they are attached to form an optionally substituted heterocyclo group;
or a pharmaceutically acceptable salt, tautomer or stereoisomer thereof.

2. The compound according to claim 1

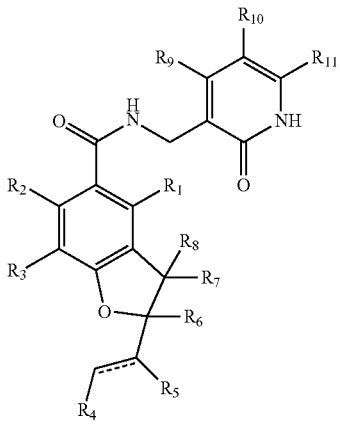

wherein
R$_1$ is hydrogen, halogen, CF$_3$ or optionally substituted C$_1$-C$_6$ alkyl;
R$_2$ is hydrogen, halogen, CF$_3$ or optionally substituted C$_1$-C$_6$ alkyl;
R$_3$ is hydrogen, halogen, —CN, —CONR$_{12}$R$_{13}$, optionally substituted C$_6$-C$_{10}$ mono or bicyclic aryl, optionally substituted C$_6$-C$_{10}$ mono or bicyclic heteroaryl, optionally substituted C$_1$-C$_6$ alkyl C$_6$aryl or optionally substituted C$_1$-C$_6$ alkyl C$_5$-C$_8$ heteroaryl, wherein the optional substituents are halogen, C$_1$-C$_6$ alkyl, C$_1$-C$_6$ alkoxy, —CONR$_{12}$R$_{13}$ or heterocyclo;
R$_4$, R$_5$, R$_6$, R$_7$ and R$_8$ are independently one or more hydrogen, flourine, CF$_3$ or optionally substituted C$_1$-C$_6$ alkyl; or
R$_6$ and R$_7$ may be taken together to form a fused C$_3$-C$_8$ cycloalkyl group, or
R$_4$ and R$_6$ may be taken together to form a spiro C$_4$-C$_8$ cycloalkyl group; or
R$_7$ and R$_8$ may be taken together to form a spiro C$_3$-C$_8$ cycloalkyl group;
R$_9$, R$_{10}$ and R$_{11}$ are independently hydrogen, halogen, CF$_3$ or optionally substituted C$_1$-C$_6$ alkyl;
R$_{12}$ and R$_{13}$ are independently hydrogen, C$_1$-C$_6$ alkyl, or
R$_{12}$ and R$_{13}$ are taken together with the nitrogen atom to which they are attached to form an optionally substituted heterocyclo group;
or a pharmaceutically acceptable salt, tautomer or stereoisomer thereof.

3. A compound of Formula (II)

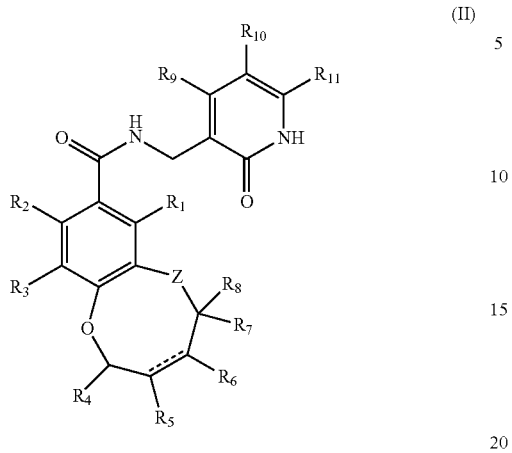

(II)

wherein
Z is O, CH$_2$ or a direct bond;
R$_1$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_2$ is hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_3$ is hydrogen, halogen, —CN, —CONR$_{12}$R$_{13}$, optionally substituted C$_6$-C$_{10}$ mono or bicyclic aryl, optionally substituted C$_6$-C$_{10}$ mono or bicyclic heteroaryl, optionally substituted C$_1$-C$_6$ alkyl C$_6$aryl or optionally substituted C$_1$-C$_6$ alkyl C$_5$-C$_8$ heteroaryl, wherein the optional substituents are halogen, C$_1$-C$_6$ alkyl, C$_1$-C$_6$ alkoxy, —CONR$_{12}$R$_{13}$ or heterocyclo;
R$_4$, R$_5$, R$_6$, R$_7$ and R$_8$ are independently one or more hydrogen, fluorine, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo; or
R$_6$ and R$_7$ may be taken together to form a fused C$_3$-C$_8$ cycloalkyl group, or
R$_7$ and R$_8$ may be taken together to form a spiro C$_3$-C$_8$ cycloalkyl group;
R$_9$, R$_{10}$ and R$_{11}$ are independently hydrogen, halogen, CF$_3$, optionally substituted C$_1$-C$_6$ alkyl, optionally substituted C$_1$-C$_6$ alkoxy, optionally substituted C$_3$-C$_8$ cycloalkyl, C$_2$-C$_6$ alkenyl, C$_2$-C$_6$ alkynyl, optionally substituted aryl or optionally substituted heterocyclo;
R$_{12}$ and R$_{13}$ are independently hydrogen, C$_1$-C$_6$ alkyl, or
R$_{12}$ and R$_{13}$ are taken together with the nitrogen atom to which they are attached to form an optionally substituted heterocyclo group;
or a pharmaceutically acceptable salt, tautomer or stereoisomer thereof.

4. The compound according to claim 3 of the formula

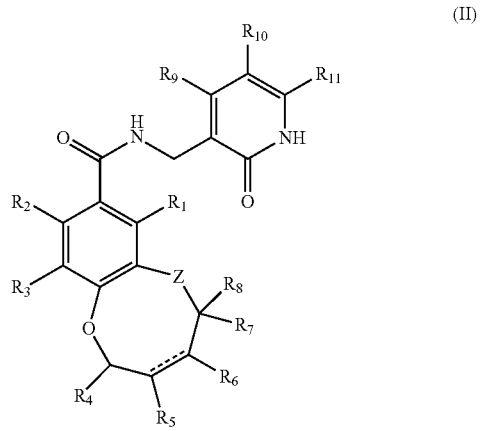

(II)

wherein
Z is O, CH$_2$ or a direct bond;
R$_1$ is hydrogen, halogen, CF$_3$ or optionally substituted C$_1$-C$_6$ alkyl;
R$_2$ is hydrogen, halogen, CF$_3$ or optionally substituted C$_1$-C$_6$ alkyl;
R$_3$ is hydrogen, halogen, —CN, —CONR$_{12}$R$_{13}$, optionally substituted C$_6$-C$_{10}$ mono or bicyclic aryl, optionally substituted C$_6$-C$_{10}$ mono or bicyclic heteroaryl, optionally substituted C$_1$-C$_6$ alkyl C$_6$aryl or optionally substituted C$_1$-C$_6$ alkyl C$_5$-C$_8$ heteroaryl, wherein the optional substituents are halogen, C$_1$-C$_6$ alkyl, C$_1$-C$_6$ alkoxy, —CONR$_{12}$R$_{13}$ or heterocyclo;
R$_4$, R$_5$, R$_6$, R$_7$ and R$_8$ are independently one or more hydrogen, fluorine, CF$_3$ or optionally substituted C$_1$-C$_6$ alkyl; or
R$_6$ and R$_7$ may be taken together to form a fused C$_3$-C$_8$ cycloalkyl group, or
R$_7$ and R$_8$ may be taken together to form a spiro C$_3$-C$_8$ cycloalkyl group;
R$_9$, R$_{10}$ and R$_{11}$ are independently hydrogen, halogen, CF$_3$ or optionally substituted C$_1$-C$_6$ alkyl;
R$_{12}$ and R$_{13}$ are independently hydrogen, C$_1$-C$_6$ alkyl, or
R$_{12}$ and R$_{13}$ are taken together with the nitrogen atom to which they are attached to form an optionally substituted heterocyclo group;
or a pharmaceutically acceptable salt, tautomer or stereoisomer thereof.

5. The compound which is
7-Bromo-N-((4,6-dimethyl-2-oxo-1,2-dihydropyridin-3-yl)methyl)-2,2-dimethyl-2,3-dihydrobenzofuran-5-carboxamide,
7-Chloro-N-((4,6-dimethyl-2-oxo-1,2-dihydropyridin-3-yl)methyl)-2,2-dimethyl-2,3-dihydrobenzofuran-5-carboxamide,
N-((4,6-Dimethyl-2-oxo-1,2-dihydropyridin-3-yl)methyl)-2,2-dimethyl-2,3-dihydrobenzofuran-5-carboxamide,
N-((4,6-Dimethyl-2-oxo-1,2-dihydropyridin-3-yl)methyl)-7-fluoro-2,2-dimethyl-2,3-dihydrobenzofuran-5-carboxamide,
N-((4,6-Dimethyl-2-oxo-1,2-dihydropyridin-3-yl)methyl)-2,2,7-trimethyl-2,3-dihydrobenzofuran-5-carboxamide,
N-((4,6-Dimethyl-2-oxo-1,2-dihydropyridin-3-yl)methyl)-2,2-dimethyl-7-(trifluoromethyl)-2,3-dihydrobenzofuran-5-carboxamide, 7-Bromo-N-((4,6-dimethyl-2-oxo-1,2-dihydropyridin-3-yl)methyl)-2,2,4-trimethyl-2,3-dihydrobenzofuran-5-carboxamide,
N-((4,6-Dimethyl-2-oxo-1,2-dihydropyridin-3-yl)methyl)-2,2,4-trimethyl-2,3-dihydrobenzofuran-5-carboxamide,
N-((4,6-Dimethyl-2-oxo-1,2-dihydropyridin-3-yl)methyl)-2,2,4,7-tetramethyl-2,3-dihydrobenzofuran-5-carboxamide,
N-((4,6-Dimethyl-2-oxo-1,2-dihydropyridin-3-yl)methyl)-2,2-dimethyl-7-(4-(morpholinomethyl)phenyl)-2,3-dihydrobenzofuran-5-carboxamide,
N-((4,6-Dimethyl-2-oxo-1,2-dihydropyridin-3-yl)methyl)-2,2-dimethyl-7-(6-(piperazin-1-yl)pyridin-3-yl)-2,3-dihydrobenzofuran-5-carboxamide,
N-((4,6-Dimethyl-2-oxo-1,2-dihydropyridin-3-yl)methyl)-2,2-dimethyl-7-(6-morpholinopyridin-3-yl)-2,3-dihydrobenzofuran-5-carboxamide,
N-((4,6-Dimethyl-2-oxo-1,2-dihydropyridin-3-yl)methyl)-2,2-dimethyl-7-(quinolin-3-yl)-2,3-dihydrobenzofuran-5-carboxamide,
N-((4,6-Dimethyl-2-oxo-1,2-dihydropyridin-3-yl)methyl)-7-(6-methoxypyridin-3-yl)-2,2-dimethyl-2,3-dihydrobenzofuran-5-carboxamide,
(E)-N-((4,6-Dimethyl-2-oxo-1,2-dihydropyridin-3-yl)methyl)-2,2-dimethyl-7-styryl-2,3-dihydrobenzofuran-5-carboxamide,
N-((4,6-Dimethyl-2-oxo-1,2-dihydropyridin-3-yl)methyl)-2,2-dimethyl-7-(4-(4-methylpiperazine-1-carbonyl)phenyl)-2,3-dihydrobenzofuran-5-carboxamide,
t-Butyl 4-(5-(5-(((4,6-dimethyl-2-oxo-1,2-dihydropyridin-3-yl)methyl)carbamoyl)-2,2-dimethyl-2,3-dihydrobenzofuran-7-yl)pyrimidin-2-yl)piperazine-1-carboxylate,
N-((4,6-Dimethyl-2-oxo-1,2-dihydropyridin-3-yl)methyl)-2,2-dimethyl-7-(4-(piperazin-1-yl)phenyl)-2,3-dihydrobenzofuran-5-carboxamide,
N-((4,6-Dimethyl-2-oxo-1,2-dihydropyridin-3-yl)methyl)-2,2-dimethyl-7-(4-(piperidin-1-ylmethyl)phenyl)-2,3-dihydrobenzofuran-5-carboxamide,
N-((4,6-Dimethyl-2-oxo-1,2-dihydropyridin-3-yl)methyl)-2,2-dimethyl-7-(2-(piperazin-1-yl)pyrimidin-5-yl)-2,3-dihydrobenzofuran-5-carboxamide,
7-Benzyl-N-((4,6-dimethyl-2-oxo-1,2-dihydropyridin-3-yl)methyl)-2,2-dimethyl-2,3-dihydrobenzofuran-5-carboxamide,
7-Cyano-N-((4,6-dimethyl-2-oxo-1,2-dihydropyridin-3-yl)methyl)-2,2-dimethyl-2,3-dihydrobenzofuran-5-carboxamide,
7-Chloro-2,2-dimethyl-N-((6-methyl-2-oxo-4-propyl-1,2-dihydropyridin-3-yl)methyl)-2,3-dihydrobenzofuran-5-carboxamide,
7-Bromo-2,2-dimethyl-N-((6-methyl-2-oxo-4-propyl-1,2-dihydropyridin-3-yl)methyl)-2,3-dihydrobenzofuran-5-carboxamide,
N-((4,6-Dimethyl-2-oxo-1,2-dihydropyridin-3-yl)methyl)-7-(6-methoxypyridin-3-yl)-2,2,4-trimethyl-2,3-dihydrobenzofuran-5-carboxamide,
N-((4,6-Dimethyl-2-oxo-1,2-dihydropyridin-3-yl)methyl)-2,2,4-trimethyl-7-(6-(piperazin-1-yl)pyridin-3-yl)-2,3-dihydrobenzofuran-5-carboxamide,
N-((4,6-Dimethyl-2-oxo-1,2-dihydropyridin-3-yl)methyl)-3-methyl-7-(6-morpholinopyridin-3-yl)-2,3-dihydrobenzofuran-5-carboxamide,
N-((4,6-Dimethyl-2-oxo-1,2-dihydropyridin-3-yl)methyl)-3-methyl-7-(4-(morpholinomethyl)phenyl)-2,3-dihydrobenzofuran-5-carboxamide,
N-((4,6-Dimethyl-2-oxo-1,2-dihydropyridin-3-yl)methyl)-3-methyl-7-(6-(piperazin-1-yl)pyridin-3-yl)-2,3-dihydrobenzofuran-5-carboxamide,
N-((4,6-Dimethyl-2-oxo-1,2-dihydropyridin-3-yl)methyl)-7-(6-methoxypyridin-3-yl)-3-methyl-2,3-dihydrobenzofuran-5-carboxamide,
7-Bromo-N-((4,6-dimethyl-2-oxo-1,2-dihydropyridin-3-yl)methyl)-2-methyl-2,3-dihydrobenzofuran-5-carboxamide,
N-((4,6-Dimethyl-2-oxo-1,2-dihydropyridin-3-yl)methyl)-7-(6-methoxypyridin-3-yl)-2-methyl-2,3-dihydrobenzofuran-5-carboxamide,
N-((4,6-Dimethyl-2-oxo-1,2-dihydropyridin-3-yl)methyl)-2-methyl-7-(6-morpholinopyridin-3-yl)-2,3-dihydrobenzofuran-5-carboxamide,
N-((4,6-Dimethyl-2-oxo-1,2-dihydropyridin-3-yl)methyl)-2-methyl-7-(6-(piperazin-1-yl)pyridin-3-yl)-2,3-dihydrobenzofuran-5-carboxamide,
N-((4,6-Dimethyl-2-oxo-1,2-dihydropyridin-3-yl)methyl)-2-methyl-7-(4-(morpholinomethyl)phenyl)-2,3-dihydrobenzofuran-5-carboxamide,
N-((4,6-Dimethyl-2-oxo-1,2-dihydropyridin-3-yl)methyl)-7-(6-methoxypyridin-3-yl)-2,3-dihydrobenzofuran-5-carboxamide,
N-((4,6-Dimethyl-2-oxo-1,2-dihydropyridin-3-yl)methyl)-7-(6-morpholinopyridin-3-yl)-2,3-dihydrobenzofuran-5-carboxamide,
N-((4,6-Dimethyl-2-oxo-1,2-dihydropyridin-3-yl)methyl)-7-(6-(piperazin-1-yl)pyridin-3-yl)-2,3-dihydrobenzofuran-5-carboxamide,
N-((4,6-Dimethyl-2-oxo-1,2-dihydropyridin-3-yl)methyl)-7-(6-methoxypyridin-3-yl)-3,3-dimethyl-2,3-dihydrobenzofuran-5-carboxamide,
(2S,3R)-7-Bromo-N-((4,6-dimethyl-2-oxo-1,2-dihydropyridin-3-yl)methyl)-2,3-dimethyl-2,3-dihydrobenzofuran-5-carboxamide,
N-((4,6-Dimethyl-2-oxo-1,2-dihydropyridin-3-yl)methyl)-2,2-dimethylchroman-6-carboxamide,
8-Bromo-N-((4,6-dimethyl-2-oxo-1,2-dihydropyridin-3-yl)methyl)-2,2-dimethylchroman-6-carboxamide,
N-((4,6-Dimethyl-2-oxo-1,2-dihydropyridin-3-yl)methyl)-8-(6-methoxypyridin-3-yl)-2,2-dimethylchroman-6-carboxamide,
9-Bromo-N-((4,6-dimethyl-2-oxo-1,2-dihydropyridin-3-yl)methyl)-4-methyl-2,5-dihydrobenzo[b]oxepine-7-carboxamide,
9-Bromo-N-((4,6-dimethyl-2-oxo-1,2-dihydropyridin-3-yl)methyl)-4-methyl-2,3,4,5-tetrahydrobenzo[b]oxepine-7-carboxamide,
N-((4,6-Dimethyl-2-oxo-1,2-dihydropyridin-3-yl)methyl)-9-(6-methoxypyridin-3-yl)-4-methyl-2,3,4,5-tetrahydrobenzo[b]oxepine-7-carboxamide,
N-((4,6-Dimethyl-2-oxo-1,2-dihydropyridin-3-yl)methyl)-2-methyl-2,3-dihydrobenzo[b]oxepine-7-carboxamide,
N-((4,6-Dimethyl-2-oxo-1,2-dihydropyridin-3-yl)methyl)-2-methyl-2,3,4,5-tetrahydrobenzo[b]oxepine-7-carboxamide,
9-Bromo-N-((4,6-dimethyl-2-oxo-1,2-dihydropyridin-3-yl)methyl)-2-methyl-2,3,4,5-tetrahydrobenzo[b]oxepine-7-carboxamide,
N-((4,6-Dimethyl-2-oxo-1,2-dihydropyridin-3-yl)methyl)-2-methyl-9-(4-(morpholinomethyl)phenyl)-2,3,4,5-tetrahydrobenzo[b]oxepine-7-carboxamide,
N-((4,6-Dimethyl-2-oxo-1,2-dihydropyridin-3-yl)methyl)-2-methyl-9-(6-(piperazin-1-yl)pyridin-3-yl)-2,3,4,5-tetrahydrobenzo[b]oxepine-7-carboxamide, N-((4,6-Dimethyl-2-oxo-1,2-dihydropyridin-3-yl)methyl)-9-(6-methoxypyridin-3-yl)-2-methyl-2,3,4,5-tetrahydrobenzo[b]oxepine-7-carboxamide, 9-Bromo-N-((4,6-dimethyl-2-oxo-1,2-dihydropyridin-3-yl)methyl)-3-methyl-2,3,4,5-tetrahydrobenzo[b]oxepine-7-carboxamide, N-((4,6-Dimethyl-2-oxo-1,2-dihydropyridin-3-yl)methyl)-3-methyl-9-(6-(piperazin-1-yl)pyridin-3-yl)-2,3,4,5-tetrahydrobenzo[b]oxepine-7-carboxamide, N-((4,6-Dimethyl-2-oxo-1,2-dihydropyridin-3-yl)methyl)-7-(6-methoxypyridin-3-yl)-2-methyl-2-vinyl-2,3-dihydrobenzofuran-5-carboxamide, 7-Bromo-N-((4,6-dimethyl-2-oxo-1,2-dihydropyridin-3-yl)methyl)-2-methyl-2-vinyl-2,3-dihydrobenzofuran-5-carboxamide, N-((4,6-Dimethyl-2-oxo-1,2-dihydropyridin-3-yl)methyl)-2-methyl-7-(4-(morpholinomethyl)phenyl)-2-vinyl-2,3-dihydrobenzofuran-5-carboxamide, N-((4,6-Dimethyl-2-oxo-1,2-dihydropyridin-3-yl)methyl)-2-methyl-7-(6-(piperazin-1-yl)pyridin-3-yl)-2-vinyl-2,3-dihydrobenzofuran-5-carboxamide, N-((4,6-Dimethyl-2-oxo-1,2-dihydropyridin-3-yl)methyl)-2-ethyl-7-(6-methoxypyridin-3-yl)-2-methyl-2,3-dihydrobenzofuran-5-carboxamide, N-((4,6-Dimethyl-2-oxo-1,2-dihydropyridin-3-yl)methyl)-2-ethyl-2-methyl-7-(6-(piperazin-1-yl)pyridin-3-yl)-2,3-dihydrobenzofuran-5-carboxamide, N-((4,6-Dimethyl-2-oxo-1,2-dihydropyridin-3-yl)methyl)-2-ethyl-2-methyl-7-(p-tolyl)-2,3-dihydrobenzofuran-5-carboxamide, rac-(3aS,8bS)-5-Bromo-N-((4,6-dimethyl-2-oxo-1,2-dihydropyridin-3-yl)methyl)-3a-methyl-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(6-(piperazin-1-yl)pyridin-3-yl)-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-5-(6-methoxypyridin-3-yl)-3a-methyl-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(4-(piperidin-1-ylmethyl)phenyl)-2,3,3a,8b-tetrahydro-1H-cyclopenta[b]benzofuran-7-carboxamide, rac-(3aS,8bS)—N-((4,6-Dimethyl-2-oxo-1,2-dihydropyridin-3-yl)methyl)-3a-methyl-5-(4-(piperazin-1-yl)phenyl)-2,3,3a,8b-tetrahydro-1H-cyclopenta[b]benzofuran-7-carboxamide, rac-(3aS,8bS)-5-Bromo-N-((4,6-dimethyl-2-oxo-1,2-dihydropyridin-3-yl)methyl)-3a,6-dimethyl-2,3,3a,8b-tetrahydro-1H-cyclopenta[b]benzofuran-7-carboxamide, 7-Bromo-N-((4,6-dimethyl-2-oxo-1,2-dihydropyridin-3-yl)methyl)-3H-spiro[benzofuran-2,1'-cyclopentane]-5-carboxamide, N-((4,6-Dimethyl-2-oxo-1,2-dihydropyridin-3-yl)methyl)-7-(6-methoxypyridin-3-yl)-3H-spiro[benzofuran-2,1'-cyclopentane]-5-carboxamide, N-((4,6-Dimethyl-2-oxo-1,2-dihydropyridin-3-yl)methyl)-7-(6-(piperazin-1-yl)pyridin-3-yl)-3H-spiro[benzofuran-2,1'-cyclopentane]-5-carboxamide, tert-Butyl 4-(5-(5-(((4,6-dimethyl-2-oxo-1,2-dihydropyridin-3-yl)methyl)carbamoyl)-3H-spiro[benzofuran-2,1'-cyclopentan]-7-yl)pyrimidin-2-yl)piperazine-1-carboxylate, N-((4,6-Dimethyl-2-oxo-1,2-dihydropyridin-3-yl)methyl)-7-(4-(piperidin-1-ylmethyl)phenyl)-3H-spiro[benzofuran-2,1'-cyclopentane]-5-carboxamide, 7-Bromo-N-((4,6-dimethyl-2-oxo-1,2-dihydropyridin-3-yl)methyl)-2H-spiro[benzofuran-3,1'-cyclopentane]-5-carboxamide, N-((4,6-Dimethyl-2-oxo-1,2-dihydropyridin-3-yl)methyl)-7-(6-methoxypyridin-3-yl)-2H-spiro[benzofuran-3,1'-cyclopentane]-5-carboxamide, N-((4,6-Dimethyl-2-oxo-1,2-dihydropyridin-3-yl)methyl)-7-(6-(piperazin-1-yl)pyridin-3-yl)-2H-spiro[benzofuran-3,1'-cyclopentane]-5-carboxamide, N-((4,6-Dimethyl-2-oxo-1,2-dihydropyridin-3-yl)methyl)-7-(4-(piperidin-1-ylmethyl)phenyl)-2H-spiro[benzofuran-3,1'-cyclopentane]-5-carboxamide, 7-Bromo-N-((4,6-dimethyl-2-oxo-1,2-dihydropyridin-3-yl)methyl)-2-isopropyl-2,3-dihydrobenzofuran-5-carboxamide, N-((4,6-Dimethyl-2-oxo-1,2-dihydropyridin-3-yl)methyl)-2-isopropyl-7-(6-(piperazin-1-yl)pyridin-3-yl)-2,3-dihydrobenzofuran-5-carboxamide, 9-Bromo-N-((4,6-dimethyl-2-oxo-1,2-dihydropyridin-3-yl)methyl)-3,4-dimethyl-2,5-dihydrobenzo[b]oxepine-7-carboxamide, 7-Bromo-N-((4,6-dimethyl-2-oxo-1,2-dihydropyridin-3-yl)methyl)-2-methyl-2-(prop-1-en-2-yl)-2,3-dihydrobenzofuran-5-carboxamide, N-((4,6-dimethyl-2-oxo-1,2-dihydropyridin-3-yl)methyl)-7-(6-methoxypyridin-3-yl)-2-methyl-2-(prop-1-en-2-yl)-2,3-dihydrobenzofuran-5-carboxamide, N-((4,6-Dimethyl-2-oxo-1,2-dihydropyridin-3-yl)methyl)-2-isopropyl-7-(6-methoxypyridin-3-yl)-2-methyl-2,3-dihydrobenzofuran-5-carboxamide, HCl, N-((4,6-Dimethyl-2-oxo-1,2-dihydropyridin-3-yl)methyl)-2-methyl-7-(6-(piperazin-1-yl)pyridin-3-yl)-2-(prop-1-en-2-yl)-2,3-dihydrobenzofuran-5-carboxamide, 2 TFA, 9-Bromo-3,4-dimethyl-N-((6-methyl-2-oxo-4-propyl-1,2-dihydropyridin-3-yl)methyl)-2,5-dihydrobenzo[b]oxepine-7-carboxamide, 2-Methyl-N-((6-methyl-2-oxo-4-propyl-1,2-dihydropyridin-3-yl)methyl)-7-(6-(piperazin-1-yl)pyridin-3-yl)-2-(prop-1-en-2-yl)-2,3-dihydrobenzofuran-5-carboxamide, 2 TFA, 2-isopropyl-2-methyl-N-((6-methyl-2-oxo-4-propyl-1,2-dihydropyridin-3-yl) methyl)-7-(6-(piperazin-1-yl)pyridin-3-yl)-2,3-dihydrobenzofuran-5-carboxamide, 2 HCl, 9-Bromo-N-((4,6-dimethyl-2-oxo-1,2-dihydropyridin-3-yl)methyl)-3,4-dimethyl-2,5-dihydrobenzo[b]oxepine-7-carboxamide, 8-Bromo-N-((4,6-dimethyl-2-oxo-1,2-dihydropyridin-3-yl)methyl)-2-vinyl-2,3-dihydrobenzo[b][1,4]dioxine-6-carboxamide, 8-Bromo-N-((4,6-dimethyl-2-oxo-1,2-dihydropyridin-3-yl)methyl)-2-ethyl-2,3-dihydrobenzo[b][1,4]dioxine-6-carboxamide, N-((4,6-Dimethyl-2-oxo-1,2-dihydropyridin-3-yl)methyl)-2-ethyl-8-(6-(piperazin-1-yl)pyridin-3-yl)-2,3-dihydrobenzo[b][1,4]dioxine-6-carboxamide, 2 TFA, 2-Isopropyl-7-(6-(4-isopropylpiperazin-1-yl)pyridin-3-yl)-2-methyl-N-((6-methyl-2-oxo-4-propyl-1,2-dihydropyridin-3-yl)methyl)-2,3-dihydrobenzofuran-5-carboxamide, 2-Methyl-N-((6-methyl-2-oxo-4-propyl-1,2-dihydropyridin-3-yl)methyl)-7-(2-(piperazin-1-yl)pyrimidin-5-yl)-2-(prop-1-en-2-yl)-2,3-dihydrobenzofuran-5-carboxamide, 2 HCl, or a pharmaceutically acceptable salt, tautomer or stereoisomer thereof.

6. A pharmaceutical composition comprising one or more compounds according to claim 1 and a pharmaceutically acceptable carrier or diluent.

7. A compound according to claim 1 for use in therapy.

* * * * *